US009999222B2

(12) United States Patent
Major et al.

(10) Patent No.: US 9,999,222 B2
(45) Date of Patent: *Jun. 19, 2018

(54) HERBICIDAL COMBINATION COMPRISING AZINES

(71) Applicant: BASF SE, Ludwigshafen (DE)

(72) Inventors: Julia Major, Freinsheim (DE); Florian Vogt, Mannheim (DE); Frederick Calo, Duesseldorf (DE); Thomas Seitz, Viernheim (DE); Doreen Schachtschabel, Mannheim (DE); Trevor William Newton, Neustadt (DE); Kristin Hanzlik, Bobenheim am Berg (DE); Johannes Hutzler, Waldsee (DE); Klaus Kreuz, Denzlingen (DE); Stefan Tresch, Kirchheim (DE)

(73) Assignee: BASF SE, Ludwigshafen (DE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/305,835

(22) PCT Filed: Apr. 22, 2015

(86) PCT No.: PCT/EP2015/058689
§ 371 (c)(1),
(2) Date: Oct. 21, 2016

(87) PCT Pub. No.: WO2015/162164
PCT Pub. Date: Oct. 29, 2015

(65) Prior Publication Data
US 2017/0042154 A1 Feb. 16, 2017

(30) Foreign Application Priority Data

Apr. 23, 2014 (EP) .................... 14165564

(51) Int. Cl.
*A01N 43/68* (2006.01)
(52) U.S. Cl.
CPC .................. *A01N 43/68* (2013.01)
(58) Field of Classification Search
None
See application file for complete search history.

(56) References Cited

U.S. PATENT DOCUMENTS

| 3,816,419 A | 6/1974 | Cross et al. | |
| 9,549,558 B2 * | 1/2017 | Newton | C07C 279/26 |
| 2003/0004064 A1 * | 1/2003 | Ahrens | A01N 43/68 504/133 |
| 2003/0087761 A1 * | 5/2003 | Ahrens et al. | A01N 43/68 504/133 |

FOREIGN PATENT DOCUMENTS

| WO | WO-2014/064094 | 5/2014 |
| WO | WO-2015/144881 | 10/2015 |
| WO | WO-2015/150541 | 10/2015 |
| WO | WO-2015/155129 | 10/2015 |
| WO | WO-2015/155271 | 10/2015 |
| WO | WO-2015/155272 | 10/2015 |
| WO | WO-2015/155273 | 10/2015 |
| WO | WO-2015/162164 | 10/2015 |
| WO | WO-2015/162169 | 10/2015 |

OTHER PUBLICATIONS

Vaughn "Cellulose Biosynthesis Inhibitor Herbicides", pp. 139-150 in Herbicide Classes in Development, ed. By Boeger, Wakabayashi, and Hirai, 2002.*
Search Report dated Mar. 19, 2015 for European Application No. 14165564.7.
International Search Report dated Jun. 10, 2015 for PCT/EP2015/058689.
International Preliminary Report on Patentability dated Jun. 28, 2016 for PCT/EP2015/058689.

* cited by examiner

*Primary Examiner* — Robert A Wax
*Assistant Examiner* — Thor Nielsen
(74) *Attorney, Agent, or Firm* — Brinks Gilson & Lione

(57) ABSTRACT

The present invention relates to herbicidal combinations comprising at least one compound of formula (I) (component a) and at least one further compound selected from herbicidally active compounds (component b) and/or safeners (component c)

(I)

wherein
$R^a$, $R^b$, $R^c$, $R^d$ are inter alia H, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, etc.;
$R^1$ is inter alia H, OH, $S(O)_2NH_2$, CN, $C_1$-$C_6$-alkyl, etc.;
$R^2$ is inter alia H, halogen, CN, $C_1$-$C_6$-alkyl, $C_1$-$C_6$-haloalkyl, $C_2$-$C_6$-alkenyl, $C_3$-$C_6$-alkynyl, etc.;
$R^3$ is inter alia H, halogen, CN, $C_1$-$C_6$-alkyl, etc;
$R^4$ is inter alia H, halogen, CN, $C_1$-$C_6$-alkyl, etc; or
$R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, and
$R^5$ is inter alia H, OH, $S(O)_2NH_2$, CN, $C_1$-$C_6$-alkyl, etc;
including their agriculturally acceptable salts or N-oxides; and at least one further compound selected from herbicide compounds b) and safeners c) and mixtures thereof.

20 Claims, No Drawings

HERBICIDAL COMBINATION COMPRISING AZINES

This application is a National Stage application of International Application No. PCT/EP2015/058689, filed Apr. 22, 2015. This application also claims priority under 35 U.S.C. § 119 to European Patent Application No. 14165564.7, filed Apr. 23, 2014.

The present invention relates to herbicidal combinations comprising at least one compound of formula (I) (component a), which is defined below and at least one further compound selected from herbicidally active compounds (component b) and/or safeners (component c).

In the case of crop protection combinations, it is desirable in principle to increase the specific activity of an active compound and the reliability of the effect. It is particularly desirable for the crop protection combination to control the harmful plants effectively, but at the same time to be compatible with the useful plants in question. Also desirable is a broad spectrum of activity allowing the simultaneous control of harmful plants. Frequently, this cannot be achieved using a single herbicidally active compound.

With many highly effective herbicides, there is the problem that their compatibility with useful plants, in particular dicotyledonous crop plants, such as cotton, oilseed rape and graminaceous plants, such as barley, millet, corn, rice, wheat and sugar cane, is not always satisfactory, i.e. in addition to the harmful plants, the crop plants, too, are damaged on a scale which cannot be tolerated. By reducing the application rates, the useful plants are spared; however, naturally, the extent of the control of harmful plants decreases, too.

Frequently, it is a problem that herbicides can only be applied within a narrow time frame in order to achieve the desired herbicidal action, which time frame may be unpredictably influenced by weather conditions.

It is known that special combinations of different specifically active herbicides result in enhanced activity of an herbicide component in the sense of a synergistic effect. In this manner, it is possible to reduce the application rates of herbicidally active compounds required for controlling the harmful plants.

Furthermore, it is known that in some cases joint application of specifically acting herbicides with organic active compounds, some of which may also have herbicidal activity, allows better crop plant compatibility to be achieved. In these cases, the active compounds act as antidotes or antagonists and are also referred to as safeners, since they reduce or even prevent damage to the crop plants.

Some compounds of formula (I) have been described for example in WO 2014/064094.

U.S. Pat. No. 3,816,419 describes structurally similar compounds for which herbicidal action is stated, which differ from the according to the present invention. This document does not describe the use of the compounds in herbicidal combinations comprising at least at least one further herbicidally active compounds and/or safeners.

US 2003/0087761 and US 2003/004064 describe combinations of a triazine diamine compounds with further herbicidally compounds. The triazine compounds of US 2003/0087761 and US 2003/004064 differ from the compounds of the present invention in the alkylene group between the phenyl group and the amino group attached to the triazine ring.

It is an object of the present invention to provide herbicidal combinations which are highly active against unwanted harmful plants. At the same time, the combinations should have good compatibility with useful plants, which thus can use applied in crops, in particular crops selected from the group consisting of wheat, sugarcane, direct seeded rice, transplanted rice, soybeans, corn, OSR, sunflower or total herbicide soy and corn. In addition, the combinations according to the invention should have a broad spectrum of activity.

This and further objects are achieved by the herbicidal combinations below.

Accordingly, the present invention relates to herbicidal combinations comprising:

a) at least one compound of the formula (I)

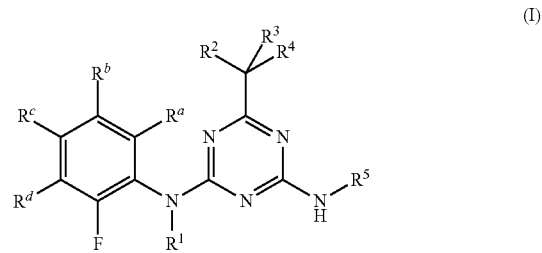

wherein $R^a$, $R^b$, $R^c$, $R^d$ independently from each other are H, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl and ($C_1$-$C_6$-alkyl)$C_3$-$C_6$-cycloalkyl;

$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;

$R^2$ is selected from the group consisting of H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, ($C_1$-$C_6$-alkyl)$C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;

$R^3$ H, halogen, CN, $C_1$-$C_6$-alkyl, $C_1$-$C_6$-haloalkyl or $C_1$-$C_6$-alkoxy;

$R^4$ H, halogen, CN, $C_1$-$C_6$-alkyl or $C_1$-$C_6$-haloalkyl; or $R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl, wherein the $C_3$-$C_6$-cycloalkyl, $C_3$-$C_6$-cycloalkenyl or three- to six-membered heterocyclyl is unsubstituted or substituted by one to three substituents selected from halogen, CN, $C_1$-$C_6$-alkyl and $C_1$-$C_6$-alkoxy, and R⁵ is selected from the group consisting of H, OH, S(O)$_2$NH$_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl, wherein phenyl in the last 6 mentioned radicals are unsubstituted or substituted by 1, 2, 3, 4 or 5 identical or different substituents selected from the group consisting of halogen, CN, NO$_2$, $C_1$-$C_6$-alkyl, $C_1$-$C_6$-haloalkyl, $C_1$-$C_6$-alkoxy and $C_1$-$C_6$-haloalkoxy including their agriculturally acceptable salts or N-oxides and at least one further compound selected from herbicide compounds b) and safeners c) and mixtures thereof;

a) where the further herbicidally active compounds b) is selected from the compounds of the following class b1) to b15):

b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyidazinol (CAS 499223-49-3) and its salts and esters including their agriculturally acceptable salts or derivatives.

The invention relates in particular to combinations in the form of herbicidal active agrochemical combinations comprising a herbicidally effective amount of an active compound combination comprising at least one compound of formula (I) (component a/compound A) and at least one further compound selected from the herbicides b) (component b/herbicide B) and/or at least one safeners c.

The invention relates in particular to combinations in the form of herbicidal active agrochemical combinations comprising a herbicidally effective amount of an active compound combination comprising at least one compound of formula (I) (component a/compound A) and at least one further compound selected from the herbicides b) (component b/herbicide B) and the safeners c, as defined above, and also at least one liquid and/or solid carrier and/or one or more surfactants and, if desired, one or more further auxiliaries customary for agrochemical combinations.

The invention also relates to combination in the form of an agrochemical composition formulated as a 1-component composition comprising an active compound composition comprising at least one compound of formula (I) (component a) or compound A) and at least one further active compound selected from the herbicides b) (herbicide B) and the safeners compound c, and at least one solid or liquid carrier and/or one or more surfactants and, if desired, one or more further auxiliaries customary for agrochemical combinations.

The invention also relates to combinations in the form of a agrochemical composition formulated as a 2-component composition comprising a first component comprising at least one compound of formula (I), (component a), compound A) a solid or liquid carrier and/or one or more surfactants, and a second component comprising at least one further active compound selected from the herbicides b) (herbicide B) and safeners c, a solid or liquid carrier and/or one or more surfactants, where additionally both components may also comprise further auxiliaries customary for agrochemical combinations.

Surprisingly, the combinations according to the invention comprising at least one compound of formula (I) (component a), compound A) and at least one herbicide b) (herbicide B) have better herbicidal activity, i.e. better activity against harmful plants, than would have been expected based on the herbicidal activity observed for the individual compounds, or a broader activity spectrum. The herbicidal activity to be expected for mixtures based on the individual compound can be calculated using Colby's formula (see below). If the activity observed exceeds the expected additive activity of the individual compounds, synergism is said to be present.

Moreover, the time frame, within which the desired herbicidal action can be achieved, may be expanded by the combinations according to the invention comprising at least one compound of formula (I) (component a), compound A) and at least one herbicide b) (herbicide B) and optionally a safener c. This allows a more flexibly timed application of the compositions according to the present invention in comparison with the single compounds.

The combinations according to the invention comprising both at least one compound of formula (I) (component a), compound A) and at least one of the compounds mentioned under C also have good herbicidal activity against harmful plants and better compatibility with useful plants.

Surprisingly, the herbicidal combinations according to the invention comprising at least one compound of formula (I) (component a), compound A), at least one herbicide b) (herbicide B) and at least one of the compounds mentioned under c have better herbicidal activity, i.e. better activity against harmful plants, than would have been expected based on the herbicidal activity observed for the individual compounds, or a broader activity spectrum, and show better compatibility with useful plants than combinations comprising only one compound of formula (I) and one herbicide b).

The invention furthermore relates to a method for controlling unwanted vegetation, in particular where crop plants are cultivated.

The invention also relates to a method for the desiccation or defoliation of plants especially for controlling unwanted vegetation in one of the following crops: wheat, sugarcane, directed rice, transplanted rice, soybeans, corn, OSR, sunflower, or total herbicide in soy and corn.

The invention furthermore relates to 6-(1-methylbutyl)-N4-(2,3,5,6-tetrafluorophenyl)-1,3,5-triazine-2,4-diamine, N4-(2,3,5,6-tetrafluorophenyl)-6-(1,2,2-trimethylpropyl)-1,3,5-triazine-2,4-diamine, 6-(cyclopropylmethyl)-N4-(2,4,6-trifluorophenyl)-1,3,5-triazine-2,4-diamine and to their agriculturally acceptable salts or N-oxides.

The invention furthermore relates to 6-(1-fluorocyclopentyl)-N4-(2,3,5,6-tetrafluorophenyl)-1,3,5-triazine-2,4-diamine and to its agriculturally acceptable salts or N-oxides.

The invention furthermore relates to agrochemical compositions comprising at least one compound selected from the group consisting of 6-(1-methylbutyl)-N4-(2,3,5,6-tetrafluorophenyl)-1,3,5-triazine-2,4-diamine, N4-(2,3,5,6-tetrafluorophenyl)-6-(1,2,2-trimethylpropyl)-1,3,5-triazine-2,4-diamine, 6-(cyclopropylmethyl)-N4-(2,4,6-trifluorophenyl)-1,3,5-triazine-2,4-diamine and to their agriculturally acceptable salts or N-oxides and at least on auxiliary customary for formulating crop protection agents.

The invention furthermore relates to the use of compounds selected from the group consisting of 6-(1-methylbutyl)-N4-(2,3,5,6-tetrafluorophenyl)-1,3,5-triazine-2,4-diamine, N4-(2,3,5,6-tetrafluorophenyl)-6-(1,2,2-trimethylpropyl)-1,3,5-triazine-2,4-diamine, 6-(cyclopropylmethyl)-N4-(2,4,6-trifluorophenyl)-1,3,5-triazine-2,4-diamine and to their agriculturally acceptable salts or N-oxides as herbicides, i.e. for controlling unwanted and/or harmful vegetation or plants.

The invention furthermore relates to the use of 6-(1-fluorocyclopentyl)-N4-(2,3,5,6-tetrafluorophenyl)-1,3,5-triazine-2,4-diamine and to its agriculturally acceptable salts or N-oxides as herbicides, i.e. for controlling unwanted and/or harmful vegetation or plants.

The invention furthermore relates to agrochemical combination comprising at least one compound selected from the group consisting of 6-(1-methylcyclobutyl)-N4-(2,3,5,6-tetrafluorophenyl)-1,3,5-triazine-2,4-diamine, 6-(1-fluorocyclopentyl)-N4-(2,3,5,6-tetrafluorophenyl)-1,3,5-triazine-2,4-diamine, 6-(1-fluoro-1-methyl-ethyl)-N4-(2,3,5,6-tetrafluorophenyl)-1,3,5-triazine-2,4-diamine, N4-(2,6-difluorophenyl)-6-(1-fluoro-1-methyl-ethyl)-1,3,5-triazine-2,4-diamine and to their agriculturally acceptable salts or N-oxides and at least on auxiliary customary for formulating crop protection agents.

As used herein, the terms "controlling" and "combating" are synonyms.

As used herein, the terms "undesirable vegetation", "unwanted vegetation", "unwanted plants" and "harmful plants" are synonyms.

In the context of substituents, the term "one or more substituents" means that the number of substituents is e.g. from 1 to 10, in particular 1, 2, 3, 4, 5, 6, 7 or 8.

If the compound of formula (I) (component a), compound A), the herbicidal compounds b) (herbicide B) and/or the safeners c as described herein are capable of forming geometrical isomers, for example E/Z isomers, it is possible to use both, the pure isomers and mixtures thereof, in the combinations according to the invention.

If the compound of formula (I) (component a), compound A), the herbicidal compounds b) (herbicide B) and/or the safeners c as described herein have one or more centers of chirality and, as a consequence, are present as enantiomers or diastereomers, it is possible to use both, the pure enantiomers and diastereomers and their mixtures, in the combinations according to the invention.

If the compound of formula (I) (component a), compound A), the herbicidal compounds b) herbicide B) and/or the safeners c as described herein have ionizable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)-ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Compound of formula (I) (component a), compound A), herbicidal compounds b) (herbicide B) and/or safeners C as described herein having a carboxyl group can be employed in the form of the acid, in the form of an agriculturally suitable salt as mentioned above or else in the form of an agriculturally acceptable derivative, for example as amides, such as mono- and di-$C_1$-$C_6$-alkylamides or arylamides, as esters, for example as allyl esters, propargyl esters, $C_1$-$C_{10}$-alkyl esters, alkoxyalkyl esters, tefuryl ((tetrahydrofuran-2-yl)methyl) esters and also as thioesters, for example as $C_1$-$C_{10}$-alkylthio esters. Preferred mono- and di-$C_1$-$C_6$-alkylamides are the methyl and the dimethylamides. Preferred arylamides are, for example, the anilides and the 2-chloroanilides. Preferred alkyl esters are, for example, the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, for example the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

The organic moieties mentioned in the definition of the variables $R^1$ to $R^5$, $R^a$, $R^b$, $R^c$, $R^d$ are—like the term halogen—collective terms for individual enumerations of the individual group members. The term halogen denotes in each case fluorine, chlorine, bromine or iodine. All hydrocarbon chains, i.e. all alkyl, haloalkyl, alkenyl, alkynyl, alkoxy, alkylthio, alkylsulfonyl, (alkyl)amino, di(alkyl) amino chains can be straight-chain or branched, the prefix $C_n$-$C_m$ denoting in each case the possible number of carbon atoms in the group. The same applies to composed radicals, such as cycloalkyl and phenylalkyl.

Examples of such meanings are:

$C_1$-$C_3$-alkyl: $CH_3$, $C_2H_5$, n-propyl, and $CH(CH_3)_2$;

$C_1$-$C_4$-alkyl and also the $C_1$-$C_4$-alkyl moieties of $C_1$-$C_4$-alkoxy, $C_1$-$C_4$-alkylthio, $C_1$-$C_4$-alkylsulfonyl, ($C_1$-$C_4$-alkyl)carbonyl, ($C_1$-$C_4$-alkyl)carbonyl, ($C_1$-$C_4$-alkoxy)carbonyl, ($C_1$-$C_4$-alkyl)carbonyloxy, $C_1$-$C_4$-alkyoxy-$C_1$-$C_4$-alkyl, $C_3$-$C_6$-cycloalkyl-$C_1$-$C_4$-alkyl, ($C_1$-$C_4$-alkylamino)carbonyl, di($C_1$-$C_4$-alkyl)aminocarbonyl, ($C_1$-$C_4$-alkylamino)sulfonyl, di($C_1$-$C_4$-alkyl)aminosulfonyl or phenyl-$C_1$-$C_4$-alkyl: for example $CH_3$, $C_2H_5$, n-propyl, $CH(CH_3)_2$, $C_1$-$C_3$-alkyl as mentioned above and also n-butyl, $CH(CH_3)$—$C_2H$, $CH_2$—$CH(CH_3)_2$, and $C(CH_3)_3$;

$C_1$-$C_6$-alkyl and also the $C_1$-$C_6$-alkyl moieties of $C_1$-$C_6$-alkoxy, $C_1$-$C_6$-alkylthio, $C_1$-$C_6$-alkylsulfonyl, ($C_1$-$C_6$-alkyl)carbonyl, ($C_1$-$C_6$-alkyl)carbonyl, ($C_1$-$C_6$-alkoxy)carbonyl, ($C_1$-$C_6$-alkyl)carbonyloxy, $C_1$-$C_4$-alkyoxy-$C_1$-$C_6$-alkyl, $C_3$-$C_6$-cycloalkyl-$C_1$-$C_6$-alkyl, phenyl ($C_1$-$C_6$-alkyl)aminocarbonyl, ($C_1$-$C_6$-alkylamino) carbonyl, di($C_1$-$C_6$-alkyl)aminocarbonyl, ($C_1$-$C_6$-alkylamino)sulfonyl, di($C_1$-$C_6$-alkyl)aminosulfonyl or phenyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_3$-haloalkyl: $C_1$-$C_3$-alkyl as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl;

$C_1$-$C_4$-haloalkyl: $C_1$-$C_3$-haloalkyl as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl, chloro-methyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_3$-$C_6$-cycloalkyl and also the cycloalkyl moieties of $C_3$-$C_6$-cycloalkyl-$C_1$-$C_4$-alkyl: monocyclic saturated hydrocarbons having 3 to 6 ring members, such as cyclopropyl, cyclobutyl, cyclopentyl and cyclohexyl;

$C_3$-$C_6$-alkenyl: for example 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkynyl and also the $C_2$-$C_6$-alkynyl moieties of ($C_1$-$C_6$-alkoxy)-$C_2$-$C_6$-alkynyl: linear or branched unsaturated hydrocarbon group having 2 to 6 carbon atoms and containing at least one C—C-triple bond, such as ethynyl, 1-propynyl, 2-propynyl (propargyl), 1-butynyl, 2-butynyl, 3-butynyl, 1-methyl-2-propynyl and the like;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_3$-alkoxy: methoxy, ethoxy, propoxy, 1-methylethoxy;

$C_1$-$C_4$-alkoxy and also the $C_1$-$C_4$-alkoxy moieties of hydroxycarbonyl-$C_1$-$C_4$-alkoxy, $C_1$-$C_6$-alkoxycarbonyl-$C_1$-$C_4$-alkoxy: for example methoxy, ethoxy, propoxy, 1-methylethoxy butoxy, 1-methylpropoxy, 2-methylpropoxy and 1,1-dimethylethoxy $C_1$-$C_6$-alkoxy and also the $C_1$-$C_6$-alkoxy moieties of ($C_1$-$C_6$-alkoxy)carbonyl, ($C_1$-$C_6$-alkoxy)sulfonyl, ($C_1$-$C_6$-alkoxy)-$C_1$-$C_6$-alkyl, ($C_1$-$C_6$-alkoxy)-$C_1$-$C_6$-alkoxy, ($C_1$-$C_6$-alkoxy)-$C_2$-$C_6$-alkenyl, ($C_1$-$C_6$-alkoxy)-$C_2$-$C_6$-alkynyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, for example, chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy2-fluoroethoxy, 2-chloroethoxy, 2-bromoethxoy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2,2-difluoropropoxy, 2,3-difluoropropoxy, 2-chloropropoxy, 3-chloropropoxy, 2,3-dichloro-propoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 4-fluorobutoxy, nonafluorobutoxy, 1,1,2,2,-tetrafluoroethoxy and 1-trifluoromethyl-1,2,2,2-tetrafluoroethoxy;

$C_1$-$C_6$-haloalkoxy $C_1$-$C_4$-alkoxy as mentioned above: $C_1$-$C_4$-haloalkoxy as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_2$-$C_6$-alkenyloxy: $C_2$-$C_6$-alkenyl as defined above, which is bound via an oxygen atom, such as ethenyloxy (vinyloxy), 1-propenyloxy, 2-propenyloxy (allyloxy), 1-butenyloxy, 2-butenyloxy, 3-butenyloxy 1-methyl-2-propenyloxy and the like;

$C_2$-$C_6$-alkynyloxy: $C_2$-$C_6$-alkynyl as defined above, which is bound via an oxygen atom, such as ethynyloxy, 1-propynyl, 2-propynyloxy (propargyloxy), 1-butynyloxy, 2-butynyloxy, 3-butynyloxy 1-methyl-2-propynyloxy and the like;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylsulfinyl ($C_1$-$C_6$-alkyl-S(=O)—): z.B. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsufinyl, 1-methylbutylsulfinyl, 2-methylbutylsufinyl, 3-methylbutylsulfinyl, 2,2-dimethylpropylsulfinyl, 1-ethylpropylsulfinyl, 1,1-dimethylpropylsufinyl, 1,2-dimethylpropylsufinyl, hexylsulfinyl, 1-methylpentylsulfinyl, 2-methylpentylsulfinyl, 3-methylpentylsulfinyl, 4-methylpentyl-sulfinyl, 1,1-dimethylbutylsufinyl, 1,2-dimethylbutylsufinyl, 1,3-dimethylbutylsulfinyl, 2,2-dimethylbutylsufinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsufinyl, 1,2,2-trimethylpropylsufinyl, 1-ethyl-1-methylpropylsulfinyl and 1-ethyl-2-methylpropylsufinyl;

$C_1$-$C_6$-alkylsulfonyl ($C_1$-$C_6$-alkyl-S(O)$_2$—): for example methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-di-methylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethyl-propylsulfonyl, 1,2,2-trimethylpropylsulfonyl, 1-ethyl-1-methylpropylsulfonyl and 1-ethyl-2-methylpropylsulfonyl;

($C_1$-$C_4$-alkyl)amino and also the ($C_1$-$C_4$-alkylamino) moieties of ($C_1$-$C_4$-alkylamino)carbonyl or ($C_1$-$C_4$-alkylamino)sulfonyl: for example methylamino, ethylamino, propylamino, 1-methylethylamino, butylamino, 1-methylpropylamino, 2-methylpropylamino or 1,1-dimethylethylamino;

($C_1$-$C_6$-alkyl)amino and also the ($C_1$-$C_6$-alkylamino) moieties of ($C_1$-$C_6$-alkylamino)carbonyl, phenyl($C_1$-$C_6$-alkyl)aminocarbonyl or ($C_1$-$C_6$-alkylamino)sulfonyl: ($C_1$-$C_4$-alkyl)amino as mentioned above, and also, for example, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino or 1-ethyl-2-methylpropylamino;

di($C_1$-$C_4$-alkyl)amino and also the di($C_1$-$C_4$-alkylamino) moieties of di($C_1$-$C_4$-alkylamino)carbonyl or di($C_1$-$C_4$-alkylamino)sulfonyl: for example N,N-dimethylamino, N,N-diethylamino, N,N-di(1-methylethyl)amino, N,N-dipropylamino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethyl-ethyl)-N-(2-methylpropyl)amino;

di($C_1$-$C_6$-alkyl)amino and also the di($C_1$-$C_6$-alkylamino) moieties of di($C_1$-$C_6$-alkylamino)carbonyl or di($C_1$-$C_6$-alkylamino)sulfonyl: di($C_1$-$C_4$-alkyl)amino as mentioned above, and also, for example, N-methyl-N-pentylamino, N-methyl-N-(1-methylbutyl)amino, N-methyl-N-(2-methylbutyl)amino, N-methyl-N-(3-methyl-butyl)amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl) amino, N-methyl-N-(1-methylpentyl)amino, N-methyl-N-(2-methylpentyl)amino, N-methyl-N-(3-methylpentyl)amino, N-methyl-N-(4-methylpentyl) amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl) amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl) amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl) amino, N-ethyl-N-(2,3-dimethylbutyl)amino, N-ethyl-N-(3,3-dimethylbutyl)amino, N-ethyl-N-(1-ethylbutyl)-amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-di-pentylamino, N-propyl-N-hexylamino, N-butyl-N-hexylamino, N-pentyl-N-hexylamino or N,N-dihexylamino;

$C_3$-$C_6$-cycloalkyl and also the $C_3$-$C_6$-cyclolalkyl moieties of ($C_3$-$C_6$-cyclolalkyl)-carbonyl, ($C_3$-$C_6$-cyclolalkyl)-$C_1$-$C_6$-alkyl, ($C_3$-$C_6$-cycloalkyl)carbonyl and ($C_3$-$C_6$-cyclolalkyl)-$C_1$-$C_6$-alkoxy: a cycloaliphatic radical having 3 to 6 carbon atoms, such as cyclopropyl, cyclobutyl, cyclopentyl and cyclohexyl;

$C_3$-$C_6$-cycloalkoxy a cycloaliphatic radical having 3 to 6 carbon atoms and bound via an oxygen atom, such as cyclopropyloxy, cyclobutyloxy, cyclopentyloxy and cyclohexyloxy;

($C_3$-$C_6$-cycloalkyl)-$C_1$-$C_6$-alkyl: $C_1$-$C_6$-alkyl, in particular $C_1$-$C_4$-alkyl as defined above, such as methyl or ethyl, wherein 1 hydrogen atom is replaced by $C_3$-$C_6$-cycloalkyl as defined above, examples including cyclopropylmethyl ($CH_2$-cyclopropyl), cyclobutylmethyl, cyclopentylmethyl, cycloexylmethyl, 1-cyclopropylethyl (CH($CH_3$)-cyclopropyl), 1-cyclobutylethyl, 1-cyclopentylethyl, 1-cycloexylethyl, 2-cyclopropylethyl ($CH_2CH_2$-cyclopropyl), 2-cyclobutylethyl, 2-cyclopentylethyl or 2-cycloexylethyl;

($C_3$-$C_6$-cycloalkyl)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_3$-$C_6$-cyclolalkyl as defined above, examples including cyclopropylmethoxy (O$CH_2$-cyclopropyl), cyclobutylmethoxy, cyclopentylmethoxy, cycloexylmethoxy, 1-cyclopropylethoxy (O—CH($CH_3$)-cyclopropyl), 1-cyclobutylethoxy, 1-cyclopentylethoxy, 1-cycloexylethoxy, 2-cyclopropylethoxy (O$CH_2CH_2$)-cyclopropyl), 2-cyclobutylethoxy, 2-cyclopentylethoxy and 2-cycloexylethoxy;

($C_1$-$C_6$-alkoxy)-$C_1$-$C_6$-alkyl: $C_1$-$C_6$-alkyl, in particular $C_1$-$C_4$-alkyl as defined above, such as methyl, ethyl or isopropyl, wherein 1 hydrogen atom is replaced by $C_1$-$C_6$-alkoxy as defined above, examples including methoxymethyl, ethoxymethyl, n-propoxymethyl, butoxymethyl, 1-methoxyethyl, 1-ethoxyethyl, 1-(n-propoxy)ethyl, 1-butoxyethyl, 2-methoxyethyl, 2-ethoxyethyl, 2-(n-propoxy)ethyl, 2-butoxyethyl, 2-methoxypropyl, 2-ethoxypropyl, 2-(n-propoxy)propyl, 2-butoxypropyl;

($C_1$-$C_6$-alkoxy)-$C_1$-$C_6$-alkoxy: $C_1$-$C_6$-alkoxy, in particular $C_1$-$C_4$-alkoxy as defined above, such as methoxy or ethoxy, wherein 1 hydrogen atom is replaced by $C_1$-$C_6$-alkoxy as defined above, examples including methoxymethoxy, ethoxymethoxy, n-propoxymethoxy, butoxymethoxy, 2-methoxyethoxy, 2-ethoxyethoxy, 2-(n-propoxy)ethoxy and 2-butoxyethoxy;

($C_1$-$C_6$-alkoxy)-$C_2$-$C_6$-alkenyl: $C_2$-$C_6$-alkenyl, in particular $C_2$-$C_4$-alkenyl as defined above, such as ethenyl, propenyl, 1-butenyl or 2-butenyl, wherein 1 hydrogen atom is replaced by $C_1$-$C_6$-alkoxy as defined above;

($C_1$-$C_6$-alkoxy)-$C_2$-$C_6$-alkynyl: $C_2$-$C_6$-alkynyl, in particular $C_2$-$C_4$-alkynyl as defined above, such as ethynyl, propynyl or 2-butynyl, wherein 1 hydrogen atom is replaced by $C_1$-$C_6$-alkoxy as defined above;

($C_1$-$C_6$-alkyl)carbonyl: $C_1$-$C_6$-alkyl as mentioned above, which is bound to the remainder of the molecule by a carbonyl group;

($C_1$-$C_6$-alkoxy)carbonyl: $C_1$-$C_6$-alkyloxy as mentioned above, which is bound to the remainder of the molecule by a carbonyl group;

($C_1$-$C_6$-alkylamino)carbonyl: ($C_1$-$C_6$-alkyl)amino as mentioned above, which is bound to the remainder of the molecule by a carbonyl group;

($C_1$-$C_6$-alkylamino)sulfonyl: ($C_1$-$C_6$-alkyl)amino as mentioned above, which is bound to the remainder of the molecule by a sulfonyl group;

di($C_1$-$C_6$-alkylamino)carbonyl: di($C_1$-$C_6$-alkyl)amino as mentioned above, which is bound to the remainder of the molecule by a carbonyl group;

di($C_1$-$C_6$-alkylamino)sulfonyl: di($C_1$-$C_6$-alkyl)amino as mentioned above, which is bound to the remainder of the molecule by a sulfonyl group;

phenyl-$C_1$-$C_6$-alkyl: $C_1$-$C_6$-alkyl, in particular $C_1$-$C_4$-alkyl as defined above, such as methyl or ethyl, wherein 1 hydrogen atom is replaced by phenyl, examples including benzyl, 1-phenylethyl, 2-phenylethyl, 1-phenylpropyl, 2-phenylpropyl, 1-phenyl-1-methylethyl etc.;

three- to six-membered heterocyclyl: monocyclic saturated or partially unsaturated hydrocarbon having three to six ring members as mentioned above which, in addition to carbon atoms, contains one or two heteroatoms selected from O, S and N;

for example saturated heterocycles such as 2-oxiranyl, 2-oxetanyl, 3-oxetanyl, 2-aziridinyl, 2-thietanyl, 1-azetidinyl, 2-azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 2-piperidinyl, 3-piperidinyl, 4-piperidinyl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,4-dithian-2-yl, 1,3-dithian-5-yl, 2-tetrahydropyranyl, 3-tetrahydropyranyl, 4-tetrahydropyranyl, 2-tetrahydrothiopyranyl, 3-tetrahydrothiopyranyl, 4-tetrahydro-thiopyranyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, tetrahydro-1,3-oxazin-2-yl, tetrahydro-1,3-oxazin-6-yl, 2-morpholinyl, 3-morpholinyl or 4-morpholinyl, for example 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl;

partially unsaturated heterocycles such as 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 4,5-dihydropyrrol-2-yl, 4,5-dihydropyrrol-3-yl, 2,5-dihydropyrrol-2-yl, 2,5-dihydropyrrol-3-yl, 4,5-dihydroisoxazol-3-yl, 2,5-dihydroisoxazol-3-yl, 2,3-dihydroisoxazol-3-yl, 4,5-dihydroisoxazol-4-yl, 2,5-dihydroisoxazol-4-yl, 2,3-dihydroisoxazol-4-yl, 4,5-dihydroisoxazol-5-yl, 2,5-dihydroisoxazol-5-yl, 2,3-dihydroisoxazol-5-yl, 4,5-dihydroisothiazol-3-yl, 2,5-dihydroisothiazol-3-yl, 2,3-dihydroisothiazol-3-yl, 4,5-dihydroisothiazol-4-yl, 2,5-dihydroisothiazol-4-yl, 2,3-dihydroisothiazol-4-yl, 4,5-dihydroisothiazol-5-yl, 2,5-dihydroisothiazol-5-yl, 2,3-dihydroisothiazol-5-yl, 2,3-dihydropyrazol-2-yl, 2,3-dihydropyrazol-3-yl, 2,3-dihydropyrazol-4-yl, 2,3-dihydropyrazol-5-yl, 3,4-di-hydropyrazol-3-yl, 3,4-dihydropyrazol-4-yl, 3,4-dihydropyrazol-5-yl, 4,5-dihydropyrazol-3-yl, 4,5-dihydropyrazol-4-yl, 4,5-dihydropyrazol-5-yl, 2,3-dihydroimidazol-2-yl, 2,3-dihydroimidazol-3-yl, 2,3-dihydroimidazol-4-yl, 2,3-dihydroimidazol-5-yl, 4,5-dihydro-imidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2,3-dihydrooxazol-3-yl, 2,3-dihydrooxazol-4-yl, 2,3-dihydrooxazol-5-yl, 3,4-dihydrooxazol-3-yl, 3,4-dihydrooxazol-4-yl, 3,4-dihydrooxazol-5-yl, 2,3-dihydrothiazol-3-yl, 2,3-dihydrothiazol-4-yl, 2,3-dihydro-thiazol-5-yl, 3,4-dihydrothiazol-3-yl, 3,4-dihydrothiazol-4-yl, 3,4-dihydrothiazol-5-yl, 3,4-dihydrothiazol-2-yl, 3,4-dihydrothiazol-3-yl, 3,4-dihydrothiazol-4-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 3,4-dihydro-2H-pyran-3-yl, 3,4-dihydro-2H-pyran-4-yl, 3,4-dihydro-2H-pyran-6-yl, 5,6-dihydro-4H-1,3-oxazin-2-yl.

The preferred embodiments of the invention mentioned herein below have to be understood as being preferred either independently from each other or in combination with one another.

According to a preferred embodiment of the invention mentioned herein below have to be understood as being preferred either independently from each other or in combination with one another. Particular groups of embodiment of the invention relates to that combination comprises as active compound A or component a) at least one, preferably exactly one, compound of formula (I), wherein the variables $R^1$, $R^2$, $R^3$, $R^4$ and $R^5$, either independently of one another or in combination with one another, have the following meanings:

Preferred are the combination of the invention, which comprises as active component a) (compound A) compounds of formula (I) wherein $R^a$ is halogen, CN, $C_1$-$C_6$-alkyl or $C_1$-$C_6$-alkoxy in particular halogen or CN; more particular halogen; especially fluorine; and $R^b$, $R^c$ and $R^d$ independently of one another are hydrogen, halogen, CN, $C_1$-$C_6$-alkyl or $C_1$-$C_6$-alkoxy; in particular hydrogen or halogen, especially hydrogen or fluorine;

in particular $R^a$ is halogen; and $R^b$ and $R^d$ are halogen; and $R^c$ is hydrogen;

most preferred $R^a$, $R^b$, $R^c$ and $R^d$ are halogen.

Also preferred are the combinations, which comprise as active component a) at least one, preferably exactly one, compound of formula (I), wherein $R^a$ is halogen or CN; and
$R^b$, $R^c$ and $R^d$ are H or halogen;
in particular $R^a$, $R^b$ and $R^d$ are halogen; and
$R^c$ is H or halogen;
especially preferred $R^a$, $R^b$ and $R^d$ are halogen; and
$R^c$ is H, F, Br or I;
more preferred $R^a$, $R^b$ and $R^d$ are F; and
$R^c$ is H, F, Br or I;
most preferred $R^a$, $R^b$ and $R^d$ are F; and
$R^c$ is H or F.

Likewise preferred are the combinations, which comprise as active component a) compound of formula (I), wherein
$R^a$ is halogen; especially fluorine; and
$R^b$ and $R^d$ are halogen; especially fluorine and
$R^c$ is hydrogen.

Likewise preferred are the combinations, which comprise as active component a) compound of formula (I), wherein
$R^a$ is halogen; especially fluorine; and
$R^b$ $R^c$ and $R^d$ are hydrogen.

Also preferred are the combinations, which comprise as active component a) at least one, preferably exactly one, compound of formula (I), wherein
$R^2$ is H, halogen, $C_1$-$C_4$-alkyl, $C_1$-$C_4$-alkoxy ($C_1$-$C_6$-alkyl) $C_3$-$C_6$-cycloalkyl or $C_1$-$C_4$-haloalkyl;
particularly preferred hydrogen, halogen, $C_1$-$C_2$-alkyl or $C_1$-$C_2$-haloalkyl; also particularly preferred H, F, Cl, $CH_3$, $OCH_3$ or $CF_3$.

Also preferred are the combinations, which comprise as active component a) at least one, preferably exactly one, compound (I) of formula (I), wherein
$R^3$ and $R^4$ are
independently of one another H, halogen, $C_1$-$C_4$-alkyl or $C_1$-$C_4$-haloalkyl; or together with the carbon atom to which they are attached form a moiety selected from the group consisting of $C_3$-$C_6$-cycloalkyl and three- to six-membered saturated heterocyclyl,
wherein the $C_3$-$C_6$-cycloalkyl or the three- to six-membered saturated heterocyclyl is unsubstituted or substituted by one to three substituents selected from halogen, CN, $C_1$-$C_6$-alkyl and $C_1$-$C_6$-alkoxy;
wherein $R^3$ and $R^4$ independently of one another are particular selected from H, halogen, $C_1$-$C_2$-alkyl or $C_1$-$C_2$-haloalkyl; or
together with the carbon atom to which they are attached form a moiety selected from the group consisting of $C_3$-$C_6$-cycloalkyl;
wherein $R^3$ and $R^4$ independently of one another are especially selected from H, halogen, $C_1$-$C_2$-alkyl or $C_1$-$C_2$-haloalkyl;
where $R^3$ is in particular different from hydrogen.

Also preferred are the combinations, which comprise as active component a) at least one, preferably exactly one, compound of formula (I), wherein
$R^2$ is H, halogen, $C_1$-$C_4$-alkyl; and
$R^3$ and $R^4$ are independently of one another H, halogen, $C_1$-$C_4$-alkyl, or together with the carbon atom to which they are attached form a $C_3$-$C_6$-cycloalkyl;
in particular $R^2$ is H, halogen or $C_1$-$C_2$-alkyl;
$R^3$ is $C_1$-$C_2$-alkyl;
$R^4$ is H, halogen or $C_1$-$C_2$-alkyl;
$R^3$ and $R^4$ together with the carbon atom to which they are attached form a $C_3$-$C_6$-cycloalkyl;
especially preferred $R^2$ is H, halogen or $C_1$-$C_2$-alkyl;
$R^3$ is $C_1$-$C_2$-alkyl;
$R^4$ is H or $C_1$-$C_2$-alkyl;
most preferred $R^2$ is halogen; and
$R^3$ and $R^4$ are $C_1$-$C_2$-alkyl.

Likewise preferred are the combinations, which comprise as active component a) at least one, preferably exactly one, compound of formula (I), wherein
$R^2$ is H, halogen, $C_1$-$C_4$-alkyl; and
$R^3$ and $R^4$ are independently of one another H, halogen, $C_1$-$C_4$-alkyl, or together with the carbon atom to which they are attached form a $C_3$-$C_6$-cycloalkyl;
in particular $R^2$ is H, halogen or $C_1$-$C_2$-alkyl;
$R^3$ and $R^4$ together with the carbon atom to which they are attached form a $C_3$-$C_6$-cycloalkyl;
especially preferred $R^2$ is H, halogen or $C_1$-$C_2$-alkyl;
$R^3$ and $R^4$ together with the carbon atom to which they are attached form a $C_4$-$C_6$-cycloalkyl;
most preferred $R^2$ is $CH_3$, halogen; and
$R^3$ and $R^4$ together with the carbon atom to which they are attached form a cyclobutyl or cyclopentyl.

Also preferred are the combinations, which comprise as active component a) at least one, preferably exactly one, compound of formula (I), wherein
$R^1$ is H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenyl-$C_1$-$C_6$-alkyl, phenylsulfonyl, phenylaminosulfonyl, phenylcarbonyl and phenoxycarbonyl,
wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy; preferably, H, CN, $C_1$-$C_6$-alkyl, ($C_1$-$C_6$-alkoxy)-$C_1$-$C_6$-alkyl, ($C_1$-$C_6$-alkyl)carbonyl or ($C_1$-$C_6$-alkyl)sulfonyl, where the aliphatic parts of the 4 aforementioned radicals unsubstituted partly or completely halogenated,
phenyl and phenyl-$C_1$-$C_6$ alkyl,
wherein phenyl in the last 2 mentioned radical is unsubstituted or substituted by 1, 2, 3, 4, or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
in particular H, CN, $C_1$-$C_6$-alkyl, $C_1$-$C_6$-haloalkyl, ($C_1$-$C_6$-alkoxy)-$C_1$-$C_6$-alkyl, $C_1$-$C_6$-alkoxy, ($C_1$-$C_6$-alkyl)carbonyl, ($C_1$-$C_6$-haloalkyl)carbonyl, ($C_1$-$C_6$-alkyl)sulfonyl or ($C_1$-$C_6$-haloalkyl)sulfonyl;
more particularly H, CN, $C_1$-$C_4$-alkyl, ($C_1$-$C_4$-alkoxy)-$C_1$-$C_4$-alkyl, $C_1$-$C_4$-alkoxy, ($C_1$-$C_4$-alkyl)carbonyl or ($C_1$-$C_4$-alkyl)sulfonyl; even more particularly H, CN, $CH_3$, $CH_2OCH_3$, $OCH_3$, $C(O)CH_3$ or $SO_2CH_3$;
especially hydrogen.

Also preferred are the combinations, which comprise as active component a) at least one, preferably exactly one, compound of formula (I), wherein
$R^5$ is H, OH, $S(O)_2NH_2$, CN, $C_1$-$C_6$-alkyl, $C_2$-$C_6$-alkenyl, $C_2$—C-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated, phenyl, phenylsulfonyl, phenylaminosulfonyl, phenyl-$C_1$-$C_6$ alkyl, phenoxy, phenylcarbonyl and phenoxycarbonyl, wherein phenyl in the last 6 mentioned radicals is unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy preferably, H, CN, $C_1$-$C_6$-alkyl, ($C_1$-$C_6$-alkoxy)-$C_1$-$C_6$-alkyl, ($C_1$-$C_6$-alkyl)carbonyl or ($C_1$-$C_6$-alkyl)sulfonyl, where the aliphatic parts of the 4 aforementioned radicals unsubstituted partly or completely halogenated;

phenyl and phenyl-$C_1$-$C_6$ alkyl, wherein phenyl in the last 2 mentioned radical is unsubstituted or substituted by 1, 2, 3, 4, or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy in particular H, CN, $C_1$-$C_6$-alkyl, ($C_1$-$C_6$-alkoxy)-$C_1$-$C_6$-alkyl, ($C_1$-$C_6$-alkyl)carbonyl or ($C_1$-$C_6$-alkyl)sulfonyl;

more particularly H, CN, $C_1$-$C_4$-alkyl, ($C_1$-$C_4$-alkoxy)-$C_1$-$C_4$-alkyl, ($C_1$-$C_4$-alkyl)carbonyl or ($C_1$-$C_4$-alkyl)sulfonyl;

even more particularly H, CN, $CH_3$, $CH_2OCH_3$, $C(O)CH_3$ or $SO_2CH_3$; especially hydrogen.

In particular the compinations comprise as active component a) at least one, preferably exactly one, compound of formula (I), wherein $R^1$ is H, CN, $C_1$-$C_4$-alkyl, $C_1$-$C_4$-alkoxy-$C_1$-$C_4$-alkyl, $C_1$-$C_4$-alkoxy, ($C_1$-$C_4$-alkyl)carbonyl or ($C_1$-$C_4$-alkyl)sulfonyl;

$R^2$ is H, halogen, $C_1$-$C_4$-alkyl, $C_1$-$C_4$-alkoxy or $C_1$-$C_4$-haloalkyl;

$R^3$ is H, halogen, CN, $C_1$-$C_6$-alkyl or $C_1$-$C_6$-haloalkyl;

$R^3$ and $R^4$ together with the carbon atom to which they are attached form a $C_3$-$C_6$-cycloalkyl;

$R^4$ is H, halogen, CN, $C_1$-$C_4$-alkyl or $C_1$-$C_4$-haloalkyl;

$R^a$ is H, halogen, CN, $NO_2$, $C_1$-$C_4$-alkyl, $C_1$-$C_4$-haloalkyl, OH, $C_1$-$C_4$-alkoxy, $C_1$-$C_4$-alkylthio, ($C_1$-$C_4$-alkyl)sulfinyl, ($C_1$-$C_4$-alkyl)sulfonyl, amino, ($C_1$-$C_4$-alkyl)amino, di($C_1$-$C_6$-alkyl)amino, ($C_1$-$C_4$-alkyl)-carbonyl and ($C_1$-$C_4$-alkoxy)-carbonyl;

$R^b$ is H, halogen, CN, $NO_2$, $C_1$-$C_4$-alkyl, $C_1$-$C_4$-haloalkyl, OH, $C_1$-$C_4$-alkoxy, $C_1$-$C_4$-alkylthio, ($C_1$-$C_4$-alkyl)sulfinyl, ($C_1$-$C_4$-alkyl)sulfonyl, amino, ($C_1$-$C_4$-alkyl)amino, di($C_1$-$C_4$-alkyl)amino, ($C_1$-$C_4$-alkyl)-carbonyl and ($C_1$-$C_4$-alkoxy)-carbonyl;

$R^c$ is H, halogen, CN, $NO_2$, $C_1$-$C_4$-alkyl, $C_1$-$C_4$-haloalkyl, OH, $C_1$-$C_4$-alkoxy, $C_1$-$C_4$-alkylthio, ($C_1$-$C_4$-alkyl)sulfinyl, ($C_1$-$C_4$-alkyl)sulfonyl, amino, ($C_1$-$C_4$-alkyl)amino, di($C_1$-$C_4$-alkyl)amino, ($C_1$-$C_4$-alkyl)-carbonyl and ($C_1$-$C_4$-alkoxy)-carbonyl;

$R^d$ H, halogen, CN, $NO_2$, $C_1$-$C_4$-alkyl, $C_1$-$C_4$-haloalkyl, OH, $C_1$-$C_4$-alkoxy, $C_1$-$C_4$-alkylthio, ($C_1$-$C_4$-alkyl)sulfinyl, ($C_1$-$C_4$-alkyl)sulfonyl, amino, ($C_1$-$C_4$-alkyl)amino, di($C_1$-$C_4$-alkyl)amino, ($C_1$-$C_4$-alkyl)-carbonyl and ($C_1$-$C_4$-alkoxy)-carbonyl;

$R^5$ is H, CN, $C_1$-$C_4$-alkyl, $C_1$-$C_4$-alkoxy-$C_1$-$C_4$-alkyl, $C_1$-$C_4$-alkoxy, ($C_1$-$C_4$-alkyl)carbonyl or ($C_1$-$C_4$-alkyl)sulfonyl More particular the combination comprise as active component a) at least one, preferably exactly one, compound of formula (I), wherein $R^1$ is H, CN, $CH_3$, $CH_2OCH_3$, $OCH_3$, $COCH_3$ or $SO_2CH_3$;

$R^2$ is halogen, $C_1$-$C_2$-alkyl or $C_1$-$C_2$-haloalkyl;

$R^3$ is H, halogen, CN, $C_1$-$C_4$-alkyl, $C_1$-$C_4$-haloalkyl or $C_1$-$C_4$-alkoxy;

$R^3$ and $R^4$ together with the carbon atom to which they are attached form a $C_3$-$C_6$-cycloalkyl;

$R^4$ is H, halogen, CN, $C_1$-$C_4$-alkyl or $C_1$-$C_4$-haloalkyl or $C_1$-$C_4$-alkoxy;

$R^a$ is H, halogen, CN, $C_1$-$C_4$-alkyl or $C_1$-$C_4$-haloalkyl or $C_1$-$C_4$-alkoxy;

$R^b$ is H, halogen, CN, $C_1$-$C_4$-alkyl or $C_1$-$C_4$-haloalkyl or $C_1$-$C_4$-alkoxy;

$R^c$ is H, halogen, CN, $C_1$-$C_4$-alkyl or $C_1$-$C_4$-haloalkyl or $C_1$-$C_4$-alkoxy;

$R^d$ is H, halogen, CN, $C_1$-$C_4$-alkyl or $C_1$-$C_4$-haloalkyl or $C_1$-$C_4$-alkoxy;

$R^5$ is H, CN, $CH_3$, $CH_2OCH_3$, $OCH_3$, $COCH_3$ or $SO_2CH_3$.

Especially the combination comprise as active component a) at least one, preferably exactly one, compound of formula (I), wherein $R^1$ is hydrogen $R^2$ is H, F, Cl, $CH_3$, $OCH_3$ or $CF_3$ $R^3$ is H, $CH_3$ $C_2H_5$;

$R^3$ and $R^4$ together with the carbon atom to which they are attached form a $C_3$-$C_6$-cycloalkyl;

$R^4$ is H, $CH_3$ $C_2H_5$;

$R^a$ is H, CN, F, Cl, Br, I;

$R^b$ is H, CN, F, Cl, Br, I;

$R^c$ is H, CN, F, Cl, Br, I;

$R^d$ is H, CN, F, Cl, Br, I;

$R^5$ is hydrogen.

Particular preference is given to compounds of formula (I) listed below in table 1 and 2 (examples 1 to 270). Compounds listed in table 1 are compounds of formula (I), wherein $R^1$ is H. Compounds listed in table 2 are compounds of formula (I).

| no | $R^a$ | $R^b$ | $R^c$ | $R^d$ | $R^2$ | $R^3$ | $R^4$ | $R^5$ | MS [m/z] |
|---|---|---|---|---|---|---|---|---|---|
| 1. | F | F | F | F | Cl | $CH_3$ | $CH_3$ | H | 354.2 |
| 2. | F | F | H | F | F | $CH_3$ | $CH_3$ | H | 320.0 |
| 3. | F | F | F | F | H | H | H | H | 292.0 |
| 4. | F | F | F | F | F | H | $CH_3$ | H | 305.9 |
| 5. | F | F | F | F | H | $CH_3$ | CN | H | 331.3 |
| 6. | F | F | H | F | H | $CH_3$ | $CH_3$ | H | 301.9 |
| 7. | F | F | F | F | H | $CH_3$ | $CH_3$ | H | 320.2 |
| 8. | F | F | H | F | F | F | $CH_3$ | H | 323.9 |
| 9. | F | F | F | F | F | F | $CH_3$ | H | 342.2 |
| 10. | F | H | H | H | F | $CH_3$ | H | H | 270.2 |
| 11. | H | F | H | H | F | $CH_3$ | H | H | 288.2 |
| 12. | F | F | H | F | F | $CH_3$ | H | H | 306.2 |
| 13. | F | F | F | F | F | $CH_3$ | H | H | 324.1 |
| 14. | F | H | Br | H | F | $CH_3$ | H | H | 349.9 |
| 15. | F | H | H | H | F | $CH_3$ | $CH_3$ | H | 284.3 |
| 16. | F | F | H | H | F | $CH_3$ | $CH_3$ | H | 302.3 |
| 17. | F | H | F | H | F | $CH_3$ | $CH_3$ | H | 302.2 |

-continued

| no | $R^a$ | $R^b$ | $R^c$ | $R^d$ | $R^2$ | $R^3$ | $R^4$ | $R^5$ | MS [m/z] |
|---|---|---|---|---|---|---|---|---|---|
| 18. | F | F | F | F | F | $CH_3$ | $CH_3$ | H | 338.1 |
| 19. | F | Cl | H | H | F | $CH_3$ | $CH_3$ | H | 317.9 |
| 20. | F | H | Br | H | F | $CH_3$ | $CH_3$ | H | 364.1 |
| 21. | Cl | H | H | H | F | $CH_3$ | $CH_3$ | H | 300.3 |
| 22. | Cl | F | H | H | F | $CH_3$ | $CH_3$ | H | 318.1 |
| 23. | F | $CH_3$ | H | H | F | $CH_3$ | $CH_3$ | H | 298.0 |
| 24. | F | $OCH_3$ | H | H | F | $CH_3$ | $CH_3$ | H | 314.0 |
| 25. | F | $OC_2H_5$ | H | H | F | $CH_3$ | $CH_3$ | H | 328.3 |
| 26. | F | F | F | F | F | $C_2H_5$ | $CH_3$ | H | 352.0 |
| 27. | F | F | F | F | F | $C_2H_5$ | $C_2H_5$ | H | 366.0 |
| 28. | F | F | F | F | F | $C_3H_7$ | $C_2H_5$ | H | 380.1 |
| 29. | F | H | H | H | $CH_3$ | $CH_3$ | $CH_3$ | H | 256.2 |
| 30. | F | F | F | F | $CH_3$ | $CH_3$ | $CH_3$ | H | 334.2 |
| 31. | F | F | F | F | $CH_3$ | | $=CH_2$ | H | 318.3 |
| 32. | F | H | H | H | H | | $—CH_2—CH_2—$ | H | 264.3 |
| 33. | F | F | H | H | H | | $—CH_2—CH_2—$ | H | 300.3 |
| 34. | F | F | F | H | H | | $—CH_2—CH_2—$ | H | 318.1 |
| 35. | F | F | F | F | H | | $—(CH_2)_3—$ | H | 332.3 |
| 36. | F | F | F | F | H | | $—(CH_2)_4—$ | H | 346.3 |
| 37. | F | F | F | F | H | | $—(CH_2)_5—$ | H | 360.3 |
| 38. | F | F | F | F | F | $CH_3$ | H | H | 323.9* |
| 39. | F | F | F | F | $CH_3$ | $CH_2CH_3$ | H | H | 334.1 |
| 40. | F | F | F | F | cyclopropyl | $CH_3$ | H | H | 346.3 |
| 41. | F | F | F | F | CN | $CH_3$ | $CH_3$ | H | 345.3 |
| 42. | F | F | F | F | $CH_3$ | | CO | H | 320.2 |
| 43. | F | H | H | H | $CH_3$ | $CH_3$ | H | H | 266.2 |
| 44. | F | Cl | H | H | $CH_3$ | $CH_3$ | H | H | 300 |
| 45. | F | F | F | F | F | F | $CF_3$ | H | 395.9 |
| 46. | F | F | F | F | OH | $CH_3$ | H | H | 322.1 |
| 47. | F | H | H | H | F | $CH_2CH_3$ | $CH_3$ | H | 298 |
| 48. | F | H | CN | H | F | $CH_3$ | $CH_3$ | H | 309 |
| 49. | F | F | F | F | $CF_3$ | H | H | H | 360 |
| 50. | F | F | F | F | $CH_2CF_3$ | H | H | H | 374 |
| 51. | F | F | F | F | 1-$CH_3$-cyclo-hexyl | H | H | H | 406 |
| 52. | F | F | F | F | 1-$CH_3$-cyclo-hexyl | H | H | CO(1-$CH_3$-cyclo-hexyl) | 526 |
| 53. | F | Cl | H | H | F | $CH_2CH_3$ | $CH_3$ | H | 332 |
| 54. | F | H | H | H | Cl | $CH_3$ | $CH_3$ | H | 300.1 |
| 55. | F | F | H | H | $CH_3$ | $CH_3$ | $CH_3$ | H | 298.1 |
| 56. | F | Cl | H | H | $CH_3$ | $CH_3$ | $CH_3$ | H | 314.1 |
| 57. | F | F | F | F | $CH_2CH_3$ | $CH_3$ | $CH_3$ | H | 348.2 |
| 58. | F | F | F | F | $CH_2CH_3$ | $CH_2CH_3$ | H | H | 348.1 |
| 59. | F | F | F | F | Cl | $CH_3$ | H | H | 340.1 |
| 60. | F | H | H | H | H | | $—(CH_2)_3—$ | H | 278.1 |
| 61. | F | H | H | H | H | | $—(CH_2)_4—$ | H | 292.2 |
| 62. | F | H | H | H | H | | $—(CH_2)_5—$ | H | 306.2 |
| 63. | F | F | F | F | $CH_3$ | | $—(CH_2)_5—$ | H | 374.2 |
| 64. | F | F | H | F | F | $CH_2CH_3$ | $CH_3$ | H | 334.1 |
| 65. | F | F | F | F | $CH_3$ | | $—(CH_2)_4—$ | H | 360.1 |
| 66. | F | F | H | F | $CH_3$ | $CH_3$ | $CH_3$ | H | 316.4 |
| 67. | F | F | F | F | $CH(CH_3)_2$ | $CH_3$ | H | H | 348.3 |
| 68. | F | H | F | H | $CH_3$ | $CH_3$ | $CH_3$ | H | 298.1 |
| 69. | F | F | $OCH_3$ | F | F | $CH_3$ | $CH_3$ | H | 350 |
| 70. | F | F | F | Cl | F | | $—(CH_2)_4—$ | H | 380 |
| 71. | F | H | Cl | H | F | $CH_3$ | $CH_3$ | H | 318 |
| 72. | F | H | C≡CH | H | F | $CH_3$ | $CH_3$ | H | 308 |
| 73. | F | $CH_3$ | Cl | H | F | $CH_3$ | $CH_3$ | H | 332 |
| 74. | F | H | $CH_3$ | H | F | $CH_3$ | $CH_3$ | H | 298 |
| 75. | F | F | F | H | F | $CH_3$ | $CH_3$ | H | 320 |
| 76. | F | F | C≡CH | F | F | $CH_3$ | $CH_3$ | H | 344 |
| 77. | F | F | Br | F | F | $CH_3$ | $CH_3$ | H | 478.1 |
| 78. | F | H | H | H | $CH_2CH_3$ | H | H | H | 252.2 |
| 79. | F | H | H | H | F | F | F | H | 292.1 |
| 80. | $CF_3$ | H | H | H | F | $CH_3$ | $CH_3$ | H | 334.2 |
| 81. | F | Cl | H | Cl | F | $CH_3$ | $CH_3$ | H | 334.1 |
| 82. | $SO_2CH_3$ | H | H | H | F | $CH_3$ | $CH_3$ | H | 344.2 |
| 83. | F | F | H | F | F | $CH_3$ | H | H | 288.1 |
| 84. | F | F | H | F | Cl | $CH_3$ | $CH_3$ | H | 336.1 |
| 85. | F | F | H | H | Cl | $CH_3$ | $CH_3$ | H | 318.1 |
| 86. | CN | H | H | H | Cl | $CH_3$ | $CH_3$ | H | 307.1 |
| 87. | F | F | H | F | F | $CH_3$ | $CH_2CH_3$ | H | 316.1 |
| 88. | F | F | F | F | F | $CH_3$ | $CH_3$ | acetyl | 380 |
| 89. | F | H | $OCH_3$ | H | F | $CH_3$ | $CH_3$ | H | 314 |
| 90. | F | H | F | H | | | $=CH—CH_2—CH_2—CH_2—$ | H | 308 |

-continued

| no | $R^a$ | $R^b$ | $R^c$ | $R^d$ | $R^2$ | $R^3$ | $R^4$ | $R^5$ | MS [m/z] |
|---|---|---|---|---|---|---|---|---|---|
| 91. | F | F | H | F | | | =CH—CH$_2$—CH$_2$—CH$_2$— | H | 326 |
| 92. | F | F | H | H | | | =CH—CH$_2$—CH$_2$—CH$_2$— | H | 308 |
| 93. | F | H | H | H | | | =CH—CH$_2$—CH$_2$—CH$_2$— | H | 290 |
| 94. | F | F | F | F | F | F | H | H | 328.1 |
| 95. | F | H | H | H | F | F | H | H | 274.1 |
| 96. | F | F | H | H | F | F | H | H | 292.1 |
| 97. | F | H | H | H | CH$_3$ | | =CHCH$_3$[(E) conf] | H | 278 |
| 98. | F | F | F | F | CH$_3$ | | =CHCH$_3$[(E) conf] | H | 332 |
| 99. | F | Cl | H | H | F | F | F | H | 326 |
| 100. | F | F | H | H | F | F | F | H | 310.1 |
| 101. | F | F | Cl | F | F | CH$_3$ | CH$_3$ | H | 354 |
| 102. | Cl | F | H | H | F | CH$_3$ | H | H | 304.1 |
| 103. | F | F | H | F | F | F | F | H | 328 |
| 104. | F | F | F | F | F | F | F | H | 346.1 |
| 105. | F | H | F | H | F | F | F | H | 310 |
| 106. | CN | H | H | H | CH$_3$ | CH$_3$ | CH$_3$ | H | 287.1 |
| 107. | F | F | H | F | CH$_3$ | CH$_3$ | CH$_2$CH$_3$ | H | 330.2 |
| 108. | F | H | H | F | CH$_3$ | | CH$_2$CH$_3$ | H | 316.1 |
| 109. | F | H | F | H | F | F | CH$_3$ | H | 306.1 |
| 110. | F | H | F | H | H | | —(CH$_2$)$_5$— | H | 324.2 |
| 111. | F | H | F | H | H | | —(CH$_2$)$_4$— | H | 310.2 |
| 112. | F | H | F | H | H | H | C$_3$H$_5$ | H | 296.2 |
| 113. | F | H | F | H | H | | —(CH$_2$)$_3$— | H | 296.2 |
| 114. | F | H | F | H | H | | —CH$_2$—CH$_2$— | H | 282.2 |
| 115. | F | H | F | H | CH$_3$ | | —(CH$_2$)$_4$— | H | 324.2 |
| 116. | F | H | F | H | CH$_3$ | | —(CH$_2$)$_5$— | H | 338.2 |
| 117. | F | F | F | F | F | F | Cl | H | 362 |
| 118. | F | F | F | F | Cl | Cl | CH$_3$ | H | 374 |
| 119. | F | F | H | H | CH$_3$ | CH$_3$ | H | H | 284.1 |
| 120. | F | F | H | F | F | F | H | H | 310.1 |
| 121. | Cl | F | H | H | F | F | H | H | 308.1 |
| 122. | F | Cl | H | H | F | F | H | H | 308.1 |
| 123. | Cl | F | H | H | F | F | F | H | 326 |
| 124. | F | F | Br | F | F | F | H | H | 389.9 |
| 125. | F | F | Br | F | CH$_3$ | CH$_3$ | CH$_3$ | H | 396 |
| 126. | F | F | H | F | Cl | | —(CH$_2$)$_5$— | H | 376 |
| 127. | F | F | F | F | Cl | | —(CH$_2$)$_5$— | H | 394 |
| 128. | F | F | H | F | Cl | | —(CH$_2$)$_4$— | H | 362 |
| 129. | F | F | F | F | Cl | CH$_2$Cl | CH$_3$ | H | 388 |
| 130. | F | F | F | F | H | | —(CH$_2$)$_2$—CHCF$_3$—(CH$_2$)$_2$— | H | 428 |
| 131. | F | F | F | F | H | | —(C$_2$)$_2$—CHCH$_2$CH$_3$—(CH$_2$)$_2$— | H | 388 |
| 132. | F | F | F | F | H | | —(CH$_2$)$_2$—CHOCH$_3$—(CH$_2$)$_2$— | H | 390 |
| 133. | F | F | F | F | OCH$_3$ | CH$_3$ | H | H | 336.1 |
| 134. | F | F | H | H | H | | —CH$_2$—CH$_2$—CH$_2$— | H | 296.2 |
| 135. | F | F | H | F | (CH$_2$)$_4$CH$_3$ | H | H | H | 330.1 |
| 136. | F | F | F | F | H | | —(CH$_2$)$_2$—CHCH$_3$—(CH$_2$)$_2$— | H | 474.1 |
| 137. | F | F | F | F | CH$_3$ | | —CH$_2$—CH$_2$— | H | 346.1 |
| 138. | F | F | F | F | F | | —(CF$_2$)$_5$— | H | 558 |
| 139. | F | F | F | F | F | CH$_3$ | CH$_3$ | CH$_3$ | 352 |
| 140. | F | F | F | F | H | | —(CH$_2$)$_2$—CHC(CH$_3$)$_3$—(CH$_2$)$_2$— | H | 416 |
| 141. | F | F | F | F | H | | —CH$_2$—CH$_2$—CH$_2$—CH$_2$— | CH$_3$ | 360 |
| 142. | F | F | H | F | CN | CH$_3$ | CH$_3$ | H | 327 |
| 143. | F | F | Br | F | F | CH$_3$ | H | H | 384 |
| 144. | F | F | H | F | CH$_2$CH$_3$ | H | H | H | 288.1 |
| 145. | F | F | Br | F | F | F | F | H | 408 |
| 146. | F | F | OH | F | F | CH$_3$ | CH$_3$ | H | 336.1 |
| 147. | F | H | OH | H | F | CH$_3$ | CH$_3$ | H | 300.1 |
| 148. | F | F | H | F | H | | —CH$_2$—CH$_2$—CH$_2$— | H | 314.1 |
| 149. | F | F | H | H | H | | —(CH$_2$)$_2$—CHCH$_3$—(CH$_2$)$_2$— | H | 356.1 |
| 150. | F | F | F | F | F | | —(CH$_2$)$_4$— | H | 364.1 |
| 151. | F | NO$_2$ | H | H | F | CH$_3$ | CH$_3$ | H | 329.1 |
| 152. | F | F | H | F | H | | —(CH$_2$)$_5$— | H | 342.2 |
| 153. | 3,5-dimethyl phenoxy | H | H | H | F | CH$_3$ | CH$_3$ | H | 386.1 |
| 154. | F | F | H | C$_6$H$_5$ | F | CH$_3$ | CH$_3$ | H | 378.1 |
| 155. | F | F | H | F | CH$_2$CH$_3$ | CH$_3$ | H | H | 316.1 |
| 156. | F | F | Br | F | CH$_3$ | | =CHCH$_3$[(Z) conf] | H | 392 |
| 157. | F | F | Br | F | Cl | CH$_2$CH$_3$ | CH$_3$ | H | 430 |
| 158. | F | F | H | F | CN | (CH$_2$)$_3$CH$_3$ | H | H | 355 |
| 159. | F | F | H | H | CN | (CH$_2$)$_3$CH$_3$ | H | H | 337 |
| 160. | F | F | H | F | F | H | H | H | 292 |
| 161. | F | H | H | H | F | H | H | H | 256 |
| 162. | F | F | F | F | Cl | CH$_2$CH$_3$ | CH$_3$ | H | 368 |

-continued

| no | $R^a$ | $R^b$ | $R^c$ | $R^d$ | $R^2$ | $R^3$ | $R^4$ | $R^5$ | MS [m/z] |
|---|---|---|---|---|---|---|---|---|---|
| 163. | F | F | H | F | CN | H | H | H | 299 |
| 164. | F | F | H | F | F | $CH_2CH_3$ | H | H | 320 |
| 165. | F | F | Br | F | $C_6H_5$ | H | H | H | 428.1 |
| 166. | F | F | Br | F | $CH_2CH_3$ | H | H | H | 368 |
| 167. | F | F | H | F | Cl | $CH_2CH_3$ | $CH_3$ | H | 350.2 |
| 168. | F | F | H | F | $CH_3$ | | $=CHCH_3$[(Z) conf] | H | 314.2 |
| 169. | F | F | H | F | F | $CH_2CH_3$ | $CH_3$ | acetyl | 376.1 |
| 170. | F | F | H | H | H | | $-(CH_2)_5-$ | H | 324.2 |
| 171. | F | F | Br | F | H | | $-(CH_2)_5-$ | H | 420.1 |
| 172. | F | F | Br | F | H | | $-(CH_2)_4-$ | | 408 |
| 173. | F | F | H | F | H | | $-(CH_2)_4-$ | H | 328.1 |
| 174. | F | F | H | H | H | | $-(CH_2)_4-$ | H | 310.2 |
| 175. | F | F | F | F | | | $=CH-(CH_2)_4-$ | H | 358.1 |
| 176. | F | F | H | H | $CH_3$ | | $=CHCH_3$[(Z) conf] | H | 296.2 |
| 177. | F | F | Br | F | $CH_2CH_3$ | $CH_3$ | H | H | 396 |
| 178. | F | F | H | F | CN | | $-CH_2-CH_2-$ | H | 325 |
| 179. | F | F | Br | F | $CH_3$ | | $=CH_2$ | H | 378 |
| 180. | F | F | Br | F | Cl | $CH_3$ | $CH_3$ | H | 416 |
| 181. | F | F | H | F | CN | $CH_2CH_3$ | $CH_2CH_3$ | H | 355 |
| 182. | F | H | $NO_2$ | H | F | $CH_3$ | $CH_3$ | H | 329 |
| 183. | F | F | CN | F | F | $CH_3$ | $CH_3$ | H | 345 |
| 184. | F | F | acetyl | H | F | $CH_3$ | $CH_3$ | H | 344 |
| 185. | F | H | acetyl | H | F | $CH_3$ | $CH_3$ | H | 326 |
| 186. | Cl | F | H | H | Cl | $CH_3$ | $CH_3$ | H | 334.1 |
| 187. | F | F | H | F | $CH_3$ | cyclopropyl | H | H | 328.1 |
| 188. | F | F | F | F | $OCH_3$ | $CH_3$ | $CH_3$ | H | 350.1 |
| 189. | F | F | H | H | $OCH_3$ | $CH_3$ | H | H | 299.8 |
| 190. | F | H | H | H | $OCH_3$ | $CH_3$ | H | H | 281.8 |
| 191. | F | F | H | F | $OCH_3$ | $CH_3$ | H | H | 317.8 |
| 192. | F | Cl | H | H | $OCH_3$ | $CH_3$ | H | H | 315.8 |
| 193. | F | H | F | H | $OCH_3$ | $CH_3$ | H | H | 299.8 |
| 194. | F | F | F | F | H | | $-(CH_2)_2-CHCF_3-(CH_2)_2-$ | H | 428.2 |
| 195. | F | F | F | F | H | | $-(CH_2)_2-CHCF_3-(CH_2)_2-$ | H | 428.2 |
| 196. | F | Cl | F | H | F | $CH_3$ | $CH_3$ | H | 336 |
| 197. | F | H | H | H | H | | $-(CH_2)_2-CHCH_3-(CH_2)_2-$ | H | 320.5 |
| 198. | F | F | H | H | H | | $-(CH_2)_2-CHCH_3-(CH_2)_2-$ | H | 338.5 |
| 199. | F | H | F | H | H | | $-(CH_2)_2-CHCH_3-(CH_2)_2-$ | H | 338.5 |
| 200. | F | F | Br | F | H | | $-(CH_2)_2-CHCH_3-(CH_2)_2-$ | H | 435.7 |
| 201. | F | Cl | H | H | H | | $-(CH_2)_2-CHCH_3-(CH_2)_2-$ | H | 353.8 |
| 202. | F | F | Br | F | Cl | | $-(CH_2)_4-$ | H | 442.2 |
| 203. | F | F | H | F | $CH_3$ | | $-(CH_2)_5-$ | H | 356.6 |
| 204. | F | H | H | H | $CH_3$ | | $-(CH_2)_5-$ | H | 320.5 |
| 205. | F | F | H | F | $O(CH_2)_2OCH_3$ | H | H | H | 347.8 |
| 206. | F | F | H | H | $OCH_2CH_3$ | H | H | H | 317.8 |
| 207. | F | F | F | F | $O(CH_2)_2OCH_3$ | H | H | H | 365.7 |
| 208. | F | F | F | F | $OCH_2CH_3$ | H | H | H | 335.7 |
| 209. | F | F | H | F | $C(CH_3)_3$ | H | H | H | 329.8 |
| 210. | F | F | F | F | $C(CH_3)_3$ | H | H | H | 347.8 |
| 211. | F | F | H | F | $CH(CH_3)_2$ | H | H | H | 315.8 |
| 212. | F | F | F | F | $CH(CH_3)_2$ | H | H | H | 333.7 |
| 213. | F | F | H | F | $OCH_3$ | H | H | H | 304.4 |
| 214. | F | F | F | F | $OCH_3$ | H | H | H | 321.8 |
| 215. | 3-methyl-phenoxy | H | H | H | F | $CH_3$ | $CH_3$ | H | 372.1 |
| 216. | F | F | F | F | H | | $-(CH_2)_5-$ | $CH_3$ | 374 |
| 217. | F | F | I | F | F | $CH_3$ | $CH_3$ | H | 446.6 |
| 218. | F | F | F | F | H | | $-(CH_2)_2-O-(CH_2)_2-$ | H | 362.5 |
| 219. | F | F | H | F | H | | $-(CH_2)_2-O-(CH_2)_2-$ | H | 344.5 |
| 220. | F | $CH_3$ | H | F | F | F | F | H | 306.1 |
| 221. | F | F | $CF_3$ | F | F | $CH_3$ | $CH_3$ | H | 387.8 |
| 222. | F | F | F | F | H | | $-CHCH_3-CH_2-CHCH_3-CH_2-CHCH_3-$ | H | 402 |
| 223. | F | F | H | F | F | $CH_3$ | $CH_3$ | $CH_3$ | 334 |
| 224. | F | F | Br | F | F | $CH_3$ | $CH_3$ | $CH_3$ | 414 |
| 225. | F | F | F | F | $CF_3$ | $CH_3$ | H | H | 374 |
| 226. | F | H | $CF_3$ | H | F | $CH_3$ | $CH_3$ | H | 352 |
| 227. | F | F | H | F | H | H | $CH_2OCH_3$ | H | 318.6 |
| 228. | F | F | F | F | H | H | $CH_2OCH_3$ | H | 335.7 |
| 229. | F | F | H | F | H | $CH_3$ | $CF_3$ | H | 374 |
| 230. | F | F | H | F | H | $CH_3$ | $C(CH_3)_3$ | H | 343.8 |
| 231. | F | F | H | F | H | $CH_3$ | $-CH-CH_2-CH_2-$ | H | 328.1 |
| 232. | F | F | H | F | $CH_3$ | | $-(CH_2)_3-$ | H | 327.8 |
| 233. | F | F | H | F | $CH_3$ | | $-(CH_2)_3-$ | H | 309.8 |
| 234. | F | H | H | F | $CH_3$ | | $-(CH_2)_3-$ | H | 291.8 |
| 235. | F | F | H | F | $CH_3$ | | $-(CH_2)_4-$ | H | 341.8 |
| 236. | F | Cl | H | H | $CH_3$ | | $-(CH_2)_4-$ | H | 339.8 |

-continued

| no | $R^a$ | $R^b$ | $R^c$ | $R^d$ | $R^2$ | $R^3$ | $R^4$ | $R^5$ | MS [m/z] |
|---|---|---|---|---|---|---|---|---|---|
| 237. | F | F | H | H | $CH_3$ | | $—(CH_2)_4—$ | H | 323.8 |
| 238. | F | H | H | H | $CH_3$ | | $—(CH_2)_4—$ | H | 305.8 |
| 239. | F | F | Br | F | F | | $—(CH_2)_4—$ | H | 426.4 |
| 240. | F | F | H | F | F | | $—(CH_2)_4—$ | H | 346.0 |

*(R)-enantiomer

Compounds listed in table 2 are compounds of formula (I).

TABLE 2

| no | $R^a$ | $R^b$ | $R^c$ | $R^d$ | $R^2$ | $R^3$ | $R^4$ | $R^5$ | $R^1$ | MS [m/z] |
|---|---|---|---|---|---|---|---|---|---|---|
| 241. | F | H | H | H | H | $—CH_2—CH_2—$ | | H | CO(cyclopropyl) | 332.3 |
| 242. | F | F | F | F | $CH_3$ | $CH_3$ | $CH_3$ | H | $COC(CH_3)_3$ | 418.3 |
| 243. | F | H | H | H | $CH_3$ | $CH_3$ | $CH_3$ | H | $COC(CH_3)_3$ | 280.2 |
| 244. | F | F | H | F | H | $—CH_2—CH_2—$ | | H | CO(cyclopropyl) | 368.2 |
| 245. | F | F | H | F | $CH_3$ | $CH_3$ | $CH_3$ | H | $COC(CH_3)_3$ | 400.3 |
| 246. | F | F | F | F | OH | $CH_3$ | H | H | $CH_3$ | 336.1 |
| 247. | F | F | F | F | F | $CH_3$ | $CH_3$ | H | $COCF(CH_3)_2$ | 426 |
| 248. | F | Cl | H | H | F | $CH_3$ | $CH_3$ | H | $COCF(CH_3)_2$ | 406 |
| 249. | F | F | F | F | F | $CH_3$ | $CH_3$ | $COCH_3$ | $COCH_3$ | 422 |
| 250. | F | F | F | F | F | $CH_3$ | $CH_3$ | H | $COCH_3$ | 380 |
| 251. | F | F | Br | F | H | $CH_3$ | H | $COCH_2CH_3$ | $COCH_2CH_3$ | 478.1 |
| 252. | F | F | Br | F | $CH_3$ | $CH_3$ | H | $COCH(CH_2)_2$ | $COCH(CH_2)_2$ | 522.2 |
| 253. | F | F | H | H | F | $CH_3$ | $CH_3$ | H | $COCH_3$ | 344.1 |
| 254. | F | F | H | F | F | $CH_2CH_3$ | $CH_3$ | H | $COCF(CH_2CH_3)CH_3$ | 436.1 |
| 255. | F | H | F | H | H | $—(CH_2)_5—$ | | H | $COCH_3$ | 366.2 |
| 256. | F | F | H | F | F | $CH_3$ | $CH_3$ | H | $COCH_3$ | 362.1 |
| 257. | F | H | H | H | F | $CH_2CH_3$ | $CH_3$ | H | $COCH_3$ | 340.1 |
| 258. | F | H | H | H | F | $CH_3$ | $CH_3$ | H | $COCH_3$ | 326.1 |
| 259. | F | F | H | F | F | $CH_2CH_3$ | $CH_3$ | $COCH_3$ | $COCH_3$ | 418.1 |
| 260. | F | F | H | F | F | $CH_2CH_3$ | $CH_3$ | H | $COCH_3$ | 376.1 |
| 261. | F | F | H | H | H | $—(CH_2)_4—$ | | H | CO(cyclopentane) | 406.2 |
| 262. | F | F | F | F | | $=CH—CH_2—(CH_2)_3—$ | | H | CO(cyclohex-1-ene) | 466.3 |
| 263. | F | F | H | F | H | $—(CH_2)_4—$ | | H | Cyclopentanecarbonyl | 424.2 |
| 264. | F | F | F | F | F | $CH_3$ | $CH_3$ | H | $CH_2OCH_3$ | 382 |
| 265. | F | F | F | F | F | $CH_3$ | $CH_3$ | H | $CH_2CH_2F$ | 384 |
| 266. | F | F | F | F | F | $CH_3$ | $CH_3$ | H | $CH_3$ | 352 |
| 267. | F | F | F | F | F | $CH_3$ | $CH_3$ | H | $CH_2CH_3$ | 366 |
| 268. | F | F | F | F | F | $CH_3$ | $CH_3$ | H | $CH_2C_6H_5$ | 428 |
| 269. | F | F | F | F | F | $CH_3$ | $CH_3$ | H | $CH_2CH_2OMe$ | 396 |
| 270. | F | F | F | F | F | $CH_3$ | $CH_3$ | H | $CH_2CF_3$ | 420 |

A special preference is given to the compounds of formula (I.a), which correspond to compound of formula (I) wherein $R^1$ and $R^5$ are H and listed below in table 3 (examples 1.A to 73.A), where the definitions of the variables $R^a$, $R^b$, $R^c$, $R^d$, $R^2$, $R^3$ and $R^4$ are of particular importance for the compounds according to the invention not only in combination with one another but in each case also on their own:

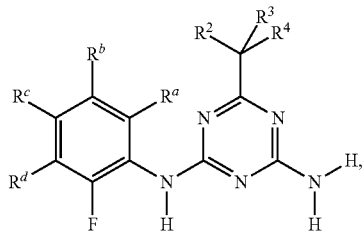

I.A

TABLE 3

| no | $R^a$ | $R^b$ | $R^c$ | $R^d$ | $R^2$ | $R^3$ | $R^4$ |
|---|---|---|---|---|---|---|---|
| 1. A | F | F | H | F | $CH_3$ | $CH_3$ | $CH_3$ |
| 2. A | F | F | F | F | $CH_3$ | $CH_3$ | $CH_3$ |
| 3. A | F | H | H | H | F | $CH_3$ | $CH_3$ |
| 4. A | CN | H | H | H | F | $CH_3$ | $CH_3$ |
| 5. A | Cl | H | H | F | F | $CH_3$ | $CH_3$ |
| 6. A | F | H | H | Cl | F | $CH_3$ | $CH_3$ |
| 7. A | F | F | H | F | F | $CH_3$ | $CH_3$ |
| 8. A | F | F | F | F | F | $CH_3$ | $CH_3$ |
| 9. A | F | F | Br | F | F | $CH_3$ | $CH_3$ |
| 10. A | F | F | I | F | F | $CH_3$ | $CH_3$ |
| 11. A | F | H | H | H | Cl | $CH_3$ | $CH_3$ |
| 12. A | F | H | H | F | Cl | $CH_3$ | $CH_3$ |
| 13. A | F | F | H | F | Cl | $CH_3$ | $CH_3$ |
| 14. A | F | F | F | F | Cl | $CH_3$ | $CH_3$ |
| 15. A | F | F | Br | F | Cl | $CH_3$ | $CH_3$ |
| 16. A | F | F | I | F | Cl | $CH_3$ | $CH_3$ |
| 17. A | F | H | H | H | F | $C_2H_5$ | $CH_3$ |
| 18. A | CN | H | H | H | F | $C_2H_5$ | $CH_3$ |
| 19. A | F | H | H | F | F | $C_2H_5$ | $CH_3$ |

TABLE 3-continued

| no | $R^a$ | $R^b$ | $R^c$ | $R^d$ | $R^2$ | $R^3$ | $R^4$ |
|---|---|---|---|---|---|---|---|
| 20. A | F | F | F | F | F | $C_2H_5$ | $CH_3$ |
| 21. A | F | F | Br | F | F | $C_2H_5$ | $CH_3$ |
| 22. A | F | F | I | F | F | $C_2H_5$ | $CH_3$ |
| 23. A | F | F | H | F | F | $C_2H_5$ | $C_2H_5$ |
| 24. A | F | F | F | F | F | $C_2H_5$ | $C_2H_5$ |
| 25. A | F | H | H | H | H | | —$(CH_2)_4$— |
| 26. A | CN | H | H | H | H | | —$(CH_2)_4$— |
| 27. A | F | F | H | F | H | | —$(CH_2)_4$— |
| 28. A | F | F | F | F | H | | —$(CH_2)_4$— |
| 29. A | F | F | Br | F | H | | —$(CH_2)_4$— |
| 30. A | F | F | I | F | H | | —$(CH_2)_4$— |
| 31. A | F | H | H | H | H | | —$(CH_2)_5$— |
| 32. A | F | F | H | F | H | | —$(CH_2)_5$— |
| 33. A | F | F | F | F | H | | —$(CH_2)_5$— |
| 34. A | F | F | Br | F | H | | —$(CH_2)_5$— |
| 35. A | F | F | I | F | H | | —$(CH_2)_5$— |
| 36. A | F | F | H | F | $CH_3$ | | —$(CH_2)_3$— |
| 37. A | F | F | F | F | $CH_3$ | | —$(CH_2)_3$— |
| 38. A | F | H | H | H | F | | —$(CH_2)_4$— |
| 39. A | CN | H | H | H | F | | —$(CH_2)_4$— |
| 40. A | F | F | H | F | F | | —$(CH_2)_4$— |
| 41. A | F | F | F | F | F | | —$(CH_2)_4$— |
| 42. A | F | F | Br | F | F | | —$(CH_2)_4$— |
| 43. A | F | F | I | F | F | | —$(CH_2)_4$— |
| 44. A | F | H | H | H | F | | —$(CH_2)_5$— |
| 45. A | CN | H | H | H | F | | —$(CH_2)_5$— |
| 46. A | F | F | H | F | F | | —$(CH_2)_5$— |
| 47. A | F | F | F | F | F | | —$(CH_2)_5$— |
| 48. A | F | F | Br | F | F | | —$(CH_2)_5$— |
| 49. A | F | F | I | F | F | | —$(CH_2)_5$— |
| 50. A | F | F | H | F | Cl | | —$(CH_2)_3$— |
| 51. A | F | F | F | F | Cl | | —$(CH_2)_3$— |
| 52. A | F | H | H | H | Cl | | —$(CH_2)_4$— |
| 53. A | CN | H | H | H | Cl | | —$(CH_2)_4$— |
| 54. A | F | F | H | F | Cl | | —$(CH_2)_4$— |
| 55. A | F | F | F | F | Cl | | —$(CH_2)_4$— |
| 56. A | F | F | Br | F | Cl | | —$(CH_2)_4$— |
| 57. A | F | F | I | F | Cl | | —$(CH_2)_4$— |
| 58. A | F | H | H | H | $C_2H_5$ | $CH_3$ | H |
| 59. A | F | F | H | F | $C_2H_5$ | $CH_3$ | H |
| 60. A | F | F | Br | F | $C_2H_5$ | $CH_3$ | H |
| 61. A | F | F | I | F | $C_2H_5$ | $CH_3$ | H |
| 62. A | F | H | H | H | $OCH_3$ | $CH_3$ | H |
| 63. A | CN | H | H | H | $OCH_3$ | $CH_3$ | H |
| 64. A | F | F | H | F | $OCH_3$ | $CH_3$ | H |
| 65. A | F | F | F | F | $OCH_3$ | $CH_3$ | H |
| 66. A | F | F | Br | F | $OCH_3$ | $CH_3$ | H |
| 67. A | F | F | I | F | $OCH_3$ | $CH_3$ | H |
| 68. A | F | H | H | H | $OCH_3$ | $CH_3$ | $CH_3$ |
| 69. A | CN | H | H | H | $OCH_3$ | $CH_3$ | $CH_3$ |
| 70. A | F | F | H | F | $OCH_3$ | $CH_3$ | $CH_3$ |
| 71. A | F | F | F | F | $OCH_3$ | $CH_3$ | $CH_3$ |
| 72. A | F | F | Br | F | $OCH_3$ | $CH_3$ | $CH_3$ |
| 73. A | F | F | I | F | $OCH_3$ | $CH_3$ | $CH_3$ |
| 74. A | F | F | H | F | H | $CH_3$ | $C(CH_3)_3$ |
| 75. A | F | F | H | F | H | $CH_3$ | $CF_3$ |
| 76. A | F | F | H | F | H | $CH_3$ | —CH—$CH_2$—$CH_2$— |
| 77. A | F | H | H | F | F | $CH_3$ | $CH_3$ |

A special preference is given to the compounds of formula (I.a) as mention above, which correspond to compound of formula (I) wherein $R^1$ and $R^5$ are H and listed below in table 4 (examples 1.B to 4.B), where the definitions of the variables $R^a$, $R^b$, $R^c$, $R^d$, $R^2$, $R^3$ and $R^4$ are of particular importance for the compounds according to the invention not only in combination with one another but in each case also on their own:

TABLE 4

| no | $R^a$ | $R^b$ | $R^c$ | $R^d$ | $R^2$ | $R^3$ | $R^4$ |
|---|---|---|---|---|---|---|---|
| 1. B | F | H | H | F | F | $CH_3$ | $CH_3$ |
| 2. B | F | F | H | F | F | $CH_3$ | $CH_3$ |
| 3. B | F | F | H | F | F | | —(CH2)$_4$— |
| 4. B | F | F | H | F | F | | —(CH2)$_3$— |

In one embodiment of the present invention the combinations according to the present invention comprise at least one compound of formula (I) (component a), compound A) and at least one further active compound b) (herbicide B, component B).

According to a first embodiment of the invention the combinations contain at least one inhibitor of the lipid biosynthesis (herbicide b1). These are compounds that inhibit lipid biosynthesis. Inhibition of the lipid biosynthesis can be affected either through inhibition of acetylCoA carboxylase (hereinafter termed ACC herbicides) or through a different mode of action (hereinafter termed non-ACC herbicides). The ACC herbicides belong to the group A of the HRAC classification system whereas the non-ACC herbicides belong to the group N of the HRAC classification.

According to a second embodiment of the invention the combinations contain at least one ALS inhibitor (herbicide b2). The herbicidal activity of these compounds is based on the inhibition of acetolactate synthase and thus on the inhibition of the branched chain amino acid biosynthesis. These inhibitors belong to the group B of the HRAC classification system.

According to a third embodiment of the invention the combinations contain at least one inhibitor of photosynthesis (herbicide b3). The herbicidal activity of these compounds is based either on the inhibition of the photosystem II in plants (so-called PSII inhibitors, groups C1, C2 and C3 of HRAC classification) or on diverting the electron transfer in photosystem I in plants (so-called PSI inhibitors, group D of HRAC classification) and thus on an inhibition of photosynthesis. Amongst these, PSII inhibitors are preferred.

According to a fourth embodiment of the invention the combinations contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

According to a fifth embodiment of the invention the combinations contain at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenylpyruvate-dioxygenase (HPPD inhibitors, group F2 of HRAC classification), compounds that inhibit DOXsynthase (group F4 of HRAC class) and compounds which inhibit carotenoid biosynthesis by an unknown mode of action (bleacher—unknown target, group F3 of HRAC classification).

According to a sixth embodiment of the invention the combinations contain at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

According to a seventh embodiment of the invention the combinations contain at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

According to an eighth embodiment of the invention the combinations contain at least one DHP synthase inhibitor (herbicide b8). The herbicidal activity of these compounds is based on the inhibition of 7,8-dihydropteroate synthase. These inhibitors belong to the group I of the HRAC classification system.

According to a ninth embodiment of the invention the combinations contain at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

According to a tenth embodiment of the invention the combinations contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

According to an eleventh embodiment of the invention the combinations contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

According to a twelfth embodiment of the invention the combinations contain at least one decoupler herbicide (herbicide b12). The herbicidal activity of these compounds is based on the disruption of the cell membrane. These inhibitors belong to the group M of the HRAC classification system.

According to a thirteenth embodiment of the invention the combinations contain at least one auxinic herbicide (herbicide b13). These include compounds that mimic auxins, i.e. plant hormones, and affect the growth of the plants. These compounds belong to the group O of the HRAC classification system.

According to a fourteenth embodiment of the invention the combinations contain at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www-.plantprotection.org/hrac/MOA.html).

Preference is given to those combinations according to the present invention comprising at least one herbicide b) selected from herbicides of classes b1, b4, b6, b9, b10 and b11.

Likewise preference is given to those combinations according to the present invention comprising at least one herbicide b) selected from herbicides of class b2, b3, b4, b5, b6, b9 and b10.

Specific preference is given to those combinations according to the present invention which comprise at least one herbicide b) selected from the herbicides of classes b1, b6 b9 and b10.

Likewise a specific preference is given to those combinations according to the present invention which comprise at least one herbicide b) selected from the herbicides of class b4, b6 b9 and b010.

Particular preference is given to those combinations according to the present invention which comprise at least one herbicide b) selected from the herbicides of classes b1, b6 and b10.

Likewise particular preference is given to those combinations according to the present invention which comprise at least one herbicide b) selected from the herbicides of class b4, b6 and b10.

Examples of herbicides b) which can be used in combination with the compounds of formula (I) according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vemolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuronmethyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pynmidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrmidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those combinations comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methyithiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those combinations comprising at least one aryl urea herbicide. Among these, likewise a preferred embodiment of the invention relates to those combinations comprising at least one triazine herbicide. Among these, likewise a preferred embodiment of the invention relates to those combinations comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, proflua-zol, pyraclonil, pyraflufen, pyraflufen-ethyl, saflufenacil, sulfentrazone, thidiazimin, tiafenacil, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100; Sumitomo; LS 5296489), N-ethyl-3-(2,6-dichloro-4-trifluoro-methylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoro-methylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) (LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3) (Isagro, IR6396), and 3-[7-chloro-5-fluoro-2-(trifluoromethyl)-1H-benzimidazol-4-yl]-1-methy-6-(trifluoromethyl-6-(tifluoromethyl)-1H-pyrimidine-2,4-dione (CAS 212754-02-4) (FMC Trifluoromethyluracil);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl) pyrimidine (CAS 180608-33-7), HPPD inhibitors: benzobicyclon, benzofenap, bicyclopyrone, clomazone, fenquintrione, isoxaflutole, mesotrione, pyrasulfotole, pyrazolynate, pyrazoxyfen, sulcotrione, tefuryltrione, tembotrione, tolpyralate, topramezone, bleacher, unknown target: aclonifen, amitrole and flumeturon;

b6) from the group of the EPSP synthase inhibitors:

glyphosate, glyphosate-isopropylammonium, glyposate-potassium and glyphosate-trimesium (sulfosate);

b7) from the group of the glutamine synthase inhibitors:

bilanaphos (bialaphos), bilanaphos-sodium, glufosinate, glufosinate-P and glufosinate-ammonium;

b8) from the group of the DHP synthase inhibitors:

asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenyichlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

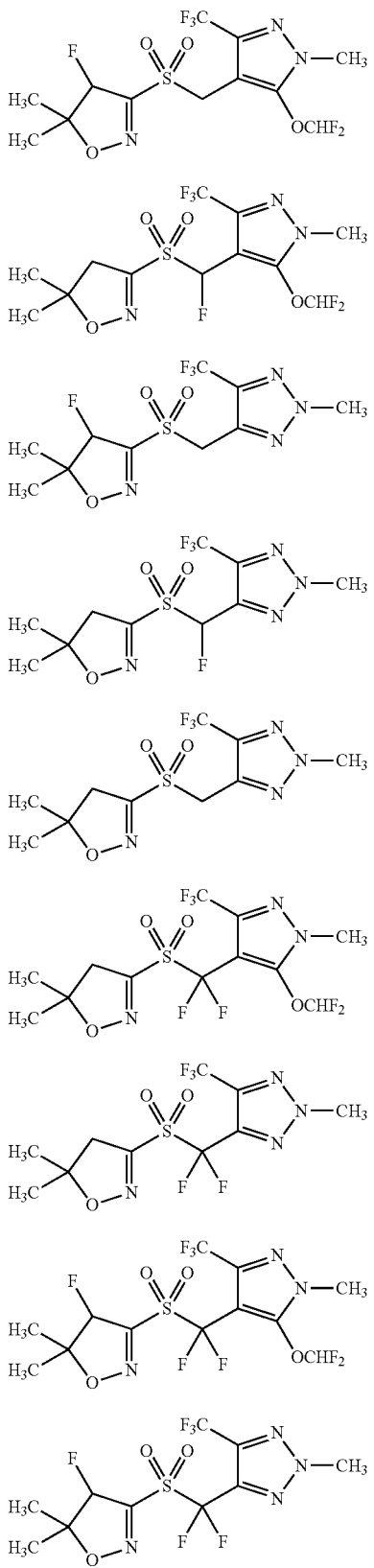

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:

chlorthiamid, dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b12) from the group of the decoupler herbicides:

dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8 DOW, LS 566509); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor");

b14) from the group of the auxin transport inhibitors:

diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3 Mitsui; SW-065; H-965) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides that can be used in combination with the compound of the formula (I) (component a), compound A) according to the present invention are:

b1) from the group of the lipid biosynthesis inhibitors:

clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine and thidiazuron;

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100; Sumitomo; LS 5296489), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) (LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4) (FMC Trifluoromethyluracil);

b5) from the group of the bleacher herbicides:
aclonifen, amitrole, beflubutamid, benzobicyclon, bicyclopyrone, clomazone, diflufenican, fenquintrione, flumeturon, flurochloridone, flurtamone, isoxaflutole, mesotrione, norflurazon, picolinafen, pyrasulfotole, pyrazolynate, sulcotrione, tefuryltrione, tembotrione, tolpyralate, topramezone and 4-(3-trifluoromethylphenoxy)-2-(4-trifluoromethylphenyl)pyrimidine (CAS 180608-33-7);

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors:
glufosinate, glufosinate-P, glufosinate-ammonium;

b8) from the group of the DHP synthase inhibitors:
asulam;

b9) from the group of the mitosis inhibitors:
benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors:
acetochlor, alachlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, fluroxypyr-meptyl, halauxifen and its salts and esters (CAS 943832-60-8 DOW, LS 566509), MCPA and its salts and esters, MCPB and its salts and esters, mecoprop-P and its salts and esters, picloram and its salts and esters, quinclorac, quinmerac, triciopyr and its salts and esters, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor");

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3 Mitsui; SW-065; H-965) and its salts and esters, dalapon, difenzoquat, difenzoquat-metilsulfate, DSMA, dymron (=daimuron), indanofan, metam, methylbromide, MSMA, oxaziclomefone, pyributicarb and tridiphane.

Particularly preferred herbicides b) that can be used in combination with the compounds of the formula (I) (component a), compound A) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn and terbuthylazine;

b4) from the group of the protoporphyrinogen-IX oxidase inhibitors: flumioxazin, oxyfluorfen, pyraflufen, pyraflufen-ethyl, saflufenacil, sulfentrazone, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100; Sumitomo; LS 5296489), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) (LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO);

b5) from the group of the bleacher herbicides: amitrole, bicyclopyrone, clomazone, diflufenican, fenquintrione, flumeturon, flurochloridone, isoxaflutole, mesotrione, picolinafen, sulcotrione, tefuryltrione, tembotrione, tolpyralate and topramezone;

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triaziflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor");

b14) from the group of the auxin transport inhibitors: diflufenzopyr and diflufenzopyr-sodium, b15) from the group of the other herbicides: dymron (=daimuron), indanofan, oxaziclomefone.

In a preferred embodiment of the invention the combinations comprise at least one compound of formula (I) and at least one further active compound b) (herbicide B), which is selected from the group consisting of triallate, pinoxaden, cycloxydim or quizalofop.

In a another preferred embodiment of the invention the combinations comprise at least one compound of formula (I) and at least one further active compound b) (herbicide B), which is selected from the group consisting of pyroxsulam, imazethypyr), imazosulfuron, pyrazosulfuron, imazamox, imazapyr or imazapic.

In an another preferred embodiment of the invention the combinations comprise at least one compound of formula (I) and at least one further active compound b) (herbicide B), which is selected from the group consisting of hexazinone, metribuzin, atrazine, diuron, isoproturon or chlorotoluron.

In an another preferred embodiment of the invention the combinations comprise at least one compound of formula (I) and at least one further active compound b) (herbicide B), which is selected from the group consisting of BAS 850 H, saflufenacil, sulfentrazone, pentoxazone or flumioxazin.

In an another preferred embodiment of the invention the combinations comprise at least one compound of formula (I) and at least one further active compound b) (herbicide B), which is selected from the group consisting of diflufenican, clomazone, picolinafen, mesotrione, isoxaflutole, bicyclopyrone or benzobicyclon.

In an another preferred embodiment of the invention the combinations comprise at least one compound of formula (I) and at least one further active compound b) (herbicide B), which is glyphosate.

In an another preferred embodiment of the invention the combinations comprise at least one compound of formula (I) and at least one further active compound b) (herbicide B), which is glufosinate.

In a another preferred embodiment of the invention the combinations comprise at least one compound of formula (I) and at least one further active compound b) (herbicide B), which is pendimethalin.

In a another preferred embodiment of the invention the combinations comprise at least one compound of formula (I) and at least one further active compound b) (herbicide B), which is selected from the group consisting of metazachlor, dmta-p, pretilachlor, pyroxasulfone, acetochlor or flufenacet.

In a another preferred embodiment of the invention the combinations comprise at least one compound of formula (I) and at least one further active compound b) (herbicide B), which is selected from the group consisting of dimethenamid or dimethenamid-P.

In a another preferred embodiment of the invention the combinations comprise at least one compound of formula (I) and at least one further active compound b) (herbicide B), which is selected from the group consisting of dicamba.

In a another preferred embodiment of the invention the combinations comprise at least one compound of formula (I) and at least one further active compound b) (herbicide B), which is selected from the group consisting of quimerac or quinclorac.

In an another preferred embodiment of the invention the combinations comprise at least one compound of formula (I) and at least one further active compound b) (herbicide B), which is cinmethylin.

Likewise in another preferred embodiment of the invention the combinations comprise at least one compound of formula (I) and at least one further active compound b) (herbicide B), which is triallate.

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is triallate.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is triallate.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is triallate.

Likewise in another preferred embodiment of the invention the combinations comprise at least N 4-(2,6-difluorophenyl)-6-(1-fluoro-1-methyl-ethyl)-1,3,5-triazine-2,4-diamine and at least one further active compound b) (herbicide B), which is triallate.

Likewise in another preferred embodiment of the invention the combinations comprise at least one compound of formula (I) and at least one further active compound b) (herbicide B), which is imazethapyr.

Likewise in another preferred embodiment of the invention the combinations comprise at least 6-(l-methycyclobutyl)-N4-(2,3,5,6-tetrafluorophenyl)-1,3,5-triazine-2,4-diamine and at least one further active compound b) (herbicide B), which is imazethapyr.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is imazethapyr.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is imazethapyr.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is imazethapyr.

Likewise in another preferred embodiment of the invention the combinations comprise at least one compound of formula (I) and at least one further active compound b) (herbicide B), which is selected from metribuzin, chlorotoluron and isoproturon.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from metribuzin, chlorotoluron and isoproturon.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from metribuzin.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from chlorotoluron.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from isoproturon.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from metribuzin, chlorotoluron and isoproturon.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from metribuzin.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from chlorotoluron.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from isoproturon.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from metribuzin, chlorotoluron and isoproturon.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from metribuzin.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from chlorotoluron.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from isoproturon.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from metribuzin, chlorotoluron and isoproturon.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from metribuzin.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from chlorotoluron.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from and isoproturon.

Likewise in another preferred embodiment of the invention the combinations comprise at least one compound of formula (I) and at least one further active compound b) (herbicide B), which is selected from sulfentrazone, saflufenacil and trifludimoxazin (BAS 850 H).

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from sulfentrazone, saflufenacil and trifludimoxazin (BAS 850 H).

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from sulfentrazone.

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from saflufenacil.

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from trifludimoxazin (BAS 850 H).

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from sulfentrazone, saflufenacil and trifludimoxazin (BAS 850 H).

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from sulfentrazone.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from saflufenacil.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from trifludimoxazin (BAS 850 H).

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from sulfentrazone, saflufenacil and trifludimoxazin (BAS 850 H).

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from sulfentrazone.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from saflufenacil.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from trifludimoxazin (BAS 850 H).

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from sulfentrazone, saflufenacil and trifludimoxazin (BAS 850 H).

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from sulfentrazone.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from saflufenacil.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from trifludimoxazin (BAS 850 H).

Likewise in another preferred embodiment of the invention the combinations comprise at least one compound of formula (I) and at least one further active compound b) (herbicide B), which is selected from picolinafen, mesotrione, diflufenican and isoxyflutole.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from picolinafen, mesotrione, diflufenican and isoxyflutole.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from picolinafen.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from mesotrione.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from diflufenican.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from isoxyflutole.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from picolinafen, mesotrione, diflufenican and isoxyflutole.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from picolinafen.

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from mesotrione.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from diflufenican.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from isoxyflutole.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from picolinafen, mesotrione, diflufenican and isoxyflutole.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from picolinafen.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from mesotrione.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from diflufenican.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from isoxyflutole.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from picolinafen, mesotrione, diflufenican and isoxyflutole.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from picolinafen.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from mesotrione.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from diflufenican.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from isoxyflutole.

Likewise in another preferred embodiment of the invention the combinations comprise at least one compound of formula (I) and at least one further active compound b) (herbicide B), which is pendimethalin.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is pendimethalin.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is pendimethalin.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is pendimethalin.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is pendimethalin.

Likewise in another preferred embodiment of the invention the combinations comprise at least one compound of formula (I) and at least one further active compound b) (herbicide B), which is selected from pyroxasulfone, flufenacet, dimethenamid, dimethenamid-P and acetochlor.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from pyroxasulfone, flufenacet, dimethenamid, dimethenamid-P and acetochlor.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from pyroxasulfone.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from flufenacet.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is selected from dimethenamid.

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from dimethenamid-P.

Likewise in another preferred embodiment of the invention the combinations comprise at least 6-(1-methycyclobutyl)-N4-(2,3,5,6-tetrafluorophenyl)-1,3,5-triazine-2,4-diamine and at least one further active compound b) (herbicide B), which is selected from acetochlor.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from pyroxasulfone, flufenacet, dimethenamid, dimethenamid-P and acetochlor.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from pyroxasulfone.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from flufenacet.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from dimethenamid.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from dimethenamid-P.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is selected from acetochlor.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from pyroxasulfone, flufenacet, dimethenamid, dimethenamid-P and acetochlor.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from pyroxasulfone.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from flufenacet.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from dimethenamid.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from dimethenamid-P.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is selected from and acetochlor.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from pyroxasulfone, flufenacet, dimethenamid, dimethenamid-P and acetochlor.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from pyroxasulfone.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from flufenacet.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from dimethenamid.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from, dimethenamid-P.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is selected from acetochlor.

Likewise in another preferred embodiment of the invention the combinations comprise at least one compound of formula (I) and at least one further active compound b) (herbicide B), which is glyphosate.

Likewise in another preferred embodiment of the invention the combinations comprise at least 6-(1-methylcyclobutyl)-N4-(2,3,5,6-tetrafluorophenyl)-1,3,5-triazine-2,4-diamine and at least one further active compound b) (herbicide B), which is glyphosate.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is glyphosate.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is glyphosate.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is glyphosate.

Likewise in another preferred embodiment of the invention the combinations comprise at least one compound of formula (I) and at least one further active compound b) (herbicide B), which is dicamba.

Likewise in another preferred embodiment of the invention the combinations comprise at least 6-(l-methycyclobutyl)-N4-(2,3,5,6-tetrafluorophenyl)-1,3,5-triazine-2,4-diamine and at least one further active compound b) (herbicide B), which is dicamba.

Likewise in another preferred embodiment of the invention the combinations comprise at least 6-(1-fluorocyclopentyl)-N4-(2,3,5,6-tetrafluorophenyl)-1,3,5-triazine-2,4-diamine and at least one further active compound b) (herbicide B), which is dicamba.

Likewise in another preferred embodiment of the invention the combinations comprise at least 6-(1-fluoro-1-methyl-ethyl)-N4-(2,3,5,6-tetrafluorophenyl)-1,3,5-triazine-2,4-diamine and at least one further active compound b) (herbicide B), which is dicamba.

Likewise in another preferred embodiment of the invention the combinations comprise at least N4-(2,6-difluorophenyl)-6-(1-fluoro-1-methyl-ethyl)-1,3,5-triazine-2,4-diamine and at least one further active compound b) (herbicide B), which is dicamba.

In an another preferred embodiment of the invention the combinations comprise at least one compound of formula (I) and at least two further active compounds b) (herbicide B), which are selected from the group consisting of diflufenican and pyroxsulam.

In an another preferred embodiment of the invention the combinations comprise at least one compound of formula (I) and at least two further active compounds b) (herbicide B), which are selected from the group consisting of hexazinone and metribuzin.

In an another preferred embodiment of the invention the combinations comprise at least one compound of formula (I) and at least two further active compounds b) (herbicide B), which are selected from the group consisting of picolinafen and pinoxaden.

Active compounds b) and c) having a carboxyl group can be employed in the form of the acid, in the form of an agriculturally suitable salt as mentioned above or else in the form of an agriculturally acceptable derivative in the combinations according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine.

Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)

ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and amino-pyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicides B are the herbicides B as defined above; in particular the herbicides B.1-B.196 listed below in table B:

TABLE B

| | Herbicide B |
|---|---|
| B-1. | clethodim |
| B-2. | clodinafop-propargyl |
| B-3. | cycloxydim |
| B-4. | cyhalofop-butyl |
| B-5. | fenoxaprop-ethyl |
| B-6. | fenoxaprop-P-ethyl |
| B-7. | metamifop |
| B-8. | pinoxaden |
| B-9. | profoxydim |
| B-10. | sethoxydim |
| B-11. | tepraloxydim |
| B-12. | tralkoxydim |
| B-13. | esprocarb |
| B-14. | ethofumesate |
| B-15. | molinate |
| B-16. | prosulfocarb |
| B-17. | thiobencarb |
| B-18. | triallate |
| B-19. | bensulfuron-methyl |
| B-20. | bispyribac-sodium |
| B-21. | cloransulam-methyl |
| B-22. | chlorsulfuron |
| B-23. | clorimuron |
| B-24. | cyclosulfamuron |
| B-25. | diclosulam |
| B-26. | florasulam |
| B-27. | flumetsulam |
| B-28. | flupyrsulfuron-methyl-sodium |
| B-29. | foramsulfuron |
| B-30. | imazamox |
| B-31. | imazamox-ammonium |
| B-32. | imazapic |
| B-33. | imazapic-ammonium |

TABLE B-continued

| | Herbicide B |
|---|---|
| B-34. | imazapic-isopropylammonium |
| B-35. | imazapyr |
| B-36. | imazapyr-ammonium |
| B-37. | imazapyr-isopropylammonium |
| B-38. | imazaquin |
| B-39. | imazaquin-ammonium |
| B-40. | imazethapyr |
| B-41. | imazethapyr-ammonium |
| B-42. | imazethapyr-isopropylammonium |
| B-43. | imazosulfuron |
| B-44. | iodosulfuron-methyl-sodium |
| B-45. | iofensulfuron |
| B-46. | iofensulfuron-sodium |
| B-47. | mesosulfuron-methyl |
| B-48. | metazosulfuron |
| B-49. | metsulfuron-methyl |
| B-50. | metosulam |
| B-51. | nicosulfuron |
| B-52. | penoxsulam |
| B-53. | propoxycarbazon-sodium |
| B-54. | pyrazosulfuron-ethyl |
| B-55. | pyribenzoxim |
| B-56. | pyriftalid |
| B-57. | pyroxsulam |
| B-58. | propyrisulfuron |
| B-59. | rimsulfuron |
| B-60. | sulfosulfuron |
| B-61. | thiencarbazone-methyl |
| B-62. | thifensulfuron-methyl |
| B-63. | tribenuron-methyl |
| B-64. | tritosulfuron |
| B-65. | triafamone |
| B-66. | ametryne |
| B-67. | atrazine |
| B-68. | bentazon |
| B-69. | bromoxynil |
| B-70. | bromoxynil-octanoate |
| B-71. | bromoxynil-heptanoate |
| B-72. | bromoxynil-potassium |
| B-73. | diuron |
| B-74. | fluometuron |
| B-75. | hexazinone |
| B-76. | isoproturon |
| B-77. | linuron |
| B-78. | metamitron |
| B-79. | metribuzin |
| B-80. | propanil |
| B-81. | simazin |
| B-82. | terbuthylazine |
| B-83. | terbutryn |
| B-84. | paraquat-dichloride |
| B-85. | acifluorfen |
| B-86. | butafenacil |
| B-87. | carfentrazone-ethyl |
| B-88. | flumioxazin |
| B-89. | fomesafen |
| B-90. | oxadiargyl |
| B-91. | oxyfluorfen |
| B-92. | pyraflufen |
| B-93. | pyraflufen-ethyl |
| B-94. | saflufenacil |
| B-95. | sulfentrazone |
| B-96. | trifludimoxazin (BAS 850 H) |
| B-97. | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) Sumitomo; LS 5296489 |
| B-98. | benzobicyclon |
| B-99. | bicyclopyrone |
| B-100. | clomazone |
| B-101. | diflufenican |
| B-102. | flurochloridone |
| B-103. | isoxaflutole |
| B-104. | mesotrione |
| B-105. | norflurazone |
| B-106. | picolinafen |
| B-107. | sulcotrione |
| B-108. | tefuryltrione |
| B-109. | tembotrione |
| B-110. | tolpyralate |
| B-111. | topramezone |
| B-112. | topramezone-sodium |
| B-113. | amitrole |
| B-114. | fluometuron |
| B-115. | fenquintrione |
| B-116. | glyphosate |
| B-117. | glyphosate-ammonium |
| B-118. | glyphosate-dimethylammonium |
| B-119. | glyphosate-isopropylammonium |
| B-120. | glyphosate-trimesium (sulfosate) |
| B-121. | glyphosate-potassium |
| B-122. | glufosinate |
| B-123. | glufosinate-ammonium |
| B-124. | glufosinate-P |
| B-125. | glufosinate-P-ammonium |
| B-126. | pendimethalin |
| B-127. | trifluralin |
| B-128. | acetochlor |
| B-129. | butachlor |
| B-130. | cafenstrole |
| B-131. | dimethenamid-P |
| B-132. | fentrazamide |
| B-133. | flufenacet |
| B-134. | mefenacet |
| B-135. | metazachlor |
| B-136. | metolachlor |
| B-137. | S-metolachlor |
| B-138. | pretilachlor |
| B-139. | fenoxasulfone |
| B-140. | indaziflam |
| B-141. | isoxaben |
| B-142. | triaziflam |
| B-143. | ipfencarbazone |
| B-144. | pyroxasulfone |
| B-145. | 2,4-D |
| B-146. | 2,4-D-isobutyl |
| B-147. | 2,4-D-dimethylammonium |
| B-148. | 2,4-D-N,N,N-trimethylethanolammonium |
| B-149. | aminopyralid |
| B-150. | aminopyralid-methyl |
| B-151. | aminopyralid-dimethyl-ammonium |
| B-152. | aminopyralid-tris(2-hydroxypropyl)ammonium |
| B-153. | clopyralid |
| B-154. | clopyralid-methyl |
| B-155. | clopyralid-olamine |
| B-156. | dicamba |
| B-157. | dicamba-butotyl |
| B-158. | dicamba-diglycolamine |
| B-159. | dicamba-dimethylammonium |
| B-160. | dicamba-diolamine |
| B-161. | dicamba-isopropylammonium |
| B-162. | dicamba-potassium |
| B-163. | dicamba-sodium |
| B-164. | dicamba-trolamine |
| B-165. | dicamba-N,N-bis-(3-aminopropyl)methylamine |
| B-166. | dicamba-diethylenetriamine |
| B-167. | fluroxypyr |
| B-168. | fluroxypyr-meptyl |
| B-169. | halauxifen |
| B-170. | halauxifen-methyl |
| B-171. | MCPA |
| B-172. | MCPA-2-ethylhexyl |
| B-173. | MCPA-dimethylammonium |
| B-174. | quinclorac |
| B-175. | quinclorac-dimethylammonium |
| B-176. | quinmerac |
| B-177. | quinmerac-dimethylammonium |
| B-178. | 4-amino-3-chloro-6-(4-chloro-2-fluoro-3-methoxyphenyl)-5-fluoropyridine-2-carboxylic acid (DOW, "Rinskor-acid") |
| B-179. | benzyl 4-amino-3-chloro-6-(4-chloro-2-fluoro-3-methoxy-phenyl)-5-fluoropyridine-2-carboxylate (CAS 1390661-72-9) (DOW, "Rinskor") |
| B-180. | aminocyclopyrachlor |

TABLE B-continued

| | Herbicide B |
|---|---|
| B-181. | aminocyclopyrachlor-potassium |
| B-182. | aminocyclopyrachlor-methyl |
| B-183. | diflufenzopyr |
| B-184. | diflufenzopyr-sodium |
| B-185. | dymron |
| B-186. | indanofan |
| B-187. | oxaziclomefone |
| B-188. | II.1 |
| B-189. | II.2 |
| B-190. | II.3 |
| B-191. | II.4 |
| B-192. | II.5 |
| B-193. | II.6 |
| B-194. | II.7 |
| B-195. | II.8 |
| B-196. | II.9 |

In a preferred embodiment of the invention the combinations comprise at least one compound of formula (I) (component a), compound A) and at least one safener c.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the compounds of formula (I) and/or the herbicides b) can be applied simultaneously or in succession.

Suitable safeners c are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners c are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Especially preferred safeners c are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro-[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners c are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and N-(2-Methoxybenzoyl)-4-[(methylaminocarbonyl)amino]benzenesulfonamide (CAS 129531-12-0).

Particularly preferred safeners c, which, as component C, are constituent of the composition according to the invention are the safeners c as defined above; in particular the safeners C.1-C.17 listed below in table C:

TABLE C

| | Safener c |
|---|---|
| C-1. | benoxacor |
| C-2. | cloquintocet |
| C-3. | cloquintocet-mexyl |
| C-4. | cyprosulfamide |
| C-5. | dichlormid |
| C-6. | fenchlorazole |
| C-7. | fenchlorazole-ethyl |
| C-8. | fenclorim |
| C-9. | furilazole |
| C-10. | isoxadifen |
| C-11. | isoxadifen-ethyl |
| C-12. | mefenpyr |
| C-13. | mefenpyr-diethyl |
| C-14. | naphtalic acid anhydride |
| C-15. | 4-(dichloroacetyl)-1-oxa-4-azaspiro[4.5]decane (MON4660, CAS 71526-07-3) |
| C-16. | 2,2,5-trimethyl-3-(dichloroacetyl)-1,3-oxazolidine (R-29148, CAS 52836-31-4) |
| C-17. | N-(2-Methoxybenzoyl)-4-[(methylaminocarbonyl)amino]benzenesulfonamide (CAS 129531-12-0) |

The active compounds b) of groups b1) to b15) and the active compounds c are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro [4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds b) and c) having a carboxyl group can be employed in the form of the acid, in the form of an agriculturally suitable salt as mentioned above or else in the form of an agriculturally acceptable derivative in the combinations according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)-ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl. Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium.

Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and amino-pyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinclorac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

The active compounds b) According to a preferred embodiment of the invention, the combination comprises as herbicidal active compound b) or component B at least one, preferably exactly one herbicide b).

According to another preferred embodiment of the invention, the combination comprises as herbicidal active compounds b) or component b) at least two, preferably exactly two herbicides b) different from each other.

According to another preferred embodiment of the invention, the combination comprises as herbicidal active compounds b) or component b) at least three, preferably exactly three herbicides b) different from each other.

According to another preferred embodiment of the invention, the combination comprises as safening component c or component c at least one, preferably exactly one safener c.

According to another preferred embodiment of the invention, the combination comprises as component b) at least one, preferably exactly one herbicide b), and as component c at least one, preferably exactly one, safener c.

According to another preferred embodiment of the invention, the combination comprises at least two, preferably exactly two, herbicides B different from each other, and as component c at least one, preferably exactly one, safener c.

According to another preferred embodiment of the invention, the combination comprises at least three, preferably exactly three, herbicides B different from each other, and as component c at least one, preferably exactly one, safener c.

According to another preferred embodiment of the invention, the combination comprises as active compound at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one, preferably exactly one, herbicide b).

According to another preferred embodiment of the invention, the combination comprises as active compound at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least two, preferably exactly two, herbicides b) different from each other.

According to another preferred embodiment of the invention, the combination comprises as active compound at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least three, preferably exactly three, herbicides b) different from each other.

According to another preferred embodiment of the invention, the combination comprises as active compound at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and as component c at least one, preferably exactly one, safener c.

According to another preferred embodiment of the invention, the combination comprises as active compound at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one, preferably exactly one, herbicide b), and as component c at least one, preferably exactly one safener c.

According to another preferred embodiment of the invention, the combination comprises as active compound at least one, preferably exactly at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least two, preferably exactly two herbicides b) different from each other, and as component c at least one, preferably exactly one, safener c.

According to another preferred embodiment of the invention, the combination comprises as component (I) at least one, preferably exactly at least one, preferably exactly one compound of formula (I), preferably one compound of the formulae 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least three, preferably exactly three herbicides b) different from each other, and as component c at least one, preferably exactly one, safener c.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and trialate.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

According to another preferred embodiment of the invention, the combination comprises, in addition to a compound of formula (I), especially an active compound from the group consisting 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b4), in particular selected from the group consisting of flumioxazin, oxyfluorfen, saflufenacil, sulfentrazone, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-310), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione), 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione (CAS 1258836-72-4), 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione and 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b4), in particular selected from the group consisting of flumioxazin, oxyfluorfen, pyraflufen, pyraflufen-ethyl, saflufenacil, sulfentrazone, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100; Sumitomo; LS 5296489), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin) and 1-methyl-6-2,7-fluoromethyl-3(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0) (LS 568 1323=Uracil-F2-PPO).

According to another preferred embodiment of the invention, the combination comprises, in addition to a compounds of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b5), in particular selected from the group consisting of clomazone, diflufenican, flurochloridone, isoxaflutole, mesotrione, picolinafen, sulcotrione, tefuryltrione, tembotrione, topramezone, bicyclopyrone, amitrole and flumeturon.

According to another preferred embodiment of the invention, the combination comprises, in addition to a compounds of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b5), in particular selected from the group consisting of amitrole, bicyclopyrone, clomazone, diflufenican, flumeturon, flurochloridone, isoxaflutole, mesotrione, picolinafen, sulcotrione, tefuryltrione, tembotrione, tolpyralate and topramezone.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b6), in particular selected from the group consisting of glyphosate, glyphosate-isopropylammonium and glyphosate-trimesium (sulfosate).

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b7), in particular selected from the group consisting of glufosinate, glufosinate-P and glufosinate-ammonium.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b9), in particular selected from the group consisting of pendimethalin and trifluralin.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone.

Likewise, preference is given to combinations comprising in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b11), in particular isoxaben.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b11), in particular indaziflam, isoxaben and triaziflam.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b13), in particular selected from the group consisting of 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, fluroxypyr-meptyl, quinclorac and quinmerac.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b13), in particular selected from the group consisting of 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor").

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b14), in particular selected from the group consisting of diflufenzopyr and diflufenzopyr-sodium.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b15), in particular selected from the group consisting of dymron (=daimuron), indanofan, indaziflam, oxaziclomefone and triaziflam.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from group b15), in particular selected from the group consisting of dymron (=daimuron), indanofan and oxaziclomefone.

According to another preferred embodiment of the invention, the combination comprises, in addition to a compound of formula (I), especially an active compound from the group consisting of 1.A, 2.A, 3.A, 4.A, 5.A, 6.A, 7.A, 8.A, 9.A, 10.A, 11.A, 12.A, 13.A, 14.A, 15.A, 16.A, 17.A, 18.A, 19.A, 20.A, 21.A, 22.A, 23.A, 24.A, 25.A, 26.A, 27.A, 28.A, 29.A, 30.A, 31.A, 32.A, 33.A, 34.A, 35.A, 36.A, 37.A, 38.A, 39.A, 40.A, 41.A, 42.A, 43.A, 44.A, 45.A, 46.A, 47.A, 48.A, 49.A, 50.A, 51.A, 52.A, 53.A, 54.A, 55.A, 56.A, 57.A, 58.A, 59.A, 60.A, 61.A, 62.A, 63.A, 64.A, 65.A, 66.A, 67.A, 68.A, 69.A, 70.A, 71.A, 72.A, 73.A, 74.A, 75.A, 76.A or 77.A and at least one and especially exactly one herbicidally active compound from the safeners c, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The following combinations indicate by the code X.Z represent particular embodiments of the invention:

1.1 to 1.3545
2.1 to 2.3545,
3.1 to 3.3545,
4.1 to 4.3545,
5.1 to 5.3545,
6.1 to 6.3545,
7.1 to 7.3545,
8.1 to 8.3545,
9.1 to 9.3545,
10.1 to 10.3545,
11.1 to 11.3545,
12.1 to 12.3545,
13.1 to 13.3545,
14.1 to 14.3545,
15.1 to 15.3545,
16.1 to 16.3545,
17.1 to 17.3545,
18.1 to 18.3545,
19.1 to 19.3545,
20.1 to 20.3545,
21.1 to 21.3545,
22.1 to 22.3545,
23.1 to 23.3545,
24.1 to 24.3545,
25.1 to 25.3545,
26.1 to 26.3545,
27.1 to 27.3545,
28.1 to 28.3545,
29.1 to 29.3545,
30.1 to 30.3545,
31.1 to 31.3545,
32.1 to 32.3545,
33.1 to 33.3545,
34.1 to 34.3545,
35.1 to 35.3545,
36.1 to 36.3545,
37.1 to 37.3545,
38.1 to 38.3545,
39.1 to 39.3545,
40.1 to 40.3545,
41.1 to 41.3545,
42.1 to 42.3545,
43.1 to 43.3545,
44.1 to 44.3545,
45.1 to 45.3545,
46.1 to 46.3545,
47.1 to 47.3545,
48.1 to 48.3545,
49.1 to 49.3545,
50.1 to 50.3545,
51.1 to 51.3545,
52.1 to 52.3545,
53.1 to 53.3545,
54.1 to 54.3545,
55.1 to 55.3545,
56.1 to 56.3545,
57.1 to 57.3545,
58.1 to 58.3545,
59.1 to 59.3545,
60.1 to 60.3545,
61.1 to 61.3545,
62.1 to 62.3545,
63.1 to 63.3545,
64.1 to 64.3545,
65.1. to 65.3545,
66.1 to 66.3545,
67.1 to 67.3545,
68.1 to 68.3545,
69.1 to 69.3545,
70.1 to 70.3545,
71.1 to 71.3545,
72.1 to 72.3545,
73.1 to 73.3545,
74.1 to 74.3545,
75.1 to 75.3545,
76.1 to 76.3545,
77.1 to 77.3545,
78.1 to 78.3545,
79.1 to 79.3545,
80.1 to 80.3545,
81.1 to 81.3545, 82.1 to 82.3545,
83.1 to 83.3545,
84.1 to 84.3545,
85.1 to 85.3545,
86.1 to 86.3545,
87.1 to 87.3545,
88.1. to 88.3545,
86.1 to 86.3545,
87.1 to 87.3545,
88.1 to 88.3545,
89.1 to 89.3545,
90.1 to 90.3545,
91.1 to 91.3545,
92.1 to 92.3545,
93.1 to 93.3545,
94.1 to 94.3545,
95.1 to 95.3545,
96.1 to 96.3545,
97.1 to 97.3545,
98.1. to 98.3545,
96.1 to 96.3545,
97.1 to 97.3545,
98.1 to 98.3545,
99.1 to 99.3545,
100.1 to 100.3545,
101.1 to 101.3545,
102.1 to 102.3545,
103.1 to 103.3545,
104.1 to 104.3545,
105.1 to 105.3545,
106.1 to 106.3545,
107.1 to 107.3545,
108.1 to 108.3545,
109.1 to 109.3545,
110.1 to 110.3545,
111.1 to 111.3545,
112.1 to 112.3545,
113.1 to 113.3545,
114.1 to 114.3545,
115.1 to 115.3545,
116.1 to 116.3545,
117.1 to 117.3545,
118.1 to 118.3545,
119.1 to 119.3545,
120.1 to 120.3545,
121.1 to 121.3545,
122.1 to 122.3545,
123.1 to 123.3545,
124.1 to 124.3545,
125.1 to 125.3545,
126.1 to 126.3545,
127.1 to 127.3545,
128.1 to 128.3545,
129.1 to 129.3545,
130.1 to 130.3545,
131.1 to 131.3545,
132.1 to 132.3545,
133.1 to 133.3545,
134.1 to 134.3545,
135.1 to 135.3545,
136.1 to 136.3545,
137.1 to 137.3545,
138.1 to 138.3545,
139.1 to 139.3545,
140.1 to 140.3545,
141.1 to 141.3545,
142.1 to 142.3545,
143.1 to 143.3545,
144.1 to 144.3545,
145.1 to 145.3545,
146.1 to 146.3545,
147.1 to 147.3545,
148.1 to 148.3545,
149.1 to 149.3545,
150.1 to 150.3545,
151.1 to 151.3545,
152.1 to 152.3545,
153.1 to 153.3545,
154.1 to 154.3545,
155.1 to 155.3545,
156.1 to 156.3545,
157.1 to 157.3545,
158.1 to 158.3545,
159.1 to 159.3545,
160.1 to 160.3545,
161.1 to 161.3545,
162.1 to 162.3545,
163.1 to 163.3545,
164.1 to 164.3545,
165.1 to 165.3545,
166.1 to 166.3545,
167.1 to 167.3545,
168.1 to 168.3545,
169.1 to 169.3545,
170.1 to 170.3545,
171.1 to 171.3545,
172.1 to 172.3545,
173.1 to 173.3545,
174.1 to 174.3545,
175.1 to 175.3545,
176.1 to 176.3545,
177.1 to 177.3545,
178.1 to 178.3545,
179.1 to 179.3545,
180.1 to 180.3545,
181.1 to 181.3545,
182.1 to 182.3545,
183.1 to 183.3545,
184.1 to 184.3545,
185.1 to 185.3545,
186.1 to 186.3545,
187.1 to 187.3545,
188.1 to 188.3545,
189.1 to 189.3545,
190.1 to 190.3545,
191.1 to 191.3545,
192.1 to 192.3545,
193.1 to 193.3545,
194.1 to 194.3545,
195.1 to 195.3545,
196.1 to 196.3545,
197.1 to 197.3545,
198.1 to 198.3545,
199.1 to 199.3545,
200.1 to 200.3545,
201.1 to 201.3545,
202.1 to 202.3545,
203.1 to 203.3545,
204.1 to 204.3545,
205.1 to 205.3545,
206.1 to 206.3545,
207.1 to 207.3545,
208.1 to 208.3545,
209.1 to 209.3545,
210.1 to 210.3545,
211.1 to 211.3545,
212.1 to 212.3545,
213.1 to 213.3545,
214.1 to 214.3545,
215.1 to 215.3545,
216.1 to 216.3545,
217.1 to 217.3545,
218.1 to 218.3545,
219.1 to 219.3545,
220.1 to 220.3545,
221.1 to 221.3545,
222.1 to 222.3545,
223.1 to 223.3545,
224.1 to 224.3545,
225.1 to 225.3545,
226.1 to 226.3545,
227.1 to 227.3545,
228.1 to 228.3545,
229.1 to 229.3545,
230.1 to 230.3545,
231.1 to 231.3545,
232.1 to 232.3545,
233.1 to 233.3545,

```
234.1 to 234.3545,
235.1 to 235.3545,
236.1 to 236.3545,
237.1 to 237.3545,
238.1 to 238.3545,
239.1 to 239.3545,
240.1 to 240.3545,
241.1 to 241.3545,
242.1 to 242.3545,
243.1 to 243.3545,
244.1 to 244.3545,
245.1 to 245.3545,
246.1 to 246.3545,
247.1 to 247.3545,
248.1 to 248.3545,
249.1 to 249.3545,
250.1 to 250.3545,
251.1 to 251.3545,
252.1 to 252.3545,
253.1 to 253.3545,
254.1 to 254.3545,
255.1 to 255.3545,
256.1 to 256.3545,
257.1 to 257.3545,
258.1 to 258.3545,
259.1 to 259.3545,
260.1 to 260.3545,
261.1 to 261.3545,
262.1 to 262.3545,
263.1 to 263.3545,
264.1 to 264.3545,
265.1 to 265.3545,
266.1 to 266.3545,
267.1 to 267.3545,
268.1 to 268.3545,
269.1 to 269.3545
270.1 to 270.3545
```

In the above codes X refers to the numbers of tables 1 to 270 of tables 1 and 2 while the integer Z refers to the row of table 5 below.

Hence, the code 1.1 refers to the combination of the compound of formula (I) of table 1 or 2, with the combination of the herbicide B and the safener c are as defined in combination no. 1.1 in table 5.

According to another preferred embodiment of the invention, the combination comprises as active compound at least one, preferably exactly one compound of formula (I), preferably one compound of selected from 1.B, 2.B, 3.B or 4.B, defined in table 4 and at least one, preferably exactly one, herbicide b).

According to another preferred embodiment of the invention, the combination comprises as active compound at least one, preferably exactly one compound of formula (I), preferably one compound of selected from 1.B, 2.B, 3.B or 4.B, defined in table 4 and at least two, preferably exactly two, herbicides b) different from each other.

According to another preferred embodiment of the invention, the combination comprises as active compound at least one, preferably exactly one compound of formula (I), preferably one compound selected from 1.B, 2.B, 3.B or 4.B defined in table 4 and at least three, preferably exactly three, herbicides b) different from each other.

According to another preferred embodiment of the invention, the combination comprises as active compound at least one, preferably exactly one compound of formula (I), preferably one compound of the selected from 1.B, 2.B, 3.B or 4.B defined in table 4 and as component c at least one, preferably exactly one, safener c.

According to another preferred embodiment of the invention, the combination comprises as active compound at least one, preferably exactly one compound of formula (I), preferably one compound of the selected from 1.B, 2.B, 3.B or 4.B defined in table 4 and at least one, preferably exactly one, herbicide b), and as component c at least one, preferably exactly one safener c.

According to another preferred embodiment of the invention, the combination comprises as active compound at least one, preferably exactly at least one, preferably exactly one compound of formula (I), preferably one compound of the formulae 1.B, 2.B, 3.B or 4.B defined in table 4 and at least two, preferably exactly two herbicides b) different from each other, and as component c at least one, preferably exactly one, safener c.

According to another preferred embodiment of the invention, the combination comprises as component (I) at least one, preferably exactly at least one, preferably exactly one compound of formula (I), preferably one compound of the formulae 1.B, 2.B, 3.B or 4.B defined in table 4 and at least three, preferably exactly three herbicides b) different from each other, and as component c at least one, preferably exactly one, safener c.

According to another preferred embodiment of the invention, the combination comprises, in addition to a compound of formula (I), especially an active compound from the group consisting of 11.B, 2.B, 3.B or 4.B defined in table 4 and at least one and especially exactly one herbicidally active compound from group b1), in particular selected from the group consisting of clodinafop-propargyl, cycloxydim, cyhalofop-butyl, fenoxaprop-P-ethyl, pinoxaden, profoxydim, tepraloxydim, tralkoxydim, esprocarb, prosulfocarb, thiobencarb and triallate.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b2), in particular selected from the group consisting of bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, mesosulfuron, metazosulfuron, nicosulfuron, penoxsulam, propoxycarbazon-sodium, pyrazosulfuron-ethyl, pyroxsulam, rimsulfuron, sulfosulfuron, thiencarbazon-methyl and tritosulfuron.

According to another preferred embodiment of the invention, the combination comprises, in addition to a compound of formula (I), especially an active compound from the group consisting 1.B, 2.B, 3.B or 4.B defined in table 4 and at least one and especially exactly one herbicidally active compound from group b3), in particular selected from the group consisting of ametryn, atrazine, diuron, fluometuron, hexazinone, isoproturon, linuron, metribuzin, paraquat, paraquat-dichloride, propanil, terbutryn and terbuthylazine.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b4), in particular selected from the group consisting of flumioxazin, oxyfluorfen, pyraflufen, pyraflufen-ethyl, saflufenacil, sulfentrazone, trifludimoxazin (BAS 850 H), ethyl [3-[2-chloro-4-fluoro-5-(1-methyl-6-trifluoromethyl-2,4-dioxo-1,2,3,4-tetrahydropyrimidin-3-yl)-phenoxy]-2-pyridyloxy]acetate (CAS 353292-31-6; S-3100; Sumitomo; LS 5296489), 3-[7-fluoro-3-oxo-4-

(prop-2-ynyl)-3,4-dihydro-2H-benzo[1,4]oxazin-6-yl]-1,5-dimethyl-6-thioxo-[1,3,5]triazinan-2,4-dione (CAS 451484-50-7) LS 4061013), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0) (LS 567 0033=F2-Flumioxazin) and 1-methyl-6-trifluoromethyl-3-(2,2,7-trifluoro-3-oxo-4-prop-2-ynyl-3,4-dihydro-2H-benzo[1,4] oxazin-6-yl)-1H-pyrimidine-2,4-dione (CAS 1304113-05-0) (LS 568 1323=Uracil-F2-PPO).

According to another preferred embodiment of the invention, the combination comprises, in addition to a compounds of formula (I), especially an active compound from the group consisting of 1.B, 2.B, 3.B or 4.B defined in table 4 and at least one and especially exactly one herbicidally active compound from group b5), in particular selected from the group consisting of amitrole, bicyclopyrone, clomazone, diflufenican, flumeturon, flurochloridone, isoxaflutole, mesotrione, picolinafen, sulcotrione, tefuryltrione, tembotrione, tolpyralate and topramezone.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b6), in particular selected from the group consisting of glyphosate, glyphosate-isopropylammonium and glyphosate-trimesium (sulfosate).

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b7), in particular selected from the group consisting of glufosinate, glufosinate-P and glufosinate-ammonium.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b9), in particular selected from the group consisting of pendimethalin and trifluralin.

According to another preferred embodiment of the invention, the combination comprises, in addition to a compound of formula (I), especially an active compound from the group consisting 1.B, 2.B, 3.B or 4.B defined in table 4 and at least one and especially exactly one herbicidally active compound from group b10), in particular selected from the group consisting of acetochlor, cafenstrole, dimethenamid-P, fentrazamide, flufenacet, mefenacet, metazachlor, metolachlor, S-metolachlor, fenoxasulfone and pyroxasulfone.

Likewise, preference is given to combinations comprising in addition to a compound of formula (I), especially an active compound from the group consisting of 1.B, 2.B, 3.B or 4.B defined in table 4 and at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b11), in particular indaziflam, isoxaben and triazifiam.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b13), in particular selected from the group consisting of 2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, fluroxypyr-meptyl, halauxifen, halauxifen-methyl, quinclorac, quinmerac, 4-amino-3-chloro-6-(4-chloro-2-fluoro-3-methoxyphenyl)-5-fluoropyridine-2-carboxylic acid (DOW, "Rinskor-acid") and benzyl 4-amino-3-chloro-6-(4-chloro-2-fluoro-3-methoxyphenyl)-5-fluoropyridine-2-carboxylate (CAS 1390661-72-9) (DOW, "Rinskor").

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b14), in particular selected from the group consisting of diflufenzopyr and diflufenzopyr-sodium.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from group b15), in particular selected from the group consisting of dymron (=daimuron), indanofan and oxaziclomefone.

According to another preferred embodiment of the invention, the combination comprises, in addition to a compound of formula (I), especially an active compound from the group consisting of 1.B, 2.B, 3.B or 4.B defined in table 4 and at least one and especially exactly one herbicidally active compound from the safeners c, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro [4.5]decane (MON4660, CAS 71526-07-3) and 2,2,5-trimethyl-3-(dichloroacetyl)-1,3-oxazolidine (R-29148, CAS 52836-31-4).

The following combinations indicate by the code X.Z represent particular embodiments of the invention:
B1.1 to B1.3545
B2.1 to B2.3545,
B3.1 to B3.3545,
B4.1 to B4.3545.

In the above codes X refers to the numbers of tables 1 to 4 of table 4 while the integer Z refers to the row of table 5 below.

Hence, the code B1.1 refers to the combination of the compound of formula (I) of table 4, with the combination of the herbicide B and the safener c are as defined in combination no. 1.1 in table 5.

TABLE 5

(compositions 1.1 to 1.3545):

| comp. no. | herbicide B | safener C |
|---|---|---|
| 1.1 | B.1 | — |
| 1.2 | B.2 | — |
| 1.3 | B.3 | — |

TABLE 5-continued

(compositions 1.1 to 1.3545):

| comp. no. | herbicide B | safener C |
|---|---|---|
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |

TABLE 5-continued (compositions 1.1 to 1.3545):

| comp. no. | herbicide B | safener C |
|---|---|---|
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | |
| 1.191 | B.191 | |
| 1.192 | B.192 | |
| 1.193 | B.193 | |
| 1.194 | B.194 | |
| 1.195 | B.195 | |
| 1.196 | B.196 | |
| 1.197 | B.1 | C.1 |
| 1.198 | B.2 | C.1 |
| 1.199 | B.3 | C.1 |
| 1.200 | B.4 | C.1 |
| 1.201 | B.5 | C.1 |
| 1.202 | B.6 | C.1 |
| 1.203 | B.7 | C.1 |
| 1.204 | B.8 | C.1 |
| 1.205 | B.9 | C.1 |
| 1.206 | B.10 | C.1 |
| 1.207 | B.11 | C.1 |
| 1.208 | B.12 | C.1 |
| 1.209 | B.13 | C.1 |
| 1.210 | B.14 | C.1 |
| 1.211 | B.15 | C.1 |
| 1.212 | B.16 | C.1 |
| 1.213 | B.17 | C.1 |
| 1.214 | B.18 | C.1 |
| 1.215 | B.19 | C.1 |
| 1.216 | B.20 | C.1 |
| 1.217 | B.21 | C.1 |
| 1.218 | B.22 | C.1 |
| 1.219 | B.23 | C.1 |
| 1.220 | B.24 | C.1 |
| 1.221 | B.25 | C.1 |
| 1.222 | B.26 | C.1 |
| 1.223 | B.27 | C.1 |
| 1.224 | B.28 | C.1 |
| 1.225 | B.29 | C.1 |
| 1.226 | B.30 | C.1 |
| 1.227 | B.31 | C.1 |
| 1.228 | B.32 | C.1 |
| 1.229 | B.33 | C.1 |
| 1.230 | B.34 | C.1 |
| 1.231 | B.35 | C.1 |
| 1.232 | B.36 | C.1 |
| 1.233 | B.37 | C.1 |
| 1.234 | B.38 | C.1 |
| 1.235 | B.39 | C.1 |
| 1.236 | B.40 | C.1 |
| 1.237 | B.41 | C.1 |
| 1.238 | B.42 | C.1 |
| 1.239 | B.43 | C.1 |
| 1.240 | B.44 | C.1 |
| 1.241 | B.45 | C.1 |
| 1.242 | B.46 | C.1 |
| 1.243 | B.47 | C.1 |
| 1.244 | B.48 | C.1 |
| 1.245 | B.49 | C.1 |
| 1.246 | B.50 | C.1 |
| 1.247 | B.51 | C.1 |
| 1.248 | B.52 | C.1 |
| 1.249 | B.53 | C.1 |
| 1.250 | B.54 | C.1 |
| 1.251 | B.55 | C.1 |
| 1.252 | B.56 | C.1 |
| 1.253 | B.57 | C.1 |
| 1.254 | B.58. | C.1 |
| 1.255 | B.59 | C.1 |
| 1.256 | B.60 | C.1 |
| 1.257 | B.61 | C.1 |
| 1.258 | B.62 | C.1 |
| 1.259 | B.63 | C.1 |
| 1.260 | B.64 | C.1 |
| 1.261 | B.65 | C.1 |
| 1.262 | B.66 | C.1 |
| 1.263 | B.67 | C.1 |
| 1.264 | B.68 | C.1 |
| 1.265 | B.69 | C.1 |
| 1.266 | B.70 | C.1 |
| 1.267 | B.71 | C.1 |
| 1.268 | B.72 | C.1 |
| 1.269 | B.73 | C.1 |
| 1.270 | B.74 | C.1 |
| 1.271 | B.75 | C.1 |
| 1.272 | B.76 | C.1 |
| 1.273 | B.77 | C.1 |
| 1.274 | B.78 | C.1 |
| 1.275 | B.79 | C.1 |
| 1.276 | B.80 | C.1 |
| 1.277 | B.81 | C.1 |
| 1.278 | B.82 | C.1 |
| 1.279 | B.83 | C.1 |
| 1.280 | B.84 | C.1 |
| 1.281 | B.85 | C.1 |
| 1.282 | B.86 | C.1 |
| 1.283 | B.87 | C.1 |
| 1.284 | B.88 | C.1 |
| 1.285 | B.89 | C.1 |
| 1.286 | B.90 | C.1 |
| 1.287 | B.91 | C.1 |
| 1.288 | B.92 | C.1 |
| 1.289 | B.93 | C.1 |
| 1.290 | B.94 | C.1 |
| 1.291 | B.95 | C.1 |
| 1.292 | B.96 | C.1 |
| 1.293 | B.97 | C.1 |
| 1.294 | B.98 | C.1 |
| 1.295 | B.99 | C.1 |
| 1.296 | B.100 | C.1 |
| 1.297 | B.101 | C.1 |
| 1.298 | B.102 | C.1 |
| 1.299 | B.103 | C.1 |
| 1.300 | B.104 | C.1 |
| 1.301 | B.105 | C.1 |
| 1.302 | B.106 | C.1 |
| 1.303 | B.107 | C.1 |

TABLE 5-continued (compositions 1.1 to 1.3545):

| comp. no. | herbicide B | safener C |
|---|---|---|
| 1.304 | B.108 | C.1 |
| 1.305 | B.109 | C.1 |
| 1.306 | B.110 | C.1 |
| 1.307 | B.111 | C.1 |
| 1.308 | B.112 | C.1 |
| 1.309 | B.113 | C.1 |
| 1.310 | B.114 | C.1 |
| 1.311 | B.115 | C.1 |
| 1.312 | B.116 | C.1 |
| 1.313 | B.117 | C.1 |
| 1.314 | B.118 | C.1 |
| 1.315 | B.119 | C.1 |
| 1.316 | B.120 | C.1 |
| 1.317 | B.121 | C.1 |
| 1.318 | B.122 | C.1 |
| 1.319 | B.123 | C.1 |
| 1.320 | B.124 | C.1 |
| 1.321 | B.125 | C.1 |
| 1.322 | B.126 | C.1 |
| 1.323 | B.127 | C.1 |
| 1.324 | B.128 | C.1 |
| 1.325 | B.129 | C.1 |
| 1.326 | B.130 | C.1 |
| 1.327 | B.131 | C.1 |
| 1.328 | B.132 | C.1 |
| 1.329 | B.133 | C.1 |
| 1.330 | B.134 | C.1 |
| 1.331 | B.135 | C.1 |
| 1.332 | B.136 | C.1 |
| 1.333 | B.137 | C.1 |
| 1.334 | B.138 | C.1 |
| 1.335 | B.139 | C.1 |
| 1.336 | B.140 | C.1 |
| 1.337 | B.141 | C.1 |
| 1.338 | B.142 | C.1 |
| 1.339 | B.143 | C.1 |
| 1.340 | B.144 | C.1 |
| 1.341 | B.145 | C.1 |
| 1.342 | B.146 | C.1 |
| 1.343 | B.147 | C.1 |
| 1.344 | B.148 | C.1 |
| 1.345 | B.149 | C.1 |
| 1.346 | B.150 | C.1 |
| 1.347 | B.151 | C.1 |
| 1.348 | B.152 | C.1 |
| 1.349 | B.153 | C.1 |
| 1.350 | B.154 | C.1 |
| 1.351 | B.155 | C.1 |
| 1.352 | B.156 | C.1 |
| 1.353 | B.157 | C.1 |
| 1.354 | B.158 | C.1 |
| 1.355 | B.159 | C.1 |
| 1.356 | B.160 | C.1 |
| 1.357 | B.161 | C.1 |
| 1.358 | B.162 | C.1 |
| 1.359 | B.163 | C.1 |
| 1.360 | B.164 | C.1 |
| 1.361 | B.165 | C.1 |
| 1.362 | B.166 | C.1 |
| 1.363 | B.167 | C.1 |
| 1.364 | B.168 | C.1 |
| 1.365 | B.169 | C.1 |
| 1.366 | B.170 | C.1 |
| 1.367 | B.171 | C.1 |
| 1.368 | B.172 | C.1 |
| 1.369 | B.173 | C.1 |
| 1.370 | B.174 | C.1 |
| 1.371 | B.175 | C.1 |
| 1.372 | B.176 | C.1 |
| 1.373 | B.177 | C.1 |
| 1.374 | B.178 | C.1 |
| 1.375 | B.179 | C.1 |
| 1.376 | B.180 | C.1 |
| 1.377 | B.181 | C.1 |
| 1.378 | B.182 | C.1 |
| 1.379 | B.183 | C.1 |
| 1.380 | B.184 | C.1 |
| 1.381 | B.185 | C.1 |
| 1.382 | B.186 | C.1 |
| 1.383 | B.187 | C.1 |
| 1.384 | B.188 | C.1 |
| 1.385 | B.189 | C.1 |
| 1.386 | B.190 | C.1 |
| 1.387 | B.191 | C.1 |
| 1.388 | B.192 | C.1 |
| 1.389 | B.193 | C.1 |
| 1.390 | B.194 | C.1 |
| 1.391 | B.195 | C.1 |
| 1.392 | B.196 | C.1 |
| 1.393 | B.1 | C.2 |
| 1.394 | B.2 | C.2 |
| 1.395 | B.3 | C.2 |
| 1.396 | B.4 | C.2 |
| 1.397 | B.5 | C.2 |
| 1.398 | B.6 | C.2 |
| 1.399 | B.7 | C.2 |
| 1.400 | B.8 | C.2 |
| 1.401 | B.9 | C.2 |
| 1.402 | B.10 | C.2 |
| 1.403 | B.11 | C.2 |
| 1.404 | B.12 | C.2 |
| 1.405 | B.13 | C.2 |
| 1.406 | B.14 | C.2 |
| 1.407 | B.15 | C.2 |
| 1.408 | B.16 | C.2 |
| 1.409 | B.17 | C.2 |
| 1.410 | B.18 | C.2 |
| 1.411 | B.19 | C.2 |
| 1.412 | B.20 | C.2 |
| 1.413 | B.21 | C.2 |
| 1.414 | B.22 | C.2 |
| 1.415 | B.23 | C.2 |
| 1.416 | B.24 | C.2 |
| 1.417 | B.25 | C.2 |
| 1.418 | B.26 | C.2 |
| 1.419 | B.27 | C.2 |
| 1.420 | B.28 | C.2 |
| 1.421 | B.29 | C.2 |
| 1.422 | B.30 | C.2 |
| 1.423 | B.31 | C.2 |
| 1.424 | B.32 | C.2 |
| 1.425 | B.33 | C.2 |
| 1.426 | B.34 | C.2 |
| 1.427 | B.35 | C.2 |
| 1.428 | B.36 | C.2 |
| 1.429 | B.37 | C.2 |
| 1.430 | B.38 | C.2 |
| 1.431 | B.39 | C.2 |
| 1.432 | B.40 | C.2 |
| 1.433 | B.41 | C.2 |
| 1.434 | B.42 | C.2 |
| 1.435 | B.43 | C.2 |
| 1.436 | B.44 | C.2 |
| 1.437 | B.45 | C.2 |
| 1.438 | B.46 | C.2 |
| 1.439 | B.47 | C.2 |
| 1.440 | B.48 | C.2 |
| 1.441 | B.49 | C.2 |
| 1.442 | B.50 | C.2 |
| 1.443 | B.51 | C.2 |
| 1.444 | B.52 | C.2 |
| 1.445 | B.53 | C.2 |
| 1.446 | B.54 | C.2 |
| 1.447 | B.55 | C.2 |
| 1.448 | B.56 | C.2 |
| 1.449 | B.57 | C.2 |
| 1.450 | B.58. | C.2 |
| 1.451 | B.59 | C.2 |
| 1.452 | B.60 | C.2 |
| 1.453 | B.61 | C.2 |

TABLE 5-continued (compositions 1.1 to 1.3545):

| comp. no. | herbicide B | safener C |
|---|---|---|
| 1.454 | B.62 | C.2 |
| 1.455 | B.63 | C.2 |
| 1.456 | B.64 | C.2 |
| 1.457 | B.65 | C.2 |
| 1.458 | B.66 | C.2 |
| 1.459 | B.67 | C.2 |
| 1.460 | B.68 | C.2 |
| 1.461 | B.69 | C.2 |
| 1.462 | B.70 | C.2 |
| 1.463 | B.71 | C.2 |
| 1.464 | B.72 | C.2 |
| 1.465 | B.73 | C.2 |
| 1.466 | B.74 | C.2 |
| 1.467 | B.75 | C.2 |
| 1.468 | B.76 | C.2 |
| 1.469 | B.77 | C.2 |
| 1.470 | B.78 | C.2 |
| 1.471 | B.79 | C.2 |
| 1.472 | B.80 | C.2 |
| 1.473 | B.81 | C.2 |
| 1.474 | B.82 | C.2 |
| 1.475 | B.83 | C.2 |
| 1.476 | B.84 | C.2 |
| 1.477 | B.85 | C.2 |
| 1.478 | B.86 | C.2 |
| 1.479 | B.87 | C.2 |
| 1.480 | B.88 | C.2 |
| 1.481 | B.89 | C.2 |
| 1.482 | B.90 | C.2 |
| 1.483 | B.91 | C.2 |
| 1.484 | B.92 | C.2 |
| 1.485 | B.93 | C.2 |
| 1.486 | B.94 | C.2 |
| 1.487 | B.95 | C.2 |
| 1.488 | B.96 | C.2 |
| 1.489 | B.97 | C.2 |
| 1.490 | B.98 | C.2 |
| 1.491 | B.99 | C.2 |
| 1.492 | B.100 | C.2 |
| 1.493 | B.101 | C.2 |
| 1.494 | B.102 | C.2 |
| 1.495 | B.103 | C.2 |
| 1.496 | B.104 | C.2 |
| 1.497 | B.105 | C.2 |
| 1.498 | B.106 | C.2 |
| 1.499 | B.107 | C.2 |
| 1.500 | B.108 | C.2 |
| 1.501 | B.109 | C.2 |
| 1.502 | B.110 | C.2 |
| 1.503 | B.111 | C.2 |
| 1.504 | B.112 | C.2 |
| 1.505 | B.113 | C.2 |
| 1.506 | B.114 | C.2 |
| 1.507 | B.115 | C.2 |
| 1.508 | B.116 | C.2 |
| 1.509 | B.117 | C.2 |
| 1.510 | B.118 | C.2 |
| 1.511 | B.119 | C.2 |
| 1.512 | B.120 | C.2 |
| 1.513 | B.121 | C.2 |
| 1.514 | B.122 | C.2 |
| 1.515 | B.123 | C.2 |
| 1.516 | B.124 | C.2 |
| 1.517 | B.125 | C.2 |
| 1.518 | B.126 | C.2 |
| 1.519 | B.127 | C.2 |
| 1.520 | B.128 | C.2 |
| 1.521 | B.129 | C.2 |
| 1.522 | B.130 | C.2 |
| 1.523 | B.131 | C.2 |
| 1.524 | B.132 | C.2 |
| 1.525 | B.133 | C.2 |
| 1.526 | B.134 | C.2 |
| 1.527 | B.135 | C.2 |
| 1.528 | B.136 | C.2 |
| 1.529 | B.137 | C.2 |
| 1.530 | B.138 | C.2 |
| 1.531 | B.139 | C.2 |
| 1.532 | B.140 | C.2 |
| 1.533 | B.141 | C.2 |
| 1.534 | B.142 | C.2 |
| 1.535 | B.143 | C.2 |
| 1.536 | B.144 | C.2 |
| 1.537 | B.145 | C.2 |
| 1.538 | B.146 | C.2 |
| 1.539 | B.147 | C.2 |
| 1.540 | B.148 | C.2 |
| 1.541 | B.149 | C.2 |
| 1.542 | B.150 | C.2 |
| 1.543 | B.151 | C.2 |
| 1.544 | B.152 | C.2 |
| 1.545 | B.153 | C.2 |
| 1.546 | B.154 | C.2 |
| 1.547 | B.155 | C.2 |
| 1.548 | B.156 | C.2 |
| 1.549 | B.157 | C.2 |
| 1.550 | B.158 | C.2 |
| 1.551 | B.159 | C.2 |
| 1.552 | B.160 | C.2 |
| 1.553 | B.161 | C.2 |
| 1.554 | B.162 | C.2 |
| 1.555 | B.163 | C.2 |
| 1.556 | B.164 | C.2 |
| 1.557 | B.165 | C.2 |
| 1.558 | B.166 | C.2 |
| 1.559 | B.167 | C.2 |
| 1.560 | B.168 | C.2 |
| 1.561 | B.169 | C.2 |
| 1.562 | B.170 | C.2 |
| 1.563 | B.171 | C.2 |
| 1.564 | B.172 | C.2 |
| 1.565 | B.173 | C.2 |
| 1.566 | B.174 | C.2 |
| 1.567 | B.175 | C.2 |
| 1.568 | B.176 | C.2 |
| 1.569 | B.177 | C.2 |
| 1.570 | B.178 | C.2 |
| 1.571 | B.179 | C.2 |
| 1.572 | B.180 | C.2 |
| 1.573 | B.181 | C.2 |
| 1.574 | B.182 | C.2 |
| 1.575 | B.183 | C.2 |
| 1.576 | B.184 | C.2 |
| 1.577 | B.185 | C.2 |
| 1.578 | B.186 | C.2 |
| 1.579 | B.187 | C.2 |
| 1.580 | B.188 | C.2 |
| 1.581 | B.189 | C.2 |
| 1.582 | B.190 | C.2 |
| 1.583 | B.191 | C.2 |
| 1.584 | B.192 | C.2 |
| 1.585 | B.193 | C.2 |
| 1.586 | B.194 | C.2 |
| 1.587 | B.195 | C.2 |
| 1.588 | B.196 | C.2 |
| 1.589 | B.1 | C.3 |
| 1.590 | B.2 | C.3 |
| 1.591 | B.3 | C.3 |
| 1.592 | B.4 | C.3 |
| 1.593 | B.5 | C.3 |
| 1.594 | B.6 | C.3 |
| 1.595 | B.7 | C.3 |
| 1.596 | B.8 | C.3 |
| 1.597 | B.9 | C.3 |
| 1.598 | B.10 | C.3 |
| 1.599 | B.11 | C.3 |
| 1.600 | B.12 | C.3 |
| 1.601 | B.13 | C.3 |
| 1.602 | B.14 | C.3 |
| 1.603 | B.15 | C.3 |

TABLE 5-continued (compositions 1.1 to 1.3545):

| comp. no. | herbicide B | safener C |
|---|---|---|
| 1.604 | B.16 | C.3 |
| 1.605 | B.17 | C.3 |
| 1.606 | B.18 | C.3 |
| 1.607 | B.19 | C.3 |
| 1.608 | B.20 | C.3 |
| 1.609 | B.21 | C.3 |
| 1.610 | B.22 | C.3 |
| 1.611 | B.23 | C.3 |
| 1.612 | B.24 | C.3 |
| 1.613 | B.25 | C.3 |
| 1.614 | B.26 | C.3 |
| 1.615 | B.27 | C.3 |
| 1.616 | B.28 | C.3 |
| 1.617 | B.29 | C.3 |
| 1.618 | B.30 | C.3 |
| 1.619 | B.31 | C.3 |
| 1.620 | B.32 | C.3 |
| 1.621 | B.33 | C.3 |
| 1.622 | B.34 | C.3 |
| 1.623 | B.35 | C.3 |
| 1.624 | B.36 | C.3 |
| 1.625 | B.37 | C.3 |
| 1.626 | B.38 | C.3 |
| 1.627 | B.39 | C.3 |
| 1.628 | B.40 | C.3 |
| 1.629 | B.41 | C.3 |
| 1.630 | B.42 | C.3 |
| 1.631 | B.43 | C.3 |
| 1.632 | B.44 | C.3 |
| 1.633 | B.45 | C.3 |
| 1.634 | B.46 | C.3 |
| 1.635 | B.47 | C.3 |
| 1.636 | B.48 | C.3 |
| 1.637 | B.49 | C.3 |
| 1.638 | B.50 | C.3 |
| 1.639 | B.51 | C.3 |
| 1.640 | B.52 | C.3 |
| 1.641 | B.53 | C.3 |
| 1.642 | B.54 | C.3 |
| 1.643 | B.55 | C.3 |
| 1.644 | B.56 | C.3 |
| 1.645 | B.57 | C.3 |
| 1.646 | B.58. | C.3 |
| 1.647 | B.59 | C.3 |
| 1.648 | B.60 | C.3 |
| 1.649 | B.61 | C.3 |
| 1.650 | B.62 | C.3 |
| 1.651 | B.63 | C.3 |
| 1.652 | B.64 | C.3 |
| 1.653 | B.65 | C.3 |
| 1.654 | B.66 | C.3 |
| 1.655 | B.67 | C.3 |
| 1.656 | B.68 | C.3 |
| 1.657 | B.69 | C.3 |
| 1.658 | B.70 | C.3 |
| 1.659 | B.71 | C.3 |
| 1.660 | B.72 | C.3 |
| 1.661 | B.73 | C.3 |
| 1.662 | B.74 | C.3 |
| 1.663 | B.75 | C.3 |
| 1.664 | B.76 | C.3 |
| 1.665 | B.77 | C.3 |
| 1.666 | B.78 | C.3 |
| 1.667 | B.79 | C.3 |
| 1.668 | B.80 | C.3 |
| 1.669 | B.81 | C.3 |
| 1.670 | B.82 | C.3 |
| 1.671 | B.83 | C.3 |
| 1.672 | B.84 | C.3 |
| 1.673 | B.85 | C.3 |
| 1.674 | B.86 | C.3 |
| 1.675 | B.87 | C.3 |
| 1.676 | B.88 | C.3 |
| 1.677 | B.89 | C.3 |
| 1.678 | B.90 | C.3 |
| 1.679 | B.91 | C.3 |
| 1.680 | B.92 | C.3 |
| 1.681 | B.93 | C.3 |
| 1.682 | B.94 | C.3 |
| 1.683 | B.95 | C.3 |
| 1.684 | B.96 | C.3 |
| 1.685 | B.97 | C.3 |
| 1.686 | B.98 | C.3 |
| 1.687 | B.99 | C.3 |
| 1.688 | B.100 | C.3 |
| 1.689 | B.101 | C.3 |
| 1.690 | B.102 | C.3 |
| 1.691 | B.103 | C.3 |
| 1.692 | B.104 | C.3 |
| 1.693 | B.105 | C.3 |
| 1.694 | B.106 | C.3 |
| 1.695 | B.107 | C.3 |
| 1.696 | B.108 | C.3 |
| 1.697 | B.109 | C.3 |
| 1.698 | B.110 | C.3 |
| 1.699 | B.111 | C.3 |
| 1.700 | B.112 | C.3 |
| 1.701 | B.113 | C.3 |
| 1.702 | B.114 | C.3 |
| 1.703 | B.115 | C.3 |
| 1.704 | B.116 | C.3 |
| 1.705 | B.117 | C.3 |
| 1.706 | B.118 | C.3 |
| 1.707 | B.119 | C.3 |
| 1.708 | B.120 | C.3 |
| 1.709 | B.121 | C.3 |
| 1.710 | B.122 | C.3 |
| 1.711 | B.123 | C.3 |
| 1.712 | B.124 | C.3 |
| 1.713 | B.125 | C.3 |
| 1.714 | B.126 | C.3 |
| 1.715 | B.127 | C.3 |
| 1.716 | B.128 | C.3 |
| 1.717 | B.129 | C.3 |
| 1.718 | B.130 | C.3 |
| 1.719 | B.131 | C.3 |
| 1.720 | B.132 | C.3 |
| 1.721 | B.133 | C.3 |
| 1.722 | B.134 | C.3 |
| 1.723 | B.135 | C.3 |
| 1.724 | B.136 | C.3 |
| 1.725 | B.137 | C.3 |
| 1.726 | B.138 | C.3 |
| 1.727 | B.139 | C.3 |
| 1.728 | B.140 | C.3 |
| 1.729 | B.141 | C.3 |
| 1.730 | B.142 | C.3 |
| 1.731 | B.143 | C.3 |
| 1.732 | B.144 | C.3 |
| 1.733 | B.145 | C.3 |
| 1.734 | B.146 | C.3 |
| 1.735 | B.147 | C.3 |
| 1.736 | B.148 | C.3 |
| 1.737 | B.149 | C.3 |
| 1.738 | B.150 | C.3 |
| 1.739 | B.151 | C.3 |
| 1.740 | B.152 | C.3 |
| 1.741 | B.153 | C.3 |
| 1.742 | B.154 | C.3 |
| 1.743 | B.155 | C.3 |
| 1.744 | B.156 | C.3 |
| 1.745 | B.157 | C.3 |
| 1.746 | B.158 | C.3 |
| 1.747 | B.159 | C.3 |
| 1.748 | B.160 | C.3 |
| 1.749 | B.161 | C.3 |
| 1.750 | B.162 | C.3 |
| 1.751 | B.163 | C.3 |
| 1.752 | B.164 | C.3 |
| 1.753 | B.165 | C.3 |

TABLE 5-continued (compositions 1.1 to 1.3545):

| comp. no. | herbicide B | safener C |
|---|---|---|
| 1.754 | B.166 | C.3 |
| 1.755 | B.167 | C.3 |
| 1.756 | B.168 | C.3 |
| 1.757 | B.169 | C.3 |
| 1.758 | B.170 | C.3 |
| 1.759 | B.171 | C.3 |
| 1.760 | B.172 | C.3 |
| 1.761 | B.173 | C.3 |
| 1.762 | B.174 | C.3 |
| 1.763 | B.175 | C.3 |
| 1.764 | B.176 | C.3 |
| 1.765 | B.177 | C.3 |
| 1.766 | B.178 | C.3 |
| 1.767 | B.179 | C.3 |
| 1.768 | B.180 | C.3 |
| 1.769 | B.181 | C.3 |
| 1.770 | B.182 | C.3 |
| 1.771 | B.183 | C.3 |
| 1.772 | B.184 | C.3 |
| 1.773 | B.185 | C.3 |
| 1.774 | B.186 | C.3 |
| 1.775 | B.187 | C.3 |
| 1.776 | B.188 | C.3 |
| 1.777 | B.189 | C.3 |
| 1.778 | B.190 | C.3 |
| 1.779 | B.191 | C.3 |
| 1.780 | B.192 | C.3 |
| 1.781 | B.193 | C.3 |
| 1.782 | B.194 | C.3 |
| 1.783 | B.195 | C.3 |
| 1.784 | B.196 | C.3 |
| 1.785 | B.1 | C.4 |
| 1.786 | B.2 | C.4 |
| 1.787 | B.3 | C.4 |
| 1.788 | B.4 | C.4 |
| 1.789 | B.5 | C.4 |
| 1.790 | B.6 | C.4 |
| 1.791 | B.7 | C.4 |
| 1.792 | B.8 | C.4 |
| 1.793 | B.9 | C.4 |
| 1.794 | B.10 | C.4 |
| 1.795 | B.11 | C.4 |
| 1.796 | B.12 | C.4 |
| 1.797 | B.13 | C.4 |
| 1.798 | B.14 | C.4 |
| 1.799 | B.15 | C.4 |
| 1.800 | B.16 | C.4 |
| 1.801 | B.17 | C.4 |
| 1.802 | B.18 | C.4 |
| 1.803 | B.19 | C.4 |
| 1.804 | B.20 | C.4 |
| 1.805 | B.21 | C.4 |
| 1.806 | B.22 | C.4 |
| 1.807 | B.23 | C.4 |
| 1.808 | B.24 | C.4 |
| 1.809 | B.25 | C.4 |
| 1.810 | B.26 | C.4 |
| 1.811 | B.27 | C.4 |
| 1.812 | B.28 | C.4 |
| 1.813 | B.29 | C.4 |
| 1.814 | B.30 | C.4 |
| 1.815 | B.31 | C.4 |
| 1.816 | B.32 | C.4 |
| 1.817 | B.33 | C.4 |
| 1.818 | B.34 | C.4 |
| 1.819 | B.35 | C.4 |
| 1.820 | B.36 | C.4 |
| 1.821 | B.37 | C.4 |
| 1.822 | B.38 | C.4 |
| 1.823 | B.39 | C.4 |
| 1.824 | B.40 | C.4 |
| 1.825 | B.41 | C.4 |
| 1.826 | B.42 | C.4 |
| 1.827 | B.43 | C.4 |
| 1.828 | B.44 | C.4 |
| 1.829 | B.45 | C.4 |
| 1.830 | B.46 | C.4 |
| 1.831 | B.47 | C.4 |
| 1.832 | B.48 | C.4 |
| 1.833 | B.49 | C.4 |
| 1.834 | B.50 | C.4 |
| 1.835 | B.51 | C.4 |
| 1.836 | B.52 | C.4 |
| 1.837 | B.53 | C.4 |
| 1.838 | B.54 | C.4 |
| 1.839 | B.55 | C.4 |
| 1.840 | B.56 | C.4 |
| 1.841 | B.57 | C.4 |
| 1.842 | B.58. | C.4 |
| 1.843 | B.59 | C.4 |
| 1.844 | B.60 | C.4 |
| 1.845 | B.61 | C.4 |
| 1.846 | B.62 | C.4 |
| 1.847 | B.63 | C.4 |
| 1.848 | B.64 | C.4 |
| 1.849 | B.65 | C.4 |
| 1.850 | B.66 | C.4 |
| 1.851 | B.67 | C.4 |
| 1.852 | B.68 | C.4 |
| 1.853 | B.69 | C.4 |
| 1.854 | B.70 | C.4 |
| 1.855 | B.71 | C.4 |
| 1.856 | B.72 | C.4 |
| 1.857 | B.73 | C.4 |
| 1.858 | B.74 | C.4 |
| 1.859 | B.75 | C.4 |
| 1.860 | B.76 | C.4 |
| 1.861 | B.77 | C.4 |
| 1.862 | B.78 | C.4 |
| 1.863 | B.79 | C.4 |
| 1.864 | B.80 | C.4 |
| 1.865 | B.81 | C.4 |
| 1.866 | B.82 | C.4 |
| 1.867 | B.83 | C.4 |
| 1.868 | B.84 | C.4 |
| 1.869 | B.85 | C.4 |
| 1.870 | B.86 | C.4 |
| 1.871 | B.87 | C.4 |
| 1.872 | B.88 | C.4 |
| 1.873 | B.89 | C.4 |
| 1.874 | B.90 | C.4 |
| 1.875 | B.91 | C.4 |
| 1.876 | B.92 | C.4 |
| 1.877 | B.93 | C.4 |
| 1.878 | B.94 | C.4 |
| 1.879 | B.95 | C.4 |
| 1.880 | B.96 | C.4 |
| 1.881 | B.97 | C.4 |
| 1.882 | B.98 | C.4 |
| 1.883 | B.99 | C.4 |
| 1.884 | B.100 | C.4 |
| 1.885 | B.101 | C.4 |
| 1.886 | B.102 | C.4 |
| 1.887 | B.103 | C.4 |
| 1.888 | B.104 | C.4 |
| 1.889 | B.105 | C.4 |
| 1.890 | B.106 | C.4 |
| 1.891 | B.107 | C.4 |
| 1.892 | B.108 | C.4 |
| 1.893 | B.109 | C.4 |
| 1.894 | B.110 | C.4 |
| 1.895 | B.111 | C.4 |
| 1.896 | B.112 | C.4 |
| 1.897 | B.113 | C.4 |
| 1.898 | B.114 | C.4 |
| 1.899 | B.115 | C.4 |
| 1.900 | B.116 | C.4 |
| 1.901 | B.117 | C.4 |
| 1.902 | B.118 | C.4 |
| 1.903 | B.119 | C.4 |

TABLE 5-continued (compositions 1.1 to 1.3545):

| comp. no. | herbicide B | safener C |
|---|---|---|
| 1.904 | B.120 | C.4 |
| 1.905 | B.121 | C.4 |
| 1.906 | B.122 | C.4 |
| 1.907 | B.123 | C.4 |
| 1.908 | B.124 | C.4 |
| 1.909 | B.125 | C.4 |
| 1.910 | B.126 | C.4 |
| 1.911 | B.127 | C.4 |
| 1.912 | B.128 | C.4 |
| 1.913 | B.129 | C.4 |
| 1.914 | B.130 | C.4 |
| 1.915 | B.131 | C.4 |
| 1.916 | B.132 | C.4 |
| 1.917 | B.133 | C.4 |
| 1.918 | B.134 | C.4 |
| 1.919 | B.135 | C.4 |
| 1.920 | B.136 | C.4 |
| 1.921 | B.137 | C.4 |
| 1.922 | B.138 | C.4 |
| 1.923 | B.139 | C.4 |
| 1.924 | B.140 | C.4 |
| 1.925 | B.141 | C.4 |
| 1.926 | B.142 | C.4 |
| 1.927 | B.143 | C.4 |
| 1.928 | B.144 | C.4 |
| 1.929 | B.145 | C.4 |
| 1.930 | B.146 | C.4 |
| 1.931 | B.147 | C.4 |
| 1.932 | B.148 | C.4 |
| 1.933 | B.149 | C.4 |
| 1.934 | B.150 | C.4 |
| 1.935 | B.151 | C.4 |
| 1.936 | B.152 | C.4 |
| 1.937 | B.153 | C.4 |
| 1.938 | B.154 | C.4 |
| 1.939 | B.155 | C.4 |
| 1.940 | B.156 | C.4 |
| 1.941 | B.157 | C.4 |
| 1.942 | B.158 | C.4 |
| 1.943 | B.159 | C.4 |
| 1.944 | B.160 | C.4 |
| 1.945 | B.161 | C.4 |
| 1.946 | B.162 | C.4 |
| 1.947 | B.163 | C.4 |
| 1.948 | B.164 | C.4 |
| 1.949 | B.165 | C.4 |
| 1.950 | B.166 | C.4 |
| 1.951 | B.167 | C.4 |
| 1.952 | B.168 | C.4 |
| 1.953 | B.169 | C.4 |
| 1.954 | B.170 | C.4 |
| 1.955 | B.171 | C.4 |
| 1.956 | B.172 | C.4 |
| 1.957 | B.173 | C.4 |
| 1.958 | B.174 | C.4 |
| 1.959 | B.175 | C.4 |
| 1.960 | B.176 | C.4 |
| 1.961 | B.177 | C.4 |
| 1.962 | B.178 | C.4 |
| 1.963 | B.179 | C.4 |
| 1.964 | B.180 | C.4 |
| 1.965 | B.181 | C.4 |
| 1.966 | B.182 | C.4 |
| 1.967 | B.183 | C.4 |
| 1.968 | B.184 | C.4 |
| 1.969 | B.185 | C.4 |
| 1.970 | B.186 | C.4 |
| 1.971 | B.187 | C.4 |
| 1.972 | B.188 | C.4 |
| 1.973 | B.189 | C.4 |
| 1.974 | B.190 | C.4 |
| 1.975 | B.191 | C.4 |
| 1.976 | B.192 | C.4 |
| 1.977 | B.193 | C.4 |
| 1.978 | B.194 | C.4 |
| 1.979 | B.195 | C.4 |
| 1.980 | B.196 | C.4 |
| 1.981 | B.1 | C.5 |
| 1.982 | B.2 | C.5 |
| 1.983 | B.3 | C.5 |
| 1.984 | B.4 | C.5 |
| 1.985 | B.5 | C.5 |
| 1.986 | B.6 | C.5 |
| 1.987 | B.7 | C.5 |
| 1.988 | B.8 | C.5 |
| 1.989 | B.9 | C.5 |
| 1.990 | B.10 | C.5 |
| 1.991 | B.11 | C.5 |
| 1.992 | B.12 | C.5 |
| 1.993 | B.13 | C.5 |
| 1.994 | B.14 | C.5 |
| 1.995 | B.15 | C.5 |
| 1.996 | B.16 | C.5 |
| 1.997 | B.17 | C.5 |
| 1.998 | B.18 | C.5 |
| 1.999 | B.19 | C.5 |
| 1.1000 | B.20 | C.5 |
| 1.1001 | B.21 | C.5 |
| 1.1002 | B.22 | C.5 |
| 1.1003 | B.23 | C.5 |
| 1.1004 | B.24 | C.5 |
| 1.1005 | B.25 | C.5 |
| 1.1006 | B.26 | C.5 |
| 1.1007 | B.27 | C.5 |
| 1.1008 | B.28 | C.5 |
| 1.1009 | B.29 | C.5 |
| 1.1010 | B.30 | C.5 |
| 1.1011 | B.31 | C.5 |
| 1.1012 | B.32 | C.5 |
| 1.1013 | B.33 | C.5 |
| 1.1014 | B.34 | C.5 |
| 1.1015 | B.35 | C.5 |
| 1.1016 | B.36 | C.5 |
| 1.1017 | B.37 | C.5 |
| 1.1018 | B.38 | C.5 |
| 1.1019 | B.39 | C.5 |
| 1.1020 | B.40 | C.5 |
| 1.1021 | B.41 | C.5 |
| 1.1022 | B.42 | C.5 |
| 1.1023 | B.43 | C.5 |
| 1.1024 | B.44 | C.5 |
| 1.1025 | B.45 | C.5 |
| 1.1026 | B.46 | C.5 |
| 1.1027 | B.47 | C.5 |
| 1.1028 | B.48 | C.5 |
| 1.1029 | B.49 | C.5 |
| 1.1030 | B.50 | C.5 |
| 1.1031 | B.51 | C.5 |
| 1.1032 | B.52 | C.5 |
| 1.1033 | B.53 | C.5 |
| 1.1034 | B.54 | C.5 |
| 1.1035 | B.55 | C.5 |
| 1.1036 | B.56 | C.5 |
| 1.1037 | B.57 | C.5 |
| 1.1038 | B.58. | C.5 |
| 1.1039 | B.59 | C.5 |
| 1.1040 | B.60 | C.5 |
| 1.1041 | B.61 | C.5 |
| 1.1042 | B.62 | C.5 |
| 1.1043 | B.63 | C.5 |
| 1.1044 | B.64 | C.5 |
| 1.1045 | B.65 | C.5 |
| 1.1046 | B.66 | C.5 |
| 1.1047 | B.67 | C.5 |
| 1.1048 | B.68 | C.5 |
| 1.1049 | B.69 | C.5 |
| 1.1050 | B.70 | C.5 |
| 1.1051 | B.71 | C.5 |
| 1.1052 | B.72 | C.5 |
| 1.1053 | B.73 | C.5 |

TABLE 5-continued (compositions 1.1 to 1.3545):

| comp. no. | herbicide B | safener C |
|---|---|---|
| 1.1054 | B.74 | C.5 |
| 1.1055 | B.75 | C.5 |
| 1.1056 | B.76 | C.5 |
| 1.1057 | B.77 | C.5 |
| 1.1058 | B.78 | C.5 |
| 1.1059 | B.79 | C.5 |
| 1.1060 | B.80 | C.5 |
| 1.1061 | B.81 | C.5 |
| 1.1062 | B.82 | C.5 |
| 1.1063 | B.83 | C.5 |
| 1.1064 | B.84 | C.5 |
| 1.1065 | B.85 | C.5 |
| 1.1066 | B.86 | C.5 |
| 1.1067 | B.87 | C.5 |
| 1.1068 | B.88 | C.5 |
| 1.1069 | B.89 | C.5 |
| 1.1070 | B.90 | C.5 |
| 1.1071 | B.91 | C.5 |
| 1.1072 | B.92 | C.5 |
| 1.1073 | B.93 | C.5 |
| 1.1074 | B.94 | C.5 |
| 1.1075 | B.95 | C.5 |
| 1.1076 | B.96 | C.5 |
| 1.1077 | B.97 | C.5 |
| 1.1078 | B.98 | C.5 |
| 1.1079 | B.99 | C.5 |
| 1.1080 | B.100 | C.5 |
| 1.1081 | B.101 | C.5 |
| 1.1082 | B.102 | C.5 |
| 1.1083 | B.103 | C.5 |
| 1.1084 | B.104 | C.5 |
| 1.1085 | B.105 | C.5 |
| 1.1086 | B.106 | C.5 |
| 1.1087 | B.107 | C.5 |
| 1.1088 | B.108 | C.5 |
| 1.1089 | B.109 | C.5 |
| 1.1090 | B.110 | C.5 |
| 1.1091 | B.111 | C.5 |
| 1.1092 | B.112 | C.5 |
| 1.1093 | B.113 | C.5 |
| 1.1094 | B.114 | C.5 |
| 1.1095 | B.115 | C.5 |
| 1.1096 | B.116 | C.5 |
| 1.1097 | B.117 | C.5 |
| 1.1098 | B.118 | C.5 |
| 1.1099 | B.119 | C.5 |
| 1.1100 | B.120 | C.5 |
| 1.1101 | B.121 | C.5 |
| 1.1102 | B.122 | C.5 |
| 1.1103 | B.123 | C.5 |
| 1.1104 | B.124 | C.5 |
| 1.1105 | B.125 | C.5 |
| 1.1106 | B.126 | C.5 |
| 1.1107 | B.127 | C.5 |
| 1.1108 | B.128 | C.5 |
| 1.1109 | B.129 | C.5 |
| 1.1110 | B.130 | C.5 |
| 1.1111 | B.131 | C.5 |
| 1.1112 | B.132 | C.5 |
| 1.1113 | B.133 | C.5 |
| 1.1114 | B.134 | C.5 |
| 1.1115 | B.135 | C.5 |
| 1.1116 | B.136 | C.5 |
| 1.1117 | B.137 | C.5 |
| 1.1118 | B.138 | C.5 |
| 1.1119 | B.139 | C.5 |
| 1.1120 | B.140 | C.5 |
| 1.1121 | B.141 | C.5 |
| 1.1122 | B.142 | C.5 |
| 1.1123 | B.143 | C.5 |
| 1.1124 | B.144 | C.5 |
| 1.1125 | B.145 | C.5 |
| 1.1126 | B.146 | C.5 |
| 1.1127 | B.147 | C.5 |
| 1.1128 | B.148 | C.5 |
| 1.1129 | B.149 | C.5 |
| 1.1130 | B.150 | C.5 |
| 1.1131 | B.151 | C.5 |
| 1.1132 | B.152 | C.5 |
| 1.1133 | B.153 | C.5 |
| 1.1134 | B.154 | C.5 |
| 1.1135 | B.155 | C.5 |
| 1.1136 | B.156 | C.5 |
| 1.1137 | B.157 | C.5 |
| 1.1138 | B.158 | C.5 |
| 1.1139 | B.159 | C.5 |
| 1.1140 | B.160 | C.5 |
| 1.1141 | B.161 | C.5 |
| 1.1142 | B.162 | C.5 |
| 1.1143 | B.163 | C.5 |
| 1.1144 | B.164 | C.5 |
| 1.1145 | B.165 | C.5 |
| 1.1146 | B.166 | C.5 |
| 1.1147 | B.167 | C.5 |
| 1.1148 | B.168 | C.5 |
| 1.1149 | B.169 | C.5 |
| 1.1150 | B.170 | C.5 |
| 1.1151 | B.171 | C.5 |
| 1.1152 | B.172 | C.5 |
| 1.1153 | B.173 | C.5 |
| 1.1154 | B.174 | C.5 |
| 1.1155 | B.175 | C.5 |
| 1.1156 | B.176 | C.5 |
| 1.1157 | B.177 | C.5 |
| 1.1158 | B.178 | C.5 |
| 1.1159 | B.179 | C.5 |
| 1.1160 | B.180 | C.5 |
| 1.1161 | B.181 | C.5 |
| 1.1162 | B.182 | C.5 |
| 1.1163 | B.183 | C.5 |
| 1.1164 | B.184 | C.5 |
| 1.1165 | B.185 | C.5 |
| 1.1166 | B.186 | C.5 |
| 1.1167 | B.187 | C.5 |
| 1.1168 | B.188 | C.5 |
| 1.1169 | B.189 | C.5 |
| 1.1170 | B.190 | C.5 |
| 1.1171 | B.191 | C.5 |
| 1.1172 | B.192 | C.5 |
| 1.1173 | B.193 | C.5 |
| 1.1174 | B.194 | C.5 |
| 1.1175 | B.195 | C.5 |
| 1.1176 | B.196 | C.5 |
| 1.1177 | B.1 | C.6 |
| 1.1178 | B.2 | C.6 |
| 1.1179 | B.3 | C.6 |
| 1.1180 | B.4 | C.6 |
| 1.1181 | B.5 | C.6 |
| 1.1182 | B.6 | C.6 |
| 1.1183 | B.7 | C.6 |
| 1.1184 | B.8 | C.6 |
| 1.1185 | B.9 | C.6 |
| 1.1186 | B.10 | C.6 |
| 1.1187 | B.11 | C.6 |
| 1.1188 | B.12 | C.6 |
| 1.1189 | B.13 | C.6 |
| 1.1190 | B.14 | C.6 |
| 1.1191 | B.15 | C.6 |
| 1.1192 | B.16 | C.6 |
| 1.1193 | B.17 | C.6 |
| 1.1194 | B.18 | C.6 |
| 1.1195 | B.19 | C.6 |
| 1.1196 | B.20 | C.6 |
| 1.1197 | B.21 | C.6 |
| 1.1198 | B.22 | C.6 |
| 1.1199 | B.23 | C.6 |
| 1.1200 | B.24 | C.6 |
| 1.1201 | B.25 | C.6 |
| 1.1202 | B.26 | C.6 |
| 1.1203 | B.27 | C.6 |

TABLE 5-continued

(compositions 1.1 to 1.3545):

| comp. no. | herbicide B | safener C |
|---|---|---|
| 1.1204 | B.28 | C.6 |
| 1.1205 | B.29 | C.6 |
| 1.1206 | B.30 | C.6 |
| 1.1207 | B.31 | C.6 |
| 1.1208 | B.32 | C.6 |
| 1.1209 | B.33 | C.6 |
| 1.1210 | B.34 | C.6 |
| 1.1211 | B.35 | C.6 |
| 1.1212 | B.36 | C.6 |
| 1.1213 | B.37 | C.6 |
| 1.1214 | B.38 | C.6 |
| 1.1215 | B.39 | C.6 |
| 1.1216 | B.40 | C.6 |
| 1.1217 | B.41 | C.6 |
| 1.1218 | B.42 | C.6 |
| 1.1219 | B.43 | C.6 |
| 1.1220 | B.44 | C.6 |
| 1.1221 | B.45 | C.6 |
| 1.1222 | B.46 | C.6 |
| 1.1223 | B.47 | C.6 |
| 1.1224 | B.48 | C.6 |
| 1.1225 | B.49 | C.6 |
| 1.1226 | B.50 | C.6 |
| 1.1227 | B.51 | C.6 |
| 1.1228 | B.52 | C.6 |
| 1.1229 | B.53 | C.6 |
| 1.1230 | B.54 | C.6 |
| 1.1231 | B.55 | C.6 |
| 1.1232 | B.56 | C.6 |
| 1.1233 | B.57 | C.6 |
| 1.1234 | B.58. | C.6 |
| 1.1235 | B.59 | C.6 |
| 1.1236 | B.60 | C.6 |
| 1.1237 | B.61 | C.6 |
| 1.1238 | B.62 | C.6 |
| 1.1239 | B.63 | C.6 |
| 1.1240 | B.64 | C.6 |
| 1.1241 | B.65 | C.6 |
| 1.1242 | B.66 | C.6 |
| 1.1243 | B.67 | C.6 |
| 1.1244 | B.68 | C.6 |
| 1.1245 | B.69 | C.6 |
| 1.1246 | B.70 | C.6 |
| 1.1247 | B.71 | C.6 |
| 1.1248 | B.72 | C.6 |
| 1.1249 | B.73 | C.6 |
| 1.1250 | B.74 | C.6 |
| 1.1251 | B.75 | C.6 |
| 1.1252 | B.76 | C.6 |
| 1.1253 | B.77 | C.6 |
| 1.1254 | B.78 | C.6 |
| 1.1255 | B.79 | C.6 |
| 1.1256 | B.80 | C.6 |
| 1.1257 | B.81 | C.6 |
| 1.1258 | B.82 | C.6 |
| 1.1259 | B.83 | C.6 |
| 1.1260 | B.84 | C.6 |
| 1.1261 | B.85 | C.6 |
| 1.1262 | B.86 | C.6 |
| 1.1263 | B.87 | C.6 |
| 1.1264 | B.88 | C.6 |
| 1.1265 | B.89 | C.6 |
| 1.1266 | B.90 | C.6 |
| 1.1267 | B.91 | C.6 |
| 1.1268 | B.92 | C.6 |
| 1.1269 | B.93 | C.6 |
| 1.1270 | B.94 | C.6 |
| 1.1271 | B.95 | C.6 |
| 1.1272 | B.96 | C.6 |
| 1.1273 | B.97 | C.6 |
| 1.1274 | B.98 | C.6 |
| 1.1275 | B.99 | C.6 |
| 1.1276 | B.100 | C.6 |
| 1.1277 | B.101 | C.6 |
| 1.1278 | B.102 | C.6 |
| 1.1279 | B.103 | C.6 |
| 1.1280 | B.104 | C.6 |
| 1.1281 | B.105 | C.6 |
| 1.1282 | B.106 | C.6 |
| 1.1283 | B.107 | C.6 |
| 1.1284 | B.108 | C.6 |
| 1.1285 | B.109 | C.6 |
| 1.1286 | B.110 | C.6 |
| 1.1287 | B.111 | C.6 |
| 1.1288 | B.112 | C.6 |
| 1.1289 | B.113 | C.6 |
| 1.1290 | B.114 | C.6 |
| 1.1291 | B.115 | C.6 |
| 1.1292 | B.116 | C.6 |
| 1.1293 | B.117 | C.6 |
| 1.1294 | B.118 | C.6 |
| 1.1295 | B.119 | C.6 |
| 1.1296 | B.120 | C.6 |
| 1.1297 | B.121 | C.6 |
| 1.1298 | B.122 | C.6 |
| 1.1299 | B.123 | C.6 |
| 1.1300 | B.124 | C.6 |
| 1.1301 | B.125 | C.6 |
| 1.1302 | B.126 | C.6 |
| 1.1303 | B.127 | C.6 |
| 1.1304 | B.128 | C.6 |
| 1.1305 | B.129 | C.6 |
| 1.1306 | B.130 | C.6 |
| 1.1307 | B.131 | C.6 |
| 1.1308 | B.132 | C.6 |
| 1.1309 | B.133 | C.6 |
| 1.1310 | B.134 | C.6 |
| 1.1311 | B.135 | C.6 |
| 1.1312 | B.136 | C.6 |
| 1.1313 | B.137 | C.6 |
| 1.1314 | B.138 | C.6 |
| 1.1315 | B.139 | C.6 |
| 1.1316 | B.140 | C.6 |
| 1.1317 | B.141 | C.6 |
| 1.1318 | B.142 | C.6 |
| 1.1319 | B.143 | C.6 |
| 1.1320 | B.144 | C.6 |
| 1.1321 | B.145 | C.6 |
| 1.1322 | B.146 | C.6 |
| 1.1323 | B.147 | C.6 |
| 1.1324 | B.148 | C.6 |
| 1.1325 | B.149 | C.6 |
| 1.1326 | B.150 | C.6 |
| 1.1327 | B.151 | C.6 |
| 1.1328 | B.152 | C.6 |
| 1.1329 | B.153 | C.6 |
| 1.1330 | B.154 | C.6 |
| 1.1331 | B.155 | C.6 |
| 1.1332 | B.156 | C.6 |
| 1.1333 | B.157 | C.6 |
| 1.1334 | B.158 | C.6 |
| 1.1335 | B.159 | C.6 |
| 1.1336 | B.160 | C.6 |
| 1.1337 | B.161 | C.6 |
| 1.1338 | B.162 | C.6 |
| 1.1339 | B.163 | C.6 |
| 1.1340 | B.164 | C.6 |
| 1.1341 | B.165 | C.6 |
| 1.1342 | B.166 | C.6 |
| 1.1343 | B.167 | C.6 |
| 1.1344 | B.168 | C.6 |
| 1.1345 | B.169 | C.6 |
| 1.1346 | B.170 | C.6 |
| 1.1347 | B.171 | C.6 |
| 1.1348 | B.172 | C.6 |
| 1.1349 | B.173 | C.6 |
| 1.1350 | B.174 | C.6 |
| 1.1351 | B.175 | C.6 |
| 1.1352 | B.176 | C.6 |
| 1.1353 | B.177 | C.6 |

TABLE 5-continued (compositions 1.1 to 1.3545):

| comp. no. | herbicide B | safener C |
|---|---|---|
| 1.1354 | B.178 | C.6 |
| 1.1355 | B.179 | C.6 |
| 1.1356 | B.180 | C.6 |
| 1.1357 | B.181 | C.6 |
| 1.1358 | B.182 | C.6 |
| 1.1359 | B.183 | C.6 |
| 1.1360 | B.184 | C.6 |
| 1.1361 | B.185 | C.6 |
| 1.1362 | B.186 | C.6 |
| 1.1363 | B.187 | C.6 |
| 1.1364 | B.188 | C.6 |
| 1.1365 | B.189 | C.6 |
| 1.1366 | B.190 | C.6 |
| 1.1367 | B.191 | C.6 |
| 1.1368 | B.192 | C.6 |
| 1.1369 | B.193 | C.6 |
| 1.1370 | B.194 | C.6 |
| 1.1371 | B.195 | C.6 |
| 1.1372 | B.196 | C.6 |
| 1.1373 | B.1 | C.7 |
| 1.1374 | B.2 | C.7 |
| 1.1375 | B.3 | C.7 |
| 1.1376 | B.4 | C.7 |
| 1.1377 | B.5 | C.7 |
| 1.1378 | B.6 | C.7 |
| 1.1379 | B.7 | C.7 |
| 1.1380 | B.8 | C.7 |
| 1.1381 | B.9 | C.7 |
| 1.1382 | B.10 | C.7 |
| 1.1383 | B.11 | C.7 |
| 1.1384 | B.12 | C.7 |
| 1.1385 | B.13 | C.7 |
| 1.1386 | B.14 | C.7 |
| 1.1387 | B.15 | C.7 |
| 1.1388 | B.16 | C.7 |
| 1.1389 | B.17 | C.7 |
| 1.1390 | B.18 | C.7 |
| 1.1391 | B.19 | C.7 |
| 1.1392 | B.20 | C.7 |
| 1.1393 | B.21 | C.7 |
| 1.1394 | B.22 | C.7 |
| 1.1395 | B.23 | C.7 |
| 1.1396 | B.24 | C.7 |
| 1.1397 | B.25 | C.7 |
| 1.1398 | B.26 | C.7 |
| 1.1399 | B.27 | C.7 |
| 1.1400 | B.28 | C.7 |
| 1.1401 | B.29 | C.7 |
| 1.1402 | B.30 | C.7 |
| 1.1403 | B.31 | C.7 |
| 1.1404 | B.32 | C.7 |
| 1.1405 | B.33 | C.7 |
| 1.1406 | B.34 | C.7 |
| 1.1407 | B.35 | C.7 |
| 1.1408 | B.36 | C.7 |
| 1.1409 | B.37 | C.7 |
| 1.1410 | B.38 | C.7 |
| 1.1411 | B.39 | C.7 |
| 1.1412 | B.40 | C.7 |
| 1.1413 | B.41 | C.7 |
| 1.1414 | B.42 | C.7 |
| 1.1415 | B.43 | C.7 |
| 1.1416 | B.44 | C.7 |
| 1.1417 | B.45 | C.7 |
| 1.1418 | B.46 | C.7 |
| 1.1419 | B.47 | C.7 |
| 1.1420 | B.48 | C.7 |
| 1.1421 | B.49 | C.7 |
| 1.1422 | B.50 | C.7 |
| 1.1423 | B.51 | C.7 |
| 1.1424 | B.52 | C.7 |
| 1.1425 | B.53 | C.7 |
| 1.1426 | B.54 | C.7 |
| 1.1427 | B.55 | C.7 |
| 1.1428 | B.56 | C.7 |
| 1.1429 | B.57 | C.7 |
| 1.1430 | B.58. | C.7 |
| 1.1431 | B.59 | C.7 |
| 1.1432 | B.60 | C.7 |
| 1.1433 | B.61 | C.7 |
| 1.1434 | B.62 | C.7 |
| 1.1435 | B.63 | C.7 |
| 1.1436 | B.64 | C.7 |
| 1.1437 | B.65 | C.7 |
| 1.1438 | B.66 | C.7 |
| 1.1439 | B.67 | C.7 |
| 1.1440 | B.68 | C.7 |
| 1.1441 | B.69 | C.7 |
| 1.1442 | B.70 | C.7 |
| 1.1443 | B.71 | C.7 |
| 1.1444 | B.72 | C.7 |
| 1.1445 | B.73 | C.7 |
| 1.1446 | B.74 | C.7 |
| 1.1447 | B.75 | C.7 |
| 1.1448 | B.76 | C.7 |
| 1.1449 | B.77 | C.7 |
| 1.1450 | B.78 | C.7 |
| 1.1451 | B.79 | C.7 |
| 1.1452 | B.80 | C.7 |
| 1.1453 | B.81 | C.7 |
| 1.1454 | B.82 | C.7 |
| 1.1455 | B.83 | C.7 |
| 1.1456 | B.84 | C.7 |
| 1.1457 | B.85 | C.7 |
| 1.1458 | B.86 | C.7 |
| 1.1459 | B.87 | C.7 |
| 1.1460 | B.88 | C.7 |
| 1.1461 | B.89 | C.7 |
| 1.1462 | B.90 | C.7 |
| 1.1463 | B.91 | C.7 |
| 1.1464 | B.92 | C.7 |
| 1.1465 | B.93 | C.7 |
| 1.1466 | B.94 | C.7 |
| 1.1467 | B.95 | C.7 |
| 1.1468 | B.96 | C.7 |
| 1.1469 | B.97 | C.7 |
| 1.1470 | B.98 | C.7 |
| 1.1471 | B.99 | C.7 |
| 1.1472 | B.100 | C.7 |
| 1.1473 | B.101 | C.7 |
| 1.1474 | B.102 | C.7 |
| 1.1475 | B.103 | C.7 |
| 1.1476 | B.104 | C.7 |
| 1.1477 | B.105 | C.7 |
| 1.1478 | B.106 | C.7 |
| 1.1479 | B.107 | C.7 |
| 1.1480 | B.108 | C.7 |
| 1.1481 | B.109 | C.7 |
| 1.1482 | B.110 | C.7 |
| 1.1483 | B.111 | C.7 |
| 1.1484 | B.112 | C.7 |
| 1.1485 | B.113 | C.7 |
| 1.1486 | B.114 | C.7 |
| 1.1487 | B.115 | C.7 |
| 1.1488 | B.116 | C.7 |
| 1.1489 | B.117 | C.7 |
| 1.1490 | B.118 | C.7 |
| 1.1491 | B.119 | C.7 |
| 1.1492 | B.120 | C.7 |
| 1.1493 | B.121 | C.7 |
| 1.1494 | B.122 | C.7 |
| 1.1495 | B.123 | C.7 |
| 1.1496 | B.124 | C.7 |
| 1.1497 | B.125 | C.7 |
| 1.1498 | B.126 | C.7 |
| 1.1499 | B.127 | C.7 |
| 1.1500 | B.128 | C.7 |
| 1.1501 | B.129 | C.7 |
| 1.1502 | B.130 | C.7 |
| 1.1503 | B.131 | C.7 |

TABLE 5-continued (compositions 1.1 to 1.3545):

| comp. no. | herbicide B | safener C |
|---|---|---|
| 1.1504 | B.132 | C.7 |
| 1.1505 | B.133 | C.7 |
| 1.1506 | B.134 | C.7 |
| 1.1507 | B.135 | C.7 |
| 1.1508 | B.136 | C.7 |
| 1.1509 | B.137 | C.7 |
| 1.1510 | B.138 | C.7 |
| 1.1511 | B.139 | C.7 |
| 1.1512 | B.140 | C.7 |
| 1.1513 | B.141 | C.7 |
| 1.1514 | B.142 | C.7 |
| 1.1515 | B.143 | C.7 |
| 1.1516 | B.144 | C.7 |
| 1.1517 | B.145 | C.7 |
| 1.1518 | B.146 | C.7 |
| 1.1519 | B.147 | C.7 |
| 1.1520 | B.148 | C.7 |
| 1.1521 | B.149 | C.7 |
| 1.1522 | B.150 | C.7 |
| 1.1523 | B.151 | C.7 |
| 1.1524 | B.152 | C.7 |
| 1.1525 | B.153 | C.7 |
| 1.1526 | B.154 | C.7 |
| 1.1527 | B.155 | C.7 |
| 1.1528 | B.156 | C.7 |
| 1.1529 | B.157 | C.7 |
| 1.1530 | B.158 | C.7 |
| 1.1531 | B.159 | C.7 |
| 1.1532 | B.160 | C.7 |
| 1.1533 | B.161 | C.7 |
| 1.1534 | B.162 | C.7 |
| 1.1535 | B.163 | C.7 |
| 1.1536 | B.164 | C.7 |
| 1.1537 | B.165 | C.7 |
| 1.1538 | B.166 | C.7 |
| 1.1539 | B.167 | C.7 |
| 1.1540 | B.168 | C.7 |
| 1.1541 | B.169 | C.7 |
| 1.1542 | B.170 | C.7 |
| 1.1543 | B.171 | C.7 |
| 1.1544 | B.172 | C.7 |
| 1.1545 | B.173 | C.7 |
| 1.1546 | B.174 | C.7 |
| 1.1547 | B.175 | C.7 |
| 1.1548 | B.176 | C.7 |
| 1.1549 | B.177 | C.7 |
| 1.1550 | B.178 | C.7 |
| 1.1551 | B.179 | C.7 |
| 1.1552 | B.180 | C.7 |
| 1.1553 | B.181 | C.7 |
| 1.1554 | B.182 | C.7 |
| 1.1555 | B.183 | C.7 |
| 1.1556 | B.184 | C.7 |
| 1.1557 | B.185 | C.7 |
| 1.1558 | B.186 | C.7 |
| 1.1559 | B.187 | C.7 |
| 1.1560 | B.188 | C.7 |
| 1.1561 | B.189 | C.7 |
| 1.1562 | B.190 | C.7 |
| 1.1563 | B.191 | C.7 |
| 1.1564 | B.192 | C.7 |
| 1.1565 | B.193 | C.7 |
| 1.1566 | B.194 | C.7 |
| 1.1567 | B.195 | C.7 |
| 1.1568 | B.196 | C.7 |
| 1.1569 | B.1 | C.8 |
| 1.1570 | B.2 | C.8 |
| 1.1571 | B.3 | C.8 |
| 1.1572 | B.4 | C.8 |
| 1.1573 | B.5 | C.8 |
| 1.1574 | B.6 | C.8 |
| 1.1575 | B.7 | C.8 |
| 1.1576 | B.8 | C.8 |
| 1.1577 | B.9 | C.8 |
| 1.1578 | B.10 | C.8 |
| 1.1579 | B.11 | C.8 |
| 1.1580 | B.12 | C.8 |
| 1.1581 | B.13 | C.8 |
| 1.1582 | B.14 | C.8 |
| 1.1583 | B.15 | C.8 |
| 1.1584 | B.16 | C.8 |
| 1.1585 | B.17 | C.8 |
| 1.1586 | B.18 | C.8 |
| 1.1587 | B.19 | C.8 |
| 1.1588 | B.20 | C.8 |
| 1.1589 | B.21 | C.8 |
| 1.1590 | B.22 | C.8 |
| 1.1591 | B.23 | C.8 |
| 1.1592 | B.24 | C.8 |
| 1.1593 | B.25 | C.8 |
| 1.1594 | B.26 | C.8 |
| 1.1595 | B.27 | C.8 |
| 1.1596 | B.28 | C.8 |
| 1.1597 | B.29 | C.8 |
| 1.1598 | B.30 | C.8 |
| 1.1599 | B.31 | C.8 |
| 1.1600 | B.32 | C.8 |
| 1.1601 | B.33 | C.8 |
| 1.1602 | B.34 | C.8 |
| 1.1603 | B.35 | C.8 |
| 1.1604 | B.36 | C.8 |
| 1.1605 | B.37 | C.8 |
| 1.1606 | B.38 | C.8 |
| 1.1607 | B.39 | C.8 |
| 1.1608 | B.40 | C.8 |
| 1.1609 | B.41 | C.8 |
| 1.1610 | B.42 | C.8 |
| 1.1611 | B.43 | C.8 |
| 1.1612 | B.44 | C.8 |
| 1.1613 | B.45 | C.8 |
| 1.1614 | B.46 | C.8 |
| 1.1615 | B.47 | C.8 |
| 1.1616 | B.48 | C.8 |
| 1.1617 | B.49 | C.8 |
| 1.1618 | B.50 | C.8 |
| 1.1619 | B.51 | C.8 |
| 1.1620 | B.52 | C.8 |
| 1.1621 | B.53 | C.8 |
| 1.1622 | B.54 | C.8 |
| 1.1623 | B.55 | C.8 |
| 1.1624 | B.56 | C.8 |
| 1.1625 | B.57 | C.8 |
| 1.1626 | B.58. | C.8 |
| 1.1627 | B.59 | C.8 |
| 1.1628 | B.60 | C.8 |
| 1.1629 | B.61 | C.8 |
| 1.1630 | B.62 | C.8 |
| 1.1631 | B.63 | C.8 |
| 1.1632 | B.64 | C.8 |
| 1.1633 | B.65 | C.8 |
| 1.1634 | B.66 | C.8 |
| 1.1635 | B.67 | C.8 |
| 1.1636 | B.68 | C.8 |
| 1.1637 | B.69 | C.8 |
| 1.1638 | B.70 | C.8 |
| 1.1639 | B.71 | C.8 |
| 1.1640 | B.72 | C.8 |
| 1.1641 | B.73 | C.8 |
| 1.1642 | B.74 | C.8 |
| 1.1643 | B.75 | C.8 |
| 1.1644 | B.76 | C.8 |
| 1.1645 | B.77 | C.8 |
| 1.1646 | B.78 | C.8 |
| 1.1647 | B.79 | C.8 |
| 1.1648 | B.80 | C.8 |
| 1.1649 | B.81 | C.8 |
| 1.1650 | B.82 | C.8 |
| 1.1651 | B.83 | C.8 |
| 1.1652 | B.84 | C.8 |
| 1.1653 | B.85 | C.8 |

TABLE 5-continued (compositions 1.1 to 1.3545):

| comp. no. | herbicide B | safener C |
|---|---|---|
| 1.1654 | B.86 | C.8 |
| 1.1655 | B.87 | C.8 |
| 1.1656 | B.88 | C.8 |
| 1.1657 | B.89 | C.8 |
| 1.1658 | B.90 | C.8 |
| 1.1659 | B.91 | C.8 |
| 1.1660 | B.92 | C.8 |
| 1.1661 | B.93 | C.8 |
| 1.1662 | B.94 | C.8 |
| 1.1663 | B.95 | C.8 |
| 1.1664 | B.96 | C.8 |
| 1.1665 | B.97 | C.8 |
| 1.1666 | B.98 | C.8 |
| 1.1667 | B.99 | C.8 |
| 1.1668 | B.100 | C.8 |
| 1.1669 | B.101 | C.8 |
| 1.1670 | B.102 | C.8 |
| 1.1671 | B.103 | C.8 |
| 1.1672 | B.104 | C.8 |
| 1.1673 | B.105 | C.8 |
| 1.1674 | B.106 | C.8 |
| 1.1675 | B.107 | C.8 |
| 1.1676 | B.108 | C.8 |
| 1.1677 | B.109 | C.8 |
| 1.1678 | B.110 | C.8 |
| 1.1679 | B.111 | C.8 |
| 1.1680 | B.112 | C.8 |
| 1.1681 | B.113 | C.8 |
| 1.1682 | B.114 | C.8 |
| 1.1683 | B.115 | C.8 |
| 1.1684 | B.116 | C.8 |
| 1.1685 | B.117 | C.8 |
| 1.1686 | B.118 | C.8 |
| 1.1687 | B.119 | C.8 |
| 1.1688 | B.120 | C.8 |
| 1.1689 | B.121 | C.8 |
| 1.1690 | B.122 | C.8 |
| 1.1691 | B.123 | C.8 |
| 1.1692 | B.124 | C.8 |
| 1.1693 | B.125 | C.8 |
| 1.1694 | B.126 | C.8 |
| 1.1695 | B.127 | C.8 |
| 1.1696 | B.128 | C.8 |
| 1.1697 | B.129 | C.8 |
| 1.1698 | B.130 | C.8 |
| 1.1699 | B.131 | C.8 |
| 1.1700 | B.132 | C.8 |
| 1.1701 | B.133 | C.8 |
| 1.1702 | B.134 | C.8 |
| 1.1703 | B.135 | C.8 |
| 1.1704 | B.136 | C.8 |
| 1.1705 | B.137 | C.8 |
| 1.1706 | B.138 | C.8 |
| 1.1707 | B.139 | C.8 |
| 1.1708 | B.140 | C.8 |
| 1.1709 | B.141 | C.8 |
| 1.1710 | B.142 | C.8 |
| 1.1711 | B.143 | C.8 |
| 1.1712 | B.144 | C.8 |
| 1.1713 | B.145 | C.8 |
| 1.1714 | B.146 | C.8 |
| 1.1715 | B.147 | C.8 |
| 1.1716 | B.148 | C.8 |
| 1.1717 | B.149 | C.8 |
| 1.1718 | B.150 | C.8 |
| 1.1719 | B.151 | C.8 |
| 1.1720 | B.152 | C.8 |
| 1.1721 | B.153 | C.8 |
| 1.1722 | B.154 | C.8 |
| 1.1723 | B.155 | C.8 |
| 1.1724 | B.156 | C.8 |
| 1.1725 | B.157 | C.8 |
| 1.1726 | B.158 | C.8 |
| 1.1727 | B.159 | C.8 |
| 1.1728 | B.160 | C.8 |
| 1.1729 | B.161 | C.8 |
| 1.1730 | B.162 | C.8 |
| 1.1731 | B.163 | C.8 |
| 1.1732 | B.164 | C.8 |
| 1.1733 | B.165 | C.8 |
| 1.1734 | B.166 | C.8 |
| 1.1735 | B.167 | C.8 |
| 1.1736 | B.168 | C.8 |
| 1.1737 | B.169 | C.8 |
| 1.1738 | B.170 | C.8 |
| 1.1739 | B.171 | C.8 |
| 1.1740 | B.172 | C.8 |
| 1.1741 | B.173 | C.8 |
| 1.1742 | B.174 | C.8 |
| 1.1743 | B.175 | C.8 |
| 1.1744 | B.176 | C.8 |
| 1.1745 | B.177 | C.8 |
| 1.1746 | B.178 | C.8 |
| 1.1747 | B.179 | C.8 |
| 1.1748 | B.180 | C.8 |
| 1.1749 | B.181 | C.8 |
| 1.1750 | B.182 | C.8 |
| 1.1751 | B.183 | C.8 |
| 1.1752 | B.184 | C.8 |
| 1.1753 | B.185 | C.8 |
| 1.1754 | B.186 | C.8 |
| 1.1755 | B.187 | C.8 |
| 1.1756 | B.188 | C.8 |
| 1.1757 | B.189 | C.8 |
| 1.1758 | B.190 | C.8 |
| 1.1759 | B.191 | C.8 |
| 1.1760 | B.192 | C.8 |
| 1.1761 | B.193 | C.8 |
| 1.1762 | B.194 | C.8 |
| 1.1763 | B.195 | C.8 |
| 1.1764 | B.196 | C.8 |
| 1.1765 | B.1 | C.9 |
| 1.1766 | B.2 | C.9 |
| 1.1767 | B.3 | C.9 |
| 1.1768 | B.4 | C.9 |
| 1.1769 | B.5 | C.9 |
| 1.1770 | B.6 | C.9 |
| 1.1771 | B.7 | C.9 |
| 1.1772 | B.8 | C.9 |
| 1.1773 | B.9 | C.9 |
| 1.1774 | B.10 | C.9 |
| 1.1775 | B.11 | C.9 |
| 1.1776 | B.12 | C.9 |
| 1.1777 | B.13 | C.9 |
| 1.1778 | B.14 | C.9 |
| 1.1779 | B.15 | C.9 |
| 1.1780 | B.16 | C.9 |
| 1.1781 | B.17 | C.9 |
| 1.1782 | B.18 | C.9 |
| 1.1783 | B.19 | C.9 |
| 1.1784 | B.20 | C.9 |
| 1.1785 | B.21 | C.9 |
| 1.1786 | B.22 | C.9 |
| 1.1787 | B.23 | C.9 |
| 1.1788 | B.24 | C.9 |
| 1.1789 | B.25 | C.9 |
| 1.1790 | B.26 | C.9 |
| 1.1791 | B.27 | C.9 |
| 1.1792 | B.28 | C.9 |
| 1.1793 | B.29 | C.9 |
| 1.1794 | B.30 | C.9 |
| 1.1795 | B.31 | C.9 |
| 1.1796 | B.32 | C.9 |
| 1.1797 | B.33 | C.9 |
| 1.1798 | B.34 | C.9 |
| 1.1799 | B.35 | C.9 |
| 1.1800 | B.36 | C.9 |
| 1.1801 | B.37 | C.9 |
| 1.1802 | B.38 | C.9 |
| 1.1803 | B.39 | C.9 |

TABLE 5-continued (compositions 1.1 to 1.3545):

| comp. no. | herbicide B | safener C |
|---|---|---|
| 1.1804 | B.40 | C.9 |
| 1.1805 | B.41 | C.9 |
| 1.1806 | B.42 | C.9 |
| 1.1807 | B.43 | C.9 |
| 1.1808 | B.44 | C.9 |
| 1.1809 | B.45 | C.9 |
| 1.1810 | B.46 | C.9 |
| 1.1811 | B.47 | C.9 |
| 1.1812 | B.48 | C.9 |
| 1.1813 | B.49 | C.9 |
| 1.1814 | B.50 | C.9 |
| 1.1815 | B.51 | C.9 |
| 1.1816 | B.52 | C.9 |
| 1.1817 | B.53 | C.9 |
| 1.1818 | B.54 | C.9 |
| 1.1819 | B.55 | C.9 |
| 1.1820 | B.56 | C.9 |
| 1.1821 | B.57 | C.9 |
| 1.1822 | B.58. | C.9 |
| 1.1823 | B.59 | C.9 |
| 1.1824 | B.60 | C.9 |
| 1.1825 | B.61 | C.9 |
| 1.1826 | B.62 | C.9 |
| 1.1827 | B.63 | C.9 |
| 1.1828 | B.64 | C.9 |
| 1.1829 | B.65 | C.9 |
| 1.1830 | B.66 | C.9 |
| 1.1831 | B.67 | C.9 |
| 1.1832 | B.68 | C.9 |
| 1.1833 | B.69 | C.9 |
| 1.1834 | B.70 | C.9 |
| 1.1835 | B.71 | C.9 |
| 1.1836 | B.72 | C.9 |
| 1.1837 | B.73 | C.9 |
| 1.1838 | B.74 | C.9 |
| 1.1839 | B.75 | C.9 |
| 1.1840 | B.76 | C.9 |
| 1.1841 | B.77 | C.9 |
| 1.1842 | B.78 | C.9 |
| 1.1843 | B.79 | C.9 |
| 1.1844 | B.80 | C.9 |
| 1.1845 | B.81 | C.9 |
| 1.1846 | B.82 | C.9 |
| 1.1847 | B.83 | C.9 |
| 1.1848 | B.84 | C.9 |
| 1.1849 | B.85 | C.9 |
| 1.1850 | B.86 | C.9 |
| 1.1851 | B.87 | C.9 |
| 1.1852 | B.88 | C.9 |
| 1.1853 | B.89 | C.9 |
| 1.1854 | B.90 | C.9 |
| 1.1855 | B.91 | C.9 |
| 1.1856 | B.92 | C.9 |
| 1.1857 | B.93 | C.9 |
| 1.1858 | B.94 | C.9 |
| 1.1859 | B.95 | C.9 |
| 1.1860 | B.96 | C.9 |
| 1.1861 | B.97 | C.9 |
| 1.1862 | B.98 | C.9 |
| 1.1863 | B.99 | C.9 |
| 1.1864 | B.100 | C.9 |
| 1.1865 | B.101 | C.9 |
| 1.1866 | B.102 | C.9 |
| 1.1867 | B.103 | C.9 |
| 1.1868 | B.104 | C.9 |
| 1.1869 | B.105 | C.9 |
| 1.1870 | B.106 | C.9 |
| 1.1871 | B.107 | C.9 |
| 1.1872 | B.108 | C.9 |
| 1.1873 | B.109 | C.9 |
| 1.1874 | B.110 | C.9 |
| 1.1875 | B.111 | C.9 |
| 1.1876 | B.112 | C.9 |
| 1.1877 | B.113 | C.9 |
| 1.1878 | B.114 | C.9 |
| 1.1879 | B.115 | C.9 |
| 1.1880 | B.116 | C.9 |
| 1.1881 | B.117 | C.9 |
| 1.1882 | B.118 | C.9 |
| 1.1883 | B.119 | C.9 |
| 1.1884 | B.120 | C.9 |
| 1.1885 | B.121 | C.9 |
| 1.1886 | B.122 | C.9 |
| 1.1887 | B.123 | C.9 |
| 1.1888 | B.124 | C.9 |
| 1.1889 | B.125 | C.9 |
| 1.1890 | B.126 | C.9 |
| 1.1891 | B.127 | C.9 |
| 1.1892 | B.128 | C.9 |
| 1.1893 | B.129 | C.9 |
| 1.1894 | B.130 | C.9 |
| 1.1895 | B.131 | C.9 |
| 1.1896 | B.132 | C.9 |
| 1.1897 | B.133 | C.9 |
| 1.1898 | B.134 | C.9 |
| 1.1899 | B.135 | C.9 |
| 1.1900 | B.136 | C.9 |
| 1.1901 | B.137 | C.9 |
| 1.1902 | B.138 | C.9 |
| 1.1903 | B.139 | C.9 |
| 1.1904 | B.140 | C.9 |
| 1.1905 | B.141 | C.9 |
| 1.1906 | B.142 | C.9 |
| 1.1907 | B.143 | C.9 |
| 1.1908 | B.144 | C.9 |
| 1.1909 | B.145 | C.9 |
| 1.1910 | B.146 | C.9 |
| 1.1911 | B.147 | C.9 |
| 1.1912 | B.148 | C.9 |
| 1.1913 | B.149 | C.9 |
| 1.1914 | B.150 | C.9 |
| 1.1915 | B.151 | C.9 |
| 1.1916 | B.152 | C.9 |
| 1.1917 | B.153 | C.9 |
| 1.1918 | B.154 | C.9 |
| 1.1919 | B.155 | C.9 |
| 1.1920 | B.156 | C.9 |
| 1.1921 | B.157 | C.9 |
| 1.1922 | B.158 | C.9 |
| 1.1923 | B.159 | C.9 |
| 1.1924 | B.160 | C.9 |
| 1.1925 | B.161 | C.9 |
| 1.1926 | B.162 | C.9 |
| 1.1927 | B.163 | C.9 |
| 1.1928 | B.164 | C.9 |
| 1.1929 | B.165 | C.9 |
| 1.1930 | B.166 | C.9 |
| 1.1931 | B.167 | C.9 |
| 1.1932 | B.168 | C.9 |
| 1.1933 | B.169 | C.9 |
| 1.1934 | B.170 | C.9 |
| 1.1935 | B.171 | C.9 |
| 1.1936 | B.172 | C.9 |
| 1.1937 | B.173 | C.9 |
| 1.1938 | B.174 | C.9 |
| 1.1939 | B.175 | C.9 |
| 1.1940 | B.176 | C.9 |
| 1.1941 | B.177 | C.9 |
| 1.1942 | B.178 | C.9 |
| 1.1943 | B.179 | C.9 |
| 1.1944 | B.180 | C.9 |
| 1.1945 | B.181 | C.9 |
| 1.1946 | B.182 | C.9 |
| 1.1947 | B.183 | C.9 |
| 1.1948 | B.184 | C.9 |
| 1.1949 | B.185 | C.9 |
| 1.1950 | B.186 | C.9 |
| 1.1951 | B.187 | C.9 |
| 1.1952 | B.188 | C.9 |
| 1.1953 | B.189 | C.9 |

TABLE 5-continued (compositions 1.1 to 1.3545):

| comp. no. | herbicide B | safener C |
|---|---|---|
| 1.1954 | B.190 | C.9 |
| 1.1955 | B.191 | C.9 |
| 1.1956 | B.192 | C.9 |
| 1.1957 | B.193 | C.9 |
| 1.1958 | B.194 | C.9 |
| 1.1959 | B.195 | C.9 |
| 1.1960 | B.196 | C.9 |
| 1.1961 | B.1 | C.10 |
| 1.1962 | B.2 | C.10 |
| 1.1963 | B.3 | C.10 |
| 1.1964 | B.4 | C.10 |
| 1.1965 | B.5 | C.10 |
| 1.1966 | B.6 | C.10 |
| 1.1967 | B.7 | C.10 |
| 1.1968 | B.8 | C.10 |
| 1.1969 | B.9 | C.10 |
| 1.1970 | B.10 | C.10 |
| 1.1971 | B.11 | C.10 |
| 1.1972 | B.12 | C.10 |
| 1.1973 | B.13 | C.10 |
| 1.1974 | B.14 | C.10 |
| 1.1975 | B.15 | C.10 |
| 1.1976 | B.16 | C.10 |
| 1.1977 | B.17 | C.10 |
| 1.1978 | B.18 | C.10 |
| 1.1979 | B.19 | C.10 |
| 1.1980 | B.20 | C.10 |
| 1.1981 | B.21 | C.10 |
| 1.1982 | B.22 | C.10 |
| 1.1983 | B.23 | C.10 |
| 1.1984 | B.24 | C.10 |
| 1.1985 | B.25 | C.10 |
| 1.1986 | B.26 | C.10 |
| 1.1987 | B.27 | C.10 |
| 1.1988 | B.28 | C.10 |
| 1.1989 | B.29 | C.10 |
| 1.1990 | B.30 | C.10 |
| 1.1991 | B.31 | C.10 |
| 1.1992 | B.32 | C.10 |
| 1.1993 | B.33 | C.10 |
| 1.1994 | B.34 | C.10 |
| 1.1995 | B.35 | C.10 |
| 1.1996 | B.36 | C.10 |
| 1.1997 | B.37 | C.10 |
| 1.1998 | B.38 | C.10 |
| 1.1999 | B.39 | C.10 |
| 1.2000 | B.40 | C.10 |
| 1.2001 | B.41 | C.10 |
| 1.2002 | B.42 | C.10 |
| 1.2003 | B.43 | C.10 |
| 1.2004 | B.44 | C.10 |
| 1.2005 | B.45 | C.10 |
| 1.2006 | B.46 | C.10 |
| 1.2007 | B.47 | C.10 |
| 1.2008 | B.48 | C.10 |
| 1.2009 | B.49 | C.10 |
| 1.2010 | B.50 | C.10 |
| 1.2011 | B.51 | C.10 |
| 1.2012 | B.52 | C.10 |
| 1.2013 | B.53 | C.10 |
| 1.2014 | B.54 | C.10 |
| 1.2015 | B.55 | C.10 |
| 1.2016 | B.56 | C.10 |
| 1.2017 | B.57 | C.10 |
| 1.2018 | B.58. | C.10 |
| 1.2019 | B.59 | C.10 |
| 1.2020 | B.60 | C.10 |
| 1.2021 | B.61 | C.10 |
| 1.2022 | B.62 | C.10 |
| 1.2023 | B.63 | C.10 |
| 1.2024 | B.64 | C.10 |
| 1.2025 | B.65 | C.10 |
| 1.2026 | B.66 | C.10 |
| 1.2027 | B.67 | C.10 |
| 1.2028 | B.68 | C.10 |
| 1.2029 | B.69 | C.10 |
| 1.2030 | B.70 | C.10 |
| 1.2031 | B.71 | C.10 |
| 1.2032 | B.72 | C.10 |
| 1.2033 | B.73 | C.10 |
| 1.2034 | B.74 | C.10 |
| 1.2035 | B.75 | C.10 |
| 1.2036 | B.76 | C.10 |
| 1.2037 | B.77 | C.10 |
| 1.2038 | B.78 | C.10 |
| 1.2039 | B.79 | C.10 |
| 1.2040 | B.80 | C.10 |
| 1.2041 | B.81 | C.10 |
| 1.2042 | B.82 | C.10 |
| 1.2043 | B.83 | C.10 |
| 1.2044 | B.84 | C.10 |
| 1.2045 | B.85 | C.10 |
| 1.2046 | B.86 | C.10 |
| 1.2047 | B.87 | C.10 |
| 1.2048 | B.88 | C.10 |
| 1.2049 | B.89 | C.10 |
| 1.2050 | B.90 | C.10 |
| 1.2051 | B.91 | C.10 |
| 1.2052 | B.92 | C.10 |
| 1.2053 | B.93 | C.10 |
| 1.2054 | B.94 | C.10 |
| 1.2055 | B.95 | C.10 |
| 1.2056 | B.96 | C.10 |
| 1.2057 | B.97 | C.10 |
| 1.2058 | B.98 | C.10 |
| 1.2059 | B.99 | C.10 |
| 1.2060 | B.100 | C.10 |
| 1.2061 | B.101 | C.10 |
| 1.2062 | B.102 | C.10 |
| 1.2063 | B.103 | C.10 |
| 1.2064 | B.104 | C.10 |
| 1.2065 | B.105 | C.10 |
| 1.2066 | B.106 | C.10 |
| 1.2067 | B.107 | C.10 |
| 1.2068 | B.108 | C.10 |
| 1.2069 | B.109 | C.10 |
| 1.2070 | B.110 | C.10 |
| 1.2071 | B.111 | C.10 |
| 1.2072 | B.112 | C.10 |
| 1.2073 | B.113 | C.10 |
| 1.2074 | B.114 | C.10 |
| 1.2075 | B.115 | C.10 |
| 1.2076 | B.116 | C.10 |
| 1.2077 | B.117 | C.10 |
| 1.2078 | B.118 | C.10 |
| 1.2079 | B.119 | C.10 |
| 1.2080 | B.120 | C.10 |
| 1.2081 | B.121 | C.10 |
| 1.2082 | B.122 | C.10 |
| 1.2083 | B.123 | C.10 |
| 1.2084 | B.124 | C.10 |
| 1.2085 | B.125 | C.10 |
| 1.2086 | B.126 | C.10 |
| 1.2087 | B.127 | C.10 |
| 1.2088 | B.128 | C.10 |
| 1.2089 | B.129 | C.10 |
| 1.2090 | B.130 | C.10 |
| 1.2091 | B.131 | C.10 |
| 1.2092 | B.132 | C.10 |
| 1.2093 | B.133 | C.10 |
| 1.2094 | B.134 | C.10 |
| 1.2095 | B.135 | C.10 |
| 1.2096 | B.136 | C.10 |
| 1.2097 | B.137 | C.10 |
| 1.2098 | B.138 | C.10 |
| 1.2099 | B.139 | C.10 |
| 1.2100 | B.140 | C.10 |
| 1.2101 | B.141 | C.10 |
| 1.2102 | B.142 | C.10 |
| 1.2103 | B.143 | C.10 |

TABLE 5-continued (compositions 1.1 to 1.3545):

| comp. no. | herbicide B | safener C |
|---|---|---|
| 1.2104 | B.144 | C.10 |
| 1.2105 | B.145 | C.10 |
| 1.2106 | B.146 | C.10 |
| 1.2107 | B.147 | C.10 |
| 1.2108 | B.148 | C.10 |
| 1.2109 | B.149 | C.10 |
| 1.2110 | B.150 | C.10 |
| 1.2111 | B.151 | C.10 |
| 1.2112 | B.152 | C.10 |
| 1.2113 | B.153 | C.10 |
| 1.2114 | B.154 | C.10 |
| 1.2115 | B.155 | C.10 |
| 1.2116 | B.156 | C.10 |
| 1.2117 | B.157 | C.10 |
| 1.2118 | B.158 | C.10 |
| 1.2119 | B.159 | C.10 |
| 1.2120 | B.160 | C.10 |
| 1.2121 | B.161 | C.10 |
| 1.2122 | B.162 | C.10 |
| 1.2123 | B.163 | C.10 |
| 1.2124 | B.164 | C.10 |
| 1.2125 | B.165 | C.10 |
| 1.2126 | B.166 | C.10 |
| 1.2127 | B.167 | C.10 |
| 1.2128 | B.168 | C.10 |
| 1.2129 | B.169 | C.10 |
| 1.2130 | B.170 | C.10 |
| 1.2131 | B.171 | C.10 |
| 1.2132 | B.172 | C.10 |
| 1.2133 | B.173 | C.10 |
| 1.2134 | B.174 | C.10 |
| 1.2135 | B.175 | C.10 |
| 1.2136 | B.176 | C.10 |
| 1.2137 | B.177 | C.10 |
| 1.2138 | B.178 | C.10 |
| 1.2139 | B.179 | C.10 |
| 1.2140 | B.180 | C.10 |
| 1.2141 | B.181 | C.10 |
| 1.2142 | B.182 | C.10 |
| 1.2143 | B.183 | C.10 |
| 1.2144 | B.184 | C.10 |
| 1.2145 | B.185 | C.10 |
| 1.2146 | B.186 | C.10 |
| 1.2147 | B.187 | C.10 |
| 1.2148 | B.188 | C.10 |
| 1.2149 | B.189 | C.10 |
| 1.2150 | B.190 | C.10 |
| 1.2151 | B.191 | C.10 |
| 1.2152 | B.192 | C.10 |
| 1.2153 | B.193 | C.10 |
| 1.2154 | B.194 | C.10 |
| 1.2155 | B.195 | C.10 |
| 1.2156 | B.196 | C.10 |
| 1.2157 | B.1 | C.11 |
| 1.2158 | B.2 | C.11 |
| 1.2159 | B.3 | C.11 |
| 1.2160 | B.4 | C.11 |
| 1.2161 | B.5 | C.11 |
| 1.2162 | B.6 | C.11 |
| 1.2163 | B.7 | C.11 |
| 1.2164 | B.8 | C.11 |
| 1.2165 | B.9 | C.11 |
| 1.2166 | B.10 | C.11 |
| 1.2167 | B.11 | C.11 |
| 1.2168 | B.12 | C.11 |
| 1.2169 | B.13 | C.11 |
| 1.2170 | B.14 | C.11 |
| 1.2171 | B.15 | C.11 |
| 1.2172 | B.16 | C.11 |
| 1.2173 | B.17 | C.11 |
| 1.2174 | B.18 | C.11 |
| 1.2175 | B.19 | C.11 |
| 1.2176 | B.20 | C.11 |
| 1.2177 | B.21 | C.11 |
| 1.2178 | B.22 | C.11 |
| 1.2179 | B.23 | C.11 |
| 1.2180 | B.24 | C.11 |
| 1.2181 | B.25 | C.11 |
| 1.2182 | B.26 | C.11 |
| 1.2183 | B.27 | C.11 |
| 1.2184 | B.28 | C.11 |
| 1.2185 | B.29 | C.11 |
| 1.2186 | B.30 | C.11 |
| 1.2187 | B.31 | C.11 |
| 1.2188 | B.32 | C.11 |
| 1.2189 | B.33 | C.11 |
| 1.2190 | B.34 | C.11 |
| 1.2191 | B.35 | C.11 |
| 1.2192 | B.36 | C.11 |
| 1.2193 | B.37 | C.11 |
| 1.2194 | B.38 | C.11 |
| 1.2195 | B.39 | C.11 |
| 1.2196 | B.40 | C.11 |
| 1.2197 | B.41 | C.11 |
| 1.2198 | B.42 | C.11 |
| 1.2199 | B.43 | C.11 |
| 1.2200 | B.44 | C.11 |
| 1.2201 | B.45 | C.11 |
| 1.2202 | B.46 | C.11 |
| 1.2203 | B.47 | C.11 |
| 1.2204 | B.48 | C.11 |
| 1.2205 | B.49 | C.11 |
| 1.2206 | B.50 | C.11 |
| 1.2207 | B.51 | C.11 |
| 1.2208 | B.52 | C.11 |
| 1.2209 | B.53 | C.11 |
| 1.2210 | B.54 | C.11 |
| 1.2211 | B.55 | C.11 |
| 1.2212 | B.56 | C.11 |
| 1.2213 | B.57 | C.11 |
| 1.2214 | B.58. | C.11 |
| 1.2215 | B.59 | C.11 |
| 1.2216 | B.60 | C.11 |
| 1.2217 | B.61 | C.11 |
| 1.2218 | B.62 | C.11 |
| 1.2219 | B.63 | C.11 |
| 1.2220 | B.64 | C.11 |
| 1.2221 | B.65 | C.11 |
| 1.2222 | B.66 | C.11 |
| 1.2223 | B.67 | C.11 |
| 1.2224 | B.68 | C.11 |
| 1.2225 | B.69 | C.11 |
| 1.2226 | B.70 | C.11 |
| 1.2227 | B.71 | C.11 |
| 1.2228 | B.72 | C.11 |
| 1.2229 | B.73 | C.11 |
| 1.2230 | B.74 | C.11 |
| 1.2231 | B.75 | C.11 |
| 1.2232 | B.76 | C.11 |
| 1.2233 | B.77 | C.11 |
| 1.2234 | B.78 | C.11 |
| 1.2235 | B.79 | C.11 |
| 1.2236 | B.80 | C.11 |
| 1.2237 | B.81 | C.11 |
| 1.2238 | B.82 | C.11 |
| 1.2239 | B.83 | C.11 |
| 1.2240 | B.84 | C.11 |
| 1.2241 | B.85 | C.11 |
| 1.2242 | B.86 | C.11 |
| 1.2243 | B.87 | C.11 |
| 1.2244 | B.88 | C.11 |
| 1.2245 | B.89 | C.11 |
| 1.2246 | B.90 | C.11 |
| 1.2247 | B.91 | C.11 |
| 1.2248 | B.92 | C.11 |
| 1.2249 | B.93 | C.11 |
| 1.2250 | B.94 | C.11 |
| 1.2251 | B.95 | C.11 |
| 1.2252 | B.96 | C.11 |
| 1.2253 | B.97 | C.11 |

TABLE 5-continued (compositions 1.1 to 1.3545):

| comp. no. | herbicide B | safener C |
|---|---|---|
| 1.2254 | B.98 | C.11 |
| 1.2255 | B.99 | C.11 |
| 1.2256 | B.100 | C.11 |
| 1.2257 | B.101 | C.11 |
| 1.2258 | B.102 | C.11 |
| 1.2259 | B.103 | C.11 |
| 1.2260 | B.104 | C.11 |
| 1.2261 | B.105 | C.11 |
| 1.2262 | B.106 | C.11 |
| 1.2263 | B.107 | C.11 |
| 1.2264 | B.108 | C.11 |
| 1.2265 | B.109 | C.11 |
| 1.2266 | B.110 | C.11 |
| 1.2267 | B.111 | C.11 |
| 1.2268 | B.112 | C.11 |
| 1.2269 | B.113 | C.11 |
| 1.2270 | B.114 | C.11 |
| 1.2271 | B.115 | C.11 |
| 1.2272 | B.116 | C.11 |
| 1.2273 | B.117 | C.11 |
| 1.2274 | B.118 | C.11 |
| 1.2275 | B.119 | C.11 |
| 1.2276 | B.120 | C.11 |
| 1.2277 | B.121 | C.11 |
| 1.2278 | B.122 | C.11 |
| 1.2279 | B.123 | C.11 |
| 1.2280 | B.124 | C.11 |
| 1.2281 | B.125 | C.11 |
| 1.2282 | B.126 | C.11 |
| 1.2283 | B.127 | C.11 |
| 1.2284 | B.128 | C.11 |
| 1.2285 | B.129 | C.11 |
| 1.2286 | B.130 | C.11 |
| 1.2287 | B.131 | C.11 |
| 1.2288 | B.132 | C.11 |
| 1.2289 | B.133 | C.11 |
| 1.2290 | B.134 | C.11 |
| 1.2291 | B.135 | C.11 |
| 1.2292 | B.136 | C.11 |
| 1.2293 | B.137 | C.11 |
| 1.2294 | B.138 | C.11 |
| 1.2295 | B.139 | C.11 |
| 1.2296 | B.140 | C.11 |
| 1.2297 | B.141 | C.11 |
| 1.2298 | B.142 | C.11 |
| 1.2299 | B.143 | C.11 |
| 1.2300 | B.144 | C.11 |
| 1.2301 | B.145 | C.11 |
| 1.2302 | B.146 | C.11 |
| 1.2303 | B.147 | C.11 |
| 1.2304 | B.148 | C.11 |
| 1.2305 | B.149 | C.11 |
| 1.2306 | B.150 | C.11 |
| 1.2307 | B.151 | C.11 |
| 1.2308 | B.152 | C.11 |
| 1.2309 | B.153 | C.11 |
| 1.2310 | B.154 | C.11 |
| 1.2311 | B.155 | C.11 |
| 1.2312 | B.156 | C.11 |
| 1.2313 | B.157 | C.11 |
| 1.2314 | B.158 | C.11 |
| 1.2315 | B.159 | C.11 |
| 1.2316 | B.160 | C.11 |
| 1.2317 | B.161 | C.11 |
| 1.2318 | B.162 | C.11 |
| 1.2319 | B.163 | C.11 |
| 1.2320 | B.164 | C.11 |
| 1.2321 | B.165 | C.11 |
| 1.2322 | B.166 | C.11 |
| 1.2323 | B.167 | C.11 |
| 1.2324 | B.168 | C.11 |
| 1.2325 | B.169 | C.11 |
| 1.2326 | B.170 | C.11 |
| 1.2327 | B.171 | C.11 |
| 1.2328 | B.172 | C.11 |
| 1.2329 | B.173 | C.11 |
| 1.2330 | B.174 | C.11 |
| 1.2331 | B.175 | C.11 |
| 1.2332 | B.176 | C.11 |
| 1.2333 | B.177 | C.11 |
| 1.2334 | B.178 | C.11 |
| 1.2335 | B.179 | C.11 |
| 1.2336 | B.180 | C.11 |
| 1.2337 | B.181 | C.11 |
| 1.2338 | B.182 | C.11 |
| 1.2339 | B.183 | C.11 |
| 1.2340 | B.184 | C.11 |
| 1.2341 | B.185 | C.11 |
| 1.2342 | B.186 | C.11 |
| 1.2343 | B.187 | C.11 |
| 1.2344 | B.188 | C.11 |
| 1.2345 | B.189 | C.11 |
| 1.2346 | B.190 | C.11 |
| 1.2347 | B.191 | C.11 |
| 1.2348 | B.192 | C.11 |
| 1.2349 | B.193 | C.11 |
| 1.2350 | B.194 | C.11 |
| 1.2351 | B.195 | C.11 |
| 1.2352 | B.196 | C.11 |
| 1.2353 | B.1 | C.12 |
| 1.2354 | B.2 | C.12 |
| 1.2355 | B.3 | C.12 |
| 1.2356 | B.4 | C.12 |
| 1.2357 | B.5 | C.12 |
| 1.2358 | B.6 | C.12 |
| 1.2359 | B.7 | C.12 |
| 1.2360 | B.8 | C.12 |
| 1.2361 | B.9 | C.12 |
| 1.2362 | B.10 | C.12 |
| 1.2363 | B.11 | C.12 |
| 1.2364 | B.12 | C.12 |
| 1.2365 | B.13 | C.12 |
| 1.2366 | B.14 | C.12 |
| 1.2367 | B.15 | C.12 |
| 1.2368 | B.16 | C.12 |
| 1.2369 | B.17 | C.12 |
| 1.2370 | B.18 | C.12 |
| 1.2371 | B.19 | C.12 |
| 1.2372 | B.20 | C.12 |
| 1.2373 | B.21 | C.12 |
| 1.2374 | B.22 | C.12 |
| 1.2375 | B.23 | C.12 |
| 1.2376 | B.24 | C.12 |
| 1.2377 | B.25 | C.12 |
| 1.2378 | B.26 | C.12 |
| 1.2379 | B.27 | C.12 |
| 1.2380 | B.28 | C.12 |
| 1.2381 | B.29 | C.12 |
| 1.2382 | B.30 | C.12 |
| 1.2383 | B.31 | C.12 |
| 1.2384 | B.32 | C.12 |
| 1.2385 | B.33 | C.12 |
| 1.2386 | B.34 | C.12 |
| 1.2387 | B.35 | C.12 |
| 1.2388 | B.36 | C.12 |
| 1.2389 | B.37 | C.12 |
| 1.2390 | B.38 | C.12 |
| 1.2391 | B.39 | C.12 |
| 1.2392 | B.40 | C.12 |
| 1.2393 | B.41 | C.12 |
| 1.2394 | B.42 | C.12 |
| 1.2395 | B.43 | C.12 |
| 1.2396 | B.44 | C.12 |
| 1.2397 | B.45 | C.12 |
| 1.2398 | B.46 | C.12 |
| 1.2399 | B.47 | C.12 |
| 1.2400 | B.48 | C.12 |
| 1.2401 | B.49 | C.12 |
| 1.2402 | B.50 | C.12 |
| 1.2403 | B.51 | C.12 |

TABLE 5-continued (compositions 1.1 to 1.3545):

| comp. no. | herbicide B | safener C |
|---|---|---|
| 1.2404 | B.52 | C.12 |
| 1.2405 | B.53 | C.12 |
| 1.2406 | B.54 | C.12 |
| 1.2407 | B.55 | C.12 |
| 1.2408 | B.56 | C.12 |
| 1.2409 | B.57 | C.12 |
| 1.2410 | B.58. | C.12 |
| 1.2411 | B.59 | C.12 |
| 1.2412 | B.60 | C.12 |
| 1.2413 | B.61 | C.12 |
| 1.2414 | B.62 | C.12 |
| 1.2415 | B.63 | C.12 |
| 1.2416 | B.64 | C.12 |
| 1.2417 | B.65 | C.12 |
| 1.2418 | B.66 | C.12 |
| 1.2419 | B.67 | C.12 |
| 1.2420 | B.68 | C.12 |
| 1.2421 | B.69 | C.12 |
| 1.2422 | B.70 | C.12 |
| 1.2423 | B.71 | C.12 |
| 1.2424 | B.72 | C.12 |
| 1.2425 | B.73 | C.12 |
| 1.2426 | B.74 | C.12 |
| 1.2427 | B.75 | C.12 |
| 1.2428 | B.76 | C.12 |
| 1.2429 | B.77 | C.12 |
| 1.2430 | B.78 | C.12 |
| 1.2431 | B.79 | C.12 |
| 1.2432 | B.80 | C.12 |
| 1.2433 | B.81 | C.12 |
| 1.2434 | B.82 | C.12 |
| 1.2435 | B.83 | C.12 |
| 1.2436 | B.84 | C.12 |
| 1.2437 | B.85 | C.12 |
| 1.2438 | B.86 | C.12 |
| 1.2439 | B.87 | C.12 |
| 1.2440 | B.88 | C.12 |
| 1.2441 | B.89 | C.12 |
| 1.2442 | B.90 | C.12 |
| 1.2443 | B.91 | C.12 |
| 1.2444 | B.92 | C.12 |
| 1.2445 | B.93 | C.12 |
| 1.2446 | B.94 | C.12 |
| 1.2447 | B.95 | C.12 |
| 1.2448 | B.96 | C.12 |
| 1.2449 | B.97 | C.12 |
| 1.2450 | B.98 | C.12 |
| 1.2451 | B.99 | C.12 |
| 1.2452 | B.100 | C.12 |
| 1.2453 | B.101 | C.12 |
| 1.2454 | B.102 | C.12 |
| 1.2455 | B.103 | C.12 |
| 1.2456 | B.104 | C.12 |
| 1.2457 | B.105 | C.12 |
| 1.2458 | B.106 | C.12 |
| 1.2459 | B.107 | C.12 |
| 1.2460 | B.108 | C.12 |
| 1.2461 | B.109 | C.12 |
| 1.2462 | B.110 | C.12 |
| 1.2463 | B.111 | C.12 |
| 1.2464 | B.112 | C.12 |
| 1.2465 | B.113 | C.12 |
| 1.2466 | B.114 | C.12 |
| 1.2467 | B.115 | C.12 |
| 1.2468 | B.116 | C.12 |
| 1.2469 | B.117 | C.12 |
| 1.2470 | B.118 | C.12 |
| 1.2471 | B.119 | C.12 |
| 1.2472 | B.120 | C.12 |
| 1.2473 | B.121 | C.12 |
| 1.2474 | B.122 | C.12 |
| 1.2475 | B.123 | C.12 |
| 1.2476 | B.124 | C.12 |
| 1.2477 | B.125 | C.12 |
| 1.2478 | B.126 | C.12 |
| 1.2479 | B.127 | C.12 |
| 1.2480 | B.128 | C.12 |
| 1.2481 | B.129 | C.12 |
| 1.2482 | B.130 | C.12 |
| 1.2483 | B.131 | C.12 |
| 1.2484 | B.132 | C.12 |
| 1.2485 | B.133 | C.12 |
| 1.2486 | B.134 | C.12 |
| 1.2487 | B.135 | C.12 |
| 1.2488 | B.136 | C.12 |
| 1.2489 | B.137 | C.12 |
| 1.2490 | B.138 | C.12 |
| 1.2491 | B.139 | C.12 |
| 1.2492 | B.140 | C.12 |
| 1.2493 | B.141 | C.12 |
| 1.2494 | B.142 | C.12 |
| 1.2495 | B.143 | C.12 |
| 1.2496 | B.144 | C.12 |
| 1.2497 | B.145 | C.12 |
| 1.2498 | B.146 | C.12 |
| 1.2499 | B.147 | C.12 |
| 1.2500 | B.148 | C.12 |
| 1.2501 | B.149 | C.12 |
| 1.2502 | B.150 | C.12 |
| 1.2503 | B.151 | C.12 |
| 1.2504 | B.152 | C.12 |
| 1.2505 | B.153 | C.12 |
| 1.2506 | B.154 | C.12 |
| 1.2507 | B.155 | C.12 |
| 1.2508 | B.156 | C.12 |
| 1.2509 | B.157 | C.12 |
| 1.2510 | B.158 | C.12 |
| 1.2511 | B.159 | C.12 |
| 1.2512 | B.160 | C.12 |
| 1.2513 | B.161 | C.12 |
| 1.2514 | B.162 | C.12 |
| 1.2515 | B.163 | C.12 |
| 1.2516 | B.164 | C.12 |
| 1.2517 | B.165 | C.12 |
| 1.2518 | B.166 | C.12 |
| 1.2519 | B.167 | C.12 |
| 1.2520 | B.168 | C.12 |
| 1.2521 | B.169 | C.12 |
| 1.2522 | B.170 | C.12 |
| 1.2523 | B.171 | C.12 |
| 1.2524 | B.172 | C.12 |
| 1.2525 | B.173 | C.12 |
| 1.2526 | B.174 | C.12 |
| 1.2527 | B.175 | C.12 |
| 1.2528 | B.176 | C.12 |
| 1.2529 | B.177 | C.12 |
| 1.2530 | B.178 | C.12 |
| 1.2531 | B.179 | C.12 |
| 1.2532 | B.180 | C.12 |
| 1.2533 | B.181 | C.12 |
| 1.2534 | B.182 | C.12 |
| 1.2535 | B.183 | C.12 |
| 1.2536 | B.184 | C.12 |
| 1.2537 | B.185 | C.12 |
| 1.2538 | B.186 | C.12 |
| 1.2539 | B.187 | C.12 |
| 1.2540 | B.188 | C.12 |
| 1.2541 | B.189 | C.12 |
| 1.2542 | B.190 | C.12 |
| 1.2543 | B.191 | C.12 |
| 1.2544 | B.192 | C.12 |
| 1.2545 | B.193 | C.12 |
| 1.2546 | B.194 | C.12 |
| 1.2547 | B.195 | C.12 |
| 1.2548 | B.196 | C.12 |
| 1.2549 | B.1 | C.13 |
| 1.2550 | B.2 | C.13 |
| 1.2551 | B.3 | C.13 |
| 1.2552 | B.4 | C.13 |
| 1.2553 | B.5 | C.13 |

TABLE 5-continued (compositions 1.1 to 1.3545):

| comp. no. | herbicide B | safener C |
|---|---|---|
| 1.2554 | B.6 | C.13 |
| 1.2555 | B.7 | C.13 |
| 1.2556 | B.8 | C.13 |
| 1.2557 | B.9 | C.13 |
| 1.2558 | B.10 | C.13 |
| 1.2559 | B.11 | C.13 |
| 1.2560 | B.12 | C.13 |
| 1.2561 | B.13 | C.13 |
| 1.2562 | B.14 | C.13 |
| 1.2563 | B.15 | C.13 |
| 1.2564 | B.16 | C.13 |
| 1.2565 | B.17 | C.13 |
| 1.2566 | B.18 | C.13 |
| 1.2567 | B.19 | C.13 |
| 1.2568 | B.20 | C.13 |
| 1.2569 | B.21 | C.13 |
| 1.2570 | B.22 | C.13 |
| 1.2571 | B.23 | C.13 |
| 1.2572 | B.24 | C.13 |
| 1.2573 | B.25 | C.13 |
| 1.2574 | B.26 | C.13 |
| 1.2575 | B.27 | C.13 |
| 1.2576 | B.28 | C.13 |
| 1.2577 | B.29 | C.13 |
| 1.2578 | B.30 | C.13 |
| 1.2579 | B.31 | C.13 |
| 1.2580 | B.32 | C.13 |
| 1.2581 | B.33 | C.13 |
| 1.2582 | B.34 | C.13 |
| 1.2583 | B.35 | C.13 |
| 1.2584 | B.36 | C.13 |
| 1.2585 | B.37 | C.13 |
| 1.2586 | B.38 | C.13 |
| 1.2587 | B.39 | C.13 |
| 1.2588 | B.40 | C.13 |
| 1.2589 | B.41 | C.13 |
| 1.2590 | B.42 | C.13 |
| 1.2591 | B.43 | C.13 |
| 1.2592 | B.44 | C.13 |
| 1.2593 | B.45 | C.13 |
| 1.2594 | B.46 | C.13 |
| 1.2595 | B.47 | C.13 |
| 1.2596 | B.48 | C.13 |
| 1.2597 | B.49 | C.13 |
| 1.2598 | B.50 | C.13 |
| 1.2599 | B.51 | C.13 |
| 1.2600 | B.52 | C.13 |
| 1.2601 | B.53 | C.13 |
| 1.2602 | B.54 | C.13 |
| 1.2603 | B.55 | C.13 |
| 1.2604 | B.56 | C.13 |
| 1.2605 | B.57 | C.13 |
| 1.2606 | B.58. | C.13 |
| 1.2607 | B.59 | C.13 |
| 1.2608 | B.60 | C.13 |
| 1.2609 | B.61 | C.13 |
| 1.2610 | B.62 | C.13 |
| 1.2611 | B.63 | C.13 |
| 1.2612 | B.64 | C.13 |
| 1.2613 | B.65 | C.13 |
| 1.2614 | B.66 | C.13 |
| 1.2615 | B.67 | C.13 |
| 1.2616 | B.68 | C.13 |
| 1.2617 | B.69 | C.13 |
| 1.2618 | B.70 | C.13 |
| 1.2619 | B.71 | C.13 |
| 1.2620 | B.72 | C.13 |
| 1.2621 | B.73 | C.13 |
| 1.2622 | B.74 | C.13 |
| 1.2623 | B.75 | C.13 |
| 1.2624 | B.76 | C.13 |
| 1.2625 | B.77 | C.13 |
| 1.2626 | B.78 | C.13 |
| 1.2627 | B.79 | C.13 |
| 1.2628 | B.80 | C.13 |
| 1.2629 | B.81 | C.13 |
| 1.2630 | B.82 | C.13 |
| 1.2631 | B.83 | C.13 |
| 1.2632 | B.84 | C.13 |
| 1.2633 | B.85 | C.13 |
| 1.2634 | B.86 | C.13 |
| 1.2635 | B.87 | C.13 |
| 1.2636 | B.88 | C.13 |
| 1.2637 | B.89 | C.13 |
| 1.2638 | B.90 | C.13 |
| 1.2639 | B.91 | C.13 |
| 1.2640 | B.92 | C.13 |
| 1.2641 | B.93 | C.13 |
| 1.2642 | B.94 | C.13 |
| 1.2643 | B.95 | C.13 |
| 1.2644 | B.96 | C.13 |
| 1.2645 | B.97 | C.13 |
| 1.2646 | B.98 | C.13 |
| 1.2647 | B.99 | C.13 |
| 1.2648 | B.100 | C.13 |
| 1.2649 | B.101 | C.13 |
| 1.2650 | B.102 | C.13 |
| 1.2651 | B.103 | C.13 |
| 1.2652 | B.104 | C.13 |
| 1.2653 | B.105 | C.13 |
| 1.2654 | B.106 | C.13 |
| 1.2655 | B.107 | C.13 |
| 1.2656 | B.108 | C.13 |
| 1.2657 | B.109 | C.13 |
| 1.2658 | B.110 | C.13 |
| 1.2659 | B.111 | C.13 |
| 1.2660 | B.112 | C.13 |
| 1.2661 | B.113 | C.13 |
| 1.2662 | B.114 | C.13 |
| 1.2663 | B.115 | C.13 |
| 1.2664 | B.116 | C.13 |
| 1.2665 | B.117 | C.13 |
| 1.2666 | B.118 | C.13 |
| 1.2667 | B.119 | C.13 |
| 1.2668 | B.120 | C.13 |
| 1.2669 | B.121 | C.13 |
| 1.2670 | B.122 | C.13 |
| 1.2671 | B.123 | C.13 |
| 1.2672 | B.124 | C.13 |
| 1.2673 | B.125 | C.13 |
| 1.2674 | B.126 | C.13 |
| 1.2675 | B.127 | C.13 |
| 1.2676 | B.128 | C.13 |
| 1.2677 | B.129 | C.13 |
| 1.2678 | B.130 | C.13 |
| 1.2679 | B.131 | C.13 |
| 1.2680 | B.132 | C.13 |
| 1.2681 | B.133 | C.13 |
| 1.2682 | B.134 | C.13 |
| 1.2683 | B.135 | C.13 |
| 1.2684 | B.136 | C.13 |
| 1.2685 | B.137 | C.13 |
| 1.2686 | B.138 | C.13 |
| 1.2687 | B.139 | C.13 |
| 1.2688 | B.140 | C.13 |
| 1.2689 | B.141 | C.13 |
| 1.2690 | B.142 | C.13 |
| 1.2691 | B.143 | C.13 |
| 1.2692 | B.144 | C.13 |
| 1.2693 | B.145 | C.13 |
| 1.2694 | B.146 | C.13 |
| 1.2695 | B.147 | C.13 |
| 1.2696 | B.148 | C.13 |
| 1.2697 | B.149 | C.13 |
| 1.2698 | B.150 | C.13 |
| 1.2699 | B.151 | C.13 |
| 1.2700 | B.152 | C.13 |
| 1.2701 | B.153 | C.13 |
| 1.2702 | B.154 | C.13 |
| 1.2703 | B.155 | C.13 |

TABLE 5-continued

(compositions 1.1 to 1.3545):

| comp. no. | herbicide B | safener C |
|---|---|---|
| 1.2704 | B.156 | C.13 |
| 1.2705 | B.157 | C.13 |
| 1.2706 | B.158 | C.13 |
| 1.2707 | B.159 | C.13 |
| 1.2708 | B.160 | C.13 |
| 1.2709 | B.161 | C.13 |
| 1.2710 | B.162 | C.13 |
| 1.2711 | B.163 | C.13 |
| 1.2712 | B.164 | C.13 |
| 1.2713 | B.165 | C.13 |
| 1.2714 | B.166 | C.13 |
| 1.2715 | B.167 | C.13 |
| 1.2716 | B.168 | C.13 |
| 1.2717 | B.169 | C.13 |
| 1.2718 | B.170 | C.13 |
| 1.2719 | B.171 | C.13 |
| 1.2720 | B.172 | C.13 |
| 1.2721 | B.173 | C.13 |
| 1.2722 | B.174 | C.13 |
| 1.2723 | B.175 | C.13 |
| 1.2724 | B.176 | C.13 |
| 1.2725 | B.177 | C.13 |
| 1.2726 | B.178 | C.13 |
| 1.2727 | B.179 | C.13 |
| 1.2728 | B.180 | C.13 |
| 1.2729 | B.181 | C.13 |
| 1.2730 | B.182 | C.13 |
| 1.2731 | B.183 | C.13 |
| 1.2732 | B.184 | C.13 |
| 1.2733 | B.185 | C.13 |
| 1.2734 | B.186 | C.13 |
| 1.2735 | B.187 | C.13 |
| 1.2736 | B.188 | C.13 |
| 1.2737 | B.189 | C.13 |
| 1.2738 | B.190 | C.13 |
| 1.2739 | B.191 | C.13 |
| 1.2740 | B.192 | C.13 |
| 1.2741 | B.193 | C.13 |
| 1.2742 | B.194 | C.13 |
| 1.2743 | B.195 | C.13 |
| 1.2744 | B.196 | C.13 |
| 1.2745 | B.1 | C.14 |
| 1.2746 | B.2 | C.14 |
| 1.2747 | B.3 | C.14 |
| 1.2748 | B.4 | C.14 |
| 1.2749 | B.5 | C.14 |
| 1.2750 | B.6 | C.14 |
| 1.2751 | B.7 | C.14 |
| 1.2752 | B.8 | C.14 |
| 1.2753 | B.9 | C.14 |
| 1.2754 | B.10 | C.14 |
| 1.2755 | B.11 | C.14 |
| 1.2756 | B.12 | C.14 |
| 1.2757 | B.13 | C.14 |
| 1.2758 | B.14 | C.14 |
| 1.2759 | B.15 | C.14 |
| 1.2760 | B.16 | C.14 |
| 1.2761 | B.17 | C.14 |
| 1.2762 | B.18 | C.14 |
| 1.2763 | B.19 | C.14 |
| 1.2764 | B.20 | C.14 |
| 1.2765 | B.21 | C.14 |
| 1.2766 | B.22 | C.14 |
| 1.2767 | B.23 | C.14 |
| 1.2768 | B.24 | C.14 |
| 1.2769 | B.25 | C.14 |
| 1.2770 | B.26 | C.14 |
| 1.2771 | B.27 | C.14 |
| 1.2772 | B.28 | C.14 |
| 1.2773 | B.29 | C.14 |
| 1.2774 | B.30 | C.14 |
| 1.2775 | B.31 | C.14 |
| 1.2776 | B.32 | C.14 |
| 1.2777 | B.33 | C.14 |
| 1.2778 | B.34 | C.14 |
| 1.2779 | B.35 | C.14 |
| 1.2780 | B.36 | C.14 |
| 1.2781 | B.37 | C.14 |
| 1.2782 | B.38 | C.14 |
| 1.2783 | B.39 | C.14 |
| 1.2784 | B.40 | C.14 |
| 1.2785 | B.41 | C.14 |
| 1.2786 | B.42 | C.14 |
| 1.2787 | B.43 | C.14 |
| 1.2788 | B.44 | C.14 |
| 1.2789 | B.45 | C.14 |
| 1.2790 | B.46 | C.14 |
| 1.2791 | B.47 | C.14 |
| 1.2792 | B.48 | C.14 |
| 1.2793 | B.49 | C.14 |
| 1.2794 | B.50 | C.14 |
| 1.2795 | B.51 | C.14 |
| 1.2796 | B.52 | C.14 |
| 1.2797 | B.53 | C.14 |
| 1.2798 | B.54 | C.14 |
| 1.2799 | B.55 | C.14 |
| 1.2800 | B.56 | C.14 |
| 1.2801 | B.57 | C.14 |
| 1.2802 | B.58. | C.14 |
| 1.2803 | B.59 | C.14 |
| 1.2804 | B.60 | C.14 |
| 1.2805 | B.61 | C.14 |
| 1.2806 | B.62 | C.14 |
| 1.2807 | B.63 | C.14 |
| 1.2808 | B.64 | C.14 |
| 1.2809 | B.65 | C.14 |
| 1.2810 | B.66 | C.14 |
| 1.2811 | B.67 | C.14 |
| 1.2812 | B.68 | C.14 |
| 1.2813 | B.69 | C.14 |
| 1.2814 | B.70 | C.14 |
| 1.2815 | B.71 | C.14 |
| 1.2816 | B.72 | C.14 |
| 1.2817 | B.73 | C.14 |
| 1.2818 | B.74 | C.14 |
| 1.2819 | B.75 | C.14 |
| 1.2820 | B.76 | C.14 |
| 1.2821 | B.77 | C.14 |
| 1.2822 | B.78 | C.14 |
| 1.2823 | B.79 | C.14 |
| 1.2824 | B.80 | C.14 |
| 1.2825 | B.81 | C.14 |
| 1.2826 | B.82 | C.14 |
| 1.2827 | B.83 | C.14 |
| 1.2828 | B.84 | C.14 |
| 1.2829 | B.85 | C.14 |
| 1.2830 | B.86 | C.14 |
| 1.2831 | B.87 | C.14 |
| 1.2832 | B.88 | C.14 |
| 1.2833 | B.89 | C.14 |
| 1.2834 | B.90 | C.14 |
| 1.2835 | B.91 | C.14 |
| 1.2836 | B.92 | C.14 |
| 1.2837 | B.93 | C.14 |
| 1.2838 | B.94 | C.14 |
| 1.2839 | B.95 | C.14 |
| 1.2840 | B.96 | C.14 |
| 1.2841 | B.97 | C.14 |
| 1.2842 | B.98 | C.14 |
| 1.2843 | B.99 | C.14 |
| 1.2844 | B.100 | C.14 |
| 1.2845 | B.101 | C.14 |
| 1.2846 | B.102 | C.14 |
| 1.2847 | B.103 | C.14 |
| 1.2848 | B.104 | C.14 |
| 1.2849 | B.105 | C.14 |
| 1.2850 | B.106 | C.14 |
| 1.2851 | B.107 | C.14 |
| 1.2852 | B.108 | C.14 |
| 1.2853 | B.109 | C.14 |

TABLE 5-continued (compositions 1.1 to 1.3545):

| comp. no. | herbicide B | safener C |
|---|---|---|
| 1.2854 | B.110 | C.14 |
| 1.2855 | B.111 | C.14 |
| 1.2856 | B.112 | C.14 |
| 1.2857 | B.113 | C.14 |
| 1.2858 | B.114 | C.14 |
| 1.2859 | B.115 | C.14 |
| 1.2860 | B.116 | C.14 |
| 1.2861 | B.117 | C.14 |
| 1.2862 | B.118 | C.14 |
| 1.2863 | B.119 | C.14 |
| 1.2864 | B.120 | C.14 |
| 1.2865 | B.121 | C.14 |
| 1.2866 | B.122 | C.14 |
| 1.2867 | B.123 | C.14 |
| 1.2868 | B.124 | C.14 |
| 1.2869 | B.125 | C.14 |
| 1.2870 | B.126 | C.14 |
| 1.2871 | B.127 | C.14 |
| 1.2872 | B.128 | C.14 |
| 1.2873 | B.129 | C.14 |
| 1.2874 | B.130 | C.14 |
| 1.2875 | B.131 | C.14 |
| 1.2876 | B.132 | C.14 |
| 1.2877 | B.133 | C.14 |
| 1.2878 | B.134 | C.14 |
| 1.2879 | B.135 | C.14 |
| 1.2880 | B.136 | C.14 |
| 1.2881 | B.137 | C.14 |
| 1.2882 | B.138 | C.14 |
| 1.2883 | B.139 | C.14 |
| 1.2884 | B.140 | C.14 |
| 1.2885 | B.141 | C.14 |
| 1.2886 | B.142 | C.14 |
| 1.2887 | B.143 | C.14 |
| 1.2888 | B.144 | C.14 |
| 1.2889 | B.145 | C.14 |
| 1.2890 | B.146 | C.14 |
| 1.2891 | B.147 | C.14 |
| 1.2892 | B.148 | C.14 |
| 1.2893 | B.149 | C.14 |
| 1.2894 | B.150 | C.14 |
| 1.2895 | B.151 | C.14 |
| 1.2896 | B.152 | C.14 |
| 1.2897 | B.153 | C.14 |
| 1.2898 | B.154 | C.14 |
| 1.2899 | B.155 | C.14 |
| 1.2900 | B.156 | C.14 |
| 1.2901 | B.157 | C.14 |
| 1.2902 | B.158 | C.14 |
| 1.2903 | B.159 | C.14 |
| 1.2904 | B.160 | C.14 |
| 1.2905 | B.161 | C.14 |
| 1.2906 | B.162 | C.14 |
| 1.2907 | B.163 | C.14 |
| 1.2908 | B.164 | C.14 |
| 1.2909 | B.165 | C.14 |
| 1.2910 | B.166 | C.14 |
| 1.2911 | B.167 | C.14 |
| 1.2912 | B.168 | C.14 |
| 1.2913 | B.169 | C.14 |
| 1.2914 | B.170 | C.14 |
| 1.2915 | B.171 | C.14 |
| 1.2916 | B.172 | C.14 |
| 1.2917 | B.173 | C.14 |
| 1.2918 | B.174 | C.14 |
| 1.2919 | B.175 | C.14 |
| 1.2920 | B.176 | C.14 |
| 1.2921 | B.177 | C.14 |
| 1.2922 | B.178 | C.14 |
| 1.2923 | B.179 | C.14 |
| 1.2924 | B.180 | C.14 |
| 1.2925 | B.181 | C.14 |
| 1.2926 | B.182 | C.14 |
| 1.2927 | B.183 | C.14 |
| 1.2928 | B.184 | C.14 |
| 1.2929 | B.185 | C.14 |
| 1.2930 | B.186 | C.14 |
| 1.2931 | B.187 | C.14 |
| 1.2932 | B.188 | C.14 |
| 1.2933 | B.189 | C.14 |
| 1.2934 | B.190 | C.14 |
| 1.2935 | B.191 | C.14 |
| 1.2936 | B.192 | C.14 |
| 1.2937 | B.193 | C.14 |
| 1.2938 | B.194 | C.14 |
| 1.2939 | B.195 | C.14 |
| 1.2940 | B.196 | C.14 |
| 1.2941 | B.1 | C.15 |
| 1.2942 | B.2 | C.15 |
| 1.2943 | B.3 | C.15 |
| 1.2944 | B.4 | C.15 |
| 1.2945 | B.5 | C.15 |
| 1.2946 | B.6 | C.15 |
| 1.2947 | B.7 | C.15 |
| 1.2948 | B.8 | C.15 |
| 1.2949 | B.9 | C.15 |
| 1.2950 | B.10 | C.15 |
| 1.2951 | B.11 | C.15 |
| 1.2952 | B.12 | C.15 |
| 1.2953 | B.13 | C.15 |
| 1.2954 | B.14 | C.15 |
| 1.2955 | B.15 | C.15 |
| 1.2956 | B.16 | C.15 |
| 1.2957 | B.17 | C.15 |
| 1.2958 | B.18 | C.15 |
| 1.2959 | B.19 | C.15 |
| 1.2960 | B.20 | C.15 |
| 1.2961 | B.21 | C.15 |
| 1.2962 | B.22 | C.15 |
| 1.2963 | B.23 | C.15 |
| 1.2964 | B.24 | C.15 |
| 1.2965 | B.25 | C.15 |
| 1.2966 | B.26 | C.15 |
| 1.2967 | B.27 | C.15 |
| 1.2968 | B.28 | C.15 |
| 1.2969 | B.29 | C.15 |
| 1.2970 | B.30 | C.15 |
| 1.2971 | B.31 | C.15 |
| 1.2972 | B.32 | C.15 |
| 1.2973 | B.33 | C.15 |
| 1.2974 | B.34 | C.15 |
| 1.2975 | B.35 | C.15 |
| 1.2976 | B.36 | C.15 |
| 1.2977 | B.37 | C.15 |
| 1.2978 | B.38 | C.15 |
| 1.2979 | B.39 | C.15 |
| 1.2980 | B.40 | C.15 |
| 1.2981 | B.41 | C.15 |
| 1.2982 | B.42 | C.15 |
| 1.2983 | B.43 | C.15 |
| 1.2984 | B.44 | C.15 |
| 1.2985 | B.45 | C.15 |
| 1.2986 | B.46 | C.15 |
| 1.2987 | B.47 | C.15 |
| 1.2988 | B.48 | C.15 |
| 1.2989 | B.49 | C.15 |
| 1.2990 | B.50 | C.15 |
| 1.2991 | B.51 | C.15 |
| 1.2992 | B.52 | C.15 |
| 1.2993 | B.53 | C.15 |
| 1.2994 | B.54 | C.15 |
| 1.2995 | B.55 | C.15 |
| 1.2996 | B.56 | C.15 |
| 1.2997 | B.57 | C.15 |
| 1.2998 | B.58. | C.15 |
| 1.2999 | B.59 | C.15 |
| 1.3000 | B.60 | C.15 |
| 1.3001 | B.61 | C.15 |
| 1.3002 | B.62 | C.15 |
| 1.3003 | B.63 | C.15 |

TABLE 5-continued (compositions 1.1 to 1.3545):

| comp. no. | herbicide B | safener C |
|---|---|---|
| 1.3004 | B.64 | C.15 |
| 1.3005 | B.65 | C.15 |
| 1.3006 | B.66 | C.15 |
| 1.3007 | B.67 | C.15 |
| 1.3008 | B.68 | C.15 |
| 1.3009 | B.69 | C.15 |
| 1.3010 | B.70 | C.15 |
| 1.3011 | B.71 | C.15 |
| 1.3012 | B.72 | C.15 |
| 1.3013 | B.73 | C.15 |
| 1.3014 | B.74 | C.15 |
| 1.3015 | B.75 | C.15 |
| 1.3016 | B.76 | C.15 |
| 1.3017 | B.77 | C.15 |
| 1.3018 | B.78 | C.15 |
| 1.3019 | B.79 | C.15 |
| 1.3020 | B.80 | C.15 |
| 1.3021 | B.81 | C.15 |
| 1.3022 | B.82 | C.15 |
| 1.3023 | B.83 | C.15 |
| 1.3024 | B.84 | C.15 |
| 1.3025 | B.85 | C.15 |
| 1.3026 | B.86 | C.15 |
| 1.3027 | B.87 | C.15 |
| 1.3028 | B.88 | C.15 |
| 1.3029 | B.89 | C.15 |
| 1.3030 | B.90 | C.15 |
| 1.3031 | B.91 | C.15 |
| 1.3032 | B.92 | C.15 |
| 1.3033 | B.93 | C.15 |
| 1.3034 | B.94 | C.15 |
| 1.3035 | B.95 | C.15 |
| 1.3036 | B.96 | C.15 |
| 1.3037 | B.97 | C.15 |
| 1.3038 | B.98 | C.15 |
| 1.3039 | B.99 | C.15 |
| 1.3040 | B.100 | C.15 |
| 1.3041 | B.101 | C.15 |
| 1.3042 | B.102 | C.15 |
| 1.3043 | B.103 | C.15 |
| 1.3044 | B.104 | C.15 |
| 1.3045 | B.105 | C.15 |
| 1.3046 | B.106 | C.15 |
| 1.3047 | B.107 | C.15 |
| 1.3048 | B.108 | C.15 |
| 1.3049 | B.109 | C.15 |
| 1.3050 | B.110 | C.15 |
| 1.3051 | B.111 | C.15 |
| 1.3052 | B.112 | C.15 |
| 1.3053 | B.113 | C.15 |
| 1.3054 | B.114 | C.15 |
| 1.3055 | B.115 | C.15 |
| 1.3056 | B.116 | C.15 |
| 1.3057 | B.117 | C.15 |
| 1.3058 | B.118 | C.15 |
| 1.3059 | B.119 | C.15 |
| 1.3060 | B.120 | C.15 |
| 1.3061 | B.121 | C.15 |
| 1.3062 | B.122 | C.15 |
| 1.3063 | B.123 | C.15 |
| 1.3064 | B.124 | C.15 |
| 1.3065 | B.125 | C.15 |
| 1.3066 | B.126 | C.15 |
| 1.3067 | B.127 | C.15 |
| 1.3068 | B.128 | C.15 |
| 1.3069 | B.129 | C.15 |
| 1.3070 | B.130 | C.15 |
| 1.3071 | B.131 | C.15 |
| 1.3072 | B.132 | C.15 |
| 1.3073 | B.133 | C.15 |
| 1.3074 | B.134 | C.15 |
| 1.3075 | B.135 | C.15 |
| 1.3076 | B.136 | C.15 |
| 1.3077 | B.137 | C.15 |
| 1.3078 | B.138 | C.15 |
| 1.3079 | B.139 | C.15 |
| 1.3080 | B.140 | C.15 |
| 1.3081 | B.141 | C.15 |
| 1.3082 | B.142 | C.15 |
| 1.3083 | B.143 | C.15 |
| 1.3084 | B.144 | C.15 |
| 1.3085 | B.145 | C.15 |
| 1.3086 | B.146 | C.15 |
| 1.3087 | B.147 | C.15 |
| 1.3088 | B.148 | C.15 |
| 1.3089 | B.149 | C.15 |
| 1.3090 | B.150 | C.15 |
| 1.3091 | B.151 | C.15 |
| 1.3092 | B.152 | C.15 |
| 1.3093 | B.153 | C.15 |
| 1.3094 | B.154 | C.15 |
| 1.3095 | B.155 | C.15 |
| 1.3096 | B.156 | C.15 |
| 1.3097 | B.157 | C.15 |
| 1.3098 | B.158 | C.15 |
| 1.3099 | B.159 | C.15 |
| 1.3100 | B.160 | C.15 |
| 1.3101 | B.161 | C.15 |
| 1.3102 | B.162 | C.15 |
| 1.3103 | B.163 | C.15 |
| 1.3104 | B.164 | C.15 |
| 1.3105 | B.165 | C.15 |
| 1.3106 | B.166 | C.15 |
| 1.3107 | B.167 | C.15 |
| 1.3108 | B.168 | C.15 |
| 1.3109 | B.169 | C.15 |
| 1.3110 | B.170 | C.15 |
| 1.3111 | B.171 | C.15 |
| 1.3112 | B.172 | C.15 |
| 1.3113 | B.173 | C.15 |
| 1.3114 | B.174 | C.15 |
| 1.3115 | B.175 | C.15 |
| 1.3116 | B.176 | C.15 |
| 1.3117 | B.177 | C.15 |
| 1.3118 | B.178 | C.15 |
| 1.3119 | B.179 | C.15 |
| 1.3120 | B.180 | C.15 |
| 1.3121 | B.181 | C.15 |
| 1.3122 | B.182 | C.15 |
| 1.3123 | B.183 | C.15 |
| 1.3124 | B.184 | C.15 |
| 1.3125 | B.185 | C.15 |
| 1.3126 | B.186 | C.15 |
| 1.3127 | B.187 | C.15 |
| 1.3128 | B.188 | C.15 |
| 1.3129 | B.189 | C.15 |
| 1.3130 | B.190 | C.15 |
| 1.3131 | B.191 | C.15 |
| 1.3132 | B.192 | C.15 |
| 1.3133 | B.193 | C.15 |
| 1.3134 | B.194 | C.15 |
| 1.3135 | B.195 | C.15 |
| 1.3136 | B.196 | C.15 |
| 1.3137 | B.1 | C.16 |
| 1.3138 | B.2 | C.16 |
| 1.3139 | B.3 | C.16 |
| 1.3140 | B.4 | C.16 |
| 1.3141 | B.5 | C.16 |
| 1.3142 | B.6 | C.16 |
| 1.3143 | B.7 | C.16 |
| 1.3144 | B.8 | C.16 |
| 1.3145 | B.9 | C.16 |
| 1.3146 | B.10 | C.16 |
| 1.3147 | B.11 | C.16 |
| 1.3148 | B.12 | C.16 |
| 1.3149 | B.13 | C.16 |
| 1.3150 | B.14 | C.16 |
| 1.3151 | B.15 | C.16 |
| 1.3152 | B.16 | C.16 |
| 1.3153 | B.17 | C.16 |

TABLE 5-continued (compositions 1.1 to 1.3545):

| comp. no. | herbicide B | safener C |
|---|---|---|
| 1.3154 | B.18 | C.16 |
| 1.3155 | B.19 | C.16 |
| 1.3156 | B.20 | C.16 |
| 1.3157 | B.21 | C.16 |
| 1.3158 | B.22 | C.16 |
| 1.3159 | B.23 | C.16 |
| 1.3160 | B.24 | C.16 |
| 1.3161 | B.25 | C.16 |
| 1.3162 | B.26 | C.16 |
| 1.3163 | B.27 | C.16 |
| 1.3164 | B.28 | C.16 |
| 1.3165 | B.29 | C.16 |
| 1.3166 | B.30 | C.16 |
| 1.3167 | B.31 | C.16 |
| 1.3168 | B.32 | C.16 |
| 1.3169 | B.33 | C.16 |
| 1.3170 | B.34 | C.16 |
| 1.3171 | B.35 | C.16 |
| 1.3172 | B.36 | C.16 |
| 1.3173 | B.37 | C.16 |
| 1.3174 | B.38 | C.16 |
| 1.3175 | B.39 | C.16 |
| 1.3176 | B.40 | C.16 |
| 1.3177 | B.41 | C.16 |
| 1.3178 | B.42 | C.16 |
| 1.3179 | B.43 | C.16 |
| 1.3180 | B.44 | C.16 |
| 1.3181 | B.45 | C.16 |
| 1.3182 | B.46 | C.16 |
| 1.3183 | B.47 | C.16 |
| 1.3184 | B.48 | C.16 |
| 1.3185 | B.49 | C.16 |
| 1.3186 | B.50 | C.16 |
| 1.3187 | B.51 | C.16 |
| 1.3188 | B.52 | C.16 |
| 1.3189 | B.53 | C.16 |
| 1.3190 | B.54 | C.16 |
| 1.3191 | B.55 | C.16 |
| 1.3192 | B.56 | C.16 |
| 1.3193 | B.57 | C.16 |
| 1.3194 | B.58. | C.16 |
| 1.3195 | B.59 | C.16 |
| 1.3196 | B.60 | C.16 |
| 1.3197 | B.61 | C.16 |
| 1.3198 | B.62 | C.16 |
| 1.3199 | B.63 | C.16 |
| 1.3200 | B.64 | C.16 |
| 1.3201 | B.65 | C.16 |
| 1.3202 | B.66 | C.16 |
| 1.3203 | B.67 | C.16 |
| 1.3204 | B.68 | C.16 |
| 1.3205 | B.69 | C.16 |
| 1.3206 | B.70 | C.16 |
| 1.3207 | B.71 | C.16 |
| 1.3208 | B.72 | C.16 |
| 1.3209 | B.73 | C.16 |
| 1.3210 | B.74 | C.16 |
| 1.3211 | B.75 | C.16 |
| 1.3212 | B.76 | C.16 |
| 1.3213 | B.77 | C.16 |
| 1.3214 | B.78 | C.16 |
| 1.3215 | B.79 | C.16 |
| 1.3216 | B.80 | C.16 |
| 1.3217 | B.81 | C.16 |
| 1.3218 | B.82 | C.16 |
| 1.3219 | B.83 | C.16 |
| 1.3220 | B.84 | C.16 |
| 1.3221 | B.85 | C.16 |
| 1.3222 | B.86 | C.16 |
| 1.3223 | B.87 | C.16 |
| 1.3224 | B.88 | C.16 |
| 1.3225 | B.89 | C.16 |
| 1.3226 | B.90 | C.16 |
| 1.3227 | B.91 | C.16 |
| 1.3228 | B.92 | C.16 |
| 1.3229 | B.93 | C.16 |
| 1.3230 | B.94 | C.16 |
| 1.3231 | B.95 | C.16 |
| 1.3232 | B.96 | C.16 |
| 1.3233 | B.97 | C.16 |
| 1.3234 | B.98 | C.16 |
| 1.3235 | B.99 | C.16 |
| 1.3236 | B.100 | C.16 |
| 1.3237 | B.101 | C.16 |
| 1.3238 | B.102 | C.16 |
| 1.3239 | B.103 | C.16 |
| 1.3240 | B.104 | C.16 |
| 1.3241 | B.105 | C.16 |
| 1.3242 | B.106 | C.16 |
| 1.3243 | B.107 | C.16 |
| 1.3244 | B.108 | C.16 |
| 1.3245 | B.109 | C.16 |
| 1.3246 | B.110 | C.16 |
| 1.3247 | B.111 | C.16 |
| 1.3248 | B.112 | C.16 |
| 1.3249 | B.113 | C.16 |
| 1.3250 | B.114 | C.16 |
| 1.3251 | B.115 | C.16 |
| 1.3252 | B.116 | C.16 |
| 1.3253 | B.117 | C.16 |
| 1.3254 | B.118 | C.16 |
| 1.3255 | B.119 | C.16 |
| 1.3256 | B.120 | C.16 |
| 1.3257 | B.121 | C.16 |
| 1.3258 | B.122 | C.16 |
| 1.3259 | B.123 | C.16 |
| 1.3260 | B.124 | C.16 |
| 1.3261 | B.125 | C.16 |
| 1.3262 | B.126 | C.16 |
| 1.3263 | B.127 | C.16 |
| 1.3264 | B.128 | C.16 |
| 1.3265 | B.129 | C.16 |
| 1.3266 | B.130 | C.16 |
| 1.3267 | B.131 | C.16 |
| 1.3268 | B.132 | C.16 |
| 1.3269 | B.133 | C.16 |
| 1.3270 | B.134 | C.16 |
| 1.3271 | B.135 | C.16 |
| 1.3272 | B.136 | C.16 |
| 1.3273 | B.137 | C.16 |
| 1.3274 | B.138 | C.16 |
| 1.3275 | B.139 | C.16 |
| 1.3276 | B.140 | C.16 |
| 1.3277 | B.141 | C.16 |
| 1.3278 | B.142 | C.16 |
| 1.3279 | B.143 | C.16 |
| 1.3280 | B.144 | C.16 |
| 1.3281 | B.145 | C.16 |
| 1.3282 | B.146 | C.16 |
| 1.3283 | B.147 | C.16 |
| 1.3284 | B.148 | C.16 |
| 1.3285 | B.149 | C.16 |
| 1.3286 | B.150 | C.16 |
| 1.3287 | B.151 | C.16 |
| 1.3288 | B.152 | C.16 |
| 1.3289 | B.153 | C.16 |
| 1.3290 | B.154 | C.16 |
| 1.3291 | B.155 | C.16 |
| 1.3292 | B.156 | C.16 |
| 1.3293 | B.157 | C.16 |
| 1.3294 | B.158 | C.16 |
| 1.3295 | B.159 | C.16 |
| 1.3296 | B.160 | C.16 |
| 1.3297 | B.161 | C.16 |
| 1.3298 | B.162 | C.16 |
| 1.3299 | B.163 | C.16 |
| 1.3300 | B.164 | C.16 |
| 1.3301 | B.165 | C.16 |
| 1.3302 | B.166 | C.16 |
| 1.3303 | B.167 | C.16 |

TABLE 5-continued (compositions 1.1 to 1.3545):

| comp. no. | herbicide B | safener C |
|---|---|---|
| 1.3304 | B.168 | C.16 |
| 1.3305 | B.169 | C.16 |
| 1.3306 | B.170 | C.16 |
| 1.3307 | B.171 | C.16 |
| 1.3308 | B.172 | C.16 |
| 1.3309 | B.173 | C.16 |
| 1.3310 | B.174 | C.16 |
| 1.3311 | B.175 | C.16 |
| 1.3312 | B.176 | C.16 |
| 1.3313 | B.177 | C.16 |
| 1.3314 | B.178 | C.16 |
| 1.3315 | B.179 | C.16 |
| 1.3316 | B.180 | C.16 |
| 1.3317 | B.181 | C.16 |
| 1.3318 | B.182 | C.16 |
| 1.3319 | B.183 | C.16 |
| 1.3320 | B.184 | C.16 |
| 1.3321 | B.185 | C.16 |
| 1.3322 | B.186 | C.16 |
| 1.3323 | B.187 | C.16 |
| 1.3324 | B.188 | C.16 |
| 1.3325 | B.189 | C.16 |
| 1.3326 | B.190 | C.16 |
| 1.3327 | B.191 | C.16 |
| 1.3328 | B.192 | C.16 |
| 1.3329 | B.193 | C.16 |
| 1.3330 | B.194 | C.16 |
| 1.3331 | B.195 | C.16 |
| 1.3332 | B.196 | C.16 |
| 1.3333 | B.1 | C.17 |
| 1.3334 | B.2 | C.17 |
| 1.3335 | B.3 | C.17 |
| 1.3336 | B.4 | C.17 |
| 1.3337 | B.5 | C.17 |
| 1.3338 | B.6 | C.17 |
| 1.3339 | B.7 | C.17 |
| 1.3340 | B.8 | C.17 |
| 1.3341 | B.9 | C.17 |
| 1.3342 | B.10 | C.17 |
| 1.3343 | B.11 | C.17 |
| 1.3344 | B.12 | C.17 |
| 1.3345 | B.13 | C.17 |
| 1.3346 | B.14 | C.17 |
| 1.3347 | B.15 | C.17 |
| 1.3348 | B.16 | C.17 |
| 1.3349 | B.17 | C.17 |
| 1.3350 | B.18 | C.17 |
| 1.3351 | B.19 | C.17 |
| 1.3352 | B.20 | C.17 |
| 1.3353 | B.21 | C.17 |
| 1.3354 | B.22 | C.17 |
| 1.3355 | B.23 | C.17 |
| 1.3356 | B.24 | C.17 |
| 1.3357 | B.25 | C.17 |
| 1.3358 | B.26 | C.17 |
| 1.3359 | B.27 | C.17 |
| 1.3360 | B.28 | C.17 |
| 1.3361 | B.29 | C.17 |
| 1.3362 | B.30 | C.17 |
| 1.3363 | B.31 | C.17 |
| 1.3364 | B.32 | C.17 |
| 1.3365 | B.33 | C.17 |
| 1.3366 | B.34 | C.17 |
| 1.3367 | B.35 | C.17 |
| 1.3368 | B.36 | C.17 |
| 1.3369 | B.37 | C.17 |
| 1.3370 | B.38 | C.17 |
| 1.3371 | B.39 | C.17 |
| 1.3372 | B.40 | C.17 |
| 1.3373 | B.41 | C.17 |
| 1.3374 | B.42 | C.17 |
| 1.3375 | B.43 | C.17 |
| 1.3376 | B.44 | C.17 |
| 1.3377 | B.45 | C.17 |
| 1.3378 | B.46 | C.17 |
| 1.3379 | B.47 | C.17 |
| 1.3380 | B.48 | C.17 |
| 1.3381 | B.49 | C.17 |
| 1.3382 | B.50 | C.17 |
| 1.3383 | B.51 | C.17 |
| 1.3384 | B.52 | C.17 |
| 1.3385 | B.53 | C.17 |
| 1.3386 | B.54 | C.17 |
| 1.3387 | B.55 | C.17 |
| 1.3388 | B.56 | C.17 |
| 1.3389 | B.57 | C.17 |
| 1.3390 | B.58. | C.17 |
| 1.3391 | B.59 | C.17 |
| 1.3392 | B.60 | C.17 |
| 1.3393 | B.61 | C.17 |
| 1.3394 | B.62 | C.17 |
| 1.3395 | B.63 | C.17 |
| 1.3396 | B.64 | C.17 |
| 1.3397 | B.65 | C.17 |
| 1.3398 | B.66 | C.17 |
| 1.3399 | B.67 | C.17 |
| 1.3400 | B.68 | C.17 |
| 1.3401 | B.69 | C.17 |
| 1.3402 | B.70 | C.17 |
| 1.3403 | B.71 | C.17 |
| 1.3404 | B.72 | C.17 |
| 1.3405 | B.73 | C.17 |
| 1.3406 | B.74 | C.17 |
| 1.3407 | B.75 | C.17 |
| 1.3408 | B.76 | C.17 |
| 1.3409 | B.77 | C.17 |
| 1.3410 | B.78 | C.17 |
| 1.3411 | B.79 | C.17 |
| 1.3412 | B.80 | C.17 |
| 1.3413 | B.81 | C.17 |
| 1.3414 | B.82 | C.17 |
| 1.3415 | B.83 | C.17 |
| 1.3416 | B.84 | C.17 |
| 1.3417 | B.85 | C.17 |
| 1.3418 | B.86 | C.17 |
| 1.3419 | B.87 | C.17 |
| 1.3420 | B.88 | C.17 |
| 1.3421 | B.89 | C.17 |
| 1.3422 | B.90 | C.17 |
| 1.3423 | B.91 | C.17 |
| 1.3424 | B.92 | C.17 |
| 1.3425 | B.93 | C.17 |
| 1.3426 | B.94 | C.17 |
| 1.3427 | B.95 | C.17 |
| 1.3428 | B.96 | C.17 |
| 1.3429 | B.97 | C.17 |
| 1.3430 | B.98 | C.17 |
| 1.3431 | B.99 | C.17 |
| 1.3432 | B.100 | C.17 |
| 1.3433 | B.101 | C.17 |
| 1.3434 | B.102 | C.17 |
| 1.3435 | B.103 | C.17 |
| 1.3436 | B.104 | C.17 |
| 1.3437 | B.105 | C.17 |
| 1.3438 | B.106 | C.17 |
| 1.3439 | B.107 | C.17 |
| 1.3440 | B.108 | C.17 |
| 1.3441 | B.109 | C.17 |
| 1.3442 | B.110 | C.17 |
| 1.3443 | B.111 | C.17 |
| 1.3444 | B.112 | C.17 |
| 1.3445 | B.113 | C.17 |
| 1.3446 | B.114 | C.17 |
| 1.3447 | B.115 | C.17 |
| 1.3448 | B.116 | C.17 |
| 1.3449 | B.117 | C.17 |
| 1.3450 | B.118 | C.17 |
| 1.3451 | B.119 | C.17 |
| 1.3452 | B.120 | C.17 |
| 1.3453 | B.121 | C.17 |

TABLE 5-continued (compositions 1.1 to 1.3545):

| comp. no. | herbicide B | safener C |
|---|---|---|
| 1.3454 | B.122 | C.17 |
| 1.3455 | B.123 | C.17 |
| 1.3456 | B.124 | C.17 |
| 1.3457 | B.125 | C.17 |
| 1.3458 | B.126 | C.17 |
| 1.3459 | B.127 | C.17 |
| 1.3460 | B.128 | C.17 |
| 1.3461 | B.129 | C.17 |
| 1.3462 | B.130 | C.17 |
| 1.3463 | B.131 | C.17 |
| 1.3464 | B.132 | C.17 |
| 1.3465 | B.133 | C.17 |
| 1.3466 | B.134 | C.17 |
| 1.3467 | B.135 | C.17 |
| 1.3468 | B.136 | C.17 |
| 1.3469 | B.137 | C.17 |
| 1.3470 | B.138 | C.17 |
| 1.3471 | B.139 | C.17 |
| 1.3472 | B.140 | C.17 |
| 1.3473 | B.141 | C.17 |
| 1.3474 | B.142 | C.17 |
| 1.3475 | B.143 | C.17 |
| 1.3476 | B.144 | C.17 |
| 1.3477 | B.145 | C.17 |
| 1.3478 | B.146 | C.17 |
| 1.3479 | B.147 | C.17 |
| 1.3480 | B.148 | C.17 |
| 1.3481 | B.149 | C.17 |
| 1.3482 | B.150 | C.17 |
| 1.3483 | B.151 | C.17 |
| 1.3484 | B.152 | C.17 |
| 1.3485 | B.153 | C.17 |
| 1.3486 | B.154 | C.17 |
| 1.3487 | B.155 | C.17 |
| 1.3488 | B.156 | C.17 |
| 1.3489 | B.157 | C.17 |
| 1.3490 | B.158 | C.17 |
| 1.3491 | B.159 | C.17 |
| 1.3492 | B.160 | C.17 |
| 1.3493 | B.161 | C.17 |
| 1.3494 | B.162 | C.17 |
| 1.3495 | B.163 | C.17 |
| 1.3496 | B.164 | C.17 |
| 1.3497 | B.165 | C.17 |
| 1.3498 | B.166 | C.17 |
| 1.3499 | B.167 | C.17 |
| 1.3500 | B.168 | C.17 |
| 1.3501 | B.169 | C.17 |
| 1.3502 | B.170 | C.17 |
| 1.3503 | B.171 | C.17 |
| 1.3504 | B.172 | C.17 |
| 1.3505 | B.173 | C.17 |
| 1.3506 | B.174 | C.17 |
| 1.3507 | B.175 | C.17 |
| 1.3508 | B.176 | C.17 |
| 1.3509 | B.177 | C.17 |
| 1.3510 | B.178 | C.17 |
| 1.3511 | B.179 | C.17 |
| 1.3512 | B.180 | C.17 |
| 1.3513 | B.181 | C.17 |
| 1.3514 | B.182 | C.17 |
| 1.3515 | B.183 | C.17 |
| 1.3516 | B.184 | C.17 |
| 1.3517 | B.185 | C.17 |
| 1.3518 | B.186 | C.17 |
| 1.3519 | B.187 | C.17 |
| 1.3520 | B.188 | C.17 |
| 1.3521 | B.189 | C.17 |
| 1.3522 | B.190 | C.17 |
| 1.3523 | B.191 | C.17 |
| 1.3524 | B.192 | C.17 |
| 1.3525 | B.193 | C.17 |
| 1.3526 | B.194 | C.17 |
| 1.3527 | B.195 | C.17 |
| 1.3528 | B.196 | C.17 |
| 1.3529 | — | C.1 |
| 1.3530 | — | C.2 |
| 1.3531 | — | C.3 |
| 1.3532 | — | C.4 |
| 1.3533 | — | C.5 |
| 1.3534 | — | C.6 |
| 1.3535 | — | C.7 |
| 1.3536 | — | C.8 |
| 1.3537 | — | C.9 |
| 1.3538 | — | C.10 |
| 1.3539 | — | C.11 |
| 1.3540 | — | C.12 |
| 1.3541 | — | C.13 |
| 1.3542 | — | C.14 |
| 1.3543 | — | C.15 |
| 1.3544 | — | C.16 |
| 1.3545 | — | C.17 |

The specific number for each single combination is deductible as follows: combinations 1.200 for example comprises the compound of formula (I), cyhalofop-butyl (B.4) and benoxacor (C.1) (see table 1, entry 1.200; as well as table B, entry B.4 and table C, entry C.1).

Combination 2.200 for example comprises the compound (I) (see the definition for combination 2.1 to 2.3545 below), cyhalofop-butyl (B.4) and benoxacor (C.1) (see table 1, entry 1.200; as well as table B, entry B.4 and table C, entry C.1).

Composition 7.200 for example comprises imazapyr (B.35) (see the definition for compositions 7.1 to 7.3545 below), and the compound (I), cyhalofop-butyl (B.4) and benoxacor (C.1) (see table 1, entry 1.200; as well as table B, entry B.4 and table C, entry C.1).

Also especially preferred are combinations 1a.1. to 1a.3545 which differ from the corresponding combinations 1.1 to 1.3545 only in that they comprise as the active compound a), which is defined in row B.1 of table 4.

Also especially preferred are combinations 11b.1. to 11b.3545 which differ from the corresponding combinations 1.1 to 1.3545 only in that they comprise as the active compound a), which is defined in row B.2 of table 4.

Also especially preferred are combinations 1c.1. to 1c.3545 which differ from the corresponding combinations 1.1 to 1.3545 only in that they comprise as the active compound a), which is defined in row B.3 of table 4.

Also especially preferred are combinations 1d.1. to 1d.3545 which differ from the corresponding combinations 1.1 to 1.3545 only in that they comprise as the active compound a), which is defined in row B.4 of table 4.

Also especially preferred are combinations 2.1. to 2.3545 which differ from the corresponding combinations 1.1 to 1.3545 only in that they comprise as the active compound a), which is a compound of formula (I).

Also especially preferred are combinations 2a.1. to 2a.3545 which differ from the corresponding combinations 1.1 to 1.3545 only in that they comprise as the active compound a), which is defined in row B.1 of table 4.

Also especially preferred are combinations 2b.1. to 2b.3545 which differ from the corresponding combinations 1.1 to 1.3545 only in that they comprise as the active compound a), which is defined in row B.2 of table 4.

Also especially preferred are combinations 2c.1. to 2c.3545 which differ from the corresponding combinations 1.1 to 1.3545 only in that they comprise as the active compound a), which is defined in row B.3 of table 4.

Also especially preferred are combinations 2d.1. to 2d.3545 which differ from the corresponding combinations 1.1 to 1.3545 only in that they comprise as the active compound a), which is defined in row B.4 of table 4.

Also especially preferred are combinations 3.1. to 3.3545 which differ from the corresponding combinations 1.1 to 1.3545 only in that they additionally comprise B.2 clodinafop-propargyl as further herbicide B.

Also especially preferred are combinations 3a.1. to 3a.3545 which differ from the corresponding combinations 1.1 to 1.3545 only in that they additionally comprise B.2 clodinafop-propargyl as further herbicide B.

Also especially preferred are combinations 3a.1. to 3a.3545 which differ from the corresponding combinations 1.1 to 1.3545 only in that they additionally comprise B.2 clodinafop-propargyl as further herbicide B and the active component a) is defined in row B.1 of table 4.

Also especially preferred are combinations 3b.1. to 3b.3545 which differ from the corresponding combinations 1.1 to 1.3545 only in that they additionally comprise B.2 clodinafop-propargyl as further herbicide B and the active component a) is defined in row B.2 of table 4.

Also especially preferred are combinations 3c.1. to 3c.3545 which differ from the corresponding combinations 1.1 to 1.3545 only in that they additionally comprise B.2 clodinafop-propargyl as further herbicide B and the active component a) is defined in row B.3 of table 4.

Also especially preferred are combinations 3d.1. to 3d.3545 which differ from the corresponding combinations 1.1 to 1.3545 only in that they additionally comprise B.2 clodinafop-propargyl as further herbicide B and the active component a) is defined in row B.4 of table 4.

Also especially preferred are combinations 4.1. to 4.3545 which differ from the corresponding combinations 1.1 to 1.3545 only in that they additionally comprise B.8 pinoxaden as further herbicide B.

Also especially preferred are combinations 4a.1. to 4a.3545 which differ from the corresponding combinations 1.1 to 1.3545 only in that they additionally comprise B.8 pinoxaden as further herbicide B and the active component a) is defined in row B.1 of table 4.

Also especially preferred are combinations 4b.1. to 4b.3545 which differ from the corresponding combinations 1.1 to 1.3545 only in that they additionally comprise B.8 pinoxaden as further herbicide B and the active component a) is defined in row B.2 of table 4.

Also especially preferred are combinations 4c.1. to 4c.3545 which differ from the corresponding combinations 1.1 to 1.3545 only in that they additionally comprise B.8 pinoxaden as further herbicide B and the active component a) is defined in row B.3 of table 4.

Also especially preferred are combinations 4d.1. to 4d.3545 which differ from the corresponding combinations 1.1 to 1.3545 only in that they additionally comprise B.8 pinoxaden as further herbicide B and the active component a) is defined in row B.4 of table 4.

Also especially preferred are combinations 5.1. to 5.3545 which differ from the corresponding combinations 1.1 to 1.3545 only in that they additionally comprise B.30 imazamox as further herbicide B.

Also especially preferred are combinations 5a.1. to 5a.3545 which differ from the corresponding combinations 1.1 to 1.3545 only in that they additionally comprise B.30 imazamox as further herbicide B and the active component a) is defined in row B.1 of table 4.

Also especially preferred are combinations 5b.1. to 5b.3545 which differ from the corresponding combinations 1.1 to 1.3545 only in that they additionally comprise B.30 imazamox as further herbicide B and the active component a) is defined in row B.2 of table 4.

Also especially preferred are combinations 5c.1. to 5c.3545 which differ from the corresponding combinations 1.1 to 1.3545 only in that they additionally comprise B.30 imazamox as further herbicide B and the active component a) is defined in row B.3 of table 4.

Also especially preferred are combinations 5d.1. to 5d.3545 which differ from the corresponding combinations 1.1 to 1.3545 only in that they additionally comprise B.30 imazamox as further herbicide B and the active component a) is defined in row B.4 of table 4.

Also especially preferred are combinations 6.1. to 6.3545 which differ from the corresponding combinations 1.1 to 1.3545 only in that they additionally comprise B.32 imazapic as further herbicide B.

Also especially preferred are combinations 6a.1. to 6a.3545 which differ from the corresponding combinations 1.1 to 1.3545 only in that they additionally comprise B.32 imazapic as further herbicide B and the active component a) is defined in row B.1 of table 4.

Also especially preferred are combinations 6b.1. to 6b.3545 which differ from the corresponding combinations 1.1 to 1.3545 only in that they additionally comprise B.32 imazapic as further herbicide B and the active component a) is defined in row B.2 of table 4.

Also especially preferred are combinations 6c.1. to 6c.3545 which differ from the corresponding combinations 1.1 to 1.3545 only in that they additionally comprise B.32 imazapic as further herbicide B and the active component a) is defined in row B.3 of table 4.

Also especially preferred are combinations 6d.1. to 6d.3545 which differ from the corresponding combinations 1.1 to 1.3545 only in that they additionally comprise B.32 imazapic as further herbicide B and the active component a) is defined in row B.4 of table 4.

Also especially preferred are combinations 7.1. to 7.3545 which differ from the corresponding combinations 1.1 to 1.3545 only in that they additionally comprise B.35 imazapyr as further herbicide B.

Also especially preferred are combinations 7a.1. to 7a.3545 which differ from the corresponding combinations 1.1 to 1.3545 only in that they additionally comprise B.35 imazapyr as further herbicide B and the active component a) is defined in row B.1 of table 4.

Also especially preferred are combinations 7b.1. to 7b.3545 which differ from the corresponding combinations 1.1 to 1.3545 only in that they additionally comprise B.35 imazapyr as further herbicide B and the active component a) is defined in row B.2 of table 4.

Also especially preferred are combinations 7c.1. to 7c.3545 which differ from the corresponding combinations 1.1 to 1.3545 only in that they additionally comprise B.35 imazapyr as further herbicide B and the active component a) is defined in row B.3 of table 4.

Also especially preferred are combinations 7d.1. to 7d.3545 which differ from the corresponding combinations 1.1 to 1.3545 only in that they additionally comprise B.35 imazapyr as further herbicide B and the active component a) is defined in row B.4 of table 4.

Also especially preferred are combinations 8.1. to 8.3545 which differ from the corresponding combinations 1.1 to 1.3545 only in that they additionally comprise B.38 imazaquin as further herbicide B.

Also especially preferred are combinations 8a.1. to 8a.3545 which differ from the corresponding combinations 1.1 to 1.3545 only in that they additionally comprise B.38 imazaquin as further herbicide B and the active component a) is defined in row B.1 of table 4.

Also especially preferred are combinations 8b.1. to 8b.3545 which differ from the corresponding combinations 1.1 to 1.3545 only in that they additionally comprise B.38 imazaquin as further herbicide B and the active component a) is defined in row B.2 of table 4.

Also especially preferred are combinations 8c.1. to 8c.3545 which differ from the corresponding combinations 1.1 to 1.3545 only in that they additionally comprise B.38 imazaquin as further herbicide B and the active component a) is defined in row B.3 of table 4.

Also especially preferred are combinations 8d.1. to 8d.3545 which differ from the corresponding combinations 1.1 to 1.3545 only in that they additionally comprise B.38 imazaquin as further herbicide B and the active component a) is defined in row B.4 of table 4.

Also especially preferred are combinations 9.1. to 9.3545 which differ from the corresponding combinations 1.1 to 1.3545 only in that they additionally comprise B.40 imazethapyr as further herbicide B.

Also especially preferred are combinations 9a.1. to 9a.3545 which differ from the corresponding combinations 1.1 to 1.3545 only in that they additionally comprise B.40 imazethapyr as further herbicide B and the active component a) is defined in row B.1 of table 4.

Also especially preferred are combinations 9b.1. to 9b.3545 which differ from the corresponding combinations 1.1 to 1.3545 only in that they additionally comprise B.40 imazethapyr as further herbicide B and the active component a) is defined in row B.2 of table 4.

Also especially preferred are combinations 9c.1. to 9c.3545 which differ from the corresponding combinations 1.1 to 1.3545 only in that they additionally comprise B.40 imazethapyr as further herbicide B and the active component a) is defined in row B.3 of table 4.

Also especially preferred are combinations 9d.1. to 9d.3545 which differ from the corresponding combinations 1.1 to 1.3545 only in that they additionally comprise B.40 imazethapyr as further herbicide B and the active component a) is defined in row B.4 of table 4.

Also especially preferred are combinations 10.1. to 10.3545 which differ from the corresponding combinations 1.1 to 1.3545 only in that they additionally comprise B.51 nicosulfuron as further herbicide B.

Also especially preferred are combinations 10a.1. to 10a.3545 which differ from the corresponding combinations 1.1 to 1.3545 only in that they additionally comprise B.51 nicosulfuron as further herbicide B and the active component a) is defined in row B.1 of table 4.

Also especially preferred are combinations 10b.1. to 10b.3545 which differ from the corresponding combinations 1.1 to 1.3545 only in that they additionally comprise B.51 nicosulfuron as further herbicide B and the active component a) is defined in row B.2 of table 4.

Also especially preferred are combinations 10c.1. to 10c.3545 which differ from the corresponding combinations 1.1 to 1.3545 only in that they additionally comprise B.51 nicosulfuron as further herbicide B and the active component a) is defined in row B.3 of table 4.

Also especially preferred are combinations 10d.1. to 10d.3545 which differ from the corresponding combinations 1.1 to 1.3545 only in that they additionally comprise B.51 nicosulfuron as further herbicide B and the active component a) is defined in row B.4 of table 4.

Also especially preferred are combinations 11.1. to 11.3545 which differ from the corresponding combinations 1.1 to 1.3545 only in that they additionally comprise B.55 pyribenzoxim as further herbicide B.

Also especially preferred are combinations 11a.1. to 11a.3545 which differ from the corresponding combinations 1.1 to 1.3545 only in that they additionally comprise B.55 pyribenzoxim as further herbicide B and the active component a) is defined in row B.1 of table 4.

Also especially preferred are combinations 11b.1. to 11b.3545 which differ from the corresponding combinations 1.1 to 1.3545 only in that they additionally comprise B.55 pyribenzoxim as further herbicide B and the active component a) is defined in row B.2 of table 4.

Also especially preferred are combinations 11c.1. to 11c.3545 which differ from the corresponding combinations 1.1 to 1.3545 only in that they additionally comprise B.55 pyribenzoxim as further herbicide B and the active component a) is defined in row B.3 of table 4.

Also especially preferred are combinations 1 d.1. to 1 d.3545 which differ from the corresponding combinations 1.1 to 1.3545 only in that they additionally comprise B.55 pyribenzoxim as further herbicide B and the active component a) is defined in row B.4 of table 4.

Also especially preferred are combinations 12.1. to 12.3545 which differ from the corresponding combinations 1.1 to 1.3545 only in that they additionally comprise B.56 pyriftalid as further herbicide B.

Also especially preferred are combinations 12a.1. to 12a.3545 which differ from the corresponding combinations 1.1 to 1.3545 only in that they additionally comprise B.56 pyriftalid as further herbicide B and the active component a) is defined in row B.1 of table 4.

Also especially preferred are combinations 12b.1. to 12b.3545 which differ from the corresponding combinations 1.1 to 1.3545 only in that they additionally comprise B.56 pyriftalid as further herbicide B and the active component a) is defined in row B.2 of table 4.

Also especially preferred are combinations 12c.1. to 12c.3545 which differ from the corresponding combinations 1.1 to 1.3545 only in that they additionally comprise B.56 pyriftalid as further herbicide B and the active component a) is defined in row B.3 of table 4.

Also especially preferred are combinations 12d.1. to 12d.3545 which differ from the corresponding combinations 1.1 to 1.3545 only in that they additionally comprise B.56 pyriftalid as further herbicide B and the active component a) is defined in row B.4 of table 4.

Also especially preferred are combinations 13.1. to 13.3545 which differ from the corresponding combinations 1.1 to 1.3545 only in that they additionally comprise B.64 tritosulfuron as further herbicide B.

Also especially preferred are combinations 13a.1. to 13a.3545 which differ from the corresponding combinations 1.1 to 1.3545 only in that they additionally comprise B.64 tritosulfuron as further herbicide B and the active component a) is defined in row B.1 of table 4.

Also especially preferred are combinations 13b.1. to 13b.3545 which differ from the corresponding combinations 1.1 to 1.3545 only in that they additionally comprise B.64 tritosulfuron as further herbicide B and the active component a) is defined in row B.2 of table 4.

Also especially preferred are combinations 13c.1. to 13c.3545 which differ from the corresponding combinations 1.1 to 1.3545 only in that they additionally comprise B.64 tritosulfuron as further herbicide B and the active component a) is defined in row B.3 of table 4.

Also especially preferred are combinations 13d.1. to 13d.3545 which differ from the corresponding combinations 1.1 to 1.3545 only in that they additionally comprise B.64 tritosulfuron as further herbicide B and the active component a) is defined in row B.4 of table 4.

Also especially preferred are combinations 14.1. to 14.3545 which differ from the corresponding combinations 1.1 to 1.3545 only in that they additionally comprise B.66 ametryne as further herbicide B.

Also especially preferred are combinations 14a.1. to 14a.3545 which differ from the corresponding combinations 1.1 to 1.3545 only in that they additionally comprise B.66 ametryne as further herbicide B and the active component a) is defined in row B.1 of table 4.

Also especially preferred are combinations 14b.1. to 14b.3545 which differ from the corresponding combinations 1.1 to 1.3545 only in that they additionally comprise B.66 ametryne as further herbicide B and the active component a) is defined in row B.2 of table 4.

Also especially preferred are combinations 14c.1. to 14c.3545 which differ from the corresponding combinations 1.1 to 1.3545 only in that they additionally comprise B.66 ametryne as further herbicide B and the active component a) is defined in row B.3 of table 4.

Also especially preferred are combinations 14d.1. to 14d.3545 which differ from the corresponding combinations 1.1 to 1.3545 only in that they additionally comprise B.66 ametryne as further herbicide B and the active component a) is defined in row B.4 of table 4.

Also especially preferred are combinations 15.1. to 15.3545 which differ from the corresponding combinations 1.1 to 1.3545 only in that they additionally comprise B.67 atrazine as further herbicide B.

Also especially preferred are combinations 15a.1. to 15a.3545 which differ from the corresponding combinations 1.1 to 1.3545 only in that they additionally comprise B.67 atrazine as further herbicide B and the active component a) is defined in row B.1 of table 4.

Also especially preferred are combinations 15b.1. to 15b.3545 which differ from the corresponding combinations 1.1 to 1.3545 only in that they additionally comprise B.67 atrazine as further herbicide B and the active component a) is defined in row B.2 of table 4.

Also especially preferred are combinations 15c.1. to 15c.3545 which differ from the corresponding combinations 1.1 to 1.3545 only in that they additionally comprise B.67 atrazine as further herbicide B and the active component a) is defined in row B.3 of table 4.

Also especially preferred are combinations 15d.1. to 15d.3545 which differ from the corresponding combinations 1.1 to 1.3545 only in that they additionally comprise B.67 atrazine as further herbicide B and the active component a) is defined in row B.4 of table 4.

Also especially preferred are combinations 16.1. to 16.3545 which differ from the corresponding combinations 1.1 to 1.3545 only in that they additionally comprise B.68 bentazon as further herbicide B.

Also especially preferred are combinations 16a.1. to 16a.3545 which differ from the corresponding combinations 1.1 to 1.3545 only in that they additionally comprise B.68 bentazon as further herbicide B and the active component a) is defined in row B.1 of table 4.

Also especially preferred are combinations 16b.1. to 16b.3545 which differ from the corresponding combinations 1.1 to 1.3545 only in that they additionally comprise B.68 bentazon as further herbicide B and the active component a) is defined in row B.2 of table 4.

Also especially preferred are combinations 16c.1. to 16c.3545 which differ from the corresponding combinations 1.1 to 1.3545 only in that they additionally comprise B.68 bentazon as further herbicide B and the active component a) is defined in row B.3 of table 4.

Also especially preferred are combinations 16d.1. to 16d.3545 which differ from the corresponding combinations 1.1 to 1.3545 only in that they additionally comprise B.68 bentazon as further herbicide B and the active component a) is defined in row B.4 of table 4.

Also especially preferred are combinations 17.1. to 17.3545 which differ from the corresponding combinations 1.1 to 1.3545 only in that they additionally comprise B.69 bromoxynil as further herbicide B.

Also especially preferred are combinations 17a.1. to 17a.3545 which differ from the corresponding combinations 1.1 to 1.3545 only in that they additionally comprise B.69 bromoxynil as further herbicide B and the active component a) is defined in row B.1 of table 4.

Also especially preferred are combinations 17b.1. to 17b.3545 which differ from the corresponding combinations 1.1 to 1.3545 only in that they additionally comprise B.69 bromoxynil as further herbicide B and the active component a) is defined in row B.2 of table 4.

Also especially preferred are combinations 17c.1. to 17c.3545 which differ from the corresponding combinations 1.1 to 1.3545 only in that they additionally comprise B.69 bromoxynil as further herbicide B and the active component a) is defined in row B.3 of table 4.

Also especially preferred are combinations 17d.1. to 17d.3545 which differ from the corresponding combinations 1.1 to 1.3545 only in that they additionally comprise B.69 bromoxynil as further herbicide B and the active component a) is defined in row B.4 of table 4.

Also especially preferred are combinations 18.1. to 18.3545 which differ from the corresponding combinations 1.1 to 1.3545 only in that they additionally comprise B.73 diuron as further herbicide B.

Also especially preferred are combinations 18a.1. to 18a.3545 which differ from the corresponding combinations 1.1 to 1.3545 only in that they additionally comprise B.73 diuron as further herbicide B and the active component a) is defined in row B.1 of table 4.

Also especially preferred are combinations 18b.1. to 18b.3545 which differ from the corresponding combinations 1.1 to 1.3545 only in that they additionally comprise B.73 diuron as further herbicide B and the active component a) is defined in row B.2 of table 4.

Also especially preferred are combinations 18c.1. to 18c.3545 which differ from the corresponding combinations 1.1 to 1.3545 only in that they additionally comprise B.73 diuron as further herbicide B and the active component a) is defined in row B.3 of table 4.

Also especially preferred are combinations 18d.1. to 18d.3545 which differ from the corresponding combinations 1.1 to 1.3545 only in that they additionally comprise B.73 diuron as further herbicide B and the active component a) is defined in row B.4 of table 4.

Also especially preferred are combinations 19.1. to 19.3545 which differ from the corresponding combinations 1.1 to 1.3545 only in that they additionally comprise B.76 isoproturon as further herbicide B.

Also especially preferred are combinations 19a.1. to 19a.3545 which differ from the corresponding combinations 1.1 to 1.3545 only in that they additionally comprise B.76 isoproturon as further herbicide B and the active component a) is defined in row B.1 of table 4.

Also especially preferred are combinations 19b.1. to 19b.3545 which differ from the corresponding combinations 1.1 to 1.3545 only in that they additionally comprise B.76 isoproturon as further herbicide B and the active component a) is defined in row B.2 of table 4.

Also especially preferred are combinations 19c.1. to 19c.3545 which differ from the corresponding combinations 1.1 to 1.3545 only in that they additionally comprise B.76 isoproturon as further herbicide B and the active component a) is defined in row B.3 of table 4.

Also especially preferred are combinations 19d.1. to 19d.3545 which differ from the corresponding combinations 1.1 to 1.3545 only in that they additionally comprise B.76 isoproturon as further herbicide B and the active component a) is defined in row B.4 of table 4.

Also especially preferred are combinations 20.1. to 20.3545 which differ from the corresponding combinations 1.1 to 1.3545 only in that they additionally comprise B.81 simazin as further herbicide B.

Also especially preferred are combinations 20a.1. to 20a.3545 which differ from the corresponding combinations 1.1 to 1.3545 only in that they additionally comprise B.81 simazin as further herbicide B and the active component a) is defined in row B.1 of table 4.

Also especially preferred are combinations 20b.1. to 20b.3545 which differ from the corresponding combinations 1.1 to 1.3545 only in that they additionally comprise B.81 simazin as further herbicide B and the active component a) is defined in row B.2 of table 4.

Also especially preferred are combinations 20c.1. to 20c.3545 which differ from the corresponding combinations 1.1 to 1.3545 only in that they additionally comprise B.81 simazin as further herbicide B and the active component a) is defined in row B.3 of table 4.

Also especially preferred are combinations 20d.1. to 20d.3545 which differ from the corresponding combinations 1.1 to 1.3545 only in that they additionally comprise B.81 simazin as further herbicide B and the active component a) is defined in row B.4 of table 4.

Also especially preferred are combinations 21.1. to 21.3545 which differ from the corresponding combinations 1.1 to 1.3545 only in that they additionally comprise B.82 terbuthylazin as further herbicide B.

Also especially preferred are combinations 21a.1. to 21a.3545 which differ from the corresponding combinations 1.1 to 1.3545 only in that they additionally comprise B.82 terbuthylazin as further herbicide B and the active component a) is defined in row B.1 of table 4.

Also especially preferred are combinations 21b.1. to 21b.3545 which differ from the corresponding combinations 1.1 to 1.3545 only in that they additionally comprise B.82 terbuthylazin as further herbicide B and the active component a) is defined in row B.2 of table 4.

Also especially preferred are combinations 21b.1. to 21b.3545 which differ from the corresponding combinations 1.1 to 1.3545 only in that they additionally comprise B.82 terbuthylazin as further herbicide B and the active component a) is defined in row B.3 of table 4.

Also especially preferred are combinations 21c.1. to 21c.3545 which differ from the corresponding combinations 1.1 to 1.3545 only in that they additionally comprise B.82 terbuthylazin as further herbicide B and the active component a) is defined in row B.4 of table 4.

Also especially preferred are combinations 22.1. to 22.3545 which differ from the corresponding combinations 1.1 to 1.3545 only in that they additionally comprise B.85 acifluorfen as further herbicide B.

Also especially preferred are combinations 22a.1. to 22a.3545 which differ from the corresponding combinations 1.1 to 1.3545 only in that they additionally comprise B.85 acifluorfen as further herbicide B and the active component a) is defined in row B.1 of table 4.

Also especially preferred are combinations 22b.1. to 22b.3545 which differ from the corresponding combinations 1.1 to 1.3545 only in that they additionally comprise B.85 acifluorfen as further herbicide B and the active component a) is defined in row B.2 of table 4.

Also especially preferred are combinations 22c.1. to 22c.3545 which differ from the corresponding combinations 1.1 to 1.3545 only in that they additionally comprise B.85 acifluorfen as further herbicide B and the active component a) is defined in row B.3 of table 4.

Also especially preferred are combinations 22d.1. to 22d.3545 which differ from the corresponding combinations 1.1 to 1.3545 only in that they additionally comprise B.85 acifluorfen as further herbicide B and the active component a) is defined in row B.4 of table 4.

Also especially preferred are combinations 23.1. to 23.3545 which differ from the corresponding combinations 1.1 to 1.3545 only in that they additionally comprise B.88 flumioxazin as further herbicide B.

Also especially preferred are combinations 23a.1. to 23a.3545 which differ from the corresponding combinations 1.1 to 1.3545 only in that they additionally comprise B.88 flumioxazin as further herbicide B and the active component a) is defined in row B.1 of table 4.

Also especially preferred are combinations 23b.1. to 23b.3545 which differ from the corresponding combinations 1.1 to 1.3545 only in that they additionally comprise B.88 flumioxazin as further herbicide B and the active component a) is defined in row B.2 of table 4.

Also especially preferred are combinations 23c.1. to 23c.3545 which differ from the corresponding combinations 1.1 to 1.3545 only in that they additionally comprise B.88 flumioxazin as further herbicide B and the active component a) is defined in row B.3 of table 4.

Also especially preferred are combinations 23d.1. to 23d.3545 which differ from the corresponding combinations 1.1 to 1.3545 only in that they additionally comprise B.88 flumioxazin as further herbicide B and the active component a) is defined in row B.4 of table 4.

Also especially preferred are combinations 24.1. to 24.3545 which differ from the corresponding combinations 1.1 to 1.3545 only in that they additionally comprise B.89 fomesafen as further herbicide B.

Also especially preferred are combinations 24a.1. to 24a.3545 which differ from the corresponding combinations 1.1 to 1.3545 only in that they additionally comprise B.89 fomesafen as further herbicide B and the active component a) is defined in row B.1 of table 4.

Also especially preferred are combinations 24b.1. to 24b.3545 which differ from the corresponding combinations 1.1 to 1.3545 only in that they additionally comprise B.89 fomesafen as further herbicide B and the active component a) is defined in row B.2 of table 4.

Also especially preferred are combinations 24c.1. to 24c.3545 which differ from the corresponding combinations 1.1 to 1.3545 only in that they additionally comprise B.89 fomesafen as further herbicide B and the active component a) is defined in row B.3 of table 4.

Also especially preferred are combinations 24d.1. to 24d.3545 which differ from the corresponding combinations 1.1 to 1.3545 only in that they additionally comprise B.89 fomesafen as further herbicide B and the active component a) is defined in row B.4 of table 4.

Also especially preferred are combinations 25.1. to 25.3545 which differ from the corresponding combinations 1.1 to 1.3545 only in that they additionally comprise B.94 saflufenacil as further herbicide B.

Also especially preferred are combinations 25a.1. to 25a.3545 which differ from the corresponding combinations 1.1 to 1.3545 only in that they additionally comprise B.94 saflufenacil as further herbicide B and the active component a) is defined in row B.1 of table 4.

Also especially preferred are combinations 25b.1. to 25b.3545 which differ from the corresponding combinations 1.1 to 1.3545 only in that they additionally comprise B.94 saflufenacil as further herbicide B and the active component a) is defined in row B.2 of table 4.

Also especially preferred are combinations 25c.1. to 25c.3545 which differ from the corresponding combinations 1.1 to 1.3545 only in that they additionally comprise B.94 saflufenacil as further herbicide B and the active component a) is defined in row B.3 of table 4.

Also especially preferred are combinations 25d.1. to 25d.3545 which differ from the corresponding combinations 1.1 to 1.3545 only in that they additionally comprise B.94 saflufenacil as further herbicide B and the active component a) is defined in row B.4 of table 4.

Also especially preferred are combinations 26.1. to 26.3545 which differ from the corresponding combinations 1.1 to 1.3545 only in that they additionally comprise B.95 sulfentrazone as further herbicide B.

Also especially preferred are combinations 26a.1. to 26a.3545 which differ from the corresponding combinations 1.1 to 1.3545 only in that they additionally comprise B.95 sulfentrazone as further herbicide B and the active component a) is defined in row B.1 of table 4.

Also especially preferred are combinations 26b.1. to 26b.3545 which differ from the corresponding combinations 1.1 to 1.3545 only in that they additionally comprise B.95 sulfentrazone as further herbicide B and the active component a) is defined in row B.2 of table 4.

Also especially preferred are combinations 26c.1. to 26c.3545 which differ from the corresponding combinations 1.1 to 1.3545 only in that they additionally comprise B.95 sulfentrazone as further herbicide B and the active component a) is defined in row B.3 of table 4.

Also especially preferred are combinations 26d.1. to 26d.3545 which differ from the corresponding combinations 1.1 to 1.3545 only in that they additionally comprise B.95 sulfentrazone as further herbicide B and the active component a) is defined in row B.4 of table 4.

Also especially preferred are combinations 27.1. to 27.3545 which differ from the corresponding combinations 1.1 to 1.3545 only in that they additionally comprise B.98 benzbicyclone as further herbicide B.

Also especially preferred are combinations 27a.1. to 27a.3545 which differ from the corresponding combinations 1.1 to 1.3545 only in that they additionally comprise B.98 benzbicyclone as further herbicide B and the active component a) is defined in row B.1 of table 4.

Also especially preferred are combinations 27b.1. to 27b.3545 which differ from the corresponding combinations 1.1 to 1.3545 only in that they additionally comprise B.98 benzbicyclone as further herbicide B and the active component a) is defined in row B.2 of table 4.

Also especially preferred are combinations 27c.1. to 27c.3545 which differ from the corresponding combinations 1.1 to 1.3545 only in that they additionally comprise B.98 benzbicyclone as further herbicide B and the active component a) is defined in row B.3 of table 4.

Also especially preferred are combinations 27d.1. to 27d.3545 which differ from the corresponding combinations 1.1 to 1.3545 only in that they additionally comprise B.98 benzbicyclone as further herbicide B and the active component a) is defined in row B.4 of table 4.

Also especially preferred are combinations 28.1. to 28.3545 which differ from the corresponding combinations 1.1 to 1.3545 only in that they additionally comprise B.100 clomazone as further herbicide B.

Also especially preferred are combinations 28a.1. to 28a.3545 which differ from the corresponding combinations 1.1 to 1.3545 only in that they additionally comprise B.100 clomazone as further herbicide B and the active component a) is defined in row B.1 of table 4.

Also especially preferred are combinations 28b.1. to 28b.3545 which differ from the corresponding combinations 1.1 to 1.3545 only in that they additionally comprise B.100 clomazone as further herbicide B and the active component a) is defined in row B.2 of table 4.

Also especially preferred are combinations 28c.1. to 28c.3545 which differ from the corresponding combinations 1.1 to 1.3545 only in that they additionally comprise B.100 clomazone as further herbicide B and the active component a) is defined in row B.3 of table 4.

Also especially preferred are combinations 28d.1. to 28d.3545 which differ from the corresponding combinations 1.1 to 1.3545 only in that they additionally comprise B.100 clomazone as further herbicide B and the active component a) is defined in row B.4 of table 4.

Also especially preferred are combinations 29.1. to 29.3545 which differ from the corresponding combinations 1.1 to 1.3545 only in that they additionally comprise B.103 isoxaflutole as further herbicide B.

Also especially preferred are combinations 29a.1. to 29a.3545 which differ from the corresponding combinations 1.1 to 1.3545 only in that they additionally comprise B.103 isoxaflutole as further herbicide B and the active component a) is defined in row B.1 of table 4.

Also especially preferred are combinations 29b.1. to 29b.3545 which differ from the corresponding combinations 1.1 to 1.3545 only in that they additionally comprise B.103 isoxaflutole as further herbicide B and the active component a) is defined in row B.2 of table 4.

Also especially preferred are combinations 29c.1. to 29c.3545 which differ from the corresponding combinations 1.1 to 1.3545 only in that they additionally comprise B.103 isoxaflutole as further herbicide B and the active component a) is defined in row B.3 of table 4.

Also especially preferred are combinations 29d.1. to 29d.3545 which differ from the corresponding combinations 1.1 to 1.3545 only in that they additionally comprise B.103 isoxaflutole as further herbicide B and the active component a) is defined in row B.4 of table 4.

Also especially preferred are combinations 30.1. to 30.3545 which differ from the corresponding combinations 1.1 to 1.3545 only in that they additionally comprise B.103 isoxaflutole and B.67 atrazine as further herbicides B.

Also especially preferred are combinations 30a.1. to 30a.3545 which differ from the corresponding combinations 1.1 to 1.3545 only in that they additionally comprise B.103 isoxaflutole and B.67 atrazine as further herbicides B and the active component a) is defined in row B.1 of table 4.

Also especially preferred are combinations 30b.1. to 30b.3545 which differ from the corresponding combinations 1.1 to 1.3545 only in that they additionally comprise B.103 isoxaflutole and B.67 atrazine as further herbicides B and the active component a) is defined in row B.2 of table 4.

Also especially preferred are combinations 30c.1. to 30c.3545 which differ from the corresponding combinations 1.1 to 1.3545 only in that they additionally comprise B.103 isoxaflutole and B.67 atrazine as further herbicides B and the active component a) is defined in row B.3 of table 4.

Also especially preferred are combinations 30d.1. to 30d.3545 which differ from the corresponding combinations 1.1 to 1.3545 only in that they additionally comprise B.103 isoxaflutole and B.67 atrazine as further herbicides B and the active component a) is defined in row B.4 of table 4.

Also especially preferred are combinations 31.1. to 31.3545 which differ from the corresponding combinations 1.1 to 1.3545 only in that they additionally comprise B.103 isoxaflutole and B.76 isoproturon as further herbicides B.

Also especially preferred are combinations 31a.1. to 31a.3545 which differ from the corresponding combinations 1.1 to 1.3545 only in that they additionally comprise B.103 isoxaflutole and B.76 isoproturon as further herbicides B and the active component a) is defined in row B.1 of table 4.

Also especially preferred are combinations 31b.1. to 31b.3545 which differ from the corresponding combinations 1.1 to 1.3545 only in that they additionally comprise B.103 isoxaflutole and B.76 isoproturon as further herbicides B and the active component a) is defined in row B.2 of table 4.

Also especially preferred are combinations 31c.1. to 31c.3545 which differ from the corresponding combinations 1.1 to 1.3545 only in that they additionally comprise B.103 isoxaflutole and B.76 isoproturon as further herbicides B and the active component a) is defined in row B.3 of table 4.

Also especially preferred are combinations 31d.1. to 31d.3545 which differ from the corresponding combinations 1.1 to 1.3545 only in that they additionally comprise B.103 isoxaflutole and B.76 isoproturon as further herbicides B and the active component a) is defined in row B.4 of table 4.

Also especially preferred are combinations 32.1. to 32.3545 which differ from the corresponding combinations 1.1 to 1.3545 only in that they additionally comprise B.103 isoxaflutole and B.82 terbutylazin as further herbicides B.

Also especially preferred are combinations 32a.1. to 32a.3545 which differ from the corresponding combinations 1.1 to 1.3545 only in that they additionally comprise B.103 isoxaflutole and B.82 terbutylazin as further herbicides B. and the active component a) is defined in row B.1 of table 4

Also especially preferred are combinations 32b.1. to 32b.3545 which differ from the corresponding combinations 1.1 to 1.3545 only in that they additionally comprise B.103 isoxaflutole and B.82 terbutylazin as further herbicides B. and the active component a) is defined in row B.2 of table 4

Also especially preferred are combinations 32c.1. to 32c.3545 which differ from the corresponding combinations 1.1 to 1.3545 only in that they additionally comprise B.103 isoxaflutole and B.82 terbutylazin as further herbicides B. and the active component a) is defined in row B.3 of table 4

Also especially preferred are combinations 32d.1. to 32d.3545 which differ from the corresponding combinations 1.1 to 1.3545 only in that they additionally comprise B.103 isoxaflutole and B.82 terbutylazin as further herbicides B. and the active component a) is defined in row B.4 of table 4

Also especially preferred are combinations 33.1. to 33.3545 which differ from the corresponding combinations 1.1 to 1.3545 only in that they additionally comprise B.104 mesotrione as further herbicide B.

Also especially preferred are combinations 33a.1. to 33a.3545 which differ from the corresponding combinations 1.1 to 1.3545 only in that they additionally comprise B.104 mesotrione as further herbicide B and the active component a) is defined in row B.1 of table 4.

Also especially preferred are combinations 33b.1. to 33b.3545 which differ from the corresponding combinations 1.1 to 1.3545 only in that they additionally comprise B.104 mesotrione as further herbicide B and the active component a) is defined in row B.2 of table 4.

Also especially preferred are combinations 33c.1. to 33c.3545 which differ from the corresponding combinations 1.1 to 1.3545 only in that they additionally comprise B.104 mesotrione as further herbicide B and the active component a) is defined in row B.3 of table 4.

Also especially preferred are combinations 33d.1. to 33d.3545 which differ from the corresponding combinations 1.1 to 1.3545 only in that they additionally comprise B.104 mesotrione as further herbicide B and the active component a) is defined in row B.4 of table 4.

Also especially preferred are combinations 34.1. to 34.3545 which differ from the corresponding combinations 1.1 to 1.3545 only in that they additionally comprise B.104 mesotrione and B.67 atrazine as further herbicides B.

Also especially preferred are combinations 34a.1. to 34a.3545 which differ from the corresponding combinations 1.1 to 1.3545 only in that they additionally comprise B.104 mesotrione and B.67 atrazine as further herbicides B and the active component a) is defined in row B.1 of table 4.

Also especially preferred are combinations 34b.1. to 34b.3545 which differ from the corresponding combinations 1.1 to 1.3545 only in that they additionally comprise B.104 mesotrione and B.67 atrazine as further herbicides B and the active component a) is defined in row B.2 of table 4.

Also especially preferred are combinations 34c.1. to 34c.3545 which differ from the corresponding combinations 1.1 to 1.3545 only in that they additionally comprise B.104 mesotrione and B.67 atrazine as further herbicides B and the active component a) is defined in row B.3 of table 4.

Also especially preferred are combinations 34d.1. to 34d.3545 which differ from the corresponding combinations 1.1 to 1.3545 only in that they additionally comprise B.104 mesotrione and B.67 atrazine as further herbicides B and the active component a) is defined in row B.4 of table 4.

Also especially preferred are combinations 35.1. to 35.3545 which differ from the corresponding combinations 1.1 to 1.3545 only in that they additionally comprise B.104 mesotrione and B.76 isoproturon as further herbicides B.

Also especially preferred are combinations 35a.1. to 35a.3545 which differ from the corresponding combinations 1.1 to 1.3545 only in that they additionally comprise B.104 mesotrione and B.76 isoproturon as further herbicides B and the active component a) is defined in row B.1 of table 4.

Also especially preferred are combinations 35b.1. to 35a.3545 which differ from the corresponding combinations 1.1 to 1.3545 only in that they additionally comprise B.104 mesotrione and B.76 isoproturon as further herbicides B and the active component a) is defined in row B.2 of table 4.

Also especially preferred are combinations 35c.1. to 35c.3545 which differ from the corresponding combinations 1.1 to 1.3545 only in that they additionally comprise B.104 mesotrione and B.76 isoproturon as further herbicides B and the active component a) is defined in row B.3 of table 4.

Also especially preferred are combinations 35d.1. to 35d.3545 which differ from the corresponding combinations 1.1 to 1.3545 only in that they additionally comprise B.104 mesotrione and B.76 isoproturon as further herbicides B and the active component a) is defined in row B.4 of table 4.

Also especially preferred are combinations 36.1. to 36.3545 which differ from the corresponding combinations 1.1 to 1.3545 only in that they additionally comprise B.104 mesotrione and B.82 terbutylazin as further herbicides B.

Also especially preferred are combinations 36a.1. to 36a.3545 which differ from the corresponding combinations 1.1 to 1.3545 only in that they additionally comprise B.104 mesotrione and B.82 terbutylazin as further herbicides B and the active component a) is defined in row B.1 of table 4.

Also especially preferred are combinations 36b.1. to 36a.3545 which differ from the corresponding combinations 1.1 to 1.3545 only in that they additionally comprise B.104 mesotrione and B.82 terbutylazin as further herbicides B and the active component a) is defined in row B.2 of table 4.

Also especially preferred are combinations 36b.1. to 36b.3545 which differ from the corresponding combinations 1.1 to 1.3545 only in that they additionally comprise B.104 mesotrione and B.82 terbutylazin as further herbicides B and the active component a) is defined in row B.3 of table 4.

Also especially preferred are combinations 36d.1. to 36d.3545 which differ from the corresponding combinations 1.1 to 1.3545 only in that they additionally comprise B.104 mesotrione and B.82 terbutylazin as further herbicides B and the active component a) is defined in row B.4 of table 4.

Also especially preferred are combinations 37.1. to 37.3545 which differ from the corresponding combinations 1.1 to 1.3545 only in that they additionally comprise B.106 picolinafen as further herbicide B.

Also especially preferred are combinations 37a.1. to 37a.3545 which differ from the corresponding combinations 1.1 to 1.3545 only in that they additionally comprise B.106 picolinafen as further herbicide B and the active component a) is defined in row B.1 of table 4.

Also especially preferred are combinations 37b.1. to 37b.3545 which differ from the corresponding combinations 1.1 to 1.3545 only in that they additionally comprise B.106 picolinafen as further herbicide B and the active component a) is defined in row B.2 of table 4.

Also especially preferred are combinations 37c.1. to 37c.3545 which differ from the corresponding combinations 1.1 to 1.3545 only in that they additionally comprise B.106 picolinafen as further herbicide B and the active component a) is defined in row B.3 of table 4.

Also especially preferred are combinations 37d.1. to 37d.3545 which differ from the corresponding combinations 1.1 to 1.3545 only in that they additionally comprise B.106 picolinafen as further herbicide B and the active component a) is defined in row B.4 of table 4.

Also especially preferred are combinations 38.1. to 38.3545 which differ from the corresponding combinations 1.1 to 1.3545 only in that they additionally comprise B.107 sulcotrione as further herbicide B.

Also especially preferred are combinations 38a.1. to 38a.3545 which differ from the corresponding combinations 1.1 to 1.3545 only in that they additionally comprise B.107 sulcotrione as further herbicide B and the active component a) is defined in row B.1 of table 4.

Also especially preferred are combinations 38b.1. to 38b.3545 which differ from the corresponding combinations 1.1 to 1.3545 only in that they additionally comprise B.107 sulcotrione as further herbicide B and the active component a) is defined in row B.2 of table 4.

Also especially preferred are combinations 38b.1. to 38b.3545 which differ from the corresponding combinations 1.1 to 1.3545 only in that they additionally comprise B.107 sulcotrione as further herbicide B and the active component a) is defined in row B.3 of table 4.

Also especially preferred are combinations 38d.1. to 38d.3545 which differ from the corresponding combinations 1.1 to 1.3545 only in that they additionally comprise B.107 sulcotrione as further herbicide B and the active component a) is defined in row B.4 of table 4.

Also especially preferred are combinations 39.1. to 39.3545 which differ from the corresponding combinations 1.1 to 1.3545 only in that they additionally comprise B.107 sulcotrione and B.67 atrazine as further herbicides B.

Also especially preferred are combinations 39a.1. to 39a.3545 which differ from the corresponding combinations 1.1 to 1.3545 only in that they additionally comprise B.107 sulcotrione and B.67 atrazine as further herbicides B and the active component a) is defined in row B.1 of table 4.

Also especially preferred are combinations 39b.1. to 39b.3545 which differ from the corresponding combinations 1.1 to 1.3545 only in that they additionally comprise B.107 sulcotrione and B.67 atrazine as further herbicides B and the active component a) is defined in row B.2 of table 4.

Also especially preferred are combinations 39c.1. to 39c.3545 which differ from the corresponding combinations 1.1 to 1.3545 only in that they additionally comprise B.107 sulcotrione and B.67 atrazine as further herbicides B and the active component a) is defined in row B.3 of table 4.

Also especially preferred are combinations 39d.1. to 39d.3545 which differ from the corresponding combinations 1.1 to 1.3545 only in that they additionally comprise B.107 sulcotrione and B.67 atrazine as further herbicides B and the active component a) is defined in row B.4 of table 4.

Also especially preferred are combinations 40.1. to 40.3545 which differ from the corresponding combinations 1.1 to 1.3545 only in that they additionally comprise B.107 sulcotrione and B.76 isoproturon as further herbicides B.

Also especially preferred are combinations 40a.1. to 40a.3545 which differ from the corresponding combinations 1.1 to 1.3545 only in that they additionally comprise B.107 sulcotrione and B.76 isoproturon as further herbicides B and the active component a) is defined in row B.1 of table 4.

Also especially preferred are combinations 40b.1. to 40b.3545 which differ from the corresponding combinations 1.1 to 1.3545 only in that they additionally comprise B.107 sulcotrione and B.76 isoproturon as further herbicides B and the active component a) is defined in row B.2 of table 4.

Also especially preferred are combinations 40c.1. to 40c.3545 which differ from the corresponding combinations 1.1 to 1.3545 only in that they additionally comprise B.107 sulcotrione and B.76 isoproturon as further herbicides B and the active component a) is defined in row B.3 of table 4.

Also especially preferred are combinations 40d.1. to 40d.3545 which differ from the corresponding combinations 1.1 to 1.3545 only in that they additionally comprise B.107 sulcotrione and B.76 isoproturon as further herbicides B and the active component a) is defined in row B.4 of table 4.

Also especially preferred are combinations 41.1. to 41.3545 which differ from the corresponding combinations 1.1 to 1.3545 only in that they additionally comprise B.107 sulcotrione and B.82 terbutylazin as further herbicides B.

Also especially preferred are combinations 41a.1. to 41a.3545 which differ from the corresponding combinations 1.1 to 1.3545 only in that they additionally comprise B. 107 sulcotrione and B.82 terbutylazin as further herbicides B and the active component a) is defined in row B.1 of table 4.

Also especially preferred are combinations 41b.1. to 41b.3545 which differ from the corresponding combinations 1.1 to 1.3545 only in that they additionally comprise B. 107 sulcotrione and B.82 terbutylazin as further herbicides B and the active component a) is defined in row B.2 of table 4.

Also especially preferred are combinations 41c.1. to 41c.3545 which differ from the corresponding combinations 1.1 to 1.3545 only in that they additionally comprise B. 107 sulcotrione and B.82 terbutylazin as further herbicides B and the active component a) is defined in row B.3 of table 4.

Also especially preferred are combinations 41d.1. to 41d.3545 which differ from the corresponding combinations 1.1 to 1.3545 only in that they additionally comprise B. 107 sulcotrione and B.82 terbutylazin as further herbicides B and the active component a) is defined in row B.4 of table 4.

Also especially preferred are combinations 42.1. to 42.3545 which differ from the corresponding combinations 1.1 to 1.3545 only in that they additionally comprise B.109 tembotrione as further herbicide B.

Also especially preferred are combinations 42a.1. to 42a.3545 which differ from the corresponding combinations 1.1 to 1.3545 only in that they additionally comprise B.109 tembotrione as further herbicide B and the active component a) is defined in row B.1 of table 4.

Also especially preferred are combinations 42b.1. to 42b.3545 which differ from the corresponding combinations 1.1 to 1.3545 only in that they additionally comprise B.109 tembotrione as further herbicide B and the active component a) is defined in row B.2 of table 4.

Also especially preferred are combinations 42c.1. to 42c.3545 which differ from the corresponding combinations 1.1 to 1.3545 only in that they additionally comprise B.109 tembotrione as further herbicide B and the active component a) is defined in row B.3 of table 4.

Also especially preferred are combinations 42d.1. to 42d.3545 which differ from the corresponding combinations 1.1 to 1.3545 only in that they additionally comprise B.109 tembotrione as further herbicide B and the active component a) is defined in row B.4 of table 4.

Also especially preferred are combinations 43.1. to 43.3545 which differ from the corresponding combinations 1.1 to 1.3545 only in that they additionally comprise B.111 topramezone as further herbicide B.

Also especially preferred are combinations 43a.1. to 43a.3545 which differ from the corresponding combinations 1.1 to 1.3545 only in that they additionally comprise B.111 topramezone as further herbicide B and the active component a) is defined in row B.1 of table 4.

Also especially preferred are combinations 43b.1. to 43b.3545 which differ from the corresponding combinations 1.1 to 1.3545 only in that they additionally comprise B.111 topramezone as further herbicide B and the active component a) is defined in row B.2 of table 4.

Also especially preferred are combinations 43c.1. to 43c.3545 which differ from the corresponding combinations 1.1 to 1.3545 only in that they additionally comprise B.111 topramezone as further herbicide B and the active component a) is defined in row B.3 of table 4.

Also especially preferred are combinations 43d.1. to 43d.3545 which differ from the corresponding combinations 1.1 to 1.3545 only in that they additionally comprise B.111 topramezone as further herbicide B and the active component a) is defined in row B.4 of table 4.

Also especially preferred are combinations 44.1. to 44.3545 which differ from the corresponding combinations 1.1 to 1.3545 only in that they additionally comprise B.111 topramezone and B.67 atrazine as further herbicides B.

Also especially preferred are combinations 44a.1. to 44a.3545 which differ from the corresponding combinations 1.1 to 1.3545 only in that they additionally comprise B.111 topramezone and B.67 atrazine as further herbicides B and the active component a) is defined in row B.1 of table 4.

Also especially preferred are combinations 44b.1. to 44b.3545 which differ from the corresponding combinations 1.1 to 1.3545 only in that they additionally comprise B.111 topramezone and B.67 atrazine as further herbicides B and the active component a) is defined in row B.2 of table 4.

Also especially preferred are combinations 44c.1. to 44c.3545 which differ from the corresponding combinations 1.1 to 1.3545 only in that they additionally comprise B.111 topramezone and B.67 atrazine as further herbicides B and the active component a) is defined in row B.3 of table 4.

Also especially preferred are combinations 44d.1. to 44d.3545 which differ from the corresponding combinations 1.1 to 1.3545 only in that they additionally comprise B.111 topramezone and B.67 atrazine as further herbicides B and the active component a) is defined in row B.4 of table 4.

Also especially preferred are combinations 45.1. to 45.3545 which differ from the corresponding combinations 1.1 to 1.3545 only in that they additionally comprise B.111 topramezone and B.76 isoproturon as further herbicides B.

Also especially preferred are combinations 45a.1. to 45a.3545 which differ from the corresponding combinations 1.1 to 1.3545 only in that they additionally comprise B.111 topramezone and B.76 isoproturon as further herbicides B and the active component a) is defined in row B.1 of table 4.

Also especially preferred are combinations 45b.1. to 45b.3545 which differ from the corresponding combinations 1.1 to 1.3545 only in that they additionally comprise B.111 topramezone and B.76 isoproturon as further herbicides B and the active component a) is defined in row B.2 of table 4.

Also especially preferred are combinations 45c.1. to 45c.3545 which differ from the corresponding combinations 1.1 to 1.3545 only in that they additionally comprise B.111 topramezone and B.76 isoproturon as further herbicides B and the active component a) is defined in row B.3 of table 4.

Also especially preferred are combinations 45d.1. to 45d.3545 which differ from the corresponding combinations 1.1 to 1.3545 only in that they additionally comprise B.111 topramezone and B.76 isoproturon as further herbicides B and the active component a) is defined in row B.4 of table 4.

Also especially preferred are combinations 46.1. to 46.3545 which differ from the corresponding combinations 1.1 to 1.3545 only in that they additionally comprise B.111 topramezone and B.82 terbutylazin as further herbicides B.

Also especially preferred are combinations 46a.1. to 46a.3545 which differ from the corresponding combinations 1.1 to 1.3545 only in that they additionally comprise B.111 topramezone and B.82 terbutylazin as further herbicides B and the active component a) is defined in row B.1 of table 4.

Also especially preferred are combinations 46b.1. to 46b.3545 which differ from the corresponding combinations 1.1 to 1.3545 only in that they additionally comprise B.111 topramezone and B.82 terbutylazin as further herbicides B and the active component a) is defined in row B.2 of table 4.

Also especially preferred are combinations 46c.1. to 46c.3545 which differ from the corresponding combinations 1.1 to 1.3545 only in that they additionally comprise B.111 topramezone and B.82 terbutylazin as further herbicides B and the active component a) is defined in row B.3 of table 4.

Also especially preferred are combinations 46d.1. to 46d.3545 which differ from the corresponding combinations 1.1 to 1.3545 only in that they additionally comprise B.111 topramezone and B.82 terbutylazin as further herbicides B and the active component a) is defined in row B.4 of table 4.

Also especially preferred are combinations 47.1. to 47.3545 which differ from the corresponding combinations 1.1 to 1.3545 only in that they additionally comprise B. 116 glyphosate as further herbicide B.

Also especially preferred are combinations 47a.1. to 47a.3545 which differ from the corresponding combinations 1.1 to 1.3545 only in that they additionally comprise B. 116 glyphosate as further herbicide B and the active component a) is defined in row B.1 of table 4.

Also especially preferred are combinations 47b.1. to 47b.3545 which differ from the corresponding combinations 1.1 to 1.3545 only in that they additionally comprise B. 116 glyphosate as further herbicide B and the active component a) is defined in row B.3 of table 4.

Also especially preferred are combinations 47c.1. to 47c.3545 which differ from the corresponding combinations 1.1 to 1.3545 only in that they additionally comprise B. 116 glyphosate as further herbicide B and the active component a) is defined in row B.3 of table 4.

Also especially preferred are combinations 47d.1. to 47d.3545 which differ from the corresponding combinations 1.1 to 1.3545 only in that they additionally comprise B. 116 glyphosate as further herbicide B and the active component a) is defined in row B.4 of table 4.

Also especially preferred are combinations 48.1. to 48.3545 which differ from the corresponding combinations 1.1 to 1.3545 only in that they additionally comprise B.116 glyphosate and B.67 atrazine as further herbicides B.

Also especially preferred are combinations 48a.1. to 48a.3545 which differ from the corresponding combinations 1.1 to 1.3545 only in that they additionally comprise B.116 glyphosate and B.67 atrazine as further herbicides B and the active component a) is defined in row B.1 of table 4.

Also especially preferred are combinations 48b.1. to 48b.3545 which differ from the corresponding combinations 1.1 to 1.3545 only in that they additionally comprise B.116 glyphosate and B.67 atrazine as further herbicides B and the active component a) is defined in row B.2 of table 4.

Also especially preferred are combinations 48c.1. to 48c.3545 which differ from the corresponding combinations 1.1 to 1.3545 only in that they additionally comprise B.116 glyphosate and B.67 atrazine as further herbicides B and the active component a) is defined in row B.3 of table 4.

Also especially preferred are combinations 48d.1. to 48d.3545 which differ from the corresponding combinations 1.1 to 1.3545 only in that they additionally comprise B.116 glyphosate and B.67 atrazine as further herbicides B and the active component a) is defined in row B.4 of table 4.

Also especially preferred are combinations 49.1. to 49.3545 which differ from the corresponding combinations 1.1 to 1.3545 only in that they additionally comprise B.116 glyphosate and B.94 saflufenacil as further herbicides B.

Also especially preferred are combinations 49a.1. to 49a.3545 which differ from the corresponding combinations 1.1 to 1.3545 only in that they additionally comprise B.116 glyphosate and B.94 saflufenacil as further herbicides B and the active component a) is defined in row B.1 of table 4.

Also especially preferred are combinations 49b.1. to 49b.3545 which differ from the corresponding combinations 1.1 to 1.3545 only in that they additionally comprise B.116 glyphosate and B.94 saflufenacil as further herbicides B and the active component a) is defined in row B.2 of table 4.

Also especially preferred are combinations 49c.1. to 49c.3545 which differ from the corresponding combinations 1.1 to 1.3545 only in that they additionally comprise B.116 glyphosate and B.94 saflufenacil as further herbicides B and the active component a) is defined in row B.3 of table 4.

Also especially preferred are combinations 49d.1. to 49d.3545 which differ from the corresponding combinations 1.1 to 1.3545 only in that they additionally comprise B.116 glyphosate and B.94 saflufenacil as further herbicides B and the active component a) is defined in row B.4 of table 4.

Also especially preferred are combinations 50.1. to 50.3545 which differ from the corresponding combinations 1.1 to 1.3545 only in that they additionally comprise B.116 glyphosate and B.103 isoxaflutole as further herbicides B.

Also especially preferred are combinations 50a.1. to 50a.3545 which differ from the corresponding combinations 1.1 to 1.3545 only in that they additionally comprise B.116 glyphosate and B.103 isoxaflutole as further herbicides B and the active component a) is defined in row B.1 of table 4.

Also especially preferred are combinations 50b.1. to 50b.3545 which differ from the corresponding combinations 1.1 to 1.3545 only in that they additionally comprise B.116 glyphosate and B.103 isoxaflutole as further herbicides B and the active component a) is defined in row B.2 of table 4.

Also especially preferred are combinations 50c.1. to 50c.3545 which differ from the corresponding combinations 1.1 to 1.3545 only in that they additionally comprise B.116 glyphosate and B.103 isoxaflutole as further herbicides B and the active component a) is defined in row B.3 of table 4.

Also especially preferred are combinations 50d.1. to 50d.3545 which differ from the corresponding combinations 1.1 to 1.3545 only in that they additionally comprise B.116 glyphosate and B.103 isoxaflutole as further herbicides B and the active component a) is defined in row B.4 of table 4.

Also especially preferred are combinations 51.1. to 51.3545 which differ from the corresponding combinations 1.1 to 1.3545 only in that they additionally comprise B.116 glyphosate and B.128 acetochlor as further herbicides B.

Also especially preferred are combinations 51a.1. to 51a.3545 which differ from the corresponding combinations 1.1 to 1.3545 only in that they additionally comprise B.116 glyphosate and B.128 acetochlor as further herbicides B and the active component a) is defined in row B.1 of table 4.

Also especially preferred are combinations 51b.1. to 51b.3545 which differ from the corresponding combinations 1.1 to 1.3545 only in that they additionally comprise B.116 glyphosate and B.128 acetochlor as further herbicides B and the active component a) is defined in row B.2 of table 4.

Also especially preferred are combinations 51c.1. to 51c.3545 which differ from the corresponding combinations 1.1 to 1.3545 only in that they additionally comprise B.116 glyphosate and B.128 acetochlor as further herbicides B and the active component a) is defined in row B.3 of table 4.

Also especially preferred are combinations 51d.1. to 51d.3545 which differ from the corresponding combinations 1.1 to 1.3545 only in that they additionally comprise B.116 glyphosate and B.128 acetochlor as further herbicides B and the active component a) is defined in row B.4 of table 4.

Also especially preferred are combinations 52.1. to 52.3545 which differ from the corresponding combinations 1.1 to 1.3545 only in that they additionally comprise B.116 glyphosate and B.104 mesotrione as further herbicides B.

Also especially preferred are combinations 52a.1. to 52a.3545 which differ from the corresponding combinations 1.1 to 1.3545 only in that they additionally comprise B.116 glyphosate and B.104 mesotrione as further herbicides B and the active component a) is defined in row B.1 of table 4.

Also especially preferred are combinations 52b.1. to 52b.3545 which differ from the corresponding combinations 1.1 to 1.3545 only in that they additionally comprise B.116 glyphosate and B.104 mesotrione as further herbicides B and the active component a) is defined in row B.2 of table 4.

Also especially preferred are combinations 52c.1. to 52c.3545 which differ from the corresponding combinations 1.1 to 1.3545 only in that they additionally comprise B.116 glyphosate and B.104 mesotrione as further herbicides B and the active component a) is defined in row B.3 of table 4.

Also especially preferred are combinations 52d.1. to 52d.3545 which differ from the corresponding combinations 1.1 to 1.3545 only in that they additionally comprise B.116 glyphosate and B.104 mesotrione as further herbicides B and the active component a) is defined in row B.4 of table 4.

Also especially preferred are combinations 53.1. to 53.3545 which differ from the corresponding combinations 1.1 to 1.3545 only in that they additionally comprise B.116 glyphosate and B.107 sulcotrione as further herbicides B.

Also especially preferred are combinations 53a.1. to 53a.3545 which differ from the corresponding combinations 1.1 to 1.3545 only in that they additionally comprise B.116 glyphosate and B.107 sulcotrione as further herbicides B and the active component a) is defined in row B.1 of table 4.

Also especially preferred are combinations 53b.1. to 53b.3545 which differ from the corresponding combinations 1.1 to 1.3545 only in that they additionally comprise B.116 glyphosate and B.107 sulcotrione as further herbicides B and the active component a) is defined in row B.2 of table 4.

Also especially preferred are combinations 53c.1. to 53c.3545 which differ from the corresponding combinations 1.1 to 1.3545 only in that they additionally comprise B.116 glyphosate and B.107 sulcotrione as further herbicides B and the active component a) is defined in row B.3 of table 4.

Also especially preferred are combinations 53d.1. to 53d.3545 which differ from the corresponding combinations 1.1 to 1.3545 only in that they additionally comprise B.116 glyphosate and B.107 sulcotrione as further herbicides B and the active component a) is defined in row B.4 of table 4.

Also especially preferred are combinations 54.1. to 54.3545 which differ from the corresponding combinations 1.1 to 1.3545 only in that they additionally comprise B.116 glyphosate and B.111 topramezone as further herbicides B.

Also especially preferred are combinations 54a.1. to 54a.3545 which differ from the corresponding combinations 1.1 to 1.3545 only in that they additionally comprise B.116 glyphosate and B.111 topramezone as further herbicides B and the active component a) is defined in row B.1 of table 4.

Also especially preferred are combinations 54b.1. to 54b.3545 which differ from the corresponding combinations 1.1 to 1.3545 only in that they additionally comprise B.116 glyphosate and B.111 topramezone as further herbicides B and the active component a) is defined in row B.2 of table 4.

Also especially preferred are combinations 54c.1. to 54c.3545 which differ from the corresponding combinations 1.1 to 1.3545 only in that they additionally comprise B.116 glyphosate and B.111 topramezone as further herbicides B and the active component a) is defined in row B.3 of table 4.

Also especially preferred are combinations 54d.1. to 54d.3545 which differ from the corresponding combinations 1.1 to 1.3545 only in that they additionally comprise B.116 glyphosate and B.111 topramezone as further herbicides B and the active component a) is defined in row B.4 of table 4.

Also especially preferred are combinations 55.1. to 55.3545 which differ from the corresponding combinations 1.1 to 1.3545 only in that they additionally comprise B.122 glufosinate as further herbicide B.

Also especially preferred are combinations 55a.1. to 55a.3545 which differ from the corresponding combinations 1.1 to 1.3545 only in that they additionally comprise B.122 glufosinate as further herbicide B and the active component a) is defined in row B.1 of table 4.

Also especially preferred are combinations 55b.1. to 55b.3545 which differ from the corresponding combinations 1.1 to 1.3545 only in that they additionally comprise B.122 glufosinate as further herbicide B and the active component a) is defined in row B.2 of table 4.

Also especially preferred are combinations 55c.1. to 55c.3545 which differ from the corresponding combinations 1.1 to 1.3545 only in that they additionally comprise B.122 glufosinate as further herbicide B and the active component a) is defined in row B.3 of table 4.

Also especially preferred are combinations 55d.1. to 55d.3545 which differ from the corresponding combinations 1.1 to 1.3545 only in that they additionally comprise B.122 glufosinate as further herbicide B and the active component a) is defined in row B.4 of table 4.

Also especially preferred are combinations 56.1. to 56.3545 which differ from the corresponding combinations 1.1 to 1.3545 only in that they additionally comprise B.126 pendimethalin as further herbicide B.

Also especially preferred are combinations 56a.1. to 56a.3545 which differ from the corresponding combinations 1.1 to 1.3545 only in that they additionally comprise B.126 pendimethalin as further herbicide B and the active component a) is defined in row B.1 of table 4.

Also especially preferred are combinations 56b.1. to 56b.3545 which differ from the corresponding combinations 1.1 to 1.3545 only in that they additionally comprise B.126 pendimethalin as further herbicide B and the active component a) is defined in row B.2 of table 4.

Also especially preferred are combinations 56c.1. to 56c.3545 which differ from the corresponding combinations 1.1 to 1.3545 only in that they additionally comprise B.126 pendimethalin as further herbicide B and the active component a) is defined in row B.3 of table 4.

Also especially preferred are combinations 56d.1. to 56d.3545 which differ from the corresponding combinations 1.1 to 1.3545 only in that they additionally comprise B.126 pendimethalin as further herbicide B and the active component a) is defined in row B.4 of table 4.

Also especially preferred are combinations 57.1. to 57.3545 which differ from the corresponding combinations 1.1 to 1.3545 only in that they additionally comprise B.128 acetochlor as further herbicide B.

Also especially preferred are combinations 57a.1. to 57a.3545 which differ from the corresponding combinations 1.1 to 1.3545 only in that they additionally comprise B.128 acetochlor as further herbicide B and the active component a) is defined in row B.1 of table 4.

Also especially preferred are combinations 57b.1. to 57b.3545 which differ from the corresponding combinations 1.1 to 1.3545 only in that they additionally comprise B.128 acetochlor as further herbicide B and the active component a) is defined in row B.2 of table 4.

Also especially preferred are combinations 57c.1. to 57c.3545 which differ from the corresponding combinations 1.1 to 1.3545 only in that they additionally comprise B.128 acetochlor as further herbicide B and the active component a) is defined in row B.3 of table 4.

Also especially preferred are combinations 57d.1. to 57d.3545 which differ from the corresponding combinations 1.1 to 1.3545 only in that they additionally comprise B.128 acetochlor as further herbicide B and the active component a) is defined in row B.4 of table 4.

Also especially preferred are combinations 58.1. to 58.3545 which differ from the corresponding combinations 1.1 to 1.3545 only in that they additionally comprise B.131 dimethenamid-P as further herbicide B.

Also especially preferred are combinations 58a.1. to 58a.3545 which differ from the corresponding combinations 1.1 to 1.3545 only in that they additionally comprise B.131 dimethenamid-P as further herbicide B and the active component a) is defined in row B.1 of table 4.

Also especially preferred are combinations 58b.1. to 58b.3545 which differ from the corresponding combinations 1.1 to 1.3545 only in that they additionally comprise B.131 dimethenamid-P as further herbicide B and the active component a) is defined in row B.2 of table 4.

Also especially preferred are combinations 58c.1. to 58c.3545 which differ from the corresponding combinations 1.1 to 1.3545 only in that they additionally comprise B.131 dimethenamid-P as further herbicide B and the active component a) is defined in row B.3 of table 4.

Also especially preferred are combinations 58d.1. to 58d.3545 which differ from the corresponding combinations 1.1 to 1.3545 only in that they additionally comprise B.131 dimethenamid-P as further herbicide B and the active component a) is defined in row B.4 of table 4.

Also especially preferred are combinations 59.1. to 59.3545 which differ from the corresponding combinations 1.1 to 1.3545 only in that they additionally comprise B.132 fentrazamide as further herbicide B.

Also especially preferred are combinations 59a.1. to 59a.3545 which differ from the corresponding combinations 1.1 to 1.3545 only in that they additionally comprise B.132 fentrazamide as further herbicide B and the active component a) is defined in row B.1 of table 4.

Also especially preferred are combinations 59b.1. to 59b.3545 which differ from the corresponding combinations 1.1 to 1.3545 only in that they additionally comprise B.132 fentrazamide as further herbicide B and the active component a) is defined in row B.2 of table 4.

Also especially preferred are combinations 59c.1. to 59c.3545 which differ from the corresponding combinations 1.1 to 1.3545 only in that they additionally comprise B.132 fentrazamide as further herbicide B and the active component a) is defined in row B.3 of table 4.

Also especially preferred are combinations 59d.1. to 59d.3545 which differ from the corresponding combinations 1.1 to 1.3545 only in that they additionally comprise B.132 fentrazamide as further herbicide B and the active component a) is defined in row B.4 of table 4.

Also especially preferred are combinations 60.1. to 60.3545 which differ from the corresponding combinations 1.1 to 1.3545 only in that they additionally comprise B.133 flufenacet as further herbicide B.

Also especially preferred are combinations 60a.1. to 60a.3545 which differ from the corresponding combinations 1.1 to 1.3545 only in that they additionally comprise B.133 flufenacet as further herbicide B and the active component a) is defined in row B.1 of table 4.

Also especially preferred are combinations 60b.1. to 60a.3545 which differ from the corresponding combinations 1.1 to 1.3545 only in that they additionally comprise B.133 flufenacet as further herbicide B and the active component a) is defined in row B.2 of table 4.

Also especially preferred are combinations 60c.1. to 60c.3545 which differ from the corresponding combinations 1.1 to 1.3545 only in that they additionally comprise B.133 flufenacet as further herbicide B and the active component a) is defined in row B.3 of table 4.

Also especially preferred are combinations 60d.1. to 60d.3545 which differ from the corresponding combinations 1.1 to 1.3545 only in that they additionally comprise B.133 flufenacet as further herbicide B and the active component a) is defined in row B.4 of table 4.

Also especially preferred are combinations 61.1. to 61.3545 which differ from the corresponding combinations 1.1 to 1.3545 only in that they additionally comprise B.135 metazachlor as further herbicide B.

Also especially preferred are combinations 61a.1. to 61a.3545 which differ from the corresponding combinations 1.1 to 1.3545 only in that they additionally comprise B.135 metazachlor as further herbicide B and the active component a) is defined in row B.1 of table 4.

Also especially preferred are combinations 61b.1. to 61b.3545 which differ from the corresponding combinations 1.1 to 1.3545 only in that they additionally comprise B.135 metazachlor as further herbicide B and the active component a) is defined in row B.2 of table 4.

Also especially preferred are combinations 61c.1. to 61c.3545 which differ from the corresponding combinations 1.1 to 1.3545 only in that they additionally comprise B.135 metazachlor as further herbicide B and the active component a) is defined in row B.3 of table 4.

Also especially preferred are combinations 61d.1. to 61d.3545 which differ from the corresponding combinations 1.1 to 1.3545 only in that they additionally comprise B.135 metazachlor as further herbicide B and the active component a) is defined in row B.4 of table 4.

Also especially preferred are combinations 62.1. to 62.3545 which differ from the corresponding combinations 1.1 to 1.3545 only in that they additionally comprise B.137 S-metolachlor as further herbicide B.

Also especially preferred are combinations 62a.1. to 62a.3545 which differ from the corresponding combinations 1.1 to 1.3545 only in that they additionally comprise B.137 S-metolachlor as further herbicide B and the active component a) is defined in row B.1 of table 4.

Also especially preferred are combinations 62b.1. to 62b.3545 which differ from the corresponding combinations 1.1 to 1.3545 only in that they additionally comprise B.137 S-metolachlor as further herbicide B and the active component a) is defined in row B.2 of table 4.

Also especially preferred are combinations 62c.1. to 62c.3545 which differ from the corresponding combinations 1.1 to 1.3545 only in that they additionally comprise B.137 S-metolachlor as further herbicide B and the active component a) is defined in row B.3 of table 4.

Also especially preferred are combinations 62d.1. to 62d.3545 which differ from the corresponding combinations 1.1 to 1.3545 only in that they additionally comprise B.137 S-metolachlor as further herbicide B and the active component a) is defined in row B.4 of table 4.

Also especially preferred are combinations 63.1. to 63.3545 which differ from the corresponding combinations 11.1 to 1.3545 only in that they additionally comprise B.138 pretilachlor as further herbicide B.

Also especially preferred are combinations 63a.1. to 63a.3545 which differ from the corresponding combinations 11.1 to 1.3545 only in that they additionally comprise B.138 pretilachlor as further herbicide B and the active component a) is defined in row B.1 of table 4.

Also especially preferred are combinations 63b.1. to 63b.3545 which differ from the corresponding combinations 11.1 to 1.3545 only in that they additionally comprise B.138 pretilachlor as further herbicide B and the active component a) is defined in row B.2 of table 4.

Also especially preferred are combinations 63c.1. to 63c.3545 which differ from the corresponding combinations 11.1 to 1.3545 only in that they additionally comprise B.138 pretilachlor as further herbicide B and the active component a) is defined in row B.3 of table 4.

Also especially preferred are combinations 63d.1. to 63d.3545 which differ from the corresponding combinations 11.1 to 1.3545 only in that they additionally comprise B.138 pretilachlor as further herbicide B and the active component a) is defined in row B.4 of table 4.

Also especially preferred are combinations 64.1. to 64.3545 which differ from the corresponding combinations 1.1 to 1.3545 only in that they additionally comprise B.140 indaziflam as further herbicide B.

Also especially preferred are combinations 64a.1. to 64a.3545 which differ from the corresponding combinations 1.1 to 1.3545 only in that they additionally comprise B.140 indaziflam as further herbicide B and the active component a) is defined in row B.1 of table 4.

Also especially preferred are combinations 64b.1. to 64b.3545 which differ from the corresponding combinations 1.1 to 1.3545 only in that they additionally comprise B.140 indaziflam as further herbicide B and the active component a) is defined in row B.2 of table 4.

Also especially preferred are combinations 64c.1. to 64c.3545 which differ from the corresponding combinations 1.1 to 1.3545 only in that they additionally comprise B.140 indaziflam as further herbicide B and the active component a) is defined in row B.3 of table 4.

Also especially preferred are combinations 64d.1. to 64d.3545 which differ from the corresponding combinations 1.1 to 1.3545 only in that they additionally comprise B.140 indaziflam as further herbicide B and the active component a) is defined in row B.4 of table 4.

Also especially preferred are combinations 65.1. to 65.3545 which differ from the corresponding combinations 1.1 to 1.3545 only in that they additionally comprise B.145 2,4-D as further herbicide B.

Also especially preferred are combinations 65a.1. to 65a.3545 which differ from the corresponding combinations 1.1 to 1.3545 only in that they additionally comprise B.145 2,4-D as further herbicide B and the active component a) is defined in row B.1 of table 4.

Also especially preferred are combinations 65b.1. to 65b.3545 which differ from the corresponding combinations 1.1 to 1.3545 only in that they additionally comprise B.145 2,4-D as further herbicide B and the active component a) is defined in row B.2 of table 4.

Also especially preferred are combinations 65c.1. to 65c.3545 which differ from the corresponding combinations 1.1 to 1.3545 only in that they additionally comprise B.145 2,4-D as further herbicide B and the active component a) is defined in row B.3 of table 4.

Also especially preferred are combinations 65d.1. to 65d.3545 which differ from the corresponding combinations 1.1 to 1.3545 only in that they additionally comprise B.145 2,4-D as further herbicide B and the active component a) is defined in row B.4 of table 4.

Also especially preferred are combinations 66.1. to 66.3545 which differ from the corresponding combinations 1.1 to 1.3545 only in that they additionally comprise B.153 clopyralid as further herbicide B.

Also especially preferred are combinations 66a.1. to 66a.3545 which differ from the corresponding combinations 1.1 to 1.3545 only in that they additionally comprise B.153 clopyralid as further herbicide B and the active component a) is defined in row B.1 of table 4.

Also especially preferred are combinations 66b.1. to 66b.3545 which differ from the corresponding combinations 1.1 to 1.3545 only in that they additionally comprise B.153 clopyralid as further herbicide B and the active component a) is defined in row B.2 of table 4.

Also especially preferred are combinations 66c.1. to 66c.3545 which differ from the corresponding combinations 1.1 to 1.3545 only in that they additionally comprise B.153 clopyralid as further herbicide B and the active component a) is defined in row B.3 of table 4.

Also especially preferred are combinations 66d.1. to 66d.3545 which differ from the corresponding combinations 1.1 to 1.3545 only in that they additionally comprise B.153 clopyralid as further herbicide B and the active component a) is defined in row B.4 of table 4.

Also especially preferred are combinations 67.1. to 67.3545 which differ from the corresponding combinations 1.1 to 1.3545 only in that they additionally comprise B.156 dicamba as further herbicide B.

Also especially preferred are combinations 67a.1. to 67a.3545 which differ from the corresponding combinations 1.1 to 1.3545 only in that they additionally comprise B.156 dicamba as further herbicide B and the active component a) is defined in row B.1 of table 4.

Also especially preferred are combinations 67b.1. to 67b.3545 which differ from the corresponding combinations 1.1 to 1.3545 only in that they additionally comprise B.156 dicamba as further herbicide B and the active component a) is defined in row B.2 of table 4.

Also especially preferred are combinations 67c.1. to 67c.3545 which differ from the corresponding combinations 1.1 to 1.3545 only in that they additionally comprise B.156 dicamba as further herbicide B and the active component a) is defined in row B.3 of table 4.

Also especially preferred are combinations 67d.1. to 67d.3545 which differ from the corresponding combinations 1.1 to 1.3545 only in that they additionally comprise B.156 dicamba as further herbicide B and the active component a) is defined in row B.4 of table 4.

Also especially preferred are combinations 68.1. to 68.3545 which differ from the corresponding combinations 1.1 to 1.3545 only in that they additionally comprise B.171 MCPA as further herbicide B.

Also especially preferred are combinations 68a.1. to 68a.3545 which differ from the corresponding combinations 1.1 to 1.3545 only in that they additionally comprise B.171 MCPA as further herbicide B and the active component a) is defined in row B.1 of table 4.

Also especially preferred are combinations 68b.1. to 68b.3545 which differ from the corresponding combinations 1.1 to 1.3545 only in that they additionally comprise B.171 MCPA as further herbicide B and the active component a) is defined in row B.2 of table 4.

Also especially preferred are combinations 68c.1. to 68c.3545 which differ from the corresponding combinations 1.1 to 1.3545 only in that they additionally comprise B.171 MCPA as further herbicide B and the active component a) is defined in row B.3 of table 4.

Also especially preferred are combinations 68d.1. to 68d.3545 which differ from the corresponding combinations 1.1 to 1.3545 only in that they additionally comprise B.171 MCPA as further herbicide B and the active component a) is defined in row B.4 of table 4.

Also especially preferred are combinations 69.1. to 69.3545 which differ from the corresponding combinations 1.1 to 1.3545 only in that they additionally comprise B.174 quinclorac as further herbicide B.

Also especially preferred are combinations 69a.1. to 69a.3545 which differ from the corresponding combinations 1.1 to 1.3545 only in that they additionally comprise B.174 quinclorac as further herbicide B and the active component a) is defined in row B.1 of table 4.

Also especially preferred are combinations 69b.1. to 69b.3545 which differ from the corresponding combinations 1.1 to 1.3545 only in that they additionally comprise B.174 quinclorac as further herbicide B and the active component a) is defined in row B.2 of table 4.

Also especially preferred are combinations 69c.1. to 69c.3545 which differ from the corresponding combinations 1.1 to 1.3545 only in that they additionally comprise B.174 quinclorac as further herbicide B and the active component a) is defined in row B.3 of table 4.

Also especially preferred are combinations 69d.1. to 69d.3545 which differ from the corresponding combinations 1.1 to 1.3545 only in that they additionally comprise B.174 quinclorac as further herbicide B and the active component a) is defined in row B.4 of table 4.

Further preferred embodiments relate to ternary combinations which correspond to the binary combinations mentioned above and additionally comprise a safener c, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary combinations" includes combinations comprising one or more, for example 1, 2 or 3, active compounds of the formula (I) and either one or more, for example 1, 2 or 3, herbicides b) or one or more safeners c.

Correspondingly, the term "ternary combinations" includes combinations comprising one or more, for example 1, 2 or 3, active compounds of the formula (I), one or more, for example 1, 2 or 3, herbicides b) and one or more, for example 1, 2 or 3, safeners c.

In binary combinations comprising at least one compound of the formula (I) as component a) (compound A) and at least one herbicide b) (herbicide B), the weight ratio of the active compounds a:b is generally in the range of from 1:1000 to 1000:1, preferably in the range of from 1:500 to 500:1, in particular in the range of from 1:250 to 250:1 and particularly preferably in the range of from 1:75 to 75:1.

In binary combination comprising at least one compound of the formula (I) as component a) and at least one safener c, the weight ratio of the active compounds a:c is generally in the range of from 1:1000 to 1000:1, preferably in the range of from 1:500 to 500:1, in particular in the range of from 1:250 to 250:1 and particularly preferably in the range of from 1:75 to 75:1.

In ternary combinations comprising at least one compound of formula (I) as component a), at least one herbicide b) and at least one safener c, the relative proportions by weight of the components a:b are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components a:c is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components b:c is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components a+b to component c is preferably in the range of from 1:500 to 500:1, in particular in the range of from 1:250 to 250:1 and particularly preferably in the range of from 1:75 to 75:1.

It may furthermore be beneficial to apply the compound of formula (I) alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

The invention also relates to agrochemical combinations comprising an auxiliary and at least one combination according to the invention.

An agrochemical composition comprises a pesticidally effective amount of at least one composition according to the invention. The term "effective amount" denotes an amount of the active ingredients, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific combination according to the invention used.

The compound of formula (I) (component a) compound A) and optionally b) and/or c, their N-oxides, salts or derivatives can be converted into customary types of agrochemical combinations, e. g. solutions, emulsions, suspensions, dusts, powders, pastes, granules, pressings, capsules, and mixtures thereof. Examples for agrochemical combination types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical combinations types are defined in the "Catalogue of pesticide formulation types and international coding system", Technical Monograph No. 2, 61 Ed. May 2008, CropLife International.

The agrochemical combinations are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof.

Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical combination types and their preparation are:

i) Water-soluble concentrates (SL, LS)

10-60 wt % of a combination according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible concentrates (DC)

5-25 wt % of a combination according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable concentrates (EC)

15-70 wt % of a combination according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a combination according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a combination according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type combination up to 40 wt % binder (e.g. polyvinylalcohol) is added.

vi) Water-dispersible granules and water-soluble granules (WG, SG)

50-80 wt % of a combination according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of a combination according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a combination according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a combination according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a combination according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS combination.

ix) Dustable powders (DP, DS)

1-10 wt % of a combination according to the invention are ground finely and mixed intimately with solid carrier (e.g. finely divided kaolin) ad 100 wt %.

x) Granules (GR, FG)

0.5-30 wt % of a combination according to the invention is ground finely and associated with solid carrier (e.g. silicate) ad 100 wt %. Granulation is achieved by extrusion, spray-drying or the fluidized bed.

xi) Ultra-low volume liquids (UL)

1-50 wt % of a combination according to the invention are dissolved in organic solvent (e.g. aromatic hydrocarbon) ad 100 wt %.

The agrochemical combinations types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical combinations generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The combinations in question give, after two-to-tenfold dilution, active substance concentrations of from 0.01 to 60% by weight, preferably from 0.1 to 40% by weight, in the ready-to-use preparations. Application can be carried out before or during sowing.

Methods for applying compounds of formula (I) or agrochemical combinations thereof, respectively, on to plant propagation material, especially seeds include dressing, coating, pelleting, dusting, soaking and in-furrow application methods of the propagation material. Preferably, compound I or the combinations thereof, respectively, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the active substances or the combinations comprising them as premix or, if appropriate not until immediately prior to use (tank mix). These agents can be admixed with the combinations according to the invention in a weight ratio of 1:100 to 100:1, preferably 1:10 to 10:1.

The user applies the agrochemical combination according to the invention usually from a predosage device, a knapsack sprayer, a spray tank, a spray plane, or an irrigation system. Usually, the agrochemical combination is made up with water, buffer, and/or further auxiliaries to the desired application concentration and the ready-to-use spray liquor or the agrochemical combination according to the invention is thus obtained. Usually, 20 to 2000 liters, preferably 50 to 400 liters, of the ready-to-use spray liquor are applied per hectare of agricultural useful area.

According to one embodiment, either individual components of the agrochemical combination according to the invention or partially premixed components, e. g. agrochemical components comprising compound of formula (I)

and/or active substances from the groups b) and/or c may be mixed by the user in a spray tank and further auxiliaries and additives may be added, if appropriate.

In a further embodiment, individual components of the agrochemical combination according to the invention such as parts of a kit or parts of a binary or ternary mixture may be mixed by the user himself in a spray tank and further auxiliaries may be added, if appropriate.

In a further embodiment, either individual components of the agrochemical combination according to the invention or partially premixed components, e. g. components comprising compound of formula (I) and active substances from the groups b and/or c, can be applied jointly (e.g. after tank mix) or consecutively.

Accordingly, a first embodiment of the invention relates to combinations in the form of a agrochemical combination formulated as a 1-component combination comprising the at least one active compound of formula (I) or the at least one active compound of formula (I) (active component a), compound A) and at least one further active compound selected from the herbicides b) and the safeners c and also a solid or liquid carrier and, if appropriate, one or more surfactants.

Accordingly, a second embodiment of the invention relates to combinations in the form of a agrochemical combination formulated as a 2-component combination comprising a first formulation (component) comprising the at least one active compound a), a solid or liquid carrier and, if appropriate, one or more surfactants, and a second component comprising at least one further active compound selected from the herbicides b) and safeners c, a solid or liquid carrier and, if appropriate, one or more surfactants. The active compound a) and the at least one further active compound b) and/or c can be formulated and applied jointly or separately, simultaneously or in succession, before, during or after the emergence of the plants. In case of separate application, the order of the application of the active compounds a), b) and/or c is of minor importance. The only thing that is important is that the at least one active compound a) and the at least one further active compound b) and/or c are present simultaneously at the site of action, i.e. are at the same time in contact with or taken up by the plant to be controlled/safened.

The combinations according to the invention are suitable as herbicides. They are suitable as such or as an appropriately formulated combination (agrochemical combination).

The combinations according to the invention control vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

The combinations according to the invention are applied to the plants mainly by spraying the leaves. Here, the application can be carried out using, for example, water as carrier by customary spraying techniques using spray liquor amounts of from about 100 to 1000 l/ha (for example from 300 to 400 l/ha). The herbicidal combinations may also be applied by the low-volume or the ultra-low-volume method, or in the form of microgranules.

Application of the herbicidal combinations according to the present invention can be done before, during and/or after, preferably during and/or after, the emergence of the undesirable plants.

The herbicidal combinations according to the present invention can be applied pre- or post-emergence or together with the seed of a crop plant. It is also possible to apply the compounds and combinations by applying seed, pretreated with a combination of the invention, of a crop plant. If the active compounds a) and b) and, if appropriate c, are less well tolerated by certain crop plants, application techniques may be used in which the herbicidal combinations are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

In a further embodiment, the combination according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the compounds of the formula (I) according to the invention or the combinations prepared therefrom. Here, the herbicidal combinations can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods. Moreover, it may be advantageous to apply the combinations of the present invention on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added. When employed in plant protection, the amounts of active substances applied, i.e. a) and b) and, if appropriate, c without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha. In another embodiment of the invention, the application rate of a) and b) and, if appropriate, c, is from 0.001 to 3 kg/ha, preferably from 0.005 to 2.5 kg/ha and in particular from 0.01 to 2 kg/ha of active substance (a.s.). In another preferred embodiment of the invention, the rates of application of the compound of formula (I) (component a), compound A) according to the present invention (total amount of compound of formula (I)) are from 0.1 g/ha to 3000 g/ha, preferably 10 g/ha to 1000 g/ha, depending on the control target, the season, the target plants and the growth stage. In another preferred embodiment of the invention, the application rates of the compound of formula (I) (component a), compound A) are in the range from 0.1 g/ha to 5000 g/ha and preferably in the range from 1 g/ha to 2500 g/ha or from 5 g/ha to 2000 g/ha. In another preferred embodiment of the invention, the application rate of the compound of formula (I) (component a), compound A) is 0.1 to 1000 g/ha, preferably 1 to 750 g/ha, more preferably 5 to 500 g/ha. The required application rates of herbicidal compounds b) are generally in the range of from 0.0005 kg/ha to 2.5 kg/ha and preferably in the range of from 0.005 kg/ha to 2 kg/ha or 0.01 kg/ha to 1.5 kg/h of a.s. The required application rates of safeners c are generally in the range of from 0.0005 kg/ha to 2.5 kg/ha and preferably in the range of from 0.005 kg/ha to 2 kg/ha or 0.01 kg/ha to 1.5 kg/h of a.s. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required.

In another embodiment of the invention, to treat the seed, the amounts of active substances applied, i.e. a) A and b) and, if appropriate, c are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

In the methods of the present invention it is immaterial whether the herbicide compound a) of formula (I), and the further herbicide component b) and/or the herbicide safener compound c are formulated and applied jointly or separately. In the case of separate application it is of minor importance, in which order the application takes place. It is only necessary, that the herbicide compound a) and the herbicide compound b) and/or the herbicide safener compound c are applied in a time frame that allows simultaneous action of the active ingredients on the plants, preferably within a time-frame of at most 14 days, in particular at most 7 days.

Depending on the application method in question, the combinations according to the invention can additionally be employed in a further number of crop plants for eliminating undesirable plants. Examples of suitable crops are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor* (s. *vulgare*), *Theobroma cacao, Trifolium pratense, Triticum aestivum, Triticale, Triticum durum, Vicia faba, Vitis vinifera, Zea mays.*

Preferred crops are *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum,* (*Gossypium arboreum, Gossypium herbaceum, Gossypium vitifolium*), *Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (S. vulgare), Triticale, Triticum aestivum, Triticum durum, Vicia faba, Vitis vinifera* and *Zea mays*

Especially preferred crops are crops of cereals, corn, soybeans, rice, oilseed rape, cotton, potatoes, peanuts or permanent crops.

The combinations according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetylCoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxinic herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow Agro-Sciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the combinations according to the invention are also suitable for the defoliation and/or desiccation of plant parts, for which crop plants such as cotton, potato, oilseed rape, sunflower, soybean or field beans, in particular cotton, are suitable. In this regard combinations have been found for the desiccation and/or defoliation of plants, processes for preparing these combinations, and methods for desiccating and/or defoliating plants using the combinations according to the invention.

As desiccants, the combinations according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

A further embodiment of the invention is the use of a combination as defined above for controlling un-desirable vegetation in crop plants, where the crop plants are resistant to compounds of formula (I).

A further embodiment of the invention is a method for controlling undesirable vegetation, which comprises allowing a composition as defined above to act on plants to be controlled their habitat.

A further embodiment of the invention is a method for controlling undesirable vegetation, which comprises allowing a composition as defined above to act on plants to be controlled their habitat, which comprises applying the composition as defined above, during and/or after the emergence of the uniserable plants; the compound a) and compound b) applied simultaneously or in succession.

Compounds of formula (I) are known from the unpublished PCT/EP2013/072055 and can be prepared by the following processes:

Process A)

The azines of formula (I), can be prepared by reacting biguanidines of formula (II) with carbonyl compounds of formula (III) in the presence of a base:

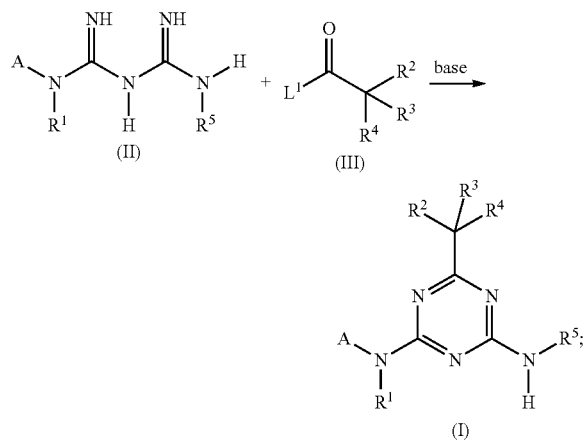

wherein A is

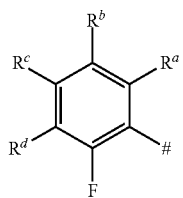

The variables $R^1$, $R^a$, $R^b$, $R^c$, $R^d$, $R^2$, $R^3$ $R^4$ and $R^5$ have the meanings, in particular the preferred meanings, as in formula (I) mentioned above, and $L^1$ is a nucleophilically displaceable leaving group such as halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy preferably halogen or $C_1$-$C_6$-alkoxy;
particularly preferred Cl or $C_1$-$C_6$-alkoxy,
also particularly preferred halogen;
especially preferred Cl;

The reaction of biguanidines of formula (II) with carbonyl compounds of formula (III) is usually carried out at temperatures from 50° C. to the boiling point of the reaction mixture, preferably from 50° C. to 200° C. (e.g. R. Sathunuru et al., J. Heterocycl. Chem. 2008, 45, 1673-1678).

The reaction can be carried out at atmospheric pressure or under elevated pressure, if appropriate under an inert gas, continuously or batchwise.

In one embodiment of the process according to the invention, the biguanidines of formula (II) and the carbonyl compounds of formula (III) are used in equimolar amounts.

In another embodiment of the process according to the invention, the carbonyl compounds of formula (III) are used in excess with regard to the biguanidines of formula (II).

Preferably the molar ratio of the carbonyl compounds of formula (III) to the biguanidines of formula (II) is in the range from 1.5:1 to 1:1, preferably 1.2:1 to 1:1, especially preferred 1.2:1, also especially preferred 1:1.

The reaction of the biguanidines of formula (II) with the carbonyl compounds of formula (III) is carried out in an organic solvent.

Suitable in principle are all solvents which are capable of dissolving the biguanidines of formula (II) and the carbonyl compounds of formula (III) at least partly and preferably fully under reaction conditions.

Examples of suitable solvents are
aliphatic hydrocarbons such as pentane, hexane, cyclohexane, nitromethane and mixtures of $C_5$-$C_8$-alkanes; romatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethytformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above. More preferred solvents are ethers as defined above.

The term solvent as used herein also includes mixtures of two or more of the above compounds.

The reaction of the biguanidines of formula (II) with the carbonyl compounds of formula (III) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the biguanidines of formula (II).

The end of the reaction can easily be determined by the skilled worker by means of routine methods.

The reaction mixtures are worked up in a customary manner, for example by mixing with water, separation of the phases and, if appropriate, chromatographic purification of the crude product.

Some of the intermediates and end products are obtained in the form of viscous oils, which can be purified or freed from volatile components under reduced pressure and at moderately elevated temperature.

If the intermediates and end products are obtained as solid, purification can also be carried out by recrystallisation or digestion.

The carbonyl compounds of formula (III) required for the preparation of azines of formula (I) are known in the art or they can be prepared in accordance and/or are commercially available.

The biguanidines of formula (II) required for the preparation of azines of formula (I) can be prepared by reacting guanidines of formula (IV) with amines of formula (V) in the presence of an acid:

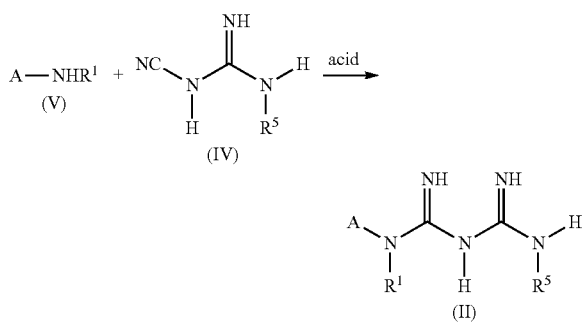

wherein A is

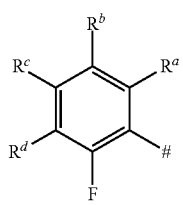

The variables $R^1$, $R^a$, $R^b$, $R^c$, $R^d$, $R^5$ has the meanings, in particular the preferred meanings, as in formula (I) mentioned above;

The reaction of guanidines of formula (IV) with amines of formula (V) is usually carried out from 50° C. to 150° C., preferably from 80° C. to 130° C.

Microwave-Technology was used where applicable (e.g. C. O. Kappe, A. Stadler, Microwaves in Organic and Medicinal Chemistry, Weinheim 2012).

The reaction can be carried out at atmospheric pressure or under elevated pressure, if appropriate under an inert gas, continuously or batchwise.

In one embodiment of the process according to the invention, the guanidines of formula (IV) and the amines of formula (V) are used in equimolar amounts.

In another embodiment of the process according to the invention, the amines of formula (V) are used in excess with regard to the guanidines of formula (IV).

Preferably the molar ratio of the amines of formula (V) to the guanidines of formula (IV) is in the range from 2:1 to 1:1, preferably 1.5:1 to 1:1, especially preferred 1:1.

The reaction of the guanidines of formula (IV) with the amines of formula (V) is carried out in an organic solvent.

Suitable in principle are all solvents which are capable of dissolving the guanidines of formula (IV) and the amines of formula (V) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethytformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles and dipolar aprotic solvents as defined above.

More preferred solvents are nitriles as defined above.

The term solvent as used herein also includes mixtures of two or more of the above compounds.

The reaction of the guanidines of formula (IV) with the amines of formula (V) is carried out in the presence of an acid.

As acids and acidic catalysts inorganic acids like hydrofluoric acid, hydrochloric acid, hydrobromic acid, hydroiodic acid, phosphoric acid, sulfuric acid; mineral acids like hydrochloric acid, sulfuric acid, phosphoric acid, Lewis acids like boron trifluoride, aluminium chloride, ferric-III-chloride, tin-IV-chloride, titanium-IV-chloride and zinc-II-chloride, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in excess or, if appropriate, can be used as solvent.

Work up can be carried out in a known manner.

The guanidines of formula (IV) required for the preparation of biguanidines of formula (II) are commercially available or can be prepared in accordance with literature procedures (e.g. J. L. LaMattina et al., J. Med. Chem. 1990, 33, 543-552; A. Perez-Medrano et al., J. Med. Chem. 2009, 52, 3366-3376).

The amines of formula (V) required for the preparation of biguanidines of formula (II) are commercially available.

Process B)

The azines of formula (I) can also be prepared by reacting halotriazines of formula (VI) with amines of formula (V) in the presence of a base and a catalyst:

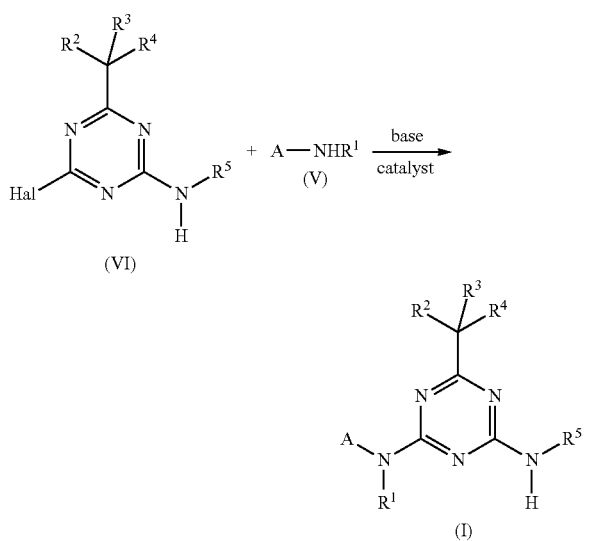

Wherein A is wherein A is

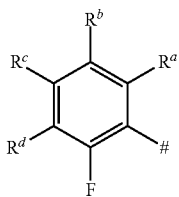

The variables $R^a$, $R^b$, $R^c$, $R^d$, A, $R^1$, $R^2$, $R^3$, $R^4$ and $R^5$ have the meanings, in particular the preferred meanings, as in formula (I) mentioned above;

Hal is halogen;

preferably Cl or Br;

particularly preferred Cl.

The reaction of the halotriazines of formula (VI) with the amines of formula (V) is usually carried out from 50° C. to the boiling point of the reaction mixture, preferably from 50° C. to 150° C., particularly preferably from 60° C. to 100° C., in an inert organic solvent (e.g. P. Dao et al., Tetrahedron 2012, 68, 3856-3860).

The reaction can be carried out at atmospheric pressure or under elevated pressure, if appropriate, under an inert gas, continuously or batchwise.

In one embodiment of the process according to the invention, the halotriazines of formula (VI) and the amines of formula (V) are used in equimolar amounts.

In another embodiment of the process according to the invention, the amines of formula (V) are used in excess with regard to the halotriazines of formula (VI).

Preferably the molar ratio of the amines of formula (V) to the halotriazines of formula (VI) is in the range from 2:1 to 1:1, preferably 1.5:1 to 1:1, especially preferred 1.2:1.

The reaction of the halotriazines of formula (VI) with the amines of formula (V) is carried out in an organic solvent.

Suitable in principle are all solvents which are capable of dissolving the halotriazines of formula (VI) and the amines of formula (V) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, as well as dipolar aprotic solvents such as sulfolane, dimethylsulfoxide, N,N-dimethytformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers as defined above.

The term solvent as used herein also includes mixtures of two or more of the above compounds.

The reaction of the halotriazines of formula (VI) with the amines of formula (V) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and also bicyclic amines such as 1,8-diazabicyclo[5.4.0]undec-7-ene (DBU) or 1,5-diazabicyclo[4.3.0]non-5-ene (DBN).

Preferred bases are alkali metal and alkaline earth metal alkoxides as defined above.

The term base as used herein also includes mixtures of two or more, preferably two of the above compounds. Particular preference is given to the use of one base.

The bases can be used in excess, preferably from 1 to 10, especially preferred from 2 to 4 base equivalents based on the halotriazines of formula (VI), and they may also be used as the solvent.

The reaction of the halotriazines of formula (VI) with the amines of formula (V) is carried out in the presence of a catalyst.

Examples of suitable catalysts include for example, palladium based catalysts like, for example, Palladium (II)acetate, tetrakis(triphenylphosphine)palladium(0), bis(triphenylphosphine)palladium(II)chloride or (1,1,-bis(diphenylphosphino)ferrocene)-dichloropalladium(II), and optionally suitable additives such as, for example, phosphines like, for example, $P(o-tolyl)_3$, triphenylphosphine or BINAP (2,2'-Bis(diphenylphospino)-1,1'-binaphthyl).

The amount of catalyst is usually 10 to 20 mol % (0.1 to 0.2 equivalents) based on the halotriazines of formula (VI).

The end of the reaction can easily be determined by the skilled worker by means of routine methods.

The reaction mixtures are worked up in a customary manner, for example by mixing with water, separation of the phases and, if appropriate, chromatographic purification of the crude product.

The amines of formula (V) required for the preparation of azines of formula (I), wherein $R^1$ is H, $C_1$-$C_6$-alkyl, $C_1$-$C_6$-alkoxy-$C_1$-$C_6$-alkyl or $C_1$-$C_6$-alkoxy, are commercially available and/or can be prepared by analogy to known literature.

The halotriazines of formula (VI) required for the preparation of azines of formula (I) are known from the literature, are commercially available and/or can be prepared by analogy (e.g. J. K. Chakrabarti et al., Tetrahedron 1975, 31, 1879-1882) by reacting thiotriazines of formula (VII) with a halogen:

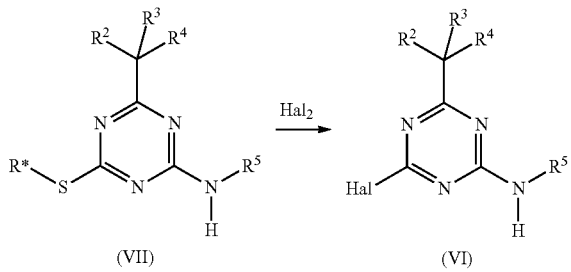

The variables $R^2$, $R^3$, $R^4$, and $R^5$ have the meanings, in particular the preferred meanings, as defined in formula (I) mentioned above;
Hal is halogen;
preferably Cl or Br;
particularly preferred Cl;
R* is $C_1$-$C_6$-alkyl, $C_2$-$C_6$-haloalkyl or phenyl;
preferably $C_1$-$C_6$-alkyl or $C_2$-$C_6$-haloalkyl;
particularly preferred $C_1$-$C_6$-alkyl;
especially preferred $CH_3$.

The reaction of the thiotriazines of formula (VII) with the halogen is usually carried out from 0° C. to the boiling point of the reaction mixture, preferably from 15° C. to the boiling point of the reaction mixture, particularly preferably from 15° C. to 400° C., in an inert organic solvent (e.g. J. K. Chakrabarti et al., Tetrahedron 1975, 31, 1879-1882).

The reaction can be carried out at atmospheric pressure or under elevated pressure, if appropriate under an inert gas, continuously or batchwise.

In the process according to the invention, the halogen is used in excess with regard to the thiotriazines of formula (VII).

The reaction of the thiotriazines of formula (VII) with the halogen is carried out in an organic solvent.

Suitable in principle are all solvents which are capable of dissolving the thiotriazines of formula (VII) and the halogen at least partly and preferably fully under reaction conditions.

Examples of suitable solvents are aliphatic hydrocarbons such as pentane, hexane, cyclohexane and mixtures of $C_5$-$C_8$-alkanes, halogenated hydrocarbons such as dichloromethane, 1,2-dichloroethane, chloroform and carbon tetrachloride; ethers such as diethyl ether, diisopropyl ether, tert.-butyl methylether (TBME), dioxane, anisole and tetrahydrofuran (THF), alcohols such as methanol, ethanol, n-propanol, isopropanol, n-butanol and tert.-butanol, as well as organic acids like formic acid, acetic acid, propionic acid, oxalic acid, citric acid, trifluoroacetic acid.

Preferred solvents are halogenated hydrocarbons and organic acids as defined above.

The term solvent as used herein also includes mixtures of two or more of the above compounds.

The end of the reaction can easily be determined by the skilled worker by means of routine methods.

The reaction mixtures are worked up in a customary manner, for example by mixing with water, separation of the phases and, if appropriate, chromatographic purification of the crude product.

The thiotriazines of formula (VII) required for the preparation of halotriazines of formula (VI) can be prepared in accordance by reacting guanidine-salts of formula (VIII) with carbonyl compounds of formula (III) in the presence of a base:

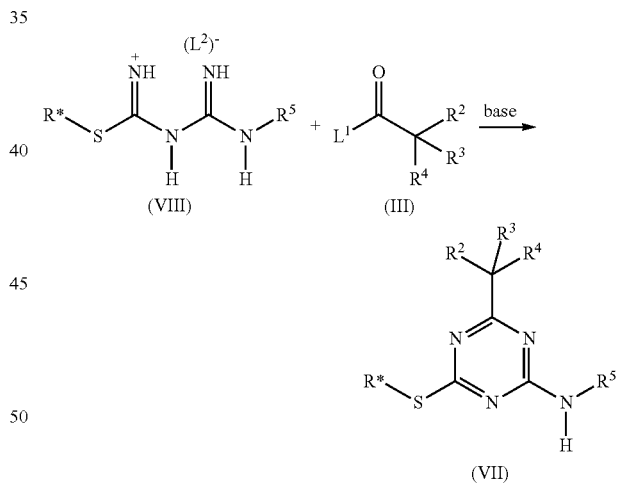

The variables $R^2$, $R^3$, $R^4$ and $R^5$ have the meanings, in particular the preferred meanings, as defined in formula (I) mentioned above;
R* is $C_1$-$C_6$-alkyl, $C_2$-$C_6$-haloalkyl or phenyl;
preferably $C_1$-$C_6$-alkyl or $C_2$-$C_6$-haloalkyl;
particularly preferred $C_1$-$C_6$-alkyl;
especially preferred $CH_3$;
$L^1$ is a nucleophilically displaceable leaving group such as halogen, CN, $C_1$-$C_6$-alkoxy, $C_1$-$C_6$-alkoxycarbonyl, $C_1$-$C_6$-alkylcarbonyloxy or $C_1$-$C_6$-alkoxycarbonyloxy
preferably halogen or $C_1$-$C_6$-alkoxy;
particularly preferred Cl or $C_1$-$C_6$-alkoxy,
also particularly preferred halogen;
especially preferred Cl; and $L^2$ is a nucleophilically displaceable leaving group such as halogen, $C_1$-$C_6$-alkylsulfonyloxy, $C_1$-$C_6$-haloalkylsufonyloxy, $C_1$-$C_6$-alkoxysulfonyloxy or phenylsulfonyloxy;
preferably halogen or $C_1$-$C_6$-haloalkylsufonyloxy;
particularly preferred halogen;
especially preferred I.

The reaction of the guanidine-salt of formula (VIII) with the carbonyl compound of formula (III) is usually carded out at temperatures from 50° C. to the boiling point of the reaction mixture, preferably from 50° C. to 100° C.

The reaction can be carried out at atmospheric pressure or under elevated pressure, if appropriate under an inert gas, continuously or batchwise.

In one embodiment of the process according to the invention, the guanidine-salts of formula (VIII) and the carbonyl compound of formula (III) are used in equimolar amounts.

In another embodiment of the process according to the invention, the carbonyl compound of formula (III) is used in excess with regard to the guanidine-salts of formula (VIII).

Preferably the molar ratio of the carbonyl compound of formula (III) to the guanidine-salt of formula (VIII) is in the range from 1.5:1 to 1:1, preferably 1.2:1 to 1:1, especially preferred 1.2:1, also especially preferred 1:1.

The reaction of the guanidine-salt of formula (VIII) with the carbonyl compound of formula (III) is usually carried out in an organic solvent.

Suitable in principle are all solvents which are capable of dissolving the guanidine-salt of formula (VIII) and the carbonyl compound of formula (III) at least partly and preferably fully under reaction conditions.

Examples of suitable solvents are halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), nitriles such as acetonitrile and propionitrile, as well as dipolar aprotic solvents such as sulfolane, dimethylsulfoxide, N,N-dimethytformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers and dipolar aprotic solvents as defined above.

More preferred solvents are ethers as defined above.

The term solvent as used herein also includes mixtures of two or more of the above compounds.

The reaction of the guanidine-salts of formula (VIII) with the carbonyl compound of formula (III) is carried out in the presence of a base.

Examples of suitable bases include metal-containing bases and nitrogen-containing bases.

Examples of suitable metal-containing bases are inorganic compounds such as alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine, and also bicyclic amines such as 1,8-diazabicyclo[5.4.0]undec-7-ene (DBU) or 1,5-diazabicyclo[4.3.0]non-5-ene (DBN).

Preferred bases are tri-$C_1$-$C_6$-alkylamines as defined above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the guanidine-salts of formula (VIII).

The end of the reaction can easily be determined by the skilled worker by means of routine methods.

The reaction mixtures are worked up in a customary manner, for example by mixing with water, separation of the phases and, if appropriate, chromatographic purification of the crude product.

The carbonyl compounds of formula (III) required for the preparation of azines of formula (I) are known from the literature. They can be prepared in accordance and/or are commercially available.

The guanidine-salt of formula (VIII), wherein $L^2$ is iodine, required for the preparation of thiotriazines of formula (VII) is known from the literature (e.g. M. Freund et al., Chem. Ber. 1901, 34, 3110-3122; H. Eilingsfeld et al., Chem. Ber. 1967, 100, 1874-1891). The guanidine-salts of formula (VIII) are commercially available and/or can be prepared in accordance with the literature cited.

Process C)

The azines of formula (I) can be prepared by reacting azines of formula (I), wherein $R^5$ is hydrogen with a compound of formula (IX):

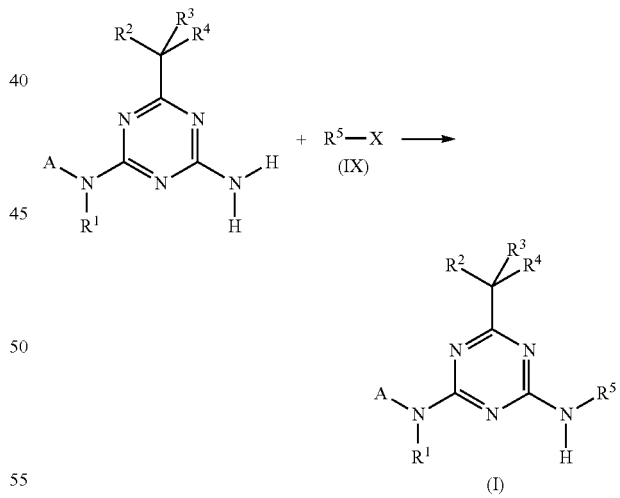

(I) wherein $R^5$ is hydrogen
Wherein A is wherein A is

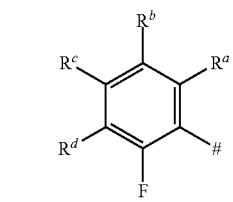

The variables $R^a$, $R^b$, $R^c$, $R^d$, $R^1$, $R^2$, $R^3$, $R^4$ and $R^5$ have the meanings, in particular the preferred meanings, as in formula (I) mentioned above, X is halogen or oxycarbonyl-$C_1$-$C_6$-alkyl;
particularly preferred halogen;
especially preferred Cl, I or Br.

Process D)

The azines of formula (I) can be prepared by reacting azines of formula (I), wherein $R^1$ is hydrogen with a compound of formula (X):

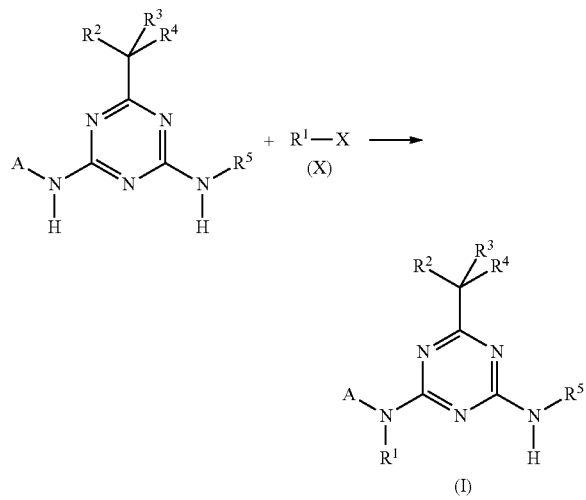

(I) wherein is hydrogen
Wherein A is wherein A is

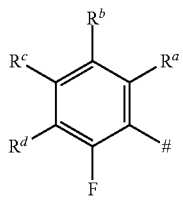

The variables $R^a$, $R^b$, $R^c$, $R^d$, $R^1$, $R^2$, $R^3$, $R^4$ and $R^5$ have the meanings, in particular the preferred meanings, as in formula (I) mentioned above, and X is halogen or oxycarbonyl-$C_1$-$C_6$-alkyl;
particularly preferred halogen;
especially preferred Cl or Br.

Both processes C and D independently of one another usually carried out at from 0° C. to the boiling point of the reaction mixture, preferably from 23° C. to 130° C., particularly preferably from 23° C. to 100° C., (e.g. Y. Yuki et al., Polym. J. 1992, 24, 791-799).

Both processes C and D independently of one another can be carried out at atmospheric pressure or under elevated pressure, if appropriate under an inert gas, continuously or batchwise.

In one embodiment of processes C and D according to the invention independently of one another, the azines of formula (I), wherein $R^5$, or $R^1$ respectively, is hydrogen are used in excess with regard to the compound of formula (IX), or (X) respectively.

In another embodiment of processes C and D according to the invention independently of one another, the azines of formula (I), wherein $R^5$, or $R^1$ respectively, is hydrogen and the compound of formula (IX), or (X) respectively, are used in equimolar amounts.

Preferably the molar ratio of the azines of formula (I), wherein $R^5$, or $R^1$ respectively, is hydrogen to the compound of formula (IX), or (X) respectively is in the range from 1:1.5 to 1:1, preferably 1:1.2 to 1:1, especially preferred 1:1.

Both processes C and D independently of one another are carried out in an organic solvent. Suitable in principle are all solvents which are capable of dissolving the azines of formula (I), wherein $R^5$, or $R^1$ respectively, is hydrogen and the compound of formula (IX), or (X) respectively, at least partly and preferably fully under reaction conditions.

Examples of suitable solvents are halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); nitriles such as acetonitrile and propionitrile; alcohols such as methanol, ethanol, n-propanol, isopropanol, n-butanol and tert.-butanol; organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are halogenated hydrocarbons, ethers and dipolar aprotic solvents as mentioned above.

More preferred solvents are dichloromethane or dioxane.

It is also possible to use mixtures of the solvents mentioned.

The term solvent as used herein also includes mixtures of two or more of the above compounds.

Both processes C and D independently of one another are optionally carried out in the presence of a base.

Examples of suitable bases include metal-containing bases and nitrogen-containing bases.

Examples of suitable metal-containing bases are inorganic compounds such as alkali metal and alkaline earth metal hydrides such as lithium hydride, sodium hydride, potassium hydride and calcium hydride, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; and furthermore organic bases, such as tertiary amines such as tri-$C_1$-$C_6$-alkylamines, for example triethylamine, trimethylamine, N-ethyldiisopropylamine, and N-methylpiperidine, pyridine, substituted pyridines such as collidine, lutidine, N-methylmorpholine and 4-dimethylaminopyridine (DMAP), and also bicyclic amines such as 1,8-diazabicyclo[5.4.0]undec-7-ene (DBU) or 1,5-diazabicyclo[4.3.0]non-5-ene (DBN).

Preferred bases are organic bases and alkali metal carbonates as mentioned above.

Especially preferred bases are organic bases as mentioned above.

The term base as used herein also includes mixtures of two or more, preferably two of the above compounds. Particular preference is given to the use of one base.

The bases are generally employed in excess; however they can also be employed in equimolar amounts, or, if appropriate, can be used as solvent.

Preferably from 1 to 5 base equivalents, particularly preferred 3 base equivalents of base are used, based on the azines of formula (I).

Work-up can be done in a known manner.

The compounds of formula (IX), or (X) respectively, are known compounds. They are commercially available or can be prepared in analogy to known methods.

The following examples serve to illustrate the invention.

A PREPARATION EXAMPLES

Example 1

Example 1

6-(1-chloro-1-methyl-ethyl)-N4-(2,3,4,5,6-pentafluorophenyl)-1,3,5-triazine-2,4-diamine

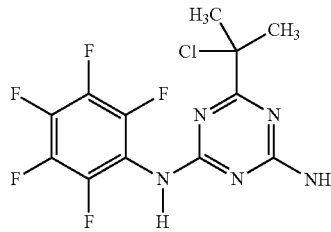

1.1: 1-Carbamimidoyl-3-(2,3,4,5,6-pentafluorophenyl)guanidine

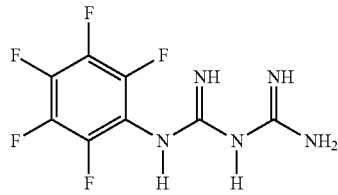 [SMILES: N=C(N)NC(=N)Nc1c(F)c(F)c(F)c(F)c1F]

A suspension of 2,3,4,5,6-pentafluoroaniline (2.00 g, 10.9 mmol) and 1-cyanoguanidine (1.10 g, 11.9 mmol) in a mixture of acetonitrile and aq. hydrochloride (38% w/w) were heated to 150° C. for 2 h in a microwave reactor. The resulting mixture was carefully added to aq. NaHCO$_3$, ethyl acetate was added and the phases were separated. The organic phase was dried over anhydrous Na$_2$SO$_4$, filtered and concentrated under reduced pressure yielding the title compound as a colorless solid (0.97 g, 33.2% yield).

MS (ESI) m/z=268.1 [M+H$^+$]

$^1$H NMR (400 MHz, de-DMSO): δ=6.75 (br s, 4H), 5.47 (s, 2H) ppm.

1.2: 6-(1-Chloro-1-methyl-ethyl)-N4-(2,3,4,5,6-pentafluorophenyl)-1,3,5-triazine-2,4-diamine 2-chloro-2-methyl-propanoyl chloride (0.69 g, 4.89 mmol) was added to a solution of 1-carbamimidoyl-3-(2,3,4,5,6-pentafluorophenyl)guanidine (1.31 g, 4.89 mmol) in a mixture of THF and triethylamine (1.49 g, 14.7 mmol). The resulting reaction mixture was heated to 60° C. for 4 h, cooled to ambient temperature and diluted with water and ethyl acetate. The phases were separated and the organic phase was dried over anhydrous Na$_2$SO$_4$, filtered and concentrated under reduced pressure. Column chromatography of the resulting crude product (ISCO-CombiFlash Rf, cyclohexane/ethyl acetate) yielded the desired title compound as colorless solid (0.72 g, 41.8% yield).

MS (ESI) m/z=354.2 [M+H$^+$].

$^1$H NMR (400 MHz, H$_3$COD): δ=1.85 (s, 6H) ppm.

Example 2

6-(1-Fluoro-1-methyl-ethyl)-N4-(2,3,5,6-tetrafluorophenyl)-1,3,5-triazine-2,4-diamine

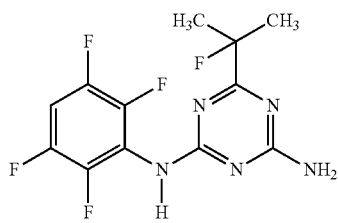 [SMILES: CC(C)(F)c1nc(N)nc(Nc2c(F)c(F)cc(F)c2F)n1]

2.1: 4-(1-fluoro-1-methyl-ethyl)-6-methylsulfanyl-1,3,5-triazin-2-amine

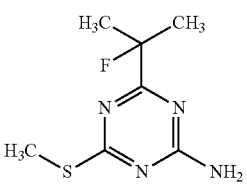

2-Fluoro-2-methyl-propanoyl chloride (23.0 g, 0.18 mol) and triethylamine (93.4 g, 0.92 mol) were added to a solution of 1-carbamimidoyl-2-methyl-isothiourea hydroiodide (48.0 g, 0.18 mol) in THF via two addition funnels. After the initial weak exothermic reaction was finished, the mixture was stirred for 3 h at 50° C. The reaction mixture was cooled to ambient temperature, diluted with water and ethyl acetate and the phases were separated. The organic phase was dried over anhydrous Na$_2$SO$_4$, filtered and concentrated under reduced pressure yielding the title compound as a colorless solid (33.3 g, 89.2% yield).

MS (ESI) m/z 203.3 [M+H$^+$]

$^1$H NMR (400 MHz, CDCl$_3$): δ=6.82 (brs, 1H), 5.64 (brs, 1H), 1.63 (d, J=21.0 Hz, 6H) ppm.

2.2: 4-chloro-6-(1-fluoro-1-methyl-ethyl)-1,3,5-triazin-2-amine

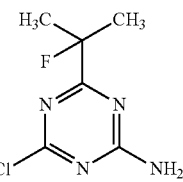

4-(1-fluoro-1-methyl-ethyl)-6-methylsulfanyl-1,3,5-triazin-2-amine (65.0 g, 0.32 mol) was dissolved in acetic acid and Cl$_2$ gas was bubbled through the solution for 30 min.

The reaction mixture was stirred for an additional hour at ambient temperature and was then carefully added to a cold solution of NaOH (130 g) in water (1 L). Ethyl acetate was added and the phases were separated. The organic phase was dried over anhydrous $Na_2SO_4$, filtered and concentrated under reduced pressure yielding the title compound as a colorless solid (41.3 g, 67.4% yield).

MS (ESI) m/z 191.3 [M+H⁺]

$^1$H NMR (400 MHz, CDCl): δ=7.12 (brs, 1H), 6.32 (brs, 1H), 1.69 (d, J=21.8 Hz, 6H) ppm.

2.3: 6-(1-fluoro-1-methyl-ethyl)-N4-(2,3,5,6-tetrafluorophenyl)-1,3,5-triazine-2,4-diamine

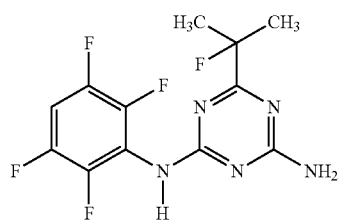 [SMILES: CC(C)(F)c1nc(N)nc(Nc2c(F)c(F)cc(F)c2F)n1]

A solution of 4-chloro-6-(1-fluoro-1-methyl-ethyl)-1,3,5-triazin-2-amine (0.64 g, 2.83 mmol), 2,3,5,6-tetrafluoroaniline (0.51 g 3.11 mmol), Pd(dppf)Cl₂ (0.21 g, 0.28 mmol) and KOtBu (0.95 g, 8.50 mmol) in dioxane was heated to 100° C. for 16 h. The reaction mixture was cooled to ambient temperature, diluted with water and ethyl acetate and the phases were separated. The organic phase was dried over anhydrous $Na_2SO_4$, filtered and concentrated under reduced pressure. Column chromatography of the resulting crude product (ISCO-CombiFlash Rf, cyclohexane/ethyl acetate) yielded the title compound as colorless solid (0.30 g, 31.9% yield).

MS (ESI) m/z 320.0 [M+H⁺].

$^1$H NMR (400 MHz, H₃COD): δ=7.42-7.29 (m, 1H), 1.61 (d, J=21.5 Hz, 6H) ppm.

Example 3

N4-(2,3,5,6-tetrafluorophenyl)-6-(2,2,2-trifluoro-1-methyl-ethyl)-1,3,5-triazine-2,4-diamine

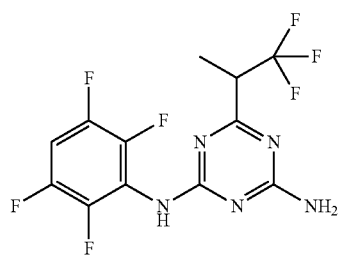 [SMILES: CC(c1nc(N)nc(Nc2c(F)c(F)cc(F)c2F)n1)C(F)(F)F]

3.1: 1-carbamimidoyl-3-(2,3,4,5,6-pentafluorophenyl)guanidine

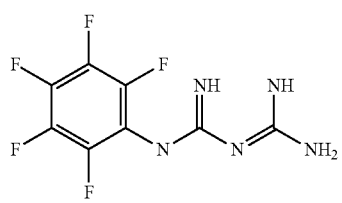 [SMILES: N=C(N=C(N)N)Nc1c(F)c(F)c(F)c(F)c1F]

Aq. HCl (38% w/w, 1.5 mL) was added, with stirring, to a solution of Pentafluoropyrdine (2.00 g, 10.9 mmol) and 1-cyanoguanidine (1.10 g, 13.1 mmol) in acetonitrile (50 mL) and the mixture was heated under microwave radiation (45 min, 140° C., 15 bar). The reaction mixture was cooled to room temperature and aq. NaOH (2M) was added until pH 12. Ethyl acetate was added and the phases were separated. The organic phase was dried over anhydrous $Na_2SO_4$, filtered and concentrated under reduced pressure to yield the desired product (2.04 g, 70.1% yield), which was directly used in the next step without any further purification.

MS (ESI) m/z 268 [M+H⁺]

3.2: N4-(2,3,5,6-tetrafluorophenyl)-6-(2,2,2-trifluoro-1-methyl-ethyl)-1,3,5-triazine-2,4-diamine

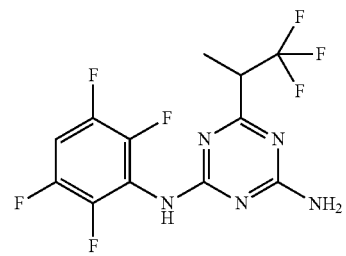 [SMILES: CC(c1nc(N)nc(Nc2c(F)c(F)cc(F)c2F)n1)C(F)(F)F]

3,3,3-trifluoro-2-methyl-propanoyl chloride (0.35 g, 2.18 mmol), which was synthesized from the commercially available carboxylic acid following literature known procedures, dissolved in $CH_2Cl_2$ (10 mL) was added to a solution of 1-carbamimidoyl-3-(2,3,4,5,6-pentafluorophenyl)guanidine (0.58 g, 2.18 mmol) and triethylamine (0.66 g, 6.54 mmol) in THF (20 mL). After the initial weak exothermic reaction was finished, the mixture was stirred for 4 h at 60° C. The reaction mixture was cooled to ambient temperature, diluted with water and ethyl acetate and the phases were separated. The organic phase was dried over anhydrous $Na_2SO_4$, filtered and concentrated under reduced pressure. Column chromatography of the resulting crude product (ISCO-CombiFlash Rf, cyclohexane/ethyl acetate) yields the desired product (0.37 g, 45.5% yield) as a white solid.

MS (ESI) m/z 374 [M+H⁺]

The compounds listed above in table 1, 2 and 3 can be prepared similar to the examples mentioned above. Likewise, the following compounds of preparation examples 4 to 10 were prepared by the protocols of examples 1 to 3.

| no | Compound | m/z [M + H⁺] |
|---|---|---|
| 4 | | 296.2 |

6-(cyclopropylmethyl)-N4-(2,4,6-trifluorophenyl)-1,3,5-triazine-2,4-diamine

-continued

| no | Compound | m/z [M + H⁺] |
|---|---|---|
| 5 | 6-(1-cyclopropylethyl)-N4-(2,3,5,6-tetrafluorophenyl)-1,3,5-triazine-2,4-diamine | 328.1 |
| 6 | 6-(1-methylbutyl)-N4-(2,3,5,6-tetrafluorophenyl)-1,3,5-triazine-2,4-diamine | 329.8 |
| 7 | N4-(2,3,5,6-tetrafluorophenyl)-6-(1,2,2-trimethylpropyl)-1,3,5-triazine-2,4-diamine | 343.8 |
| 8 | 6-(1-methylcyclobutyl)-N4-(2,3,5,6-tetrafluorophenyl)-1,3,5-triazine-2,4-diamine | 327.8 |
| 9 | 6-(1-fluorocyclopentyl)-N4-(2,3,5,6-tetrafluorophenyl)-1,3,5-triazine-2,4-diamine | 346.0 |

-continued

| no | Compound | m/z [M + H⁺] |
|---|---|---|
| 10 | N4-(2,6-difluorophenyl)-6-(1-fluoro-1-methyl-ethyl)-1,3,5-triazine-2,4-diamine | 284.3 |

B Use Examples

The herbicidal activity of the azines of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 278 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A moderate herbicidal activity is given at values of at least 60, a good herbicidal activity is given at values of at least 70, and a very good herbicidal activity is given at values of at least 85.

The plants used in the greenhouse experiments were of the following species:

| Bayer code | Scientific name |
|---|---|
| ABUTH | Abutilon theophrasti |
| ALOMY | Alopecurus myosuroides |
| AMARE | Amaranthus retroflexus |
| APESV | Apera spica-venti |
| ECHCG | Echinocloa crus-galli |
| LAMPU | Lamium purpureum |
| POLCO | Polygonum convolvulus |
| SETFA | Setaria faberi |
| SETVI | Setaria viridis |

-continued

| Bayer code | Scientific name |
|---|---|
| STEME | *Stellaria media* |
| VIOAR | *Viola arvensis* |

Example 4 applied by post-emergence method at an application rate of 1.0 kg/ha, showed very good herbicidal activity against AMARE and good herbicidal activity against POLCO.

Example 5 applied by post-emergence method at an application rate of 0.5 kg/ha, showed very good herbicidal activity against ABUTH, AMARE and ECHCG.

Example 6 applied by pre-emergence method at an application rate of 0.25 kg/ha, showed very good herbicidal activity against ABUTH, AMARE and SETFA.

Example 7 applied by pre-emergence method at an application rate of 0.25 kg/ha, showed very good herbicidal activity against AMARE, ECHCG and SETFA.

The respective stated components a and b, and if appropriate, c were formulated as a 10% by weight strength emulsion concentrate and, with addition of the amount of solvent system, introduced into the spray liquor used for applying the active compound.

In the examples, the solvent used was water.

In the examples below, using the method of S. R. Colby (1967) "Calculating synergistic and antagonistic responses of herbicide combinations", Weeds 15, p. 22ff., the value E, which is expected if the activity of the individual active compounds is only additive, was calculated.

$$E = X + Y - (X \cdot Y/100)$$

where
X=percent activity using active compound a at an application rate A;
Y=percent activity using active compound b at an application rate B;
E=expected activity (in %) by a+b at application rates A+B.

If the value found experimentally is higher than the value E calculated according to Colby, a synergistic effect is present.

The results of these tests are given below in the use examples and demonstrate the synergistic effect of the mixtures comprising at least one compound of the formula (I) and at least one herbicide B. In this context, a.s. means active substance, based on 100% active ingredient.

The plants uses in the greenhouse experiments with combination of compound 2 illustrated in the following table 1a/b to 9 a/b belonged to the following species:

| Scientific Name | Code | Common Name |
|---|---|---|
| *Abutilon theophrasti* | ABUTH | velvetleaf |
| *Alopecurus myosuroides* | ALOMY | blackgrass |
| *Anthemis arvensis* | ANTAR | field chamomile |
| *Avena fatua* | AVEFA | wild oat |
| *Brachiaria decumbens* | BRADC | surinam grass |
| *Commelina benghalensis* | COMBE | tropical spiderwort |
| *Eleusine indica* | ELEIN | goosegrass |
| *Euphorbia heterophylla* | EPHHL | wild spurge |
| *Galium aparine* | GALAP | cleaver |
| *Geranium pusillum* | GERPU | small-flowered cranesbill |
| *Kochia scoparia* | KCHSC | kochia |
| *Lolium multiflorum* | LOLMU | italian ryegrass |
| *Phalaris canariensis* | PHACA | canarygrass |
| *Ipomoea hederacea* | IPOHE | ivy-leave morning glory |
| *Polygonum convolvulus* | POLCO | wild buckwheat |
| *Sida rhombifolia* | SIDRH | common sida |
| *Sorghum halepense* | SORHA | johnsongrass |

TABLE 1a

Application in Pre-Emergence of compound 2 and Saflufenacil (individual activities)

| | compound 2 (A) | | Saflufenacil (B) | |
|---|---|---|---|---|
| Weed | use rate [g ai/ha] | observed % activity 20 DAT | use rate [g ai/ha] | observed % activity 20 DAT |
| ALOMY | 8 | 50 | 3.125 | 0 |
| APESV | 2 | 95 | 3.125 | 0 |
| ECHCG | 1 | 65 | 3.125 | 0 |
| POLCO | 2 | 70 | 6.25 | 70 |

TABLE 1b

Application in Pre-Emergence of compound 2 and Saflufenacil (combined activities)

| | compound 2 + Saflufenacil (C) | | | |
|---|---|---|---|---|
| Weed | use rate [g ai/ha] | observed % activity 20 DAT | expected % activity 20 DAT | Synergism Y/N 20 DAT |
| ALOMY | 8 + 3.125 | 85 | 80 | Y |
| APESV | 2 + 3.125 | 98 | 95 | Y |
| ECHCG | 1 + 3.125 | 70 | 65 | Y |
| POLCO | 2 + 6.25 | 100 | 91 | Y |

TABLE 2a

Application in Pre-Emergence of compound 2 and Dicamba (individual activities)

| | compound 2 (A) | | DICAMBA (B) | |
|---|---|---|---|---|
| Weed | use rate [g ai/ha] | observed % activity 20 DAT | use rate [g ai/ha] | observed % activity 20 DAT |
| ALOMY | 8 | 80 | 100 | 40 |
| ALOMY | 4 | 90 | 50 | 20 |
| APESV | 2 | 95 | 100 | 35 |
| LOLMU | 4 | 95 | 100 | 45 |
| LOLMU | 4 | 95 | 50 | 40 |
| ECHCG | 1 | 65 | 50 | 0 |
| POLCO | 2 | 70 | 50 | 40 |

TABLE 2b

Application in Pre-Emergence of compound 2 and Dicamba (combined activities)

| | compound 2 + DICAMBA (C) | | | |
|---|---|---|---|---|
| Weed | use rate [g ai/ha] | observed % activity 20 DAT | expected % activity 20 DAT | Synergism Y/N 20 DAT |
| ALOMY | 8 + 100 | 98 | 88 | Y |
| ALOMY | 4 + 50 | 95 | 92 | Y |
| ALOMY | 2 + 100 | 100 | 97 | Y |
| LOLMU | 4 + 100 | 98 | 97 | Y |
| LOLMU | 4 + 50 | 98 | 97 | Y |
| ECHCG | 1 + 50 | 70 | 65 | Y |
| POLCO | 2 + 50 | 95 | 82 | Y |

TABLE 3a

Application in Pre-Emergence of compound 2 and Picolinafen (individual activities)

| | compound 2 (A) | | Picolinafen (B) | |
|---|---|---|---|---|
| Weed | use rate [g ai/ha] | observed % activity 20 DAT | use rate [g ai/ha] | observed % activity 20 DAT |
| SETFA | 4 | 95 | 25 | 10 |
| POLCO | 1 | 15 | 50 | 0 |
| POLCO | 1 | 15 | 25 | 0 |
| KCHSC | 8 | 80 | 50 | 30 |

TABLE 3b

Application in Pre-Emergence of compound 2 and Picolinafen (combined activities)

| | compound 2 + Picolinafen (C) | | | |
|---|---|---|---|---|
| Weed | use rate [g ai/ha] | observed % activity 20 DAT | expected % activity 20 DAT | Synergism Y/N 20 DAT |
| SETFA | 4 + 25 | 100 | 96 | Y |
| POLCO | 1 + 50 | 25 | 15 | Y |
| POLCO | 1 + 25 | 30 | 15 | Y |
| KCHSC | 8 + 50 | 90 | 86 | Y |

TABLE 4a

Application in Pre-Emergence of compound 2 and Pyroxasulfone (individual activities)

| | compound 2 (A) | | Pyroxasulfone (B) | |
|---|---|---|---|---|
| Weed | use rate [g ai/ha] | observed % activity 20 DAT | use rate [g ai/ha] | observed % activity 20 DAT |
| ALOMY | 1 | 60 | 25 | 20 |
| ALOMY | 8 | 95 | 12.5 | 20 |
| ALOMY | 4 | 95 | 12.5 | 20 |
| ALOMY | 2 | 70 | 12.5 | 20 |
| ALOMY | 1 | 60 | 12.5 | 20 |
| APESV | 1 | 95 | 25 | 50 |
| APESV | 1 | 95 | 12.5 | 40 |
| LOLMU | 1 | 40 | 25 | 40 |
| LOLMU | 2 | 80 | 12.5 | 30 |
| LOLMU | 1 | 40 | 12.5 | 30 |
| SETFA | 2 | 95 | 25 | 95 |
| SETFA | 2 | 95 | 12.5 | 80 |
| SETFA | 1 | 80 | 12.5 | 80 |
| ECHCG | 2 | 98 | 25 | 90 |
| ECHCG | 2 | 98 | 12.5 | 50 |
| ECHCG | 1 | 65 | 12.5 | 50 |
| PHACA | 1 | 20 | 25 | 55 |
| PHACA | 2 | 70 | 12.5 | 40 |
| PHACA | 1 | 20 | 12.5 | 40 |
| POLCO | 4 | 95 | 12.5 | 0 |
| POLCO | 1 | 50 | 12.5 | 0 |

TABLE 4b

Application in Pre-Emergence of compound 2 and Pyroxasulfone (combined activities)

| | compound 2 + Pyroxasulfone (C) | | | |
|---|---|---|---|---|
| Weed | use rate [g ai/ha] | observed % activity 20 DAT | expected % activity 20 DAT | Synergism Y/N 20 DAT |
| ALOMY | 1 + 25 | 85 | 68 | Y |
| ALOMY | 8 + 12.5 | 98 | 96 | Y |
| ALOMY | 4 + 12.5 | 98 | 96 | Y |
| ALOMY | 2 + 12.5 | 90 | 76 | Y |
| ALOMY | 1 + 12.5 | 85 | 68 | Y |
| APESV | 1 + 25 | 100 | 98 | Y |
| APESV | 1 + 12.5 | 100 | 98 | Y |
| LOLMU | 1 + 25 | 95 | 64 | Y |
| LOLMU | 2 + 12.5 | 98 | 86 | Y |
| LOLMU | 1 + 12.5 | 65 | 58 | Y |
| SETFA | 2 + 25 | 100 | 100 | Y |
| SETFA | 2 + 12.5 | 100 | 99 | Y |
| SETFA | 1 + 12.5 | 100 | 96 | Y |
| ECHCG | 2 + 25 | 100 | 100 | Y |
| ECHCG | 2 + 12.5 | 100 | 99 | Y |
| ECHCG | 1 + 12.5 | 90 | 83 | Y |
| PHACA | 1 + 25 | 95 | 64 | Y |
| PHACA | 2 + 12.5 | 98 | 82 | Y |
| PHACA | 1 + 12.5 | 90 | 52 | Y |
| POLCO | 4 + 12.5 | 100 | 95 | Y |
| POLCO | 1 + 12.5 | 60 | 50 | Y |

TABLE 5a

Application in Pre-Emergence of compound 2 and PPO (BAS 850) (individual activities)

| | compound 2 (A) | | PPO (B) | |
|---|---|---|---|---|
| Weed | use rate [g ai/ha] | observed % activity 20 DAT | use rate [g ai/ha] | observed % activity 20 DAT |
| POLCO | 4 | 95 | 25 | 0 |
| POLCO | 1 | 50 | 25 | 0 |
| POLCO | 4 | 95 | 12.5 | 0 |
| KCHSC | 8 | 95 | 12.5 | 25 |
| KCHSC | 4 | 90 | 12.5 | 25 |
| KCHSC | 2 | 80 | 12.5 | 25 |
| KCHSC | 1 | 45 | 12.5 | 25 |

TABLE 5b

Application in Pre-Emergence of compound 2 and PPO (BAS 850) (combined activities)

| | compound 2 + PPO (C) | | | |
|---|---|---|---|---|
| Weed | use rate [g ai/ha] | observed % activity 20 DAT | expected % activity 20 DAT | Synergism Y/N 20 DAT |
| POLCO | 4 + 25 | 100 | 95 | Y |
| POLCO | 1 + 25 | 80 | 50 | Y |
| POLCO | 4 + 12.5 | 100 | 95 | Y |
| KCHSC | 8 + 12.5 | 100 | 96 | Y |
| KCHSC | 4 + 12.5 | 100 | 93 | Y |
| KCHSC | 2 + 12.5 | 98 | 85 | Y |
| KCHSC | 1 + 12.5 | 65 | 59 | Y |

TABLE 6a

Application in Pre-Emergence of compound 2 and glyphosate (individual activities)

| | compound 2 (A) | | Glyphosate (B) | |
|---|---|---|---|---|
| Weed | use rate [g ai/ha] | observed % activity 20 DAT | use rate [g ai/ha] | observed % activity 20 DAT |
| ALOMY | 4 | 90 | 125 | 0 |

TABLE 6b

Application in Pre-Emergence of compound 2 and Glyphosate (combined activities)

| | compound 2 + Glyphosate (C) | | | |
|---|---|---|---|---|
| Weed | use rate [g ai/ha] | observed % activity 20 DAT | expected % activity 20 DAT | Synergism Y/N 20 DAT |
| ALOMY | 4 + 125 | 95 | 90 | Y |

TABLE 7a

Application in Pre-Emergence of compound 2 and Flufenacet (individual activities)

| | compound 2 (A) | | Flufenacet (B) | |
|---|---|---|---|---|
| Weed | use rate [g ai/ha] | observed % activity 20 DAT | use rate [g ai/ha] | observed % activity 20 DAT |
| ALOMY | 4 | 90 | 60 | 80 |
| LOLMU | 4 | 95 | 60 | 30 |
| LOLMU | 1 | 20 | 60 | 30 |
| LOLMU | 1 | 20 | 30 | 0 |
| ECHCG | 2 | 95 | 30 | 85 |
| ECHCG | 1 | 65 | 30 | 85 |
| PHACA | 8 | 85 | 60 | 98 |
| VIOAR | 1 | 75 | 30 | 0 |

TABLE 7b

Application in Pre-Emergence of compound 2 and Flufenacet (combined activities)

| | compound 2 + Flufenacet (C) | | | |
|---|---|---|---|---|
| Weed | use rate [g ai/ha] | observed % activity 20 DAT | expected % activity 20 DAT | Synergism Y/N 20 DAT |
| ALOMY | 4 + 60 | 100 | 98 | Y |
| LOLMU | 4 + 60 | 98 | 97 | Y |
| LOLMU | 1 + 60 | 65 | 44 | Y |
| LOLMU | 1 + 30 | 60 | 36 | Y |
| ECHCG | 2 + 30 | 100 | 99 | Y |
| ECHCG | 1 + 30 | 98 | 95 | Y |
| PHACA | 8 + 60 | 100 | 100 | Y |
| VIOAR | 1 + 30 | 90 | 75 | Y |

TABLE 8a

Application in Pre-Emergence of compound 2 and Pendimethalin (individual activities)

| | compound 2 (A) | | Pendimethalin (B) | |
|---|---|---|---|---|
| Weed | use rate [g ai/ha] | observed % activity 20 DAT | use rate [g ai/ha] | observed % activity 20 DAT |
| ALOMY | 4 | 90 | 250 | 15 |
| ALOMY | 2 | 75 | 250 | 15 |
| ALOMY | 1 | 45 | 1000 | 95 |
| APESV | 4 | 98 | 250 | 75 |
| APESV | 4 | 98 | 125 | 60 |
| APESV | 2 | 90 | 500 | 95 |
| APESV | 2 | 90 | 250 | 75 |
| APESV | 2 | 90 | 125 | 60 |
| LOLMU | 2 | 80 | 500 | 15 |
| LOLMU | 2 | 70 | 1000 | 55 |
| LOLMU | 2 | 70 | 500 | 0 |
| LOLMU | 1 | 30 | 1000 | 55 |
| LOLMU | 1 | 30 | 500 | 0 |
| SETFA | 2 | 75 | 500 | 98 |
| ECHCG | 2 | 70 | 250 | 98 |
| PHACA | 2 | 50 | 250 | 55 |
| PHACA | 1 | 20 | 250 | 55 |
| POLCO | 2 | 70 | 500 | 60 |
| POLCO | 1 | 60 | 500 | 60 |
| KCHSC | 1 | 0 | 500 | 80 |
| VIOAR | 1 | 0 | 500 | 80 |
| GERPU | 2 | 0 | 125 | 90 |
| GERPU | 1 | 0 | 500 | 70 |

TABLE 8b

Application in Pre-Emergence of compound 2 and Pendimethalin (combined activities)

| | compound 2 + Pendimethalin (C) | | | |
|---|---|---|---|---|
| Weed | use rate [g ai/ha] | observed % activity 20 DAT | expected % activity 20 DAT | Synergism Y/N 20 DAT |
| ALOMY | 4 + 250 | 98 | 92 | Y |
| ALOMY | 2 + 250 | 80 | 79 | Y |
| ALOMY | 1 + 1000 | 98 | 97 | Y |
| APESV | 4 + 250 | 100 | 100 | Y |
| APESV | 4 + 125 | 100 | 99 | Y |
| APESV | 2 + 500 | 100 | 100 | Y |
| APESV | 2 + 250 | 100 | 98 | Y |
| APESV | 2 + 125 | 98 | 96 | Y |
| LOLMU | 2 + 500 | 95 | 83 | Y |
| LOLMU | 2 + 1000 | 90 | 87 | Y |
| LOLMU | 2 + 500 | 80 | 70 | Y |
| LOLMU | 1 + 1000 | 80 | 69 | Y |
| LOLMU | 1 + 500 | 50 | 30 | Y |
| SETFA | 2 + 500 | 100 | 100 | Y |
| ECHCG | 2 + 250 | 100 | 99 | Y |
| PHACA | 2 + 250 | 95 | 78 | Y |
| PHACA | 1 + 250 | 65 | 64 | Y |
| POLCO | 2 + 500 | 98 | 88 | Y |
| POLCO | 1 + 500 | 90 | 84 | Y |
| KCHSC | 1 + 500 | 90 | 80 | Y |
| VIOAR | 1 + 500 | 90 | 80 | Y |
| GERPU | 2 + 125 | 80 | 70 | Y |
| GERPU | 1 + 500 | 95 | 90 | Y |

TABLE 9a

Application in Pre-Emergence of compound 2 and Dimethenamid (individual activities)

| | compound 2 (A) | | DMTA (B) | |
|---|---|---|---|---|
| Weed | use rate [g ai/ha] | observed % activity 20 DAT | use rate [g ai/ha] | observed % activity 20 DAT |
| ALOMY | 4 | 90 | 62.5 | 0 |
| ALOMY | 1 | 45 | 62.5 | 0 |
| APESV | 2 | 95 | 62.5 | 95 |
| LOLMU | 4 | 95 | 125 | 95 |
| LOLMU | 2 | 70 | 125 | 95 |
| LOLMU | 1 | 30 | 62.5 | 85 |
| LOLMU | 1 | 30 | 15.625 | 0 |
| SETFA | 2 | 75 | 31.25 | 98 |
| SETFA | 2 | 65 | 31.25 | 98 |
| ECHCG | 2 | 70 | 31.25 | 98 |
| PHACA | 4 | 95 | 15.625 | 10 |
| PHACA | 2 | 85 | 62.5 | 65 |
| PHACA | 1 | 20 | 125 | 80 |
| PHACA | 1 | 20 | 62.5 | 70 |
| PHACA | 1 | 20 | 31.25 | 55 |
| POLCO | 2 | 70 | 125 | 0 |
| POLCO | 2 | 70 | 62.5 | 0 |
| POLCO | 2 | 70 | 31.25 | 0 |
| POLCO | 1 | 60 | 125 | 0 |
| POLCO | 1 | 60 | 62.5 | 0 |
| POLCO | 1 | 60 | 31.25 | 0 |
| KCHSC | 2 | 50 | 62.5 | 0 |
| KCHSC | 2 | 50 | 125 | 0 |
| KCHSC | 2 | 50 | 62.5 | 0 |
| KCHSC | 2 | 50 | 31.25 | 0 |
| KCHSC | 1 | 0 | 125 | 0 |
| KCHSC | 1 | 0 | 62.5 | 0 |
| VIOAR | 2 | 50 | 125 | 0 |
| VIOAR | 2 | 50 | 62.5 | 0 |
| VIOAR | 2 | 50 | 31.25 | 0 |
| VIOAR | 1 | 0 | 125 | 0 |
| VIOAR | 1 | 0 | 62.5 | 0 |
| GERPU | 2 | 0 | 125 | 95 |
| GERPU | 2 | 0 | 62.5 | 85 |
| GERPU | 1 | 0 | 125 | 95 |
| GERPU | 1 | 0 | 62.5 | 85 |
| MATIN | 1 | 98 | 125 | 90 |
| MATIN | 1 | 98 | 62.5 | 70 |

TABLE 9b

Application in Pre-Emergence of compound 2 and Dimethenamid (combined activities)

| | compound 2 + DMTA (C) | | | |
|---|---|---|---|---|
| Weed | use rate [g ai/ha] | observed % activity 20 DAT | expected % activity 20 DAT | Synergism Y/N 20 DAT |
| ALOMY | 4 + 62.5 | 95 | 90 | Y |
| ALOMY | 1 + 62.5 | 65 | 45 | Y |
| APESV | 2 + 62.5 | 100 | 100 | Y |
| LOLMU | 4 + 125 | 100 | 100 | Y |
| LOLMU | 2 + 125 | 100 | 99 | Y |
| LOLMU | 1 + 62.5 | 95 | 90 | Y |
| LOLMU | 1 + 15.625 | 40 | 30 | Y |
| SETFA | 2 + 31.25 | 100 | 100 | Y |
| SETFA | 2 + 31.25 | 100 | 99 | Y |
| ECHCG | 2 + 31.25 | 100 | 99 | Y |
| PHACA | 1 + 15.625 | 98 | 96 | Y |
| PHACA | 2 + 62.5 | 95 | 95 | Y |
| PHACA | 1 + 125 | 90 | 84 | Y |
| PHACA | 1 + 62.5 | 90 | 76 | Y |
| PHACA | 1 + 31.25 | 65 | 64 | Y |
| POLCO | 2 + 125 | 95 | 70 | Y |
| POLCO | 2 + 62.5 | 100 | 70 | Y |
| POLCO | 2 + 31.25 | 90 | 70 | Y |

TABLE 9b-continued

Application in Pre-Emergence of compound 2 and Dimethenamid (combined activities)

| | compound 2 + DMTA (C) | | | |
|---|---|---|---|---|
| Weed | use rate [g ai/ha] | observed % activity 20 DAT | expected % activity 20 DAT | Synergism Y/N 20 DAT |
| POLCO | 1 + 125 | 75 | 60 | Y |
| POLCO | 1 + 62.5 | 90 | 60 | Y |
| POLCO | 1 + 31.25 | 65 | 60 | Y |
| KCHSC | 2 + 62.5 | 65 | 50 | Y |
| KCHSC | 2 + 125 | 70 | 50 | Y |
| KCHSC | 2 + 62.5 | 55 | 50 | Y |
| KCHSC | 2 + 31.25 | 55 | 50 | Y |
| KCHSC | 1 + 125 | 50 | 0 | Y |
| KCHSC | 1 + 62.5 | 40 | 0 | Y |
| VIOAR | 2 + 125 | 70 | 50 | Y |
| VIOAR | 2 + 62.5 | 55 | 50 | Y |
| VIOAR | 2 + 31.25 | 55 | 50 | Y |
| VIOAR | 1 + 125 | 50 | 0 | Y |
| VIOAR | 1 + 62.5 | 40 | 0 | Y |
| GERPU | 2 + 125 | 100 | 98 | Y |
| GERPU | 2 + 62.5 | 95 | 85 | Y |
| GERPU | 1 + 125 | 98 | 95 | Y |
| GERPU | 1 + 62.5 | 95 | 85 | Y |
| MATIN | 1 + 125 | 100 | 100 | Y |
| MATIN | 1 + 62.5 | 100 | 99 | Y |

The plants used in the greenhouse experiments with the combinations of compound 8 illustrated in the following table 10 a/b to 24 a/b belonged to the following species.

| Scientific Name | Code | Common Name |
|---|---|---|
| *Abutilon theophrasti* | ABUTH | velvetleaf |
| *Alopecurus myosuroides* | ALOMY | blackgrass |
| *Anthemis arvensis* | ANTAR | field chamomile |
| *Avena fatua* | AVEFA | wild oat |
| *Brachiaria decumbens* | BRADC | surinam grass |
| *Commelina benghalensis* | COMBE | tropical spiderwort |
| *Eleusine indica* | ELEIN | goosegrass |
| *Euphorbia heterophylla* | EPHHL | wild spurge |
| *Galium aparine* | GALAP | cleaver |
| *Geranium pusillum* | GERPU | small-flowered cranesbill |
| *Kochia scoparia* | KCHSC | kochia |
| *Lolium multiflorum* | LOLMU | italian ryegrass |
| *Phalaris canariensis* | PHACA | canarygrass |
| *Ipomoea hederacea* | IPOHE | ivy-leave morning glory |
| *Polygonum convolvulus* | POLCO | wild buckwheat |
| *Sida rhombifolia* | SIDRH | common sida |
| *Sorghum halepense* | SORHA | johnsongrass |

TABLE 10a

Application in Pre-Emergence of compound 8 and flufenacet (individual activities)

| | compound 8 (A) | | | flufenacet (B) | | |
|---|---|---|---|---|---|---|
| weed | use rate [g ai/ha] | observed % activity 8 DAT | 20 DAT | use rate g ai/ha | observed % activity 8 DAT | 20 DAT |
| ALOMY | 8 | | 55 | 10 | | 28 |
| AVEFA | 16 | | 10 | 40 | | 10 |
| AVEFA | 8 | | 5 | 40 | | 10 |
| PHACA | 16 | | 50 | 20 | | 33 |
| PHACA | 8 | | 28 | 20 | | 33 |
| PHACA | 16 | | 50 | 10 | | 0 |
| PHACA | 8 | | 28 | 10 | | 0 |
| BRADC | 16 | | 70 | 40 | | 65 |
| BRADC | 8 | | 78 | 40 | | 65 |

TABLE 10a-continued

Application in Pre-Emergence of compound 8 and flufenacet (individual activities)

| | compound 8 (A) | | flufenacet (B) | | |
|---|---|---|---|---|---|
| weed | use rate [g ai/ha] | observed % activity 8 DAT | observed % activity 20 DAT | use rate g ai/ha | observed % activity 8 DAT | observed % activity 20 DAT |

| weed | use rate [g ai/ha] | 8 DAT | 20 DAT | g ai/ha | 8 DAT | 20 DAT |
|---|---|---|---|---|---|---|
| SORHA | 8 | | 90 | 40 | | 95 |
| GALAP | 16 | | 0 | 40 | | 40 |
| GALAP | 8 | | 0 | 40 | | 40 |
| POLCO | 8 | | 65 | 20 | | 0 |
| KCHSC | 16 | | 85 | 40 | | 0 |
| KCHSC | 16 | | 85 | 20 | | 0 |
| KCHSC | 16 | | 85 | 10 | | 0 |

TABLE 10b

Application in Pre-Emergence of compound 8 and flufenacet (combined activities)

| | compound 8 + flufenacet | | | | | |
|---|---|---|---|---|---|---|
| | | Observed % activity | | expected % activity | | Synergism Y/N |
| weed | use rate [g ai/ha] | 8 DAT | 20 DAT | 8 DAT | 20 DAT | 8 DAT | 20 DAT |
| ALOMY | 8 + 10 | | 83 | | 67 | | Y |
| AVEFA | 16 + 40 | | 43 | | 19 | | Y |
| AVEFA | 8 + 40 | | 35 | | 15 | | Y |
| PHACA | 16 + 20 | | 70 | | 66 | | Y |
| PHACA | 8 + 20 | | 65 | | 51 | | Y |
| PHACA | 16 + 10 | | 60 | | 50 | | Y |
| PHACA | 8 + 10 | | 45 | | 28 | | Y |
| BRADC | 16 + 40 | | 93 | | 90 | | Y |
| BRADC | 8 + 40 | | 93 | | 92 | | Y |
| SORHA | 8 + 40 | | 100 | | 100 | | Y |
| GALAP | 16 + 40 | | 60 | | 40 | | Y |
| GALAP | 8 + 40 | | 50 | | 40 | | Y |
| POLCO | 8 + 20 | | 80 | | 65 | | Y |
| KCHSC | 16 + 40 | | 90 | | 85 | | Y |
| KCHSC | 16 + 20 | | 90 | | 85 | | Y |
| KCHSC | 16 + 10 | | 95 | | 85 | | Y |

TABLE 11a

Application in Pre-Emergence of compound 8 and pyroxasulfone (individual activities)

| | compound 8 (A) | | | pyroxasulfone (B) | | |
|---|---|---|---|---|---|---|
| weed | use rate [g ai/ha] | observed % activity 8 DAT | 20 DAT | use rate g ai/ha | observed % activity 8 DAT | 20 DAT |
| ALOMY | 16 | | 90 | 24 | | 98 |
| ALOMY | 8 | | 50 | 12 | | 95 |
| AVEFA | 16 | | 10 | 24 | | 60 |
| AVEFA | 8 | | 0 | 6 | | 0 |
| LOLMU | 16 | | 40 | 24 | | 98 |
| LOLMU | 8 | | 30 | 6 | | 35 |
| PHACA | 16 | | 40 | 24 | | 95 |
| PHACA | 8 | | 25 | 24 | | 95 |
| PHACA | 16 | | 40 | 6 | | 80 |
| BRADC | 16 | | 70 | 6 | | 53 |
| SORHA | 16 | | 90 | 24 | | 98 |
| SORHA | 16 | | 90 | 6 | | 75 |
| GALAP | 16 | | 0 | 24 | | 75 |

TABLE 11a-continued

Application in Pre-Emergence of compound 8 and pyroxasulfone (individual activities)

| | compound 8 (A) | | | pyroxasulfone (B) | | |
|---|---|---|---|---|---|---|
| weed | use rate [g ai/ha] | 8 DAT | 20 DAT | g ai/ha | 8 DAT | 20 DAT |
| GALAP | 8 | | 0 | 12 | | 75 |
| POLCO | 8 | | 65 | 12 | | 0 |
| KCHSC | 16 | | 85 | 12 | | 85 |
| KCHSC | 16 | | 85 | 6 | | 0 |

TABLE 11b

Application in Pre-Emergence of compound 8 and pyroxasulfone (combined activities)

| | compound 8 + pyroxasulfone | | | | | |
|---|---|---|---|---|---|---|
| | | Observed % activity | | expected % activity | | Synergism Y/N |
| weed | use rate [g ai/ha] | 8 DAT | 20 DAT | 8 DAT | 20 DAT | 8 DAT | 20 DAT |
| ALOMY | 16 + 24 | | 100 | | 100 | | Y |
| ALOMY | 8 + 12 | | 98 | | 98 | | Y |
| AVEFA | 16 + 24 | | 80 | | 65 | | Y |
| AVEFA | 8 + 6 | | 35 | | 0 | | Y |
| LOLMU | 16 + 24 | | 100 | | 99 | | Y |
| LOLMU | 8 + 6 | | 60 | | 55 | | Y |
| PHACA | 16 + 24 | | 98 | | 97 | | Y |
| PHACA | 8 + 24 | | 98 | | 96 | | Y |
| PHACA | 16 + 6 | | 90 | | 85 | | Y |
| BRADC | 16 + 6 | | 99 | | 86 | | Y |
| SORHA | 16 + 24 | | 100 | | 100 | | Y |
| SORHA | 16 + 6 | | 98 | | 98 | | Y |
| GALAP | 16 + 24 | | 100 | | 75 | | Y |
| GALAP | 8 + 12 | | 98 | | 75 | | Y |
| POLCO | 8 + 12 | | 80 | | 65 | | Y |
| KCHSC | 16 + 12 | | 98 | | 98 | | Y |
| KCHSC | 16 + 6 | | 95 | | 85 | | Y |

TABLE 12a

Application in Pre-Emergence of compound 8 and dimethenamid-P (individual activities)

| | compound 8 (A) | | | dimethenamid-P (B) | | |
|---|---|---|---|---|---|---|
| Weed | use rate [g ai/ha] | observed % activity 8 DAT | 20 DAT | use rate g ai/ha | observed % activity 8 DAT | 20 DAT |
| ALOMY | 16 | | 90 | 125 | | 45 |
| ALOMY | 8 | | 50 | 125 | | 45 |
| AVEFA | 16 | | 0 | 250 | | 65 |
| AVEFA | 8 | | 0 | 250 | | 65 |
| LOLMU | 16 | | 40 | 250 | | 95 |
| LOLMU | 8 | | 30 | 250 | | 95 |
| LOLMU | 16 | | 40 | 125 | | 95 |
| LOLMU | 8 | | 30 | 125 | | 95 |
| PHACA | 16 | | 60 | 125 | | 80 |
| SORHA | 16 | | 90 | 125 | | 98 |
| GALAP | 16 | | 0 | 250 | | 50 |
| GALAP | 8 | | 0 | 250 | | 50 |
| GALAP | 16 | | 0 | 125 | | 30 |
| GALAP | 8 | | 0 | 125 | | 30 |

TABLE 12a-continued

Application in Pre-Emergence of compound 8 and dimethenamid-P (individual activities)

| | | compound 8 (A) | | | dimethenamid-P (B) | |
| --- | --- | --- | --- | --- | --- | --- |
| | | | observed % activity | | | observed % activity |
| Weed | use rate [g ai/ha] | 8 DAT | 20 DAT | use rate [g ai/ha] | 8 DAT | 20 DAT |
| POLCO | 8 | | 65 | 250 | | 50 |
| POLCO | 8 | | 65 | 125 | | 55 |
| KCHSC | 16 | | 85 | 250 | | 85 |
| KCHSC | 8 | | 90 | 250 | | 85 |
| KCHSC | 16 | | 85 | 125 | | 40 |
| KCHSC | 8 | | 90 | 125 | | 40 |

TABLE 12b

Application in Pre-Emergence of compound 8 and dimethenamid-P (combined activities)

| | | compound 8 + dimethenamd-P | | | | |
| --- | --- | --- | --- | --- | --- | --- |
| | | Observed % activity | | expected % activity | | Synergism Y/N |
| Weed | use rate [g ai/ha] | 8 DAT | 20 DAT | 8 DAT | 20 DAT | 8 DAT | 20 DAT |
| ALOMY | 16 + 125 | | 95 | | 95 | | Y |
| ALOMY | 8 + 125 | | 95 | | 73 | | Y |
| AVEFA | 16 + 250 | | 70 | | 65 | | Y |
| AVEFA | 8 + 250 | | 70 | | 65 | | Y |
| LOLMU | 16 + 250 | | 100 | | 97 | | Y |
| LOLMU | 8 + 250 | | 100 | | 97 | | Y |
| LOLMU | 16 + 125 | | 98 | | 97 | | Y |
| LOLMU | 8 + 125 | | 98 | | 97 | | Y |
| PHACA | 16 + 125 | | 95 | | 92 | | Y |
| SORHA | 16 + 125 | | 100 | | 100 | | Y |
| GALAP | 16 + 250 | | 90 | | 50 | | Y |
| GALAP | 8 + 250 | | 90 | | 50 | | Y |
| GALAP | 16 + 125 | | 65 | | 30 | | Y |
| GALAP | 8 + 125 | | 50 | | 30 | | Y |
| POLCO | 8 + 250 | | 100 | | 83 | | Y |
| POLCO | 8 + 125 | | 95 | | 84 | | Y |
| KCHSC | 16 + 125 | | 100 | | 98 | | Y |
| KCHSC | 8 + 125 | | 100 | | 99 | | Y |
| KCHSC | 8 + 250 | | 100 | | 91 | | Y |
| KCHSC | 8 + 125 | | 95 | | 94 | | Y |

TABLE 13a

Application in Pre-Emergence of compound 8 and acetochlor (individual activities)

| | | compound 8 (A) | | | acetochlor (B) | |
| --- | --- | --- | --- | --- | --- | --- |
| | | | observed % activity | | | observed % activity |
| Weed | use rate [g ai/ha] | 8 DAT | 20 DAT | g ai/ha | 8 DAT | 20 DAT |
| ALOMY | 8 | | 50 | 125 | | 0 |
| ALOMY | 8 | | 50 | 62, 5 | | 0 |
| GALAP | 8 | | 0 | 125 | | 60 |
| KCHSC | 16 | | 85 | 125 | | 0 |

TABLE 13b

Application in Pre-Emergence of compound 8 and acetochlor (combined activities)

| | | compound 8 + acetochlor | | | | |
| --- | --- | --- | --- | --- | --- | --- |
| | | Observed % activity | | expected % activity | | Synergism Y/N |
| Weed | use rate [g ai/ha] | 8 DAT | 20 DAT | 8 DAT | 20 DAT | 8 DAT | 20 DAT |
| ALOMY | 8 + 125 | | 80 | | 50 | | Y |
| ALOMY | 8 + 62, 5 | | 75 | | 50 | | Y |
| GALAP | 8 + 125 | | 85 | | 60 | | Y |
| KCHSC | 16 + 125 | | 95 | | 85 | | Y |

TABLE 14a

Application in Pre-Emergence of compound 8 and metribuzin (individual activities)

| | | compound 8 (A) | | | metribuzin (B) | |
| --- | --- | --- | --- | --- | --- | --- |
| | | | observed % activity | | | observed % activity |
| Weed | use rate [g ai/ha] | 8 DAT | 20 DAT | g ai/ha | 8 DAT | 20 DAT |
| ALOMY | 16 | | 90 | 250 | | 98 |
| ALOMY | 8 | | 50 | 62, 5 | | 35 |
| AVEFA | 16 | | 0 | 250 | | 55 |
| AVEFA | 8 | | 0 | 250 | | 55 |
| AVEFA | 16 | | 0 | 125 | | 10 |
| AVEFA | 8 | | 0 | 125 | | 10 |
| AVEFA | 16 | | 0 | 62, 5 | | 0 |
| LOLMU | 8 | | 30 | 250 | | 90 |
| LOLMU | 16 | | 40 | 125 | | 60 |
| LOLMU | 8 | | 30 | 125 | | 60 |
| PHACA | 16 | | 40 | 250 | | 90 |
| PHACA | 8 | | 25 | 250 | | 90 |
| PHACA | 16 | | 40 | 125 | | 70 |
| PHACA | 8 | | 25 | 125 | | 70 |
| PHACA | 16 | | 40 | 62, 5 | | 30 |
| BRADC | 16 | | 60 | 62, 5 | | 50 |
| SORHA | 16 | | 90 | 250 | | 45 |
| SORHA | 8 | | 90 | 250 | | 45 |
| GALAP | 16 | | 0 | 250 | | 30 |
| GALAP | 16 | | 0 | 125 | | 30 |
| GALAP | 16 | | 0 | 62, 5 | | 30 |
| POLCO | 8 | | 65 | 62, 5 | | 0 |

TABLE 14b

Application in Pre-Emergence of compound 8 and metribuzin (combined activities)

| | | compound 8 + metribuzin | | | | |
| --- | --- | --- | --- | --- | --- | --- |
| | | Observed % activity | | expected % activity | | Synergism Y/N |
| Weed | use rate [g ai/ha] | 8 DAT | 20 DAT | 8 DAT | 20 DAT | 8 DAT | 20 DAT |
| ALOMY | 16 + 250 | | 100 | | 100 | | Y |
| ALOMY | 8 + 62, 5 | | 85 | | 68 | | Y |
| AVEFA | 16 + 250 | | 90 | | 55 | | Y |
| AVEFA | 8 + 250 | | 90 | | 55 | | Y |
| AVEFA | 16 + 125 | | 75 | | 10 | | Y |
| AVEFA | 8 + 125 | | 70 | | 10 | | Y |
| AVEFA | 16 + 62, 5 | | 35 | | 0 | | Y |
| LOLMU | 8 + 250 | | 95 | | 93 | | Y |

TABLE 14b-continued

Application in Pre-Emergence of compound 8 and metribuzin (combined activities)

| | | compound 8 + metribuzin | | | | | |
|---|---|---|---|---|---|---|---|
| | | Observed | | expected | | Synergism | |
| | | % activity | | % activity | | Y/N | Y/N |
| Weed | use rate [g ai/ha] | 8 DAT | 20 DAT | 8 DAT | 20 DAT | 8 DAT | 20 DAT |
| LOLMU | 16 + 125 | | 90 | | 76 | | Y |
| LOLMU | 8 + 125 | | 95 | | 72 | | Y |
| PHACA | 16 + 250 | | 100 | | 94 | | Y |
| PHACA | 8 + 250 | | 100 | | 93 | | Y |
| PHACA | 16 + 125 | | 90 | | 82 | | Y |
| PHACA | 8 + 125 | | 85 | | 78 | | Y |
| PHACA | 16 + 62, 5 | | 65 | | 58 | | Y |
| BRADC | 16 + 62, 5 | | 85 | | 80 | | Y |
| SORHA | 16 + 250 | | 95 | | 95 | | Y |
| SORHA | 8 + 250 | | 95 | | 95 | | Y |
| GALAP | 16 + 250 | | 65 | | 30 | | Y |
| GALAP | 16 + 125 | | 65 | | 30 | | Y |
| GALAP | 16 + 62, 5 | | 80 | | 30 | | Y |
| POLCO | 8 + 62, 5 | | 85 | | 65 | | Y |

TABLE 15a

Application in Pre-Emergence of compound 8 and pendimethalin (individual activities)

| | | compound 8 (A) | | pendimethalin (B) | | |
|---|---|---|---|---|---|---|
| | | observed % activity | | | observed % activity | |
| Weed | use rate [g ai/ha] | 8 DAT | 20 DAT | use rate [g ai/ha] | 8 DAT | 20 DAT |
| ALOMY | 8 | | 50 | 500 | | 85 |
| ALOMY | 16 | | 90 | 250 | | 60 |
| ALOMY | 8 | | 50 | 250 | | 60 |
| AVEFA | 16 | | 0 | 500 | | 0 |
| AVEFA | 8 | | 10 | 500 | | 0 |
| BRADC | 16 | | 60 | 500 | | 75 |
| SORHA | 16 | | 90 | 500 | | 85 |
| SORHA | 16 | | 90 | 250 | | 75 |
| GALAP | 16 | | 0 | 500 | | 30 |
| GALAP | 8 | | 0 | 500 | | 30 |
| POLCO | 8 | | 65 | 500 | | 60 |
| POLCO | 8 | | 65 | 250 | | 50 |

TABLE 15b

Application in Pre-Emergence of compound 8 and pendimethalin (combined activities)

| | | compound 8 + pendimethalin | | | | | |
|---|---|---|---|---|---|---|---|
| | | Observed | | expected | | Synergism | |
| | | % activity | | % activity | | Y/N | Y/N |
| Weed | use rate [g ai/ha] | 8 DAT | 20 DAT | 8 DAT | 20 DAT | 8 DAT | 20 DAT |
| ALOMY | 8 + 500 | | 95 | | 93 | | Y |
| ALOMY | 16 + 250 | | 98 | | 96 | | Y |
| ALOMY | 8 + 250 | | 90 | | 80 | | Y |
| AVEFA | 16 + 500 | | 25 | | 0 | | Y |
| AVEFA | 8 + 500 | | 40 | | 10 | | Y |
| BRADC | 16 + 500 | | 100 | | 90 | | Y |
| SORHA | 16 + 500 | | 100 | | 99 | | Y |
| SORHA | 16 + 250 | | 98 | | 98 | | Y |

TABLE 15b-continued

Application in Pre-Emergence of compound 8 and pendimethalin (combined activities)

| | | compound 8 + pendimethalin | | | | | |
|---|---|---|---|---|---|---|---|
| | | Observed | | expected | | Synergism | |
| | | % activity | | % activity | | Y/N | Y/N |
| Weed | use rate [g ai/ha] | 8 DAT | 20 DAT | 8 DAT | 20 DAT | 8 DAT | 20 DAT |
| GALAP | 16 + 500 | | 60 | | 30 | | Y |
| GALAP | 8 + 500 | | 60 | | 30 | | Y |
| POLCO | 8 + 500 | | 95 | | 86 | | Y |
| POLCO | 8 + 250 | | 85 | | 83 | | Y |

TABLE 16a

Application in Pre-Emergence of compound 8 and Sulfentrazone (individual activities)

| | | compound 8 (A) | | Sulfentrazone (B) | | |
|---|---|---|---|---|---|---|
| | | observed % activity | | | observed % activity | |
| Weed | use rate [g ai/ha] | 8 DAT | 20 DAT | g ai/ha | 8 DAT | 20 DAT |
| GALAP | 8 | | 35 | 6 | | 0 |
| POLCO | 16 | | 80 | 12 | | 0 |
| POLCO | 8 | | 0 | 12 | | 0 |
| POLCO | 16 | | 80 | 6 | | 0 |
| POLCO | 8 | | 0 | 6 | | 0 |
| ANTAR | 16 | | 85 | 12 | | 60 |
| ANTAR | 16 | | 85 | 6 | | 30 |
| KCHSC | 16 | | 80 | 12 | | 98 |
| KCHSC | 8 | | 70 | 12 | | 98 |
| GERPU | 16 | | 60 | 12 | | 45 |
| GERPU | 8 | | 20 | 12 | | 45 |
| GERPU | 8 | | 45 | 6 | | 40 |
| COMBE | 16 | | 65 | 12 | | 45 |
| COMBE | 8 | | 60 | 12 | | 45 |
| COMBE | 16 | | 65 | 6 | | 20 |
| SIDRH | 16 | | 85 | 6 | | 20 |
| ABUTH | 16 | | 70 | 12 | | 45 |
| ABUTH | 16 | | 70 | 6 | | 20 |
| ABUTH | 8 | | 80 | 6 | | 20 |

TABLE 16b

Application in Pre-Emergence of compound 8 and Sulfentrazone (combined activities)

| | | compound 8 + sulfentrazone | | | | | |
|---|---|---|---|---|---|---|---|
| | | Observed | | expected | | Synergism | |
| | | % activity | | % activity | | Y/N | Y/N |
| Weed | use rate [g ai/ha] | 8 DAT | 20 DAT | 8 DAT | 20 DAT | 8 DAT | 20 DAT |
| GALAP | 8 + 6 | | 45 | | 35 | | Y |
| POLCO | 16 + 12 | | 100 | | 80 | | Y |
| POLCO | 8 + 12 | | 60 | | 0 | | Y |
| POLCO | 16 + 6 | | 100 | | 80 | | Y |
| POLCO | 8 + 6 | | 65 | | 0 | | Y |
| ANTAR | 16 + 12 | | 100 | | 94 | | Y |
| ANTAR | 16 + 6 | | 95 | | 90 | | Y |
| KCHSC | 16 + 12 | | 100 | | 100 | | Y |
| KCHSC | 8 + 12 | | 100 | | 99 | | Y |
| GERPU | 16 + 12 | | 90 | | 78 | | Y |
| GERPU | 8 + 12 | | 70 | | 56 | | Y |

TABLE 16b-continued

Application in Pre-Emergence of compound 8 and Sulfentrazone (combined activities)

| | compound 8 + sulfentrazone | | | | | |
|---|---|---|---|---|---|---|
| | | Observed | | expected | | Synergism |
| | | % activity | | % activity | | Y/N   Y/N |
| Weed | use rate [g ai/ha] | 8 DAT | 20 DAT | 8 DAT | 20 DAT | 8 DAT   20 DAT |
| GERPU | 8 + 6 | | 75 | | 67 | Y |
| COMBE | 16 + 12 | | 85 | | 81 | Y |
| COMBE | 8 + 12 | | 90 | | 78 | Y |
| COMBE | 16 + 6 | | 90 | | 72 | Y |
| SIDRH | 16 + 6 | | 98 | | 88 | Y |
| ABUTH | 16 + 12 | | 85 | | 84 | Y |
| ABUTH | 16 + 6 | | 95 | | 76 | Y |
| ABUTH | 8 + 6 | | 85 | | 84 | Y |

TABLE 17a

Application in Pre-Emergence of compound 8 and Saflufenacil (individual activities)

| | compound 8 (A) | | | Saflufenacil (B) | | |
|---|---|---|---|---|---|---|
| | | observed % activity | | | observed % activity | |
| Weed | use rate [g ai/ha] | 8 DAT | 20 DAT | use rate g ai/ha | 8 DAT | 20 DAT |
| POLCO | 16 | | 70 | 10 | | 65 |
| POLCO | 8 | | 35 | 10 | | 65 |
| POLCO | 16 | | 70 | 5 | | 60 |
| POLCO | 8 | | 35 | 5 | | 60 |
| ANTAR | 16 | | 85 | 5 | | 98 |
| POLCO | 16 | | 70 | 10 | | 65 |
| POLCO | 8 | | 35 | 10 | | 65 |
| POLCO | 16 | | 70 | 5 | | 60 |
| POLCO | 8 | | 35 | 5 | | 60 |
| ANTAR | 16 | | 85 | 5 | | 98 |
| ANTAR | 8 | | 80 | 5 | | 98 |
| KCHSC | 16 | | 80 | 5 | | 70 |
| KCHSC | 8 | | 80 | 5 | | 85 |
| GERPU | 16 | | 80 | 10 | | 25 |
| GERPU | 8 | | 45 | 10 | | 25 |
| GERPU | 16 | | 80 | 5 | | 25 |
| GERPU | 8 | | 45 | 5 | | 25 |
| COMBE | 16 | | 65 | 10 | | 98 |
| COMBE | 16 | | 65 | 5 | | 65 |
| COMBE | 8 | | 60 | 5 | | 65 |
| SIDRH | 16 | | 80 | 10 | | 90 |
| SIDRH | 8 | | 65 | 10 | | 90 |
| SIDRH | 16 | | 80 | 5 | | 55 |
| SIDRH | 8 | | 65 | 5 | | 55 |
| EPHHL | 16 | | 70 | 10 | | 95 |
| EPHHL | 8 | | 45 | 5 | | 80 |
| ABUTH | 16 | | 80 | 10 | | 90 |
| ABUTH | 8 | | 70 | 10 | | 90 |

TABLE 17b

Application in Pre-Emergence of compound 8 and Saflufenacil (combined activities)

| | compound 8 + saflufenacil | | | | | |
|---|---|---|---|---|---|---|
| | | Observed | | expected | | Synergism |
| | | % activity | | % activity | | Y/N   Y/N |
| Weed | use rate [g ai/ha] | 8 DAT | 20 DAT | 8 DAT | 20 DAT | 8 DAT   20 DAT |
| POLCO | 16 + 10 | | 98 | | 90 | Y |
| POLCO | 8 + 10 | | 95 | | 77 | Y |
| POLCO | 16 + 5 | | 100 | | 88 | Y |
| POLCO | 8 + 5 | | 80 | | 74 | Y |
| ANTAR | 16 + 5 | | 100 | | 100 | Y |
| ANTAR | 8 + 5 | | 100 | | 100 | Y |
| KCHSC | 16 + 5 | | 95 | | 94 | Y |
| KCHSC | 8 + 5 | | 100 | | 97 | Y |
| GERPU | 16 + 10 | | 100 | | 85 | Y |
| GERPU | 8 + 10 | | 100 | | 59 | Y |
| GERPU | 16 + 5 | | 100 | | 85 | Y |
| GERPU | 8 + 5 | | 75 | | 59 | Y |
| COMBE | 16 + 10 | | 100 | | 99 | Y |
| COMBE | 16 + 5 | | 100 | | 99 | Y |
| COMBE | 8 + 5 | | 100 | | 88 | Y |
| SIDRH | 16 + 10 | | 100 | | 98 | Y |
| SIDRH | 8 + 10 | | 100 | | 97 | Y |
| SIDRH | 16 + 5 | | 100 | | 91 | Y |
| SIDRH | 8 + 5 | | 90 | | 84 | Y |
| EPHHL | 16 + 10 | | 100 | | 99 | Y |
| EPHHL | 8 + 5 | | 100 | | 89 | Y |
| ABUTH | 16 + 10 | | 100 | | 98 | Y |
| ABUTH | 8 + 10 | | 100 | | 97 | Y |

TABLE 18a

Application in Pre-Emergence of compound 8 and Isoproturon (individual activities)

| | compound 8 (A) | | | Isoproturon (B) | | |
|---|---|---|---|---|---|---|
| | | observed % activity | | | observed % activity | |
| Weed | use rate [g ai/ha] | 8 DAT | 20 DAT | use rate g ai/ha | 8 DAT | 20 DAT |
| POLCO | 16 | | 70 | 750 | | 25 |
| POLCO | 8 | | 35 | 750 | | 25 |
| POLCO | 16 | | 70 | 375 | | 0 |
| POLCO | 8 | | 35 | 375 | | 0 |
| KCHSC | 16 | | 90 | 750 | | 98 |
| KCHSC | 8 | | 80 | 750 | | 98 |
| GERPU | 16 | | 60 | 750 | | 40 |
| GERPU | 8 | | 20 | 750 | | 40 |
| GERPU | 16 | | 60 | 375 | | 20 |
| GERPU | 8 | | 20 | 375 | | 20 |
| COMBE | 8 | | 60 | 750 | | 45 |
| COMBE | 16 | | 65 | 375 | | 0 |
| COMBE | 8 | | 60 | 375 | | 0 |
| SIDRH | 16 | | 80 | 375 | | 0 |
| SIDRH | 8 | | 80 | 375 | | 0 |
| IPOHE | 16 | | 35 | 750 | | 40 |
| ABUTH | 16 | | 70 | 750 | | 65 |
| ABUTH | 8 | | 80 | 750 | | 65 |
| ABUTH | 16 | | 70 | 375 | | 20 |

TABLE 18b

Application in Pre-Emergence of compound 8 and Isoproturon (combined activities)

| | | compound 8 + isoproturon | | | Synergism | |
|---|---|---|---|---|---|---|
| | | Observed % activity | | expected % activity | Y/N | Y/N |
| | use rate | | | | | |
| Weed | [g ai/ha] | 8 DAT | 20 DAT | 8 DAT 20 DAT | 8 DAT | 20 DAT |
| POLCO | 16 + 750 | 80 | | 78 | | Y |
| POLCO | 8 + 750 | 60 | | 51 | | Y |
| POLCO | 16 + 375 | 75 | | 70 | | Y |
| POLCO | 8 + 375 | 45 | | 35 | | Y |
| KCHSC | 16 + 750 | 100 | | 100 | | Y |
| KCHSC | 8 + 750 | 100 | | 100 | | Y |
| GERPU | 16 + 750 | 80 | | 76 | | Y |
| GERPU | 8 + 750 | 90 | | 52 | | Y |
| GERPU | 16 + 375 | 90 | | 68 | | Y |
| GERPU | 8 + 375 | 65 | | 36 | | Y |
| COMBE | 8 + 750 | 80 | | 78 | | Y |
| COMBE | 16 + 375 | 80 | | 65 | | Y |
| COMBE | 8 + 375 | 65 | | 60 | | Y |
| SIDRH | 16 + 375 | 85 | | 80 | | Y |
| IPOHE | 16 + 750 | 70 | | 61 | | Y |
| ABUTH | 16 + 750 | 100 | | 90 | | Y |
| ABUTH | 8 + 750 | 100 | | 93 | | Y |
| ABUTH | 16 + 375 | 95 | | 76 | | Y |

TABLE 19a

Application in Pre-Emergence of compound 8 and Mesotrione (individual activities)

| | compound 8 (A) | | | Mesotrione (B) | | |
|---|---|---|---|---|---|---|
| | use rate | observed % activity | | use rate | observed % activity | |
| Weed | [g ai/ha] | 8 DAT | 20 DAT | [g ai/ha] | 8 DAT | 20 DAT |
| GALAP | 16 | | 65 | 50 | | 75 |
| GALAP | 8 | | 35 | 50 | | 75 |
| POLCO | 8 | | 0 | 50 | | 30 |
| POLCO | 16 | | 80 | 25 | | 20 |
| ANTAR | 16 | | 85 | 50 | | 95 |
| ANTAR | 8 | | 80 | 50 | | 95 |
| ANTAR | 16 | | 85 | 25 | | 85 |
| ANTAR | 8 | | 80 | 25 | | 85 |
| KCHSC | 8 | | 70 | 50 | | 90 |
| KCHSC | 16 | | 80 | 25 | | 70 |
| GERPU | 16 | | 60 | 50 | | 0 |
| GERPU | 8 | | 20 | 50 | | 0 |
| GERPU | 16 | | 60 | 25 | | 0 |
| GERPU | 8 | | 20 | 25 | | 0 |

TABLE 19a-continued

Application in Pre-Emergence of compound 8 and Mesotrione (individual activities)

| | compound 8 (A) | | | Mesotrione (B) | | |
|---|---|---|---|---|---|---|
| | use rate | observed % activity | | use rate | observed % activity | |
| Weed | [g ai/ha] | 8 DAT | 20 DAT | [g ai/ha] | 8 DAT | 20 DAT |
| COMBE | 16 | | 80 | 50 | | 98 |
| COMBE | 8 | | 50 | 50 | | 98 |
| COMBE | 16 | | 80 | 25 | | 65 |
| COMBE | 8 | | 50 | 25 | | 65 |
| SIDRH | 8 | | 65 | 50 | | 85 |
| SIDRH | 16 | | 80 | 25 | | 60 |
| SIDRH | 8 | | 80 | 25 | | 55 |
| IPOHE | 16 | | 35 | 50 | | 30 |
| EPHHL | 16 | | 65 | 50 | | 70 |
| EPHHL | 8 | | 45 | 50 | | 70 |
| EPHHL | 16 | | 65 | 25 | | 60 |
| EPHHL | 8 | | 45 | 25 | | 60 |
| ABUTH | 16 | | 70 | 25 | | 95 |

TABLE 19b

Application in Pre-Emergence of compound 8 and mesotrione (combined activities)

| | | compound 8 + mesotrione | | | Synergism | |
|---|---|---|---|---|---|---|
| | | Observed % activity | | expected % activity | Y/N | Y/N |
| | use rate | | | | | |
| Weed | [g ai/ha] | 8 DAT | 20 DAT | 8 DAT 20 DAT | 8 DAT | 20 DAT |
| GALAP | 16 + 50 | | 95 | 91 | | Y |
| GALAP | 8 + 50 | | 90 | 84 | | Y |
| POLCO | 8 + 50 | | 85 | 30 | | Y |
| POLCO | 16 + 25 | | 90 | 84 | | Y |
| ANTAR | 16 + 50 | | 100 | 99 | | Y |
| ANTAR | 8 + 50 | | 100 | 99 | | Y |
| ANTAR | 16 + 25 | | 100 | 98 | | Y |
| ANTAR | 8 + 25 | | 100 | 97 | | Y |
| KCHSC | 8 + 50 | | 98 | 97 | | Y |
| KCHSC | 16 + 25 | | 95 | 94 | | Y |
| GERPU | 16 + 50 | | 80 | 60 | | Y |
| GERPU | 8 + 50 | | 40 | 20 | | Y |

TABLE 19b-continued

Application in Pre-Emergence of compound 8 and mesotrione (combined activities)

| | | compound 8 + mesotrione | | | | Synergism | |
|---|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| GERPU | 16 + 25 | | 75 | | 60 | | Y |
| GERPU | 8 + 25 | | 60 | | 20 | | Y |
| COMBE | 16 + 50 | | 100 | | 100 | | Y |
| COMBE | 8 + 50 | | 100 | | 99 | | Y |
| COMBE | 16 + 25 | | 98 | | 93 | | Y |
| COMBE | 8 + 25 | | 90 | | 83 | | Y |
| SIDRH | 8 + 50 | | 98 | | 95 | | Y |
| SIDRH | 16 + 25 | | 95 | | 92 | | Y |
| SIDRH | 8 + 25 | | 95 | | 91 | | Y |
| IPOHE | 16 + 50 | | 75 | | 55 | | Y |
| EPHHL | 16 + 50 | | 100 | | 90 | | Y |
| EPHHL | 8 + 50 | | 95 | | 84 | | Y |
| EPHHL | 16 + 25 | | 98 | | 86 | | Y |
| EPHHL | 8 + 25 | | 80 | | 70 | | Y |
| ABUTH | 16 + 25 | | 100 | | 99 | | Y |

TABLE 20a

Application in Pre-Emergence of compound 8 and isoxaflutole (individual activities)

| | compound 8 (A) | | | isoxaflutole (B) | | |
|---|---|---|---|---|---|---|
| | use rate | observed % activity | | use rate g ai/ha | observed % activity | |
| Weed | [g ai/ha] | 8 DAT | 20 DAT | | 8 DAT | 20 DAT |
| GALAP | 16 | | 20 | 25 | | 40 |
| POLCO | 8 | | 35 | 50 | | 30 |
| POLCO | 16 | | 70 | 25 | | 0 |
| POLCO | 8 | | 35 | 25 | | 0 |
| ANTAR | 16 | | 85 | 50 | | 98 |
| ANTAR | 8 | | 80 | 50 | | 98 |
| ANTAR | 16 | | 85 | 25 | | 95 |
| ANTAR | 8 | | 80 | 25 | | 95 |
| KCHSC | 16 | | 80 | 50 | | 98 |
| KCHSC | 8 | | 70 | 50 | | 98 |
| KCHSC | 16 | | 80 | 25 | | 98 |
| KCHSC | 8 | | 70 | 25 | | 98 |
| GERPU | 16 | | 60 | 50 | | 45 |
| GERPU | 8 | | 20 | 50 | | 45 |
| GERPU | 16 | | 60 | 25 | | 0 |
| GERPU | 8 | | 20 | 25 | | 0 |
| COMBE | 16 | | 80 | 50 | | 80 |
| COMBE | 8 | | 50 | 50 | | 80 |
| COMBE | 16 | | 80 | 25 | | 85 |
| COMBE | 8 | | 50 | 25 | | 85 |
| SIDRH | 16 | | 80 | 50 | | 98 |
| SIDRH | 8 | | 65 | 50 | | 98 |
| SIDRH | 16 | | 80 | 25 | | 90 |
| EPHHL | 16 | | 65 | 50 | | 85 |
| EPHHL | 8 | | 45 | 50 | | 85 |
| EPHHL | 16 | | 65 | 25 | | 85 |
| ABUTH | 16 | | 70 | 25 | | 98 |
| ABUTH | 8 | | 80 | 25 | | 98 |

TABLE 20b

Application in Pre-Emergence of compound 8 and isoxaflutole (combined activities)

| | | compound 8 + isoxaflutole | | | | Synergism | |
|---|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| GALAP | 16 + 25 | | 90 | | 88 | | Y |
| POLCO | 8 + 50 | | 65 | | 55 | | Y |
| POLCO | 16 + 25 | | 80 | | 70 | | Y |
| POLCO | 8 + 25 | | 40 | | 35 | | Y |
| ANTAR | 16 + 50 | | 100 | | 100 | | Y |
| ANTAR | 8 + 50 | | 100 | | 100 | | Y |
| ANTAR | 16 + 25 | | 100 | | 99 | | Y |
| ANTAR | 8 + 25 | | 100 | | 99 | | Y |
| KCHSC | 16 + 50 | | 100 | | 100 | | Y |
| KCHSC | 8 + 50 | | 100 | | 99 | | Y |
| KCHSC | 16 + 25 | | 100 | | 100 | | Y |
| KCHSC | 8 + 25 | | 100 | | 99 | | Y |
| GERPU | 16 + 50 | | 95 | | 78 | | Y |
| GERPU | 8 + 50 | | 65 | | 56 | | Y |

TABLE 20b-continued

Application in Pre-Emergence of compound 8 and isoxaflutole (combined activities)

| | | compound 8 + isoxaflutole | | | | Synergism | |
|---|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| GERPU | 16 + 25 | | 75 | | 60 | | Y |
| GERPU | 8 + 25 | | 75 | | 20 | | Y |
| COMBE | 16 + 50 | | 98 | | 96 | | Y |
| COMBE | 8 + 50 | | 98 | | 90 | | Y |
| COMBE | 16 + 25 | | 100 | | 97 | | Y |
| COMBE | 8 + 25 | | 98 | | 93 | | Y |
| SIDRH | 16 + 50 | | 100 | | 100 | | Y |
| SIDRH | 8 + 50 | | 100 | | 99 | | Y |
| SIDRH | 16 + 25 | | 100 | | 98 | | Y |
| EPHHL | 16 + 50 | | 98 | | 95 | | Y |
| EPHHL | 8 + 50 | | 95 | | 92 | | Y |
| EPHHL | 16 + 25 | | 98 | | 95 | | Y |
| ABUTH | 16 + 25 | | 100 | | 99 | | Y |
| ABUTH | 8 + 25 | | 100 | | 100 | | Y |

TABLE 21a

Application in Pre-Emergence of compound 8 and chlorotoluron (individual activities)

| | compound 8 (A) | | | chlorotoluron (B) | | |
|---|---|---|---|---|---|---|
| | use rate | observed % activity | | use rate | observed % activity | |
| Weed | [g ai/ha] | 8 DAT | 20 DAT | g ai/ha | 8 DAT | 20 DAT |
| GALAP | 16 | | 65 | 500 | | 30 |
| GALAP | 8 | | 20 | 500 | | 50 |
| POLCO | 16 | | 80 | 500 | | 20 |
| POLCO | 8 | | 0 | 500 | | 20 |
| POLCO | 16 | | 80 | 250 | | 0 |
| POLCO | 8 | | 0 | 250 | | 0 |
| ANTAR | 16 | | 85 | 500 | | 45 |
| ANTAR | 8 | | 80 | 500 | | 45 |
| ANTAR | 16 | | 85 | 250 | | 45 |
| ANTAR | 8 | | 80 | 250 | | 45 |
| KCHSC | 16 | | 80 | 500 | | 50 |
| KCHSC | 8 | | 70 | 500 | | 50 |
| KCHSC | 16 | | 80 | 250 | | 20 |
| KCHSC | 8 | | 70 | 250 | | 20 |
| GERPU | 16 | | 60 | 500 | | 20 |
| GERPU | 8 | | 20 | 500 | | 20 |
| GERPU | 16 | | 60 | 250 | | 25 |
| GERPU | 8 | | 20 | 250 | | 25 |
| COMBE | 16 | | 65 | 250 | | 20 |
| SIDRH | 16 | | 80 | 500 | | 0 |
| SIDRH | 16 | | 80 | 250 | | 0 |
| IPOHE | 16 | | 35 | 500 | | 0 |
| EPHHL | 8 | | 45 | 250 | | 0 |
| ABUTH | 16 | | 80 | 500 | | 0 |
| ABUTH | 8 | | 70 | 500 | | 0 |
| ABUTH | 16 | | 80 | 250 | | 0 |
| ABUTH | 8 | | 70 | 250 | | 0 |

TABLE 21b

Application in Pre-Emergence of compound 8 and chlorotoluron (combined activities)

| | | compound 8 + chlorotoluron | | | | Synergism | |
|---|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| GALAP | 16 + 500 | | 98 | | 76 | | Y |
| GALAP | 8 + 500 | | 65 | | 60 | | Y |
| POLCO | 16 + 500 | | 85 | | 84 | | Y |
| POLCO | 8 + 500 | | 90 | | 20 | | Y |
| POLCO | 16 + 250 | | 95 | | 80 | | Y |
| POLCO | 8 + 250 | | 30 | | 0 | | Y |
| ANTAR | 16 + 500 | | 100 | | 92 | | Y |
| ANTAR | 8 + 500 | | 100 | | 89 | | Y |
| ANTAR | 16 + 250 | | 98 | | 92 | | Y |
| ANTAR | 8 + 250 | | 90 | | 89 | | Y |
| KCHSC | 16 + 500 | | 95 | | 90 | | Y |
| KCHSC | 8 + 500 | | 95 | | 85 | | Y |
| KCHSC | 16 + 250 | | 100 | | 84 | | Y |
| KCHSC | 8 + 250 | | 90 | | 76 | | Y |
| GERPU | 16 + 500 | | 85 | | 68 | | Y |
| GERPU | 8 + 500 | | 40 | | 36 | | Y |

TABLE 21b-continued

Application in Pre-Emergence of compound 8 and chlorotoluron (combined activities)

| | | compound 8 + chlorotoluron | | | | Synergism | |
|---|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| GERPU | 16 + 250 | 100 | | 70 | | | Y |
| GERPU | 8 + 250 | 75 | | 40 | | | Y |
| COMBE | 16 + 250 | 80 | | 72 | | | Y |
| SIDRH | 16 + 500 | 95 | | 80 | | | Y |
| SIDRH | 16 + 250 | 90 | | 80 | | | Y |
| IPOHE | 16 + 500 | 40 | | 35 | | | Y |
| EPHHL | 8 + 250 | 60 | | 45 | | | Y |
| ABUTH | 16 + 500 | 90 | | 80 | | | Y |
| ABUTH | 8 + 500 | 85 | | 70 | | | Y |
| ABUTH | 16 + 250 | 95 | | 80 | | | Y |
| ABUTH | 8 + 250 | 95 | | 70 | | | Y |

TABLE 22a

Application in Pre-Emergence of compound 8 and dicamba (individual activities)

| | compound 8 (A) | | | dicamba (B) | | |
|---|---|---|---|---|---|---|
| | use rate | observed % activity | | use rate | observed % activity | |
| Weed | [g ai/ha] | 8 DAT | 20 DAT | g ai/ha | 8 DAT | 20 DAT |
| POLCO | 8 | | 35 | 40 | | 90 |
| POLCO | 16 | | 70 | 20 | | 35 |
| ANTAR | 16 | | 85 | 40 | | 30 |
| ANTAR | 16 | | 85 | 20 | | 30 |
| GERPU | 16 | | 80 | 40 | | 85 |
| GERPU | 8 | | 45 | 40 | | 85 |
| GERPU | 16 | | 80 | 20 | | 20 |
| GERPU | 8 | | 45 | 20 | | 20 |
| COMBE | 16 | | 65 | 40 | | 65 |
| COMBE | 8 | | 60 | 40 | | 65 |
| COMBE | 16 | | 65 | 20 | | 45 |
| SIDRH | 16 | | 80 | 40 | | 80 |
| SIDRH | 16 | | 80 | 20 | | 45 |
| ABUTH | 16 | | 80 | 40 | | 80 |
| ABUTH | 16 | | 80 | 20 | | 60 |

TABLE 22b

Application in Pre-Emergence of compound 8 and dicamba (combined activities)

| | | compound 8 + dicamba | | | | Synergism | |
|---|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| POLCO | 8 + 40 | | 95 | | 91 | | Y |
| POLCO | 16 + 20 | | 90 | | 84 | | Y |
| ANTAR | 16 + 40 | | 100 | | 90 | | Y |
| ANTAR | 16 + 20 | | 100 | | 90 | | Y |
| GERPU | 16 + 40 | | 98 | | 97 | | Y |
| GERPU | 8 + 40 | | 95 | | 92 | | Y |
| GERPU | 16 + 20 | | 98 | | 84 | | Y |
| GERPU | 8 + 20 | | 98 | | 56 | | Y |
| COMBE | 16 + 40 | | 95 | | 88 | | Y |
| COMBE | 8 + 40 | | 90 | | 86 | | Y |
| COMBE | 16 + 20 | | 90 | | 81 | | Y |
| SIDRH | 16 + 40 | | 98 | | 96 | | Y |
| SIDRH | 16 + 20 | | 90 | | 89 | | Y |
| ABUTH | 16 + 40 | | 98 | | 96 | | Y |
| ABUTH | 16 + 20 | | 95 | | 92 | | Y |

TABLE 23a

Application in Pre-Emergence of compound 8 and diflufenican (individual activities)

| | compound 8 (A) | | | diflufenican (B) | | |
|---|---|---|---|---|---|---|
| | use rate | observed % activity | | use rate g ai/ha | observed % activity | |
| Weed | [g ai/ha] | 8 DAT | 20 DAT | [g ai/ha] | 8 DAT | 20 DAT |
| GALAP | 8 | | 20 | 80 | | 40 |
| POLCO | 16 | | 70 | 40 | | 20 |
| POLCO | 8 | | 35 | 40 | | 20 |
| ANTAR | 16 | | 85 | 40 | | 85 |
| GERPU | 8 | | 20 | 80 | | 50 |
| GERPU | 16 | | 60 | 40 | | 40 |
| COMBE | 8 | | 50 | 80 | | 55 |
| SIDRH | 16 | | 85 | 40 | | 0 |
| SIDRH | 8 | | 65 | 40 | | 0 |
| EPHHL | 16 | | 65 | 40 | | 20 |
| ABUTH | 8 | | 80 | 80 | | 50 |
| ABUTH | 16 | | 80 | 40 | | 25 |

TABLE 23b

Application in Pre-Emergence of compound 8 and diflufenican (combined activities)

| | compound 8 + diflufenican | | | | Synergism | |
|---|---|---|---|---|---|---|
| | use rate | Observed % activity | | expected % activity | | Y/N | Y/N |
| Weed | [g ai/ha] | 8 DAT | 20 DAT | 8 DAT | 20 DAT | 8 DAT | 20 DAT |
| GALAP | 20 + 40 | | 60 | | 52 | | Y |
| POLCO | 16 + 40 | | 90 | | 76 | | Y |
| POLCO | 8 + 40 | | 75 | | 48 | | Y |
| ANTAR | 16 + 40 | | 100 | | 95 | | Y |
| GERPU | 8 + 80 | | 80 | | 60 | | Y |
| GERPU | 16 + 40 | | 98 | | 76 | | Y |
| COMBE | 8 + 80 | | 80 | | 78 | | Y |
| SIDRH | 16 + 40 | | 90 | | 85 | | Y |
| SIDRH | 8 + 40 | | 90 | | 65 | | Y |
| EPHHL | 16 + 40 | | 80 | | 72 | | Y |
| ABUTH | 8 + 80 | | 98 | | 90 | | Y |
| ABUTH | 16 + 40 | | 85 | | 84 | | Y |

TABLE 24a

Application in Pre-Emergence of compound 8 and imazethapyr (individual activities)

| | compound 8 (A) | | | imazethapyr (B) | | |
|---|---|---|---|---|---|---|
| | use rate | observed % activity | | use rate g ai/ha | observed % activity | |
| Weed | [g ai/ha] | 8 DAT | 20 DAT | [g ai/ha] | 8 DAT | 20 DAT |
| POLCO | 8 | | 35 | 40 | | 90 |
| POLCO | 16 | | 70 | 20 | | 35 |
| ANTAR | 16 | | 85 | 40 | | 30 |
| ANTAR | 16 | | 85 | 20 | | 30 |
| GERPU | 16 | | 80 | 40 | | 85 |
| GERPU | 8 | | 45 | 40 | | 85 |
| GERPU | 16 | | 80 | 20 | | 20 |
| GERPU | 8 | | 45 | 20 | | 20 |
| COMBE | 16 | | 65 | 40 | | 65 |
| COMBE | 8 | | 60 | 40 | | 65 |
| COMBE | 16 | | 65 | 20 | | 45 |
| SIDRH | 16 | | 80 | 40 | | 80 |
| SIDRH | 16 | | 80 | 20 | | 45 |
| ABUTH | 16 | | 80 | 40 | | 80 |
| ABUTH | 16 | | 80 | 20 | | 60 |

TABLE 24b

Application in Pre-Emergence of compound 8 and imazethapyr (combined activities)

| | | compound 8 + imazethapyr | | Synergism |
|---|---|---|---|---|
| | use rate | Observed % activity | expected % activity | Y/N | Y/N |
| Weed | [g ai/ha] | 8 DAT | 20 DAT | 8 DAT | 20 DAT | 8 DAT | 20 DAT |
| POLCO | 8 + 40 | | 95 | | 94 | | Y |
| POLCO | 16 + 20 | | 90 | | 81 | | Y |
| ANTAR | 16 + 40 | | 100 | | 90 | | Y |
| ANTAR | 16 + 20 | | 90 | | 90 | | Y |
| GERPU | 16 + 40 | | 98 | | 97 | | Y |
| GERPU | 8 + 40 | | 95 | | 92 | | Y |
| GERPU | 16 + 20 | | 98 | | 86 | | Y |
| GERPU | 8 + 20 | | 98 | | 52 | | Y |
| COMBE | 16 + 40 | | 95 | | 88 | | Y |
| COMBE | 8 + 40 | | 90 | | 86 | | Y |
| COMBE | 16 + 20 | | 90 | | 81 | | Y |
| SIDRH | 16 + 40 | | 98 | | 96 | | Y |
| SIDRH | 16 + 20 | | 90 | | 89 | | Y |
| ABUTH | 16 + 40 | | 98 | | 96 | | Y |
| ABUTH | 16 + 20 | | 95 | | 92 | | Y |

The plants used in the greenhouse experiments of combinations with compound 9 illustrated in the following tables 25a/b to 41 a/b belonged to the following species:

| Scientific Name | Code | Common Name |
|---|---|---|
| *Avena fatua* | AVEFA | wild oat |
| *Brachiaria decumbens* | BRADC | surinam grass |
| *Lolium multiflorum* | LOLMU | italian ryegrass |
| *Phalaris canariensis* | PHACA | canarygrass |
| *Echinochloa crus-galli* | ECHCG | cockspurgrass |
| *Setaria viridis* | SETVI | green bristlegrass |
| *Digitaria sanguinalis* | DIGSA | hairy fingergrass |
| *Eleusine indica* | ELEIN | Indian goosegrass |
| *Polygonum convolvulus* | POLCO | black knotweed |
| *Galium aparine* | GALAP | goosegrass |
| *Centaurea cyanus* | CENCY | cornflower |
| *Kochia scoparia* | KCHSC | summer cypress |
| *Commelina benghalensis* | COMBE | Bengal day flower |
| *Geranium pusillum* | GERPU | small-flower geranium |
| *Sida rhombifolia* | SIDRH | arrow-leaf sida |
| *Abutilon theophrasti* | ABUTH | Chinese lantern |
| *Euphorbia heterophylla* | EPHHL | Mexican fire plant |

TABLE 25a

Application in Pre-Emergence of compound 9 and flufenacet (individual activities)

| | compound 9 (A) | | flufenacet(B) | |
|---|---|---|---|---|
| Weed | use rate [g ai/ha] | observed % activity 20 DAT | use rate [g ai/ha] | observed % activity 20 DAT |
| BRADC | 4 | 50 | 30 | 0 |
| BRADC | 2 | 75 | 30 | 0 |
| BRADC | 4 | 50 | 60 | 98 |
| BRADC | 2 | 75 | 60 | 98 |
| BRADC | 8 | 35 | 40 | 25 |
| BRADC | 4 | 40 | 40 | 25 |
| BRADC | 8 | 95 | 20 | 40 |
| BRADC | 8 | 35 | 10 | 45 |
| PHACA | 4 | 0 | 30 | 80 |
| PHACA | 8 | 70 | 40 | 75 |
| PHACA | 8 | 60 | 20 | 65 |
| PHACA | 4 | 25 | 20 | 65 |
| PHACA | 8 | 60 | 10 | 10 |
| PHACA | 4 | 25 | 10 | 10 |

TABLE 25a-continued

Application in Pre-Emergence of compound 9 and flufenacet (individual activities)

| | compound 9 (A) | | flufenacet(B) | |
|---|---|---|---|---|
| Weed | use rate [g ai/ha] | observed % activity 20 DAT | use rate [g ai/ha] | observed % activity 20 DAT |
| LOLMU | 4 | 0 | 30 | 30 |
| LOLMU | 8 | 75 | 40 | 55 |
| LOLMU | 4 | 65 | 40 | 55 |
| LOLMU | 8 | 80 | 20 | 20 |
| LOLMU | 8 | 80 | 10 | 0 |
| AVEFA | 4 | 0 | 30 | 0 |
| AVEFA | 8 | 30 | 40 | 55 |
| ECHCG | 4 | 85 | 60 | 95 |
| ECHCG | 4 | 85 | 30 | 75 |
| ALOMY | 4 | 20 | 40 | 75 |
| ALOMY | 4 | 45 | 20 | 70 |
| ALOMY | 4 | 45 | 10 | 25 |

TABLE 25b

Application in Pre-Emergence of compound 9 and flufenacet (combined activities)

| | compound 9 + flufenacet (A) | | | Synergism |
|---|---|---|---|---|
| Weed | use rate [g ai/ha] | observed % activity 20 DAT | expected % activity 20 DAT | Y/N 20 DAT |
| BRADC | 4 + 30 | 98 | 50 | Y |
| BRADC | 2 + 30 | 95 | 75 | Y |
| BRADC | 4 + 60 | 99 | 100 | Y |
| BRADC | 2 + 60 | 100 | 100 | Y |
| BRADC | 8 + 40 | 95 | 51 | Y |
| BRADC | 4 + 40 | 80 | 55 | Y |
| BRADC | 8 + 20 | 98 | 97 | Y |
| BRADC | 8 + 10 | 70 | 64 | Y |
| PHACA | 4 + 30 | 98 | 80 | Y |
| PHACA | 8 + 40 | 100 | 93 | Y |
| PHACA | 8 + 20 | 90 | 86 | Y |
| PHACA | 4 + 20 | 75 | 74 | Y |
| PHACA | 8 + 10 | 75 | 64 | Y |
| PHACA | 4 + 10 | 50 | 33 | Y |
| LOLMU | 4 + 30 | 65 | 30 | Y |
| LOLMU | 8 + 40 | 90 | 89 | Y |

TABLE 25b-continued

Application in Pre-Emergence of compound 9 and flufenacet (combined activities)

| Weed | compound 9 + flufenacet (A) use rate [g ai/ha] | observed % activity 20 DAT | expected % activity 20 DAT | Synergism Y/N 20 DAT |
|---|---|---|---|---|
| LOLMU | 4 + 40 | 90 | 84 | Y |
| LOLMU | 8 + 20 | 90 | 84 | Y |
| LOLMU | 8 + 10 | 95 | 80 | Y |
| AVEFA | 4 + 30 | 20 | 0 | Y |
| AVEFA | 8 + 40 | 75 | 69 | Y |
| ECHCG | 4 + 60 | 100 | 99 | Y |
| ECHCG | 4 + 30 | 100 | 96 | Y |
| ALOMY | 4 + 40 | 85 | 80 | Y |
| ALOMY | 4 + 20 | 90 | 84 | Y |
| ALOMY | 4 + 10 | 70 | 59 | Y |

TABLE 26a

Application in Pre-Emergence of compound 9 and Pendimethalin (individual activities)

| Weed | compound 9 (A) use rate [g ai/ha] | observed % activity 20 DAT | Pendimethalin(B) use rate [g ai/ha] | observed % activity 20 DAT |
|---|---|---|---|---|
| AVEFA | 4 | 15 | 250 | 0 |
| BRADC | 4 | 50 | 500 | 55 |
| BRADC | 4 | 40 | 250 | 35 |
| PHACA | 2 | 0 | 500 | 45 |
| PHACA | 2 | 0 | 250 | 0 |
| PHACA | 4 | 0 | 250 | 0 |
| PHACA | 8 | 60 | 500 | 45 |
| PHACA | 4 | 25 | 500 | 45 |
| LOLMU | 4 | 0 | 250 | 0 |
| LOLMU | 4 | 40 | 250 | 35 |
| ELEIN | 2 | 95 | 500 | 100 |
| ELEIN | 2 | 95 | 250 | 90 |
| ELEIN | 4 | 98 | 250 | 98 |
| CENCY | 8 | 20 | 1000 | 0 |
| CENCY | 8 | 20 | 500 | 25 |
| CENCY | 4 | 40 | 500 | 25 |
| COMBE | 8 | 65 | 1000 | 40 |
| COMBE | 4 | 25 | 1000 | 40 |
| COMBE | 4 | 25 | 500 | 10 |
| ERICA | 8 | 98 | 1000 | 90 |
| ERICA | 4 | 98 | 1000 | 90 |
| ERICA | 8 | 98 | 500 | 90 |
| ERICA | 4 | 98 | 500 | 90 |
| IPOHE | 8 | 0 | 1000 | 0 |
| IPOHE | 4 | 0 | 1000 | 0 |
| IPOHE | 4 | 0 | 500 | 0 |
| EPHHL | 4 | 25 | 1000 | 55 |
| ALOMY | 4 | 20 | 1000 | 80 |
| ALOMY | 4 | 20 | 500 | 65 |
| ALOMY | 4 | 20 | 250 | 45 |

TABLE 26b

Application in Pre-Emergence of compound 9 and pendimethalin (combined activities)

| Weed | compound 9 + Pendimethalin (C) use rate [g ai/ha] | observed % activity 20 DAT | expected % activity 20 DAT | Synergism Y/N 20 DAT |
|---|---|---|---|---|
| AVEFA | 4 + 250 | 25 | 15 | Y |
| BRADC | 4 + 500 | 85 | 78 | Y |
| BRADC | 4 + 250 | 65 | 61 | Y |
| PHACA | 2 + 500 | 50 | 45 | Y |
| PHACA | 2 + 250 | 30 | 0 | Y |
| PHACA | 4 + 250 | 45 | 0 | Y |
| PHACA | 8 + 500 | 85 | 78 | Y |
| PHACA | 4 + 500 | 90 | 59 | Y |
| LOLMU | 4 + 250 | 40 | 0 | Y |
| LOLMU | 4 + 250 | 85 | 79 | Y |
| ELEIN | 2 + 500 | 100 | 100 | Y |
| ELEIN | 2 + 250 | 100 | 100 | Y |
| ELEIN | 4 + 250 | 100 | 100 | Y |
| CENCY | 8 + 1000 | 25 | 20 | Y |
| CENCY | 8 + 500 | 50 | 40 | Y |
| CENCY | 4 + 500 | 65 | 55 | Y |
| COMBE | 8 + 1000 | 80 | 79 | Y |
| COMBE | 4 + 1000 | 70 | 55 | Y |
| COMBE | 4 + 500 | 35 | 33 | Y |
| ERICA | 8 + 1000 | 100 | 100 | Y |
| ERICA | 4 + 1000 | 100 | 100 | Y |
| ERICA | 8 + 500 | 100 | 100 | Y |
| ERICA | 4 + 500 | 100 | 100 | Y |
| IPOHE | 8 + 1000 | 10 | 0 | Y |
| IPOHE | 4 + 1000 | 30 | 0 | Y |
| IPOHE | 4 + 500 | 20 | 0 | Y |
| EPHHL | 4 + 1000 | 70 | 66 | Y |
| ALOMY | 4 + 1000 | 90 | 84 | Y |
| ALOMY | 4 + 500 | 80 | 72 | Y |
| ALOMY | 4 + 250 | 75 | 56 | Y |

TABLE 27a

Application in Pre-Emergence of compound 9 and Dimethenamid (individual activities)

| Weed | compound 9 (A) use rate [g ai/ha] | observed % activity 20 DAT | Dimethenamid(B) use rate [g ai/ha] | observed % activity 20 DAT |
|---|---|---|---|---|
| ALOMY | 4 | 85 | 250 | 25 |
| ALOMY | 2 | 75 | 250 | 25 |
| ALOMY | 8 | 98 | 500 | 75 |
| ALOMY | 4 | 20 | 500 | 75 |
| ALOMY | 4 | 20 | 250 | 55 |
| ALOMY | 8 | 95 | 125 | 25 |
| ALOMY | 4 | 45 | 125 | 25 |
| AVEFA | 4 | 0 | 125 | 20 |
| AVEFA | 8 | 0 | 125 | 0 |
| AVEFA | 4 | 0 | 125 | 0 |
| AVEFA | 4 | 0 | 55 | 95 |
| AVEFA | 8 | 0 | 250 | 85 |
| AVEFA | 4 | 0 | 250 | 85 |
| BRADC | 8 | 35 | 500 | 98 |
| BRADC | 4 | 40 | 500 | 98 |
| BRADC | 8 | 35 | 250 | 98 |
| BRADC | 4 | 40 | 250 | 98 |
| BRADC | 8 | 35 | 125 | 98 |
| LOLMU | 4 | 0 | 125 | 85 |
| LOLMU | 8 | 75 | 250 | 98 |
| LOLMU | 8 | 95 | 125 | 98 |
| PHACA | 8 | 50 | 500 | 98 |
| PHACA | 4 | 20 | 500 | 98 |
| PHACA | 8 | 60 | 125 | 70 |
| PHACA | 4 | 25 | 125 | 70 |
| KCHSC | 4 | 50 | 250 | 75 |
| GERPU | 8 | 60 | 250 | 98 |
| GERPU | 4 | 20 | 250 | 98 |

TABLE 27a-continued

Application in Pre-Emergence of compound 9 and Dimethenamid (individual activities)

| | compound 9 (A) | | Dimethenamid(B) | |
|---|---|---|---|---|
| Weed | use rate [g ai/ha] | observed % activity 20 DAT | use rate [g ai/ha] | observed % activity 20 DAT |
| SIDRH | 8 | 10 | 250 | 70 |
| SIDRH | 4 | 10 | 250 | 70 |
| EPHHL | 8 | 10 | 250 | 25 |

TABLE 27b

Application in Pre-Emergence of compound 9 and Dimethenamid (combined activities)

| | compound 9 + Dimethenamid (C) | | |
|---|---|---|---|
| Weed | use rate [g ai/ha] | observed % activity 20 DAT | expected % activity 20 DAT | Synergism Y/N 20 DAT |
| ALOMY | 4 + 250 | 90 | 89 | Y |
| ALOMY | 2 + 250 | 95 | 81 | Y |
| ALOMY | 8 + 500 | 100 | 99 | Y |
| ALOMY | 4 + 500 | 90 | 80 | Y |
| ALOMY | 4 + 250 | 95 | 64 | Y |
| ALOMY | 8 + 125 | 98 | 96 | Y |
| ALOMY | 4 + 125 | 95 | 59 | Y |
| AVEFA | 4 + 125 | 25 | 20 | Y |
| AVEFA | 8 + 125 | 20 | 0 | Y |
| AVEFA | 4 + 125 | 20 | 0 | Y |
| AVEFA | 4 + 500 | 98 | 95 | Y |
| AVEFA | 8 + 250 | 90 | 85 | Y |
| AVEFA | 4 + 250 | 90 | 85 | Y |
| BRADC | 8 + 500 | 100 | 99 | Y |
| BRADC | 4 + 500 | 100 | 99 | Y |
| BRADC | 8 + 250 | 100 | 99 | Y |
| BRADC | 4 + 250 | 100 | 99 | Y |
| BRADC | 8 + 125 | 100 | 99 | Y |
| LOLMU | 4 + 125 | 100 | 85 | Y |
| LOLMU | 8 + 250 | 100 | 100 | Y |
| LOLMU | 8 + 125 | 100 | 100 | Y |
| PHACA | 8 + 500 | 100 | 99 | Y |
| PHACA | 4 + 500 | 100 | 98 | Y |
| PHACA | 8 + 125 | 90 | 88 | Y |
| PHACA | 4 + 125 | 95 | 78 | Y |
| KCHSC | 4 + 250 | 90 | 88 | Y |
| GERPU | 8 + 250 | 100 | 99 | Y |
| GERPU | 4 + 250 | 100 | 98 | Y |
| SIDRH | 8 + 250 | 95 | 73 | Y |
| SIDRH | 4 + 250 | 85 | 73 | Y |
| EPHHL | 8 + 250 | 45 | 33 | Y |

TABLE 28a

Application in Pre-Emergence of compound 9 and Pyroxasulfone (individual activities)

| | compound 9 (A) | | pyroxasulfone(B) | |
|---|---|---|---|---|
| Weed | use rate [g ai/ha] | observed % activity 20 DAT | use rate [g ai/ha] | observed % activity 20 DAT |
| AVEFA | 4 | 15 | 16 | 35 |
| AVEFA | 2 | 35 | 16 | 60 |
| AVEFA | 4 | 0 | 8 | 40 |
| AVEFA | 8 | 0 | 24 | 70 |
| AVEFA | 4 | 0 | 24 | 70 |
| AVEFA | 8 | 0 | 12 | 20 |
| AVEFA | 4 | 0 | 12 | 30 |
| ALOMY | 8 | 95 | 24 | 98 |
| ALOMY | 4 | 20 | 24 | 98 |
| ALOMY | 4 | 45 | 12 | 95 |
| ALOMY | 8 | 95 | 6 | 80 |
| ALOMY | 4 | 20 | 6 | 80 |
| BRADC | 4 | 55 | 16 | 55 |
| BRADC | 4 | 50 | 8 | 45 |
| BRADC | 2 | 20 | 16 | 55 |
| BRADC | 2 | 20 | 8 | 75 |
| BRADC | 8 | 95 | 24 | 95 |
| BRADC | 4 | 80 | 24 | 95 |
| BRADC | 8 | 35 | 12 | 30 |
| BRADC | 4 | 40 | 12 | 30 |
| BRADC | 8 | 35 | 6 | 35 |
| BRADC | 4 | 40 | 6 | 35 |
| PHACA | 4 | 0 | 16 | 75 |
| PHACA | 4 | 0 | 8 | 70 |
| PHACA | 2 | 0 | 16 | 75 |
| PHACA | 2 | 0 | 8 | 70 |
| PHACA | 4 | 45 | 24 | 95 |
| PHACA | 8 | 50 | 12 | 75 |
| PHACA | 4 | 20 | 12 | 75 |
| PHACA | 8 | 50 | 6 | 70 |
| PHACA | 4 | 20 | 6 | 70 |
| LOLMU | 4 | 0 | 8 | 50 |
| LOLMU | 2 | 0 | 8 | 30 |
| LOLMU | 8 | 80 | 24 | 95 |
| LOLMU | 4 | 60 | 24 | 95 |
| LOLMU | 4 | 60 | 12 | 80 |
| LOLMU | 8 | 80 | 6 | 70 |
| SETVI | 4 | 90 | 8 | 85 |
| DIGSA | 4 | 80 | 8 | 95 |
| ECHCG | 4 | 85 | 8 | 70 |
| GALAP | 4 | 55 | 24 | 50 |
| GALAP | 8 | 90 | 12 | 35 |
| GALAP | 4 | 55 | 12 | 35 |
| POLCO | 8 | 80 | 24 | 20 |
| POLCO | 4 | 20 | 24 | 20 |
| POLCO | 8 | 80 | 12 | 20 |
| POLCO | 4 | 20 | 12 | 20 |
| CENCY | 8 | 20 | 24 | 15 |
| KCHSC | 4 | 50 | 24 | 80 |
| KCHSC | 8 | 85 | 12 | 50 |
| KCHSC | 4 | 50 | 12 | 50 |
| COMBE | 8 | 65 | 12 | 90 |
| COMBE | 4 | 25 | 12 | 90 |
| GERPU | 8 | 25 | 24 | 20 |
| GERPU | 4 | 20 | 12 | 10 |
| GERPU | 4 | 25 | 12 | 10 |
| SIDRH | 8 | 10 | 24 | 95 |
| SIDRH | 4 | 10 | 24 | 95 |
| SIDRH | 8 | 10 | 12 | 45 |
| SIDRH | 4 | 10 | 12 | 45 |
| IPOHE | 8 | 10 | 24 | 10 |
| IPOHE | 8 | 0 | 12 | 20 |
| IPOHE | 4 | 0 | 12 | 0 |
| EPHHL | 8 | 20 | 24 | 70 |
| EPHHL | 8 | 20 | 12 | 40 |
| ABUTH | 8 | 40 | 24 | 40 |
| ABUTH | 4 | 55 | 24 | 40 |

TABLE 28b

Application in Pre-Emergence of compound 9 and Pyroxasulfone (combined activities)

compound 9 + pyroxasulfone (C)

| Weed | use rate [g ai/ha] | observed % activity 20 DAT | expected % activity 20 DAT | Synergism Y/N 20 DAT |
|---|---|---|---|---|
| AVEFA | 4 + 16 | 75 | 45 | Y |
| AVEFA | 2 + 16 | 75 | 74 | Y |
| AVEFA | 4 + 8 | 50 | 40 | Y |
| AVEFA | 8 + 24 | 98 | 70 | Y |
| AVEFA | 4 + 24 | 75 | 70 | Y |
| AVEFA | 8 + 12 | 60 | 20 | Y |
| AVEFA | 4 + 12 | 75 | 30 | Y |
| ALOMY | 8 + 24 | 100 | 100 | Y |
| ALOMY | 4 + 24 | 100 | 98 | Y |
| ALOMY | 4 + 12 | 98 | 97 | Y |
| ALOMY | 8 + 6 | 100 | 99 | Y |
| ALOMY | 4 + 6 | 90 | 84 | Y |
| BRADC | 4 + 16 | 95 | 80 | Y |
| BRADC | 4 + 8 | 80 | 73 | Y |
| BRADC | 2 + 16 | 85 | 64 | Y |
| BRADC | 2 + 8 | 98 | 80 | Y |
| BRADC | 8 + 24 | 100 | 100 | Y |
| BRADC | 4 + 24 | 100 | 99 | Y |
| BRADC | 8 + 12 | 90 | 55 | Y |
| BRADC | 4 + 12 | 98 | 58 | Y |
| BRADC | 8 + 6 | 98 | 58 | Y |
| BRADC | 4 + 6 | 90 | 61 | Y |
| PHACA | 4 + 16 | 90 | 75 | Y |
| PHACA | 4 + 8 | 75 | 70 | Y |
| PHACA | 2 + 16 | 90 | 75 | Y |
| PHACA | 2 + 8 | 90 | 70 | Y |
| PHACA | 4 + 24 | 98 | 97 | Y |
| PHACA | 8 + 12 | 90 | 88 | Y |
| PHACA | 4 + 12 | 98 | 80 | Y |
| PHACA | 8 + 6 | 95 | 85 | Y |
| PHACA | 4 + 6 | 90 | 76 | Y |
| LOLMU | 4 + 8 | 98 | 50 | Y |
| LOLMU | 2 + 8 | 55 | 30 | Y |
| LOLMU | 8 + 24 | 100 | 99 | Y |
| LOLMU | 4 + 24 | 100 | 98 | Y |
| LOLMU | 4 + 12 | 98 | 92 | Y |
| LOLMU | 8 + 6 | 95 | 94 | Y |
| SETVI | 4 + 8 | 100 | 99 | Y |
| DIGSA | 4 + 8 | 100 | 99 | Y |
| ECHCG | 4 + 8 | 98 | 96 | Y |
| GALAP | 4 + 24 | 95 | 78 | Y |
| GALAP | 8 + 12 | 98 | 94 | Y |
| GALAP | 4 + 12 | 98 | 71 | Y |
| POLCO | 8 + 24 | 95 | 84 | Y |
| POLCO | 4 + 24 | 90 | 36 | Y |
| POLCO | 8 + 12 | 95 | 84 | Y |
| POLCO | 4 + 12 | 65 | 36 | Y |
| CENCY | 8 + 24 | 60 | 32 | Y |
| KCHSC | 4 + 24 | 98 | 90 | Y |
| KCHSC | 8 + 12 | 98 | 93 | Y |
| KCHSC | 4 + 12 | 90 | 75 | Y |
| COMBE | 8 + 12 | 100 | 97 | Y |
| COMBE | 4 + 12 | 95 | 93 | Y |
| GERPU | 8 + 24 | 60 | 40 | Y |
| GERPU | 8 + 12 | 60 | 36 | Y |
| GERPU | 4 + 12 | 50 | 33 | Y |
| SIDRH | 8 + 24 | 100 | 96 | Y |
| SIDRH | 4 + 24 | 100 | 96 | Y |
| SIDRH | 8 + 12 | 85 | 51 | Y |
| SIDRH | 4 + 12 | 70 | 51 | Y |
| IPOHE | 8 + 24 | 20 | 10 | Y |
| IPOHE | 8 + 12 | 45 | 20 | Y |
| IPOHE | 4 + 12 | 25 | 0 | Y |
| EPHHL | 8 + 24 | 90 | 76 | Y |
| EPHHL | 8 + 12 | 55 | 52 | Y |
| ABUTH | 8 + 24 | 75 | 64 | Y |
| ABUTH | 4 + 24 | 85 | 73 | Y |

TABLE 29a

Application in Pre-Emergence of compound 9 and Metribuzin (individual activities)

| | compound 9 (A) | | metribuzin (B) | |
|---|---|---|---|---|
| Weed | use rate [g ai/ha] | observed % activity 20 DAT | use rate [g ai/ha] | observed % activity 20 DAT |
| ALOMY | 2 | 75 | 250 | 75 |
| ALOMY | 4 | 20 | 250 | 90 |
| ALOMY | 4 | 45 | 125 | 80 |
| ALOMY | 4 | 45 | 62.5 | 0 |
| AVEFA | 2 | 0 | 250 | 70 |
| AVEFA | 2 | 0 | 125 | 80 |
| AVEFA | 8 | 0 | 250 | 65 |
| BRADC | 4 | 55 | 250 | 90 |
| BRADC | 4 | 55 | 125 | 15 |
| BRADC | 2 | 20 | 250 | 90 |
| BRADC | 8 | 35 | 250 | 40 |
| BRADC | 4 | 40 | 250 | 40 |
| BRADC | 8 | 30 | 125 | 75 |
| BRADC | 8 | 35 | 62.5 | 45 |
| PHACA | 4 | 0 | 125 | 65 |
| PHACA | 2 | 0 | 125 | 65 |
| PHACA | 8 | 50 | 250 | 95 |
| PHACA | 4 | 20 | 250 | 95 |
| PHACA | 8 | 50 | 125 | 75 |
| PHACA | 4 | 20 | 125 | 75 |
| PHACA | 8 | 50 | 62.5 | 15 |
| LOLMU | 4 | 0 | 250 | 45 |
| LOLMU | 4 | 0 | 125 | 55 |
| LOLMU | 2 | 0 | 250 | 45 |
| LOLMU | 8 | 75 | 250 | 75 |
| LOLMU | 4 | 65 | 250 | 75 |
| LOLMU | 8 | 80 | 125 | 65 |
| LOLMU | 4 | 60 | 125 | 65 |
| LOLMU | 4 | 65 | 62.5 | 0 |
| SETVI | 4 | 80 | 250 | 95 |
| SETVI | 4 | 80 | 125 | 65 |
| SETVI | 2 | 70 | 250 | 95 |
| SETVI | 2 | 70 | 125 | 65 |
| ECHCG | 4 | 90 | 250 | 95 |
| ECHCG | 4 | 90 | 125 | 80 |
| ECHCG | 2 | 75 | 250 | 95 |
| ECHCG | 2 | 70 | 125 | 80 |
| ELEIN | 4 | 98 | 250 | 98 |
| ELEIN | 4 | 98 | 125 | 98 |
| ELEIN | 2 | 95 | 250 | 98 |
| ELEIN | 2 | 95 | 125 | 98 |
| GALAP | 4 | 55 | 125 | 20 |
| POLCO | 8 | 80 | 250 | 20 |
| POLCO | 4 | 20 | 250 | 20 |
| POLCO | 4 | 20 | 125 | 20 |
| CENCY | 4 | 40 | 250 | 85 |
| CENCY | 8 | 20 | 125 | 75 |
| KCHSC | 4 | 70 | 125 | 95 |
| COMBE | 8 | 65 | 250 | 90 |
| COMBE | 4 | 25 | 250 | 90 |
| ERICA | 8 | 98 | 125 | 98 |
| ERICA | 4 | 98 | 125 | 98 |
| IPOHE | 4 | 0 | 250 | 20 |
| EPHHL | 8 | 10 | 250 | 85 |

TABLE 29b

Application in Pre-Emergence of compound 9 and Metribuzin (combined activities)

compound 9 + metribuzin (A)

| Weed | use rate [g ai/ha] | observed % activity 20 DAT | expected % activity 20 DAT | Synergism Y/N 20 DAT |
|---|---|---|---|---|
| ALOMY | 2 + 250 | 95 | 94 | Y |
| ALOMY | 4 + 250 | 95 | 92 | Y |

TABLE 29b-continued

Application in Pre-Emergence of compound 9 and Metribuzin (combined activities)

compound 9 + metribuzin (A)

| Weed | use rate [g ai/ha] | observed % activity 20 DAT | expected % activity 20 DAT | Synergism Y/N 20 DAT |
|---|---|---|---|---|
| ALOMY | 4 + 125 | 95 | 89 | Y |
| ALOMY | 4 + 62.5 | 65 | 45 | Y |
| AVEFA | 2 + 250 | 90 | 70 | Y |
| AVEFA | 2 + 125 | 90 | 80 | Y |
| AVEFA | 8 + 250 | 80 | 65 | Y |
| BRADC | 4 + 250 | 98 | 96 | Y |
| BRADC | 4 + 125 | 90 | 62 | Y |
| BRADC | 2 + 250 | 98 | 92 | Y |
| BRADC | 8 + 250 | 90 | 61 | Y |
| BRADC | 4 + 250 | 75 | 64 | Y |
| BRADC | 8 + 125 | 95 | 83 | Y |
| BRADC | 8 + 62.5 | 65 | 64 | Y |
| PHACA | 4 + 125 | 95 | 65 | Y |
| PHACA | 2 + 125 | 70 | 65 | Y |
| PHACA | 8 + 250 | 100 | 98 | Y |
| PHACA | 4 + 250 | 98 | 96 | Y |
| PHACA | 8 + 125 | 98 | 88 | Y |
| PHACA | 4 + 125 | 98 | 80 | Y |
| PHACA | 8 + 62.5 | 85 | 58 | Y |
| LOLMU | 4 + 250 | 65 | 45 | Y |
| LOLMU | 4 + 125 | 98 | 55 | Y |
| LOLMU | 2 + 250 | 90 | 45 | Y |
| LOLMU | 8 + 250 | 95 | 94 | Y |
| LOLMU | 4 + 250 | 95 | 91 | Y |
| LOLMU | 8 + 125 | 95 | 93 | Y |
| LOLMU | 4 + 125 | 90 | 86 | Y |
| LOLMU | 4 + 62.5 | 70 | 65 | Y |
| SETVI | 4 + 250 | 100 | 99 | Y |
| SETVI | 4 + 125 | 100 | 93 | Y |
| SETVI | 2 + 250 | 100 | 99 | Y |
| SETVI | 2 + 125 | 100 | 90 | Y |
| ECHCG | 4 + 250 | 100 | 100 | Y |
| ECHCG | 4 + 125 | 100 | 98 | Y |
| ECHCG | 2 + 250 | 100 | 99 | Y |
| ECHCG | 2 + 125 | 95 | 94 | Y |
| ELEIN | 4 + 250 | 100 | 100 | Y |
| ELEIN | 4 + 125 | 100 | 100 | Y |
| ELEIN | 2 + 250 | 100 | 100 | Y |
| ELEIN | 2 + 125 | 100 | 100 | Y |
| GALAP | 4 + 125 | 65 | 64 | Y |
| POLCO | 8 + 250 | 90 | 84 | Y |
| POLCO | 4 + 250 | 85 | 36 | Y |
| POLCO | 4 + 125 | 65 | 36 | Y |
| CENCY | 4 + 250 | 98 | 91 | Y |
| CENCY | 8 + 125 | 85 | 80 | Y |
| KCHSC | 4 + 125 | 100 | 99 | Y |
| COMBE | 8 + 250 | 98 | 97 | Y |
| COMBE | 4 + 250 | 98 | 93 | Y |
| ERICA | 8 + 125 | 100 | 100 | Y |
| ERICA | 4 + 125 | 100 | 100 | Y |
| IPOHE | 4 + 250 | 25 | 20 | Y |
| EPHHL | 8 + 250 | 95 | 35 | Y |

TABLE 30a

Application in Pre-Emergence of compound 9 and BAS 850 (PPO) (individual activities)

| | compound 9 (A) | | BAS 850 (PPO)(B) | |
|---|---|---|---|---|
| Weed | use rate [g ai/ha] | observed % activity 20 DAT | use rate [g ai/ha] | observed % activity 20 DAT |
| ALOMY | 4 | 20 | 25 | 60 |
| AVEFA | 4 | 15 | 36 | 15 |
| AVEFA | 2 | 0 | 36 | 15 |
| AVEFA | 8 | 0 | 50 | 0 |
| AVEFA | 8 | 0 | 25 | 0 |
| AVEFA | 4 | 0 | 25 | 0 |
| BRADC | 4 | 55 | 36 | 25 |
| BRADC | 8 | 35 | 25 | 65 |
| LOLMU | 4 | 0 | 36 | 35 |
| LOLMU | 2 | 0 | 36 | 35 |
| LOLMU | 8 | 75 | 50 | 55 |
| LOLMU | 4 | 65 | 25 | 0 |
| PHACA | 4 | 0 | 36 | 70 |
| PHACA | 4 | 0 | 18 | 45 |
| PHACA | 2 | 0 | 36 | 65 |
| PHACA | 2 | 0 | 18 | 45 |
| PHACA | 8 | 50 | 25 | 35 |
| PHACA | 4 | 20 | 25 | 35 |
| SETVI | 4 | 90 | 36 | 90 |
| SETVI | 2 | 90 | 36 | 90 |
| SETVI | 4 | 90 | 18 | 95 |
| DIGSA | 4 | 60 | 36 | 90 |
| DIGSA | 4 | 60 | 18 | 85 |
| DIGSA | 2 | 75 | 36 | 90 |
| DIGSA | 2 | 75 | 18 | 85 |
| ECHCG | 4 | 85 | 18 | 0 |
| ECHCG | 2 | 70 | 18 | 0 |
| ELEIN | 4 | 98 | 36 | 90 |
| ELEIN | 4 | 98 | 18 | 55 |
| ELEIN | 2 | 95 | 36 | 90 |
| ELEIN | 2 | 95 | 18 | 55 |

TABLE 30b

Application in Pre-Emergence of compound 9 and BAS 850 (PPO) (combined activities)

compound 9 + BAS 850 (PPO) (C)

| Weed | use rate [g ai/ha] | observed % activity 20 DAT | expected % activity 20 DAT | Synergism Y/N 20 DAT |
|---|---|---|---|---|
| ALOMY | 4 + 25 | 75 | 68 | Y |
| AVEFA | 4 + 36 | 75 | 28 | Y |
| AVEFA | 2 + 36 | 60 | 15 | Y |
| AVEFA | 8 + 50 | 35 | 0 | Y |
| AVEFA | 8 + 25 | 40 | 0 | Y |
| AVEFA | 4 + 25 | 20 | 0 | Y |
| BRADC | 4 + 36 | 75 | 66 | Y |
| BRADC | 8 + 25 | 80 | 77 | Y |
| LOLMU | 4 + 36 | 95 | 35 | Y |
| LOLMU | 2 + 36 | 50 | 35 | Y |
| LOLMU | 8 + 50 | 90 | 89 | Y |
| LOLMU | 4 + 25 | 70 | 65 | Y |
| PHACA | 4 + 36 | 75 | 70 | Y |
| PHACA | 4 + 18 | 65 | 45 | Y |
| PHACA | 2 + 36 | 90 | 65 | Y |
| PHACA | 2 + 18 | 75 | 45 | Y |
| PHACA | 8 + 25 | 90 | 68 | Y |
| PHACA | 4 + 25 | 75 | 48 | Y |
| SETVI | 4 + 36 | 100 | 99 | Y |
| SETVI | 4 + 18 | 100 | 100 | Y |
| SETVI | 2 + 36 | 100 | 99 | Y |
| DIGSA | 4 + 36 | 100 | 96 | Y |
| DIGSA | 4 + 18 | 98 | 94 | Y |
| DIGSA | 2 + 36 | 100 | 98 | Y |
| DIGSA | 2 + 18 | 100 | 96 | Y |
| ECHCG | 4 + 18 | 90 | 85 | Y |
| ECHCG | 2 + 18 | 75 | 70 | Y |
| ELEIN | 4 + 36 | 100 | 100 | Y |
| ELEIN | 4 + 18 | 100 | 99 | Y |

TABLE 30b-continued

Application in Pre-Emergence of compound
9 and BAS 850 (PPO) (combined activities)

compound 9 + BAS 850 (PPO) (C)

| Weed | use rate [g ai/ha] | observed % activity 20 DAT | expected % activity 20 DAT | Synergism Y/N 20 DAT |
|---|---|---|---|---|
| ELEIN | 2 + 36 | 100 | 100 | Y |
| ELEIN | 2 + 18 | 100 | 98 | Y |

TABLE 31a

Application in Pre-Emergence of compound
9 and Tri-allate (individual activities)

| | compound 9 (A) | | tri-allate(B) | |
|---|---|---|---|---|
| Weed | use rate [g ai/ha] | observed % activity 20 DAT | use rate [g ai/ha] | observed % activity 20 DAT |
| ALOMY | 4 | 80 | 400 | 5 |
| ALOMY | 2 | 70 | 400 | 5 |
| AVEFA | 4 | 15 | 400 | 75 |
| AVEFA | 4 | 0 | 200 | 45 |
| AVEFA | 2 | 0 | 400 | 75 |
| BRADC | 4 | 55 | 200 | 0 |
| DIGSA | 4 | 60 | 400 | 0 |
| PHACA | 2 | 0 | 400 | 0 |
| PHACA | 2 | 0 | 200 | 0 |
| ELEIN | 4 | 98 | 400 | 0 |

TABLE 31b

Application in Pre-Emergence of compound
9 and Tri-allate (combined activities)

compound 9 + tri-allate (C)

| Weed | use rate [g ai/ha] | observed % activity 20 DAT | expected % activity 20 DAT | Synergism Y/N 20 DAT |
|---|---|---|---|---|
| ALOMY | 4 + 400 | 90 | 81 | Y |
| ALOMY | 2 + 400 | 80 | 72 | Y |
| AVEFA | 4 + 400 | 90 | 79 | Y |
| AVEFA | 4 + 200 | 50 | 45 | Y |
| AVEFA | 2 + 400 | 85 | 75 | Y |
| BRADC | 4 + 200 | 70 | 50 | Y |
| DIGSA | 4 + 400 | 65 | 60 | Y |
| PHACA | 2 + 400 | 25 | 0 | Y |
| PHACA | 2 + 200 | 35 | 0 | Y |
| ELEIN | 4 + 400 | 100 | 98 | Y |

TABLE 32a

Application in Pre-Emergence of compound 9
and Saflufenacil (individual activities)

| | compound 9 (A) | | saflufenacil(B) | |
|---|---|---|---|---|
| Weed | use rate [g ai/ha] | observed % activity 20 DAT | use rate [g ai/ha] | observed % activity 20 DAT |
| BRADC | 2 | 20 | 36 | 90 |
| DIGSA | 4 | 60 | 36 | 65 |
| DIGSA | 4 | 60 | 18 | 0 |
| ELEIN | 4 | 98 | 36 | 95 |
| ELEIN | 4 | 98 | 18 | 35 |
| ELEIN | 2 | 95 | 36 | 95 |
| ELEIN | 2 | 95 | 18 | 35 |
| GALAP | 16 | 60 | 10 | 50 |
| GALAP | 16 | 60 | 5 | 25 |
| POLCO | 16 | 80 | 10 | 25 |
| POLCO | 8 | 50 | 10 | 25 |
| POLCO | 16 | 70 | 5 | 40 |
| POLCO | 8 | 50 | 5 | 0 |
| CENCY | 16 | 10 | 10 | 30 |
| CENCY | 8 | 20 | 10 | 20 |
| CENCY | 16 | 15 | 5 | 20 |
| CENCY | 8 | 20 | 5 | 20 |
| KCHSC | 16 | 90 | 10 | 65 |
| KCHSC | 8 | 75 | 10 | 65 |
| KCHSC | 16 | 90 | 5 | 70 |
| KCHSC | 8 | 75 | 5 | 70 |
| COMBE | 16 | 20 | 10 | 15 |
| COMBE | 16 | 20 | 5 | 0 |
| SIDRH | 16 | 30 | 10 | 20 |
| ABUTH | 16 | 20 | 10 | 25 |
| ABUTH | 8 | 20 | 10 | 25 |

TABLE 32b

Application in Pre-Emergence of compound
9 and Saflufenacil (combined activities)

compound 9 + saflufenacil (C)

| Weed | use rate [g ai/ha] | observed % activity 20 DAT | expected % activity 20 DAT | Synergism Y/N 20 DAT |
|---|---|---|---|---|
| BRADC | 2 + 36 | 95 | 92 | Y |
| DIGSA | 4 + 36 | 90 | 86 | Y |
| DIGSA | 4 + 18 | 75 | 60 | Y |
| ELEIN | 4 + 36 | 100 | 100 | Y |
| ELEIN | 4 + 18 | 100 | 99 | Y |
| ELEIN | 2 + 36 | 100 | 100 | Y |
| ELEIN | 2 + 18 | 100 | 97 | Y |
| GALAP | 16 + 10 | 85 | 80 | Y |
| GALAP | 16 + 5 | 90 | 70 | Y |
| POLCO | 16 + 10 | 100 | 85 | Y |
| POLCO | 8 + 10 | 90 | 63 | Y |
| POLCO | 16 + 5 | 90 | 82 | Y |
| POLCO | 8 + 5 | 80 | 50 | Y |
| CENCY | 16 + 10 | 40 | 37 | Y |
| CENCY | 8 + 10 | 40 | 36 | Y |
| CENCY | 16 + 5 | 65 | 32 | Y |
| CENCY | 8 + 5 | 40 | 36 | Y |
| KCHSC | 16 + 10 | 98 | 97 | Y |
| KCHSC | 8 + 10 | 100 | 91 | Y |
| KCHSC | 16 + 5 | 98 | 97 | Y |
| KCHSC | 8 + 5 | 95 | 93 | Y |
| COMBE | 16 + 10 | 60 | 32 | Y |
| COMBE | 16 + 5 | 25 | 20 | Y |
| SIDRH | 16 + 10 | 50 | 44 | Y |
| ABUTH | 16 + 10 | 50 | 40 | Y |
| ABUTH | 8 + 10 | 80 | 40 | Y |

TABLE 33a

Application in Pre-Emergence of compound 9 and Imazethapyr (individual activities)

| | compound 9 (A) | | Imazethapyr (B) | |
|---|---|---|---|---|
| Weed | use rate [g ai/ha] | observed % activity 20 DAT | use rate [g ai/ha] | observed % activity 20 DAT |
| GALAP | 16 | 60 | 30 | 60 |
| GALAP | 16 | 60 | 15 | 50 |
| POLCO | 16 | 80 | 30 | 65 |
| POLCO | 8 | 75 | 30 | 60 |
| POLCO | 16 | 80 | 15 | 30 |
| POLCO | 8 | 50 | 15 | 30 |
| KCHSC | 16 | 80 | 30 | 85 |
| KCHSC | 8 | 75 | 30 | 70 |
| KCHSC | 16 | 90 | 15 | 70 |
| KCHSC | 8 | 75 | 15 | 70 |
| COMBE | 16 | 35 | 30 | 35 |
| COMBE | 8 | 30 | 30 | 35 |
| COMBE | 16 | 35 | 15 | 0 |
| COMBE | 8 | 30 | 15 | 0 |
| GERPU | 16 | 60 | 30 | 30 |
| GERPU | 8 | 40 | 30 | 30 |
| GERPU | 16 | 30 | 15 | 30 |
| SIDRH | 8 | 25 | 30 | 60 |
| SIDRH | 16 | 30 | 15 | 15 |
| SIDRH | 8 | 15 | 15 | 15 |
| IPOHE | 16 | 10 | 30 | 0 |
| EPHHL | 16 | 20 | 30 | 65 |
| ABUTH | 16 | 20 | 30 | 15 |
| ABUTH | 8 | 20 | 30 | 15 |
| ABUTH | 16 | 20 | 15 | 0 |
| ABUTH | 8 | 20 | 15 | 0 |

TABLE 33b

Application in Pre-Emergence of compound 9 and Imazethapyr (combined activities)

| | compound 9 + Imazethapyr (C) | | | |
|---|---|---|---|---|
| Weed | use rate [g ai/ha] | observed % activity 20 DAT | expected % activity 20 DAT | Synergism Y/N 20 DAT |
| GALAP | 16 + 30 | 85 | 84 | Y |
| GALAP | 16 + 15 | 98 | 80 | Y |
| POLCO | 16 + 30 | 98 | 93 | Y |
| POLCO | 8 + 30 | 100 | 90 | Y |
| POLCO | 16 + 15 | 98 | 86 | Y |
| POLCO | 8 + 15 | 70 | 65 | Y |
| KCHSC | 16 + 30 | 98 | 97 | Y |
| KCHSC | 8 + 30 | 98 | 93 | Y |
| KCHSC | 16 + 15 | 100 | 97 | Y |
| KCHSC | 8 + 15 | 95 | 93 | Y |
| COMBE | 16 + 30 | 70 | 58 | Y |
| COMBE | 8 + 30 | 65 | 55 | Y |
| COMBE | 16 + 15 | 60 | 35 | Y |
| COMBE | 8 + 15 | 50 | 30 | Y |
| GERPU | 16 + 30 | 75 | 72 | Y |
| GERPU | 8 + 30 | 80 | 58 | Y |
| GERPU | 16 + 15 | 60 | 51 | Y |
| SIDRH | 8 + 30 | 75 | 70 | Y |
| SIDRH | 16 + 15 | 60 | 41 | Y |
| SIDRH | 8 + 15 | 40 | 28 | Y |
| IPOHE | 16 + 30 | 35 | 24 | Y |
| EPHHL | 16 + 30 | 75 | 72 | Y |
| ABUTH | 16 + 30 | 50 | 32 | Y |
| ABUTH | 8 + 30 | 75 | 32 | Y |
| ABUTH | 16 + 15 | 25 | 20 | Y |
| ABUTH | 8 + 15 | 50 | 20 | Y |

TABLE 34a

Application in Pre-Emergence of compound 9 and Diflufenican (individual activities)

| | compound 9 (A) | | Diflufenican (B) | |
|---|---|---|---|---|
| Weed | use rate [g ai/ha] | observed % activity 20 DAT | use rate [g ai/ha] | observed % activity 20 DAT |
| GALAP | 16 | 60 | 60 | 25 |
| GALAP | 8 | 70 | 60 | 25 |
| GALAP | 16 | 60 | 30 | 20 |
| GALAP | 8 | 70 | 30 | 20 |
| POLCO | 16 | 80 | 60 | 60 |
| POLCO | 8 | 50 | 60 | 60 |
| POLCO | 16 | 70 | 30 | 0 |
| POLCO | 8 | 50 | 30 | 30 |
| CENCY | 16 | 10 | 60 | 0 |
| CENCY | 8 | 35 | 60 | 0 |
| CENCY | 16 | 10 | 30 | 0 |
| CENCY | 8 | 35 | 30 | 0 |
| KCHSC | 16 | 90 | 60 | 80 |
| COMBE | 16 | 20 | 60 | 35 |
| COMBE | 8 | 20 | 60 | 35 |
| GERPU | 16 | 30 | 60 | 60 |
| GERPU | 8 | 40 | 60 | 50 |
| IPOHE | 16 | 15 | 60 | 15 |
| EPHHL | 16 | 20 | 60 | 15 |
| ABUTH | 16 | 20 | 60 | 0 |
| ABUTH | 8 | 20 | 60 | 0 |
| ABUTH | 16 | 20 | 30 | 0 |

TABLE 34b

Application in Pre-Emergence of compound 9 and Diflufenican (combined activities)

| | compound 9 + Diflufenican (C) | | | |
|---|---|---|---|---|
| Weed | use rate [g ai/ha] | observed % activity 20 DAT | expected % activity 20 DAT | Synergism Y/N 20 DAT |
| GALAP | 16 + 60 | 100 | 70 | Y |
| GALAP | 8 + 60 | 80 | 78 | Y |
| GALAP | 16 + 30 | 98 | 68 | Y |
| GALAP | 8 + 30 | 85 | 76 | Y |
| POLCO | 16 + 60 | 100 | 90 | Y |
| POLCO | 8 + 60 | 100 | 75 | Y |
| POLCO | 16 + 30 | 80 | 70 | Y |
| POLCO | 8 + 30 | 70 | 65 | Y |
| CENCY | 16 + 60 | 70 | 10 | Y |
| CENCY | 8 + 60 | 80 | 35 | Y |
| CENCY | 16 + 30 | 30 | 10 | Y |
| CENCY | 8 + 30 | 40 | 35 | Y |
| KCHSC | 16 + 60 | 100 | 98 | Y |
| COMBE | 16 + 60 | 65 | 48 | Y |
| COMBE | 8 + 60 | 60 | 48 | Y |
| GERPU | 16 + 60 | 75 | 72 | Y |
| GERPU | 8 + 60 | 35 | 20 | Y |
| IPOHE | 16 + 60 | 40 | 28 | Y |
| EPHHL | 16 + 60 | 50 | 32 | Y |
| ABUTH | 16 + 60 | 40 | 20 | Y |
| ABUTH | 8 + 60 | 30 | 20 | Y |
| ABUTH | 16 + 30 | 30 | 20 | Y |

TABLE 35a

Application in Pre-Emergence of compound 9 and Dicamba (individual activities)

| | compound 9 (A) | | Dicamba (B) | |
|---|---|---|---|---|
| Weed | use rate [g ai/ha] | observed % activity 20 DAT | use rate [g ai/ha] | observed % activity 20 DAT |
| CENCY | 16 | 15 | 70 | 30 |
| CENCY | 8 | 20 | 70 | 30 |
| CENCY | 16 | 15 | 35 | 0 |
| CENCY | 8 | 20 | 35 | 0 |
| KCHSC | 7 | 75 | 70 | 75 |
| KCHSC | 16 | 90 | 35 | 75 |
| COMBE | 16 | 35 | 70 | 50 |
| COMBE | 16 | 20 | 35 | 15 |
| COMBE | 8 | 20 | 35 | 15 |
| GERPU | 8 | 40 | 35 | 40 |
| SIDRH | 16 | 55 | 70 | 15 |
| SIDRH | 8 | 25 | 70 | 15 |
| SIDRH | 16 | 30 | 35 | 20 |
| SIDRH | 8 | 15 | 35 | 20 |
| IPOHE | 16 | 10 | 70 | 40 |
| IPOHE | 16 | 10 | 35 | 40 |
| EPHHL | 16 | 15 | 35 | 20 |
| ABUTH | 16 | 20 | 70 | 20 |
| ABUTH | 16 | 20 | 35 | 0 |

TABLE 35b

Application in Pre-Emergence of compound 9 and Dicamba (combined activities)

| | compound 9 + Dicamba (C) | | | |
|---|---|---|---|---|
| Weed | use rate [g ai/ha] | observed % activity 20 DAT | expected % activity 20 DAT | Synergism Y/N 20 DAT |
| CENCY | 16 + 70 | 50 | 41 | Y |
| CENCY | 8 + 70 | 50 | 44 | Y |
| CENCY | 16 + 35 | 50 | 15 | Y |
| CENCY | 8 + 35 | 40 | 20 | Y |
| KCHSC | 8 + 70 | 98 | 94 | Y |
| KCHSC | 16 + 35 | 98 | 98 | Y |
| COMBE | 16 + 70 | 70 | 68 | Y |
| COMBE | 16 + 35 | 40 | 32 | Y |
| COMBE | 8 + 35 | 40 | 32 | Y |
| GERPU | 8 + 35 | 75 | 64 | Y |
| SIDRH | 16 + 70 | 65 | 62 | Y |
| SIDRH | 8 + 70 | 95 | 36 | Y |
| SIDRH | 16 + 35 | 60 | 44 | Y |
| SIDRH | 8 + 35 | 40 | 32 | Y |
| IPOHE | 16 + 70 | 65 | 46 | Y |
| IPOHE | 16 + 35 | 65 | 46 | Y |
| EPHHL | 16 + 35 | 35 | 32 | Y |
| ABUTH | 16 + 70 | 50 | 36 | Y |
| ABUTH | 16 + 35 | 40 | 20 | Y |

TABLE 36a

Application in Pre-Emergence of compound 9 and Chlorotoluron (individual activities)

| | compound 9 (A) | | Chlorotoluron (B) | |
|---|---|---|---|---|
| Weed | use rate [g ai/ha] | observed % activity 20 DAT | use rate [g ai/ha] | observed % activity 20 DAT |
| GALAP | 16 | 60 | 250 | 30 |
| GALAP | 8 | 70 | 250 | 30 |
| GALAP | 16 | 60 | 125 | 25 |
| POLCO | 16 | 70 | 250 | 0 |
| POLCO | 8 | 50 | 250 | 0 |
| CENCY | 16 | 10 | 250 | 0 |
| CENCY | 8 | 35 | 250 | 0 |
| CENCY | 16 | 10 | 125 | 20 |
| KCHSC | 16 | 80 | 125 | 15 |
| KCHSC | 8 | 90 | 125 | 15 |
| COMBE | 16 | 35 | 250 | 0 |
| COMBE | 16 | 35 | 125 | 0 |
| GERPU | 16 | 30 | 250 | 25 |
| GERPU | 16 | 30 | 125 | 25 |
| IPOHE | 16 | 15 | 250 | 0 |
| EPHHL | 16 | 15 | 250 | 15 |
| EPHHL | 8 | 25 | 250 | 15 |
| ABUTH | 16 | 20 | 250 | 0 |
| ABUTH | 8 | 20 | 250 | 0 |
| ABUTH | 16 | 20 | 125 | 0 |

TABLE 36b

Application in Pre-Emergence of compound 9 and Chlortoluron (combined activities)

| | compound 9 + Chlorotoluron (C) | | | |
|---|---|---|---|---|
| Weed | use rate [g ai/ha] | observed % activity 20 DAT | expected % activity 20 DAT | Synergism Y/N 20 DAT |
| GALAP | 16 + 250 | 100 | 75 | Y |
| GALAP | 8 + 250 | 85 | 79 | Y |
| GALAP | 16 + 125 | 85 | 70 | Y |
| POLCO | 16 + 250 | 100 | 70 | Y |
| POLCO | 8 + 250 | 80 | 50 | Y |
| CENCY | 16 + 250 | 70 | 10 | Y |
| CENCY | 8 + 250 | 40 | 35 | Y |
| CENCY | 16 + 125 | 65 | 28 | Y |
| KCHSC | 16 + 125 | 85 | 83 | Y |
| KCHSC | 8 + 125 | 98 | 92 | Y |
| COMBE | 16 + 250 | 50 | 35 | Y |
| COMBE | 16 + 125 | 50 | 35 | Y |
| GERPU | 16 + 250 | 60 | 48 | Y |
| GERPU | 16 + 125 | 50 | 48 | Y |
| IPOHE | 16 + 250 | 20 | 15 | Y |
| EPHHL | 16 + 250 | 40 | 28 | Y |
| EPHHL | 8 + 250 | 40 | 36 | Y |
| ABUTH | 16 + 250 | 50 | 20 | Y |
| ABUTH | 8 + 250 | 35 | 20 | Y |
| ABUTH | 16 + 125 | 60 | 20 | Y |

TABLE 37a

Application in Pre-Emergence of compound 9 and Isoxaflutole (individual activities)

| | compound 9 (A) | | Isoxaflutole (B) | |
|---|---|---|---|---|
| Weed | use rate [g ai/ha] | observed % activity 20 DAT | use rate [g ai/ha] | observed % activity 20 DAT |
| GALAP | 16 | 60 | 50 | 70 |
| GALAP | 8 | 70 | 50 | 70 |
| GALAP | 16 | 60 | 25 | 40 |
| GALAP | 8 | 70 | 25 | 40 |
| POLCO | 16 | 80 | 50 | 0 |
| POLCO | 8 | 50 | 50 | 0 |

TABLE 37a-continued

Application in Pre-Emergence of compound 9 and Isoxaflutole (individual activities)

| | compound 9 (A) | | Isoxaflutole (B) | |
|---|---|---|---|---|
| Weed | use rate [g ai/ha] | observed % activity 20 DAT | use rate [g ai/ha] | observed % activity 20 DAT |
| POLCO | 16 | 80 | 25 | 0 |
| POLCO | 8 | 50 | 25 | 0 |
| CENCY | 8 | 20 | 50 | 60 |
| CENCY | 16 | 15 | 25 | 20 |
| CENCY | 8 | 20 | 25 | 20 |
| KCHSC | 16 | 80 | 50 | 98 |
| KCHSC | 8 | 90 | 50 | 98 |
| KCHSC | 16 | 80 | 25 | 98 |
| KCHSC | 8 | 90 | 25 | 98 |
| COMBE | 16 | 35 | 50 | 45 |
| GERPU | 16 | 60 | 50 | 50 |
| GERPU | 8 | 40 | 50 | 50 |
| GERPU | 16 | 60 | 25 | 70 |
| GERPU | 8 | 40 | 25 | 70 |
| IPOHE | 16 | 10 | 50 | 35 |
| EPHHL | 16 | 15 | 50 | 70 |
| EPHHL | 8 | 25 | 50 | 70 |
| EPHHL | 16 | 15 | 25 | 65 |
| EPHHL | 8 | 25 | 25 | 65 |
| ABUTH | 16 | 20 | 50 | 95 |
| ABUTH | 8 | 20 | 50 | 95 |

TABLE 37b

Application in Pre-Emergence of compound 9 and Isoxaflutole (combined activities)

| | compound 9 + Isoxaflutole (C) | | | |
|---|---|---|---|---|
| Weed | use rate [g ai/ha] | observed % activity 20 DAT | expected % activity 20 DAT | Synergism Y/N 20 DAT |
| GALAP | 16 + 50 | 98 | 88 | Y |
| GALAP | 8 + 50 | 95 | 91 | Y |
| GALAP | 16 + 25 | 95 | 76 | Y |
| GALAP | 8 + 25 | 85 | 82 | Y |
| POLCO | 16 + 50 | 100 | 80 | Y |
| POLCO | 8 + 50 | 85 | 50 | Y |
| POLCO | 16 + 25 | 100 | 80 | Y |
| POLCO | 8 + 25 | 85 | 50 | Y |
| CENCY | 8 + 50 | 80 | 68 | Y |
| CENCY | 16 + 25 | 65 | 32 | Y |
| CENCY | 8 + 25 | 65 | 36 | Y |
| KCHSC | 16 + 50 | 100 | 100 | Y |
| KCHSC | 8 + 50 | 100 | 100 | Y |
| KCHSC | 16 + 25 | 100 | 100 | Y |
| KCHSC | 8 + 25 | 100 | 100 | Y |
| COMBE | 16 + 50 | 65 | 64 | Y |
| GERPU | 16 + 50 | 95 | 80 | Y |
| GERPU | 8 + 50 | 98 | 70 | Y |
| GERPU | 16 + 25 | 90 | 88 | Y |
| GERPU | 8 + 25 | 90 | 82 | Y |
| IPOHE | 16 + 50 | 50 | 42 | Y |
| EPHHL | 16 + 50 | 85 | 75 | Y |
| EPHHL | 8 + 50 | 85 | 78 | Y |
| EPHHL | 16 + 25 | 80 | 70 | Y |
| EPHHL | 8 + 25 | 75 | 74 | Y |
| ABUTH | 16 + 50 | 98 | 96 | Y |
| ABUTH | 8 + 50 | 98 | 96 | Y |

TABLE 38a

Application in Pre-Emergence of compound 9 and Mesotrione (individual activities)

| | compound 9 (A) | | Mesotrione (B) | |
|---|---|---|---|---|
| Weed | use rate [g ai/ha] | observed % activity 20 DAT | use rate [g ai/ha] | observed % activity 20 DAT |
| GALAP | 16 | 60 | 50 | 80 |
| GALAP | 8 | 70 | 50 | 80 |
| GALAP | 16 | 60 | 25 | 65 |
| POLCO | 8 | 50 | 50 | 0 |
| POLCO | 8 | 50 | 25 | 0 |
| POLCO | 16 | 70 | 25 | 0 |
| CENCY | 16 | 15 | 50 | 40 |
| CENCY | 8 | 20 | 50 | 40 |
| CENCY | 16 | 10 | 25 | 60 |
| COMBE | 16 | 20 | 50 | 0 |
| COMBE | 16 | 20 | 25 | 0 |
| GERPU | 16 | 30 | 25 | 70 |
| GERPU | 8 | 40 | 25 | 70 |
| EPHHL | 16 | 15 | 50 | 60 |
| EPHHL | 8 | 30 | 25 | 50 |

TABLE 38b

Application in Pre-Emergence of compound 9 and Mesotrione (combined activities)

| | compound 9 + Mesotrione (C) | | | |
|---|---|---|---|---|
| Weed | use rate [g ai/ha] | observed % activity 20 DAT | expected % activity 20 DAT | Synergism Y/N 20 DAT |
| GALAP | 16 + 50 | 100 | 92 | Y |
| GALAP | 8 + 50 | 98 | 94 | Y |
| GALAP | 16 + 25 | 90 | 86 | Y |
| POLCO | 8 + 50 | 70 | 50 | Y |
| POLCO | 8 + 25 | 60 | 50 | Y |
| POLCO | 16 + 25 | 75 | 70 | Y |
| CENCY | 16 + 50 | 85 | 49 | Y |
| CENCY | 8 + 50 | 75 | 52 | Y |
| CENCY | 16 + 25 | 65 | 64 | Y |
| COMBE | 16 + 50 | 40 | 20 | Y |
| COMBE | 16 + 25 | 40 | 20 | Y |
| GERPU | 16 + 25 | 90 | 79 | Y |
| GERPU | 8 + 25 | 90 | 82 | Y |
| EPHHL | 16 + 50 | 70 | 66 | Y |
| EPHHL | 8 + 25 | 80 | 65 | Y |

TABLE 39a

Application in Pre-Emergence of compound 9 and Isoproturon (individual activities)

| | compound 9 (A) | | Isoproturon (B) | |
|---|---|---|---|---|
| Weed | use rate [g ai/ha] | observed % activity 20 DAT | use rate [g ai/ha] | observed % activity 20 DAT |
| GALAP | 16 | 60 | 500 | 15 |
| GALAP | 8 | 50 | 500 | 65 |
| GALAP | 8 | 50 | 250 | 30 |
| POLCO | 16 | 70 | 500 | 25 |
| POLCO | 8 | 50 | 500 | 10 |
| POLCO | 16 | 80 | 250 | 10 |
| POLCO | 8 | 50 | 250 | 10 |
| CENCY | 8 | 20 | 500 | 30 |
| CENCY | 8 | 20 | 250 | 30 |
| KCHSC | 16 | 80 | 500 | 98 |
| KCHSC | 8 | 90 | 500 | 98 |
| KCHSC | 16 | 80 | 250 | 98 |

TABLE 39a-continued

Application in Pre-Emergence of compound 9 and Isoproturon (individual activities)

| | compound 9 (A) | | Isoproturon (B) | |
|---|---|---|---|---|
| Weed | use rate [g ai/ha] | observed % activity 20 DAT | use rate [g ai/ha] | observed % activity 20 DAT |
| KCHSC | 8 | 90 | 250 | 98 |
| COMBE | 16 | 20 | 500 | 10 |
| COMBE | 8 | 20 | 500 | 10 |
| COMBE | 16 | 15 | 250 | 0 |
| GERPU | 8 | 40 | 500 | 0 |
| SIDRH | 16 | 30 | 500 | 40 |
| SIDRH | 8 | 25 | 250 | 0 |
| EPHHL | 16 | 20 | 500 | 35 |
| EPHHL | 16 | 15 | 250 | 10 |
| EPHHL | 8 | 30 | 250 | 25 |
| ABUTH | 16 | 20 | 500 | 15 |
| ABUTH | 16 | 20 | 250 | 50 |

TABLE 39b

Application in Pre-Emergence of compound 9 and Isoproturon (combined activities)

| | compound 9 + Isoproturon (C) | | | |
|---|---|---|---|---|
| Weed | use rate [g ai/ha] | observed % activity 20 DAT | expected % activity 20 DAT | Synergism Y/N 20 DAT |
| GALAP | 16 + 500 | 98 | 66 | Y |
| GALAP | 8 + 500 | 85 | 83 | Y |
| GALAP | 8 + 250 | 80 | 65 | Y |
| POLCO | 16 + 500 | 80 | 78 | Y |
| POLCO | 8 + 500 | 70 | 55 | Y |
| POLCO | 16 + 250 | 98 | 82 | Y |
| POLCO | 8 + 250 | 90 | 55 | Y |
| CENCY | 8 + 500 | 75 | 44 | Y |
| CENCY | 8 + 250 | 45 | 44 | Y |
| KCHSC | 16 + 500 | 100 | 100 | Y |
| KCHSC | 8 + 500 | 100 | 100 | Y |
| KCHSC | 16 + 250 | 100 | 100 | Y |
| KCHSC | 8 + 250 | 100 | 100 | Y |
| COMBE | 16 + 500 | 55 | 28 | Y |
| COMBE | 8 + 500 | 30 | 28 | Y |
| COMBE | 16 + 250 | 45 | 35 | Y |
| GERPU | 8 + 500 | 65 | 40 | Y |
| SIDRH | 16 + 500 | 75 | 58 | Y |
| SIDRH | 8 + 250 | 35 | 25 | Y |
| EPHHL | 16 + 500 | 50 | 48 | Y |
| EPHHL | 16 + 250 | 30 | 24 | Y |
| EPHHL | 8 + 250 | 50 | 48 | Y |
| ABUTH | 16 + 500 | 60 | 32 | Y |
| ABUTH | 16 + 250 | 65 | 60 | Y |

TABLE 40a

Application in Pre-Emergence of compound 9 and Saflufenacil (individual activities)

| | compound 9 (A) | | Saflufenacil (B) | |
|---|---|---|---|---|
| Weed | use rate [g ai/ha] | observed % activity 20 DAT | use rate [g ai/ha] | observed % activity 20 DAT |
| GALAP | 16 | 60 | 10 | 50 |
| GALAP | 16 | 60 | 5 | 25 |
| POLCO | 16 | 80 | 10 | 25 |
| POLCO | 8 | 50 | 10 | 25 |
| POLCO | 16 | 70 | 5 | 40 |
| POLCO | 8 | 50 | 5 | 0 |

TABLE 40a-continued

Application in Pre-Emergence of compound 9 and Saflufenacil (individual activities)

| | compound 9 (A) | | Saflufenacil (B) | |
|---|---|---|---|---|
| Weed | use rate [g ai/ha] | observed % activity 20 DAT | use rate [g ai/ha] | observed % activity 20 DAT |
| CENCY | 16 | 10 | 10 | 30 |
| CENCY | 8 | 20 | 10 | 20 |
| CENCY | 16 | 15 | 5 | 20 |
| CENCY | 8 | 20 | 5 | 20 |
| KCHSC | 16 | 90 | 10 | 65 |
| KCHSC | 8 | 75 | 10 | 65 |
| KCHSC | 16 | 90 | 5 | 70 |
| KCHSC | 8 | 75 | 5 | 70 |
| COMBE | 16 | 20 | 10 | 15 |
| COMBE | 16 | 20 | 5 | 0 |
| SIDRH | 16 | 30 | 10 | 20 |
| ABUTH | 16 | 20 | 10 | 25 |
| ABUTH | 8 | 20 | 10 | 25 |

TABLE 40b

Application in Pre-Emergence of compound 9 and Saflufenacil (combined activities)

| | compound 9 + Saflufenacil (C) | | | |
|---|---|---|---|---|
| Weed | use rate [g ai/ha] | observed % activity 20 DAT | expected % activity 20 DAT | Synergism Y/N 20 DAT |
| GALAP | 16 + 10 | 85 | 80 | Y |
| GALAP | 16 + 5 | 90 | 70 | Y |
| POLCO | 16 + 10 | 100 | 85 | Y |
| POLCO | 8 + 10 | 90 | 63 | Y |
| POLCO | 16 + 5 | 90 | 82 | Y |
| POLCO | 8 + 5 | 80 | 50 | Y |
| CENCY | 16 + 10 | 40 | 37 | Y |
| CENCY | 8 + 10 | 40 | 36 | Y |
| CENCY | 16 + 5 | 65 | 32 | Y |
| CENCY | 8 + 5 | 40 | 36 | Y |
| KCHSC | 16 + 10 | 98 | 97 | Y |
| KCHSC | 8 + 10 | 100 | 91 | Y |
| KCHSC | 16 + 5 | 98 | 97 | Y |
| KCHSC | 8 + 5 | 95 | 93 | Y |
| COMBE | 16 + 10 | 60 | 32 | Y |
| COMBE | 16 + 5 | 25 | 20 | Y |
| SIDRH | 16 + 10 | 50 | 44 | Y |
| ABUTH | 16 + 10 | 50 | 40 | Y |
| ABUTH | 8 + 10 | 80 | 40 | Y |

TABLE 41a

Application in Pre-Emergence of compound 9 and Sulfentrazone (individual activities)

| | compound 9 (A) | | Sulfentrazone (B) | |
|---|---|---|---|---|
| Weed | use rate [g ai/ha] | observed % activity 20 DAT | use rate [g ai/ha] | observed % activity 20 DAT |
| GALAP | 16 | 60 | 10 | 50 |
| GALAP | 16 | 60 | 5 | 25 |
| POLCO | 16 | 80 | 10 | 25 |
| POLCO | 8 | 50 | 10 | 25 |
| POLCO | 16 | 70 | 5 | 40 |
| POLCO | 8 | 50 | 5 | 0 |
| CENCY | 16 | 10 | 10 | 30 |
| CENCY | 8 | 20 | 10 | 20 |
| CENCY | 16 | 15 | 5 | 20 |
| CENCY | 8 | 20 | 5 | 20 |

TABLE 41a-continued

Application in Pre-Emergence of compound 9 and Sulfentrazone (individual activities)

| | compound 9 (A) | | Sulfentrazone (B) | |
|---|---|---|---|---|
| Weed | use rate [g ai/ha] | observed % activity 20 DAT | use rate [g ai/ha] | observed % activity 20 DAT |
| KCHSC | 16 | 90 | 10 | 65 |
| KCHSC | 8 | 75 | 10 | 65 |
| KCHSC | 16 | 90 | 5 | 70 |
| KCHSC | 8 | 75 | 5 | 70 |
| COMBE | 16 | 20 | 10 | 15 |
| SIDRH | 16 | 30 | 10 | 30 |
| ABUTH | 16 | 20 | 10 | 25 |
| ABUTH | 8 | 20 | 10 | 25 |

TABLE 41b

Application in Pre-Emergence of compound 9 and Sulfentrazone (combined activities)

| | compound 9 + Sulfentrazone (C) | | | |
|---|---|---|---|---|
| Weed | use rate [g ai/ha] | observed % activity 20 DAT | expected % activity 20 DAT | Synergism Y/N 20 DAT |
| GALAP | 16 + 10 | 85 | 80 | Y |
| GALAP | 16 + 5 | 90 | 70 | Y |
| POLCO | 16 + 10 | 100 | 85 | Y |
| POLCO | 8 + 10 | 90 | 63 | Y |
| POLCO | 16 + 5 | 90 | 82 | Y |
| POLCO | 8 + 5 | 80 | 50 | Y |
| CENCY | 16 + 10 | 40 | 37 | Y |
| CENCY | 8 + 10 | 40 | 36 | Y |
| CENCY | 16 + 5 | 65 | 32 | Y |
| CENCY | 8 + 5 | 40 | 36 | Y |
| KCHSC | 16 + 10 | 98 | 97 | Y |
| KCHSC | 8 + 10 | 100 | 91 | Y |
| KCHSC | 16 + 5 | 98 | 97 | Y |
| KCHSC | 8 + 5 | 95 | 93 | Y |
| COMBE | 16 + 10 | 60 | 32 | Y |
| SIDRH | 16 + 10 | 50 | 44 | Y |
| ABUTH | 16 + 10 | 50 | 40 | Y |
| ABUTH | 8 + 10 | 80 | 40 | Y |

The plants used in the greenhouse experiments with combination of compound 10 illustrated in the following tables 42a/b to 49a/b belonged to the following species:

| Scientific Name | Code | Common Name |
|---|---|---|
| Abutilon theophrasti | ABUTH | velvetleaf |
| Alopecurus myosuroides | ALOMY | blackgrass |
| Anthemis arvensis | ANTAR | field chamomile |
| Avena fatua | AVEFA | wild oat |
| Brachiaria decumbens | BRADC | surinam grass |
| Commelina benghalensis | COMBE | tropical spiderwort |
| Eleusine indica | ELEIN | goosegrass |
| Euphorbia heterophylla | EPHHL | wild spurge |
| Galium aparine | GALAP | cleaver |
| Geranium pusillum | GERPU | small-flowered cranesbill |
| Kochia scoparia | KCHSC | kochia |
| Lolium multiflorum | LOLMU | italian ryegrass |
| Phalaris canariensis | PHACA | canarygrass |
| Ipomoea hederacea | IPOHE | ivy-leave morning glory |
| Polygonum convolvulus | POLCO | wild buckwheat |
| Sida rhombifolia | SIDRH | common sida |
| Sorghum halepense | SORHA | johnsongrass |

TABLE 42a

Application in Pre-Emergence of compound 10 and Saflufenacil (individual activities)

| | compound 10 (A) | | Saflufenacil (B) | |
|---|---|---|---|---|
| Weed | use rate [g ai/ha] | observed % activity 20 DAT | use rate [g ai/ha] | observed % activity 20 DAT |
| ALOMY | 62 | 90 | 12.5 | 0 |
| ALOMY | 15.5 | 65 | 12.5 | 0 |
| ALOMY | 62 | 90 | 6.25 | 0 |
| ALOMY | 31 | 90 | 6.25 | 0 |
| LOLMU | 31 | 70 | 6.25 | 0 |
| LOLMU | 7.75 | 30 | 6.25 | 0 |
| SETFA | 15.5 | 98 | 12.5 | 0 |
| SETFA | 7.75 | 90 | 12.5 | 0 |
| SETFA | 15.5 | 98 | 6.25 | 0 |
| SETFA | 15.5 | 98 | 6.25 | 0 |
| POLCO | 62 | 95 | 12.5 | 85 |
| POLCO | 62 | 95 | 6.25 | 70 |
| KCHSC | 31 | 75 | 12.5 | 70 |
| KCHSC | 62 | 90 | 6.25 | 30 |

TABLE 42b

Application in Pre-Emergence of compound 10 and Saflufenacil (combined activities)

| | compound 10 + KIXOR (C) | | | |
|---|---|---|---|---|
| Weed | use rate [g ai/ha] | observed % activity 20 DAT | expected % activity 20 DAT | Synergism Y/N 20 DAT |
| ALOMY | 62 + 12.5 | 98 | 90 | Y |
| ALOMY | 15.5 + 12.5 | 80 | 65 | Y |
| ALOMY | 62 + 6.25 | 98 | 90 | Y |
| ALOMY | 31 + 6.25 | 95 | 90 | Y |
| LOLMU | 31 + 6.25 | 75 | 70 | Y |
| LOLMU | 7.75 + 6.25 | 40 | 30 | Y |
| SETFA | 15.5 + 12.5 | 100 | 98 | Y |
| SETFA | 7.75 + 12.5 | 100 | 90 | Y |
| SETFA | 15.5 + 6.25 | 100 | 98 | Y |
| SETFA | 15.5 + 6.25 | 100 | 98 | Y |
| POLCO | 62 + 12.5 | 100 | 99 | Y |
| POLCO | 62 + 6.25 | 100 | 99 | Y |
| KCHSC | 31 + 12.5 | 95 | 93 | Y |
| KCHSC | 62 + 6.25 | 95 | 93 | Y |

TABLE 43a

Application in Pre-Emergence of compound 10 and Dicamba (individual activities)

| | compound 10 (A) | | Dicamba (B) | |
|---|---|---|---|---|
| Weed | use rate [g ai/ha] | observed % activity 20 DAT | use rate [g ai/ha] | observed % activity 20 DAT |
| ALOMY | 15.5 | 65 | 100 | 40 |
| ALOMY | 62 | 90 | 50 | 20 |
| ALOMY | 31 | 90 | 50 | 20 |
| LOLMU | 31 | 70 | 100 | 45 |
| LOLMU | 7.75 | 30 | 100 | 45 |
| POLCO | 62 | 95 | 100 | 60 |
| POLCO | 62 | 95 | 50 | 40 |
| KCHSC | 62 | 90 | 100 | 90 |
| KCHSC | 7.75 | 75 | 100 | 90 |
| KCHSC | 62 | 90 | 50 | 85 |

TABLE 43b

Application in Pre-Emergence of compound
10 and Dicamba (combined activities)

compound 10 + Dicamba (C)

| Weed | use rate [g ai/ha] | observed % activity 20 DAT | expected % activity 20 DAT | Synergism Y/N 20 DAT |
|---|---|---|---|---|
| ALOMY | 15.5 + 100 | 85 | 79 | Y |
| ALOMY | 62 + 50 | 98 | 92 | Y |
| ALOMY | 31 + 50 | 95 | 92 | Y |
| LOLMU | 31 + 100 | 95 | 82 | Y |
| LOLMU | 7.75 + 100 | 65 | 58 | Y |
| POLCO | 62 + 100 | 100 | 98 | Y |
| POLCO | 62 + 50 | 100 | 97 | Y |
| KCHSC | 62 + 100 | 100 | 99 | Y |
| KCHSC | 7.75 + 100 | 98 | 98 | Y |
| KCHSC | 62 + 50 | 100 | 99 | Y |

TABLE 44a

Application in Pre-Emergence of compound 10
and Pyroxasulfone (individual activities)

| | compound 10 (A) | | Pyroxasulfone (B) | |
|---|---|---|---|---|
| Weed | use rate [g ai/ha] | observed % activity 20 DAT | use rate [g ai/ha] | observed % activity 20 DAT |
| ALOMY | 31 | 98 | 25 | 20 |
| ALOMY | 15.5 | 90 | 25 | 20 |
| ALOMY | 7.75 | 65 | 25 | 20 |
| ALOMY | 62 | 95 | 12.5 | 20 |
| ALOMY | 31 | 98 | 12.5 | 20 |
| ALOMY | 15.5 | 90 | 12.5 | 20 |
| ALOMY | 7.75 | 65 | 12.5 | 20 |
| APESV | 7.75 | 95 | 25 | 60 |
| APESV | 7.75 | 95 | 12.5 | 50 |
| LOLMU | 62 | 90 | 25 | 40 |
| LOLMU | 31 | 70 | 25 | 40 |
| LOLMU | 15.5 | 35 | 25 | 40 |
| LOLMU | 7.75 | 15 | 25 | 40 |
| LOLMU | 62 | 90 | 12.5 | 30 |
| LOLMU | 31 | 70 | 12.5 | 30 |
| LOLMU | 15.5 | 35 | 12.5 | 30 |
| LOLMU | 7.75 | 15 | 12.5 | 30 |
| ECHCG | 7.75 | 90 | 12.5 | 50 |
| PHACA | 62 | 75 | 25 | 55 |
| PHACA | 31 | 80 | 25 | 55 |
| PHACA | 7.75 | 30 | 25 | 55 |
| PHACA | 62 | 75 | 12.5 | 40 |
| PHACA | 31 | 80 | 12.5 | 40 |
| PHACA | 7.75 | 30 | 12.5 | 40 |
| POLCO | 7.75 | 70 | 12.5 | 0 |
| KCHSC | 31 | 95 | 25 | 0 |
| KCHSC | 15.5 | 90 | 25 | 0 |

TABLE 44b

Application in Pre-Emergence of compound 10
and Pyroxasulfone (combined activities)

compound 10 + Pyroxasulfone (C)

| Weed | use rate [g ai/ha] | observed % activity 20 DAT | expected % activity 20 DAT | Synergism Y/N 20 DAT |
|---|---|---|---|---|
| ALOMY | 31 + 25 | 100 | 98 | Y |
| ALOMY | 15.5 + 25 | 95 | 92 | Y |
| ALOMY | 7.75 + 25 | 98 | 72 | Y |
| ALOMY | 62 + 12.5 | 100 | 96 | Y |
| ALOMY | 31 + 12.5 | 100 | 98 | Y |

TABLE 44b-continued

Application in Pre-Emergence of compound 10
and Pyroxasulfone (combined activities)

compound 10 + Pyroxasulfone (C)

| Weed | use rate [g ai/ha] | observed % activity 20 DAT | expected % activity 20 DAT | Synergism Y/N 20 DAT |
|---|---|---|---|---|
| ALOMY | 15.5 + 12.5 | 98 | 92 | Y |
| ALOMY | 7.75 + 12.5 | 95 | 72 | Y |
| APESV | 7.75 + 25 | 100 | 98 | Y |
| APESV | 7.75 + 12.5 | 100 | 98 | Y |
| LOLMU | 62 + 25 | 100 | 94 | Y |
| LOLMU | 31 + 25 | 95 | 82 | Y |
| LOLMU | 15.5 + 25 | 95 | 61 | Y |
| LOLMU | 7.75 + 25 | 95 | 49 | Y |
| LOLMU | 62 + 12.5 | 95 | 93 | Y |
| LOLMU | 31 + 12.5 | 90 | 79 | Y |
| LOLMU | 15.5 + 12.5 | 95 | 55 | Y |
| LOLMU | 7.75 + 12.5 | 80 | 41 | Y |
| ECHCG | 7.75 + 12.5 | 100 | 95 | Y |
| PHACA | 62 + 25 | 100 | 98 | Y |
| PHACA | 31 + 25 | 100 | 91 | Y |
| PHACA | 7.75 + 25 | 70 | 69 | Y |
| PHACA | 62 + 12.5 | 95 | 85 | Y |
| PHACA | 31 + 12.5 | 98 | 88 | Y |
| PHACA | 7.75 + 12.5 | 70 | 58 | Y |
| POLCO | 7.75 + 12.5 | 100 | 70 | Y |
| KCHSC | 31 + 25 | 100 | 95 | Y |
| KCHSC | 15.5 + 25 | 98 | 90 | Y |

TABLE 45a

Application in Pre-Emergence of compound 10
and PPO (BAS 850) (individual activities)

| | compound 10 (A) | | PPO (B) | |
|---|---|---|---|---|
| Weed | use rate [g ai/ha] | observed % activity 20 DAT | use rate [g ai/ha] | observed % activity 20 DAT |
| PHACA | 62 | 75 | 12.5 | 85 |
| KCHSC | 31 | 95 | 25 | 85 |
| KCHSC | 15.5 | 90 | 25 | 85 |
| KCHSC | 31 | 95 | 12.5 | 25 |
| KCHSC | 15.5 | 90 | 12.5 | 25 |
| KCHSC | 7.75 | 85 | 12.5 | 25 |

TABLE 45b

Application in Pre-Emergence of compound 10
and PPO (BAS 850) (combined activities)

compound 10 + PPO (C)

| Weed | use rate [g ai/ha] | observed % activity 20 DAT | expected % activity 20 DAT | Synergism Y/N 20 DAT |
|---|---|---|---|---|
| PHACA | 62 + 12.5 | 100 | 96 | Y |
| KCHSC | 31 + 25 | 100 | 99 | Y |
| KCHSC | 15.5 + 25 | 100 | 99 | Y |
| KCHSC | 31 + 12.5 | 100 | 96 | Y |
| KCHSC | 15.5 + 12.5 | 98 | 93 | Y |
| KCHSC | 7.75 + 12.5 | 98 | 89 | Y |

TABLE 46a

Application in Pre-Emergence of compound 10 and glyphosate (individual activities)

| | compound 10 (A) | | ROUNDUP (B) | |
|---|---|---|---|---|
| Weed | use rate [g ai/ha] | observed % activity 20 DAT | use rate [g ai/ha] | observed % activity 20 DAT |
| ALOMY | 15.5 | 70 | 250 | 20 |
| ALOMY | 62 | 98 | 125 | 0 |
| ALOMY | 31 | 98 | 125 | 0 |
| APESV | 15.5 | 95 | 250 | 0 |
| APESV | 15.5 | 95 | 125 | 0 |
| LOLMU | 15.5 | 35 | 250 | 0 |
| LOLMU | 62 | 85 | 125 | 0 |
| LOLMU | 15.5 | 35 | 125 | 0 |
| LOLMU | 7.75 | 20 | 125 | 0 |
| SETFA | 7.75 | 75 | 250 | 0 |
| SETFA | 15.5 | 95 | 125 | 0 |
| SETFA | 7.75 | 75 | 125 | 0 |
| ECHCG | 7.75 | 95 | 250 | 0 |
| PHACA | 62 | 70 | 250 | 0 |
| PHACA | 31 | 85 | 250 | 0 |
| PHACA | 15.5 | 25 | 250 | 0 |
| PHACA | 7.75 | 25 | 250 | 0 |
| PHACA | 62 | 70 | 125 | 0 |
| PHACA | 31 | 85 | 125 | 0 |
| KCHSC | 62 | 90 | 250 | 0 |
| KCHSC | 16.5 | 65 | 250 | 0 |
| KCHSC | 7.75 | 55 | 250 | 0 |
| KCHSC | 62 | 90 | 125 | 0 |
| KCHSC | 7.75 | 55 | 125 | 0 |

TABLE 46b

Application in Pre-Emergence of compound 10 and Glyphosate (combined activities)

| | compound 10 + ROUNDUP (C) | | |
|---|---|---|---|
| Weed | use rate [g ai/ha] | observed % activity 20 DAT | expected % activity 20 DAT | Synergism Y/N 20 DAT |
| ALOMY | 15.5 + 250 | 80 | 76 | Y |
| ALOMY | 62 + 125 | 100 | 98 | Y |
| ALOMY | 31 + 125 | 100 | 98 | Y |
| APESV | 15.5 + 250 | 98 | 95 | Y |
| APESV | 15.5 + 125 | 98 | 95 | Y |
| LOLMU | 15.5 + 250 | 40 | 35 | Y |
| LOLMU | 62 + 125 | 90 | 85 | Y |
| LOLMU | 15.5 + 125 | 45 | 35 | Y |
| LOLMU | 7.75 + 125 | 25 | 20 | Y |
| SETFA | 7.75 + 250 | 90 | 75 | Y |
| SETFA | 15.5 + 125 | 100 | 95 | Y |
| SETFA | 7.75 + 125 | 80 | 75 | Y |
| ECHCG | 7.75 + 250 | 98 | 95 | Y |
| PHACA | 62 + 250 | 80 | 70 | Y |
| PHACA | 31 + 250 | 95 | 85 | Y |
| PHACA | 15.5 + 250 | 35 | 25 | Y |
| PHACA | 7.75 + 250 | 30 | 25 | Y |
| PHACA | 62 + 125 | 75 | 70 | Y |
| PHACA | 31 + 125 | 90 | 85 | Y |
| KCHSC | 62 + 250 | 95 | 90 | Y |
| KCHSC | 15.5 + 250 | 80 | 65 | Y |
| KCHSC | 7.75 + 250 | 60 | 55 | Y |
| KCHSC | 62 + 125 | 95 | 90 | Y |
| KCHSC | 7.75 + 125 | 65 | 55 | Y |

TABLE 47a

Application in Pre-Emergence of compound 10 and Flufenacet (individual activities)

| | compound 10 (A) | | Flufenacet (B) | |
|---|---|---|---|---|
| Weed | use rate [g ai/ha] | observed % activity 20 DAT | use rate [g ai/ha] | observed % activity 20 DAT |
| ALOMY | 62 | 98 | 60 | 80 |
| ALOMY | 31 | 98 | 60 | 80 |
| ALOMY | 15.5 | 70 | 60 | 80 |
| ALOMY | 15.5 | 70 | 30 | 75 |
| LOLMU | 62 | 85 | 60 | 30 |
| LOLMU | 31 | 70 | 60 | 30 |
| LOLMU | 15.5 | 35 | 60 | 30 |
| LOLMU | 7.75 | 20 | 60 | 30 |
| LOLMU | 62 | 85 | 30 | 20 |
| LOLMU | 31 | 70 | 30 | 20 |
| LOLMU | 15.5 | 35 | 30 | 20 |
| SETFA | 15.5 | 95 | 30 | 98 |
| ECHCG | 7.75 | 95 | 30 | 85 |
| PHACA | 62 | 70 | 60 | 98 |
| PHACA | 31 | 85 | 60 | 98 |
| PHACA | 62 | 70 | 30 | 65 |
| PHACA | 15.5 | 25 | 30 | 65 |
| KCHSC | 62 | 90 | 60 | 0 |
| KCHSC | 15.5 | 65 | 60 | 0 |
| KCHSC | 7.75 | 55 | 60 | 0 |
| KCHSC | 62 | 90 | 30 | 0 |

TABLE 47b

Application in Pre-Emergence of compound 10 and Flufenacet (combined activities)

| | compound 10 + Flufenacet (C) | | |
|---|---|---|---|
| Weed | use rate [g ai/ha] | observed % activity 20 DAT | expected % activity 20 DAT | Synergism Y/N 20 DAT |
| ALOMY | 62 + 60 | 100 | 100 | Y |
| ALOMY | 31 + 60 | 100 | 100 | Y |
| ALOMY | 15.5 + 60 | 95 | 94 | Y |
| ALOMY | 15.5 + 30 | 95 | 93 | Y |
| LOLMU | 62 + 60 | 100 | 90 | Y |
| LOLMU | 31 + 60 | 95 | 75 | Y |
| LOLMU | 15.5 + 60 | 70 | 55 | Y |
| LOLMU | 7.75 + 60 | 70 | 44 | Y |
| LOLMU | 62 + 30 | 90 | 88 | Y |
| LOLMU | 31 + 30 | 90 | 76 | Y |
| LOLMU | 15.5 + 30 | 75 | 48 | Y |
| SETFA | 15.5 + 30 | 100 | 100 | Y |
| ECHCG | 7.75 + 30 | 100 | 99 | Y |
| PHACA | 62 + 60 | 100 | 99 | Y |
| PHACA | 31 + 60 | 100 | 100 | Y |
| PHACA | 62 + 30 | 95 | 90 | Y |
| PHACA | 15.5 + 30 | 90 | 74 | Y |
| KCHSC | 62 + 60 | 95 | 90 | Y |
| KCHSC | 15.5 + 60 | 80 | 65 | Y |
| KCHSC | 7.75 + 60 | 80 | 55 | Y |
| KCHSC | 62 + 30 | 95 | 90 | Y |

TABLE 48a

Application in Pre-Emergence of compound 10 and Pendimethalin (individual activities)

| | compound 10 (A) | | Pendimethalin (B) | |
|---|---|---|---|---|
| Weed | use rate [g ai/ha] | observed % activity 20 DAT | use rate [g ai/ha] | observed % activity 20 DAT |
| ALOMY | 31 | 98 | 1000 | 75 |
| ALOMY | 31 | 98 | 500 | 65 |
| ALOMY | 31 | 98 | 250 | 10 |
| ALOMY | 7.75 | 75 | 1000 | 95 |
| ALOMY | 7.75 | 75 | 500 | 90 |
| ALOMY | 7.75 | 75 | 250 | 85 |
| ALOMY | 7.75 | 75 | 125 | 55 |
| APESV | 15.5 | 98 | 500 | 95 |
| APESV | 15.5 | 98 | 250 | 75 |
| APESV | 7.75 | 30 | 125 | 85 |
| LOLMU | 15.5 | 50 | 500 | 15 |
| LOLMU | 15.5 | 50 | 250 | 0 |
| LOLMU | 15.5 | 25 | 1000 | 55 |
| LOLMU | 15.5 | 25 | 500 | 0 |
| LOLMU | 15.5 | 25 | 250 | 0 |
| LOLMU | 15.5 | 25 | 125 | 0 |
| LOLMU | 7.75 | 0 | 1000 | 55 |
| LOLMU | 7.75 | 0 | 500 | 0 |
| LOLMU | 7.75 | 0 | 250 | 0 |
| LOLMU | 7.75 | 0 | 125 | 0 |
| SETFA | 7.75 | 65 | 500 | 98 |
| SETFA | 7.75 | 65 | 125 | 98 |
| ECHCG | 15.5 | 95 | 250 | 98 |
| ECHCG | 15.5 | 95 | 125 | 95 |
| ECHCG | 7.75 | 95 | 250 | 98 |
| ECHCG | 7.75 | 95 | 125 | 98 |
| PHACA | 15.5 | 60 | 250 | 55 |
| PHACA | 7.75 | 55 | 500 | 65 |
| PHACA | 7.75 | 55 | 250 | 55 |
| PHACA | 7.75 | 55 | 125 | 35 |
| POLCO | 15.5 | 90 | 500 | 60 |
| POLCO | 7.75 | 75 | 500 | 45 |
| POLCO | 7.75 | 75 | 125 | 0 |
| KCHSC | 15.5 | 85 | 125 | 60 |
| GERPU | 15.5 | 75 | 250 | 90 |
| GERPU | 15.5 | 75 | 125 | 70 |
| GERPU | 7.75 | 75 | 125 | 70 |

TABLE 48b

Application in Pre-Emergence of compound 10 and Pendimethalin (combined activities)

| | compound 10 + Pendimethalin (C) | | | |
|---|---|---|---|---|
| Weed | use rate [g ai/ha] | observed % activity 20 DAT | expected % activity 20 DAT | Synergism Y/N 20 DAT |
| ALOMY | 31 + 1000 | 100 | 100 | Y |
| ALOMY | 31 + 500 | 100 | 99 | Y |
| ALOMY | 31 + 250 | 100 | 98 | Y |
| ALOMY | 7.75 + 1000 | 100 | 99 | Y |
| ALOMY | 7.75 + 500 | 98 | 98 | Y |
| ALOMY | 7.75 + 250 | 98 | 96 | Y |
| ALOMY | 7.75 + 125 | 98 | 89 | Y |
| APESV | 15.5 + 500 | 100 | 100 | Y |
| APESV | 15.5 + 250 | 100 | 100 | Y |
| APESV | 7.75 + 125 | 98 | 96 | Y |
| LOLMU | 15.5 + 500 | 65 | 58 | Y |
| LOLMU | 15.5 + 250 | 65 | 50 | Y |
| LOLMU | 15.5 + 1000 | 75 | 66 | Y |
| LOLMU | 15.5 + 500 | 70 | 25 | Y |
| LOLMU | 15.5 + 250 | 65 | 25 | Y |
| LOLMU | 15.5 + 125 | 60 | 25 | Y |
| LOLMU | 7.75 + 1000 | 100 | 55 | Y |
| LOLMU | 7.75 + 500 | 90 | 0 | Y |
| LOLMU | 7.75 + 250 | 100 | 0 | Y |
| LOLMU | 7.75 + 125 | 98 | 0 | Y |
| SETFA | 7.75 + 500 | 100 | 99 | Y |
| SETFA | 7.75 + 125 | 100 | 99 | Y |
| ECHCG | 15.5 + 250 | 100 | 100 | Y |
| ECHCG | 15.5 + 125 | 100 | 100 | Y |
| ECHCG | 7.75 + 250 | 100 | 100 | Y |
| ECHCG | 7.75 + 125 | 100 | 100 | Y |
| PHACA | 15.5 + 250 | 90 | 82 | Y |
| PHACA | 7.75 + 500 | 90 | 84 | Y |
| PHACA | 7.75 + 250 | 100 | 80 | Y |
| PHACA | 7.75 + 125 | 85 | 71 | Y |
| POLCO | 15.5 + 500 | 100 | 96 | Y |
| POLCO | 7.75 + 500 | 95 | 90 | Y |
| POLCO | 7.75 + 125 | 100 | 75 | Y |
| KCHSC | 15.5 + 125 | 98 | 94 | Y |
| GERPU | 15.5 + 250 | 100 | 98 | Y |
| GERPU | 15.5 + 125 | 100 | 93 | Y |
| GERPU | 7.75 + 125 | 95 | 93 | Y |

TABLE 49a

Application in Pre-Emergence of compound 10 and Dimethenamid (individual activities)

| | compound 10 (A) | | DMTA (B) | |
|---|---|---|---|---|
| Weed | use rate [g ai/ha] | observed % activity 20 DAT | use rate [g ai/ha] | observed % activity 20 DAT |
| ALOMY | 31 | 98 | 62.5 | 0 |
| ALOMY | 15.5 | 95 | 125 | 35 |
| LOLMU | 31 | 80 | 15.625 | 35 |
| LOLMU | 15.5 | 50 | 125 | 95 |
| LOLMU | 15.5 | 50 | 15.625 | 35 |
| LOLMU | 15.5 | 25 | 125 | 95 |
| LOLMU | 15.5 | 25 | 62.5 | 85 |
| LOLMU | 15.5 | 25 | 31.25 | 55 |
| LOLMU | 15.5 | 25 | 15.625 | 0 |
| LOLMU | 7.75 | 0 | 31.25 | 55 |
| LOLMU | 7.75 | 0 | 15.625 | 0 |
| ECHCG | 15.5 | 95 | 31.25 | 98 |
| SETFA | 7.75 | 65 | 31.25 | 98 |
| SETFA | 7.75 | 65 | 15.625 | 85 |
| PHACA | 15.5 | 60 | 125 | 80 |
| PHACA | 15.5 | 60 | 31.25 | 55 |
| POLCO | 15.5 | 90 | 125 | 0 |
| POLCO | 15.5 | 90 | 31.25 | 0 |
| POLCO | 7.75 | 75 | 125 | 0 |
| POLCO | 7.75 | 75 | 62.5 | 0 |
| POLCO | 7.75 | 75 | 31.25 | 0 |
| KCHSC | 15.5 | 85 | 62.5 | 0 |
| KCHSC | 15.5 | 85 | 31.25 | 0 |
| KCHSC | 15.5 | 85 | 125 | 0 |
| KCHSC | 15.5 | 85 | 62.5 | 0 |
| KCHSC | 15.5 | 85 | 31.25 | 0 |
| KCHSC | 7.75 | 90 | 125 | 0 |
| KCHSC | 7.75 | 90 | 31.25 | 0 |
| VIOAR | 15.5 | 85 | 125 | 0 |
| VIOAR | 15.5 | 85 | 62.5 | 0 |
| VIOAR | 15.5 | 85 | 31.25 | 0 |
| VIOAR | 7.75 | 90 | 125 | 0 |
| VIOAR | 7.75 | 90 | 31.25 | 0 |
| GERPU | 15.5 | 75 | 62.5 | 85 |
| GERPU | 15.5 | 75 | 31.25 | 70 |
| GERPU | 15.5 | 75 | 15.625 | 50 |
| GERPU | 7.75 | 50 | 62.5 | 85 |

TABLE 49b

Application in Pre-Emergence of compound
10 and Dimethenamid (combined activities)

compound 10 + DMTA (C)

| Weed | use rate [g ai/ha] | observed % activity 20 DAT | expected % activity 20 DAT | Synergism Y/N 20 DAT |
|---|---|---|---|---|
| ALOMY | 31 + 62.5 | 100 | 98 | Y |
| ALOMY | 15.5 + 125 | 98 | 97 | Y |
| LOLMU | 31 + 15.625 | 90 | 87 | Y |
| LOLMU | 15.5 + 125 | 100 | 98 | Y |
| LOLMU | 15.5 + 15.625 | 75 | 68 | Y |
| LOLMU | 15.5 + 125 | 100 | 96 | Y |
| LOLMU | 15.5 + 62.5 | 95 | 89 | Y |
| LOLMU | 15.5 + 31.25 | 90 | 66 | Y |
| LOLMU | 15.5 + 15.625 | 45 | 25 | Y |
| LOLMU | 7.75 + 31.25 | 60 | 55 | Y |
| LOLMU | 7.75 + 15.625 | 40 | 0 | Y |
| ECHCG | 15.5 + 31.25 | 100 | 100 | Y |
| SETFA | 7.75 + 31.25 | 100 | 99 | Y |
| SETFA | 7.75 + 15.625 | 100 | 95 | Y |
| PHACA | 15.5 + 125 | 98 | 92 | Y |
| PHACA | 15.5 + 31.25 | 90 | 82 | Y |
| POLCO | 15.5 + 125 | 100 | 90 | Y |
| POLCO | 15.5 + 31.25 | 100 | 90 | Y |
| POLCO | 7.75 + 125 | 100 | 75 | Y |
| POLCO | 7.75 + 62.5 | 95 | 75 | Y |
| POLCO | 7.75 + 31.25 | 80 | 75 | Y |
| KCHSC | 15.5 + 62.5 | 90 | 85 | Y |
| KCHSC | 15.5 + 31.25 | 100 | 85 | Y |
| KCHSC | 15.5 + 125 | 98 | 85 | Y |
| KCHSC | 15.5 + 62.5 | 95 | 85 | Y |
| KCHSC | 15.5 + 31.25 | 98 | 85 | Y |
| KCHSC | 7.75 + 125 | 95 | 90 | Y |
| KCHSC | 7.75 + 31.25 | 95 | 90 | Y |
| VIOAR | 15.5 + 125 | 98 | 85 | Y |
| VIOAR | 15.5 + 62.5 | 95 | 85 | Y |
| VIOAR | 15.5 + 31.25 | 98 | 85 | Y |
| VIOAR | 7.75 + 125 | 95 | 90 | Y |
| VIOAR | 7.75 + 31.25 | 95 | 90 | Y |
| GERPU | 15.5 + 62.5 | 100 | 96 | Y |
| GERPU | 15.5 + 31.25 | 100 | 93 | Y |
| GERPU | 15.5 + 15.625 | 100 | 88 | Y |
| GERPU | 7.75 + 62.5 | 100 | 96 | Y |

The invention claimed is:

1. A herbicidal combination comprising:
a) at least one compound a) of the formula (I)

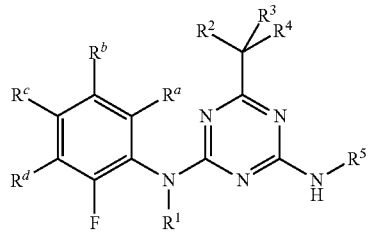

(I)

wherein
$R^a$, $R^b$, $R^c$, $R^d$ independently from each other are H, halogen, CN, $NO_2$, $C_1$-$C_6$-alkyl, $C_1$-$C_6$-haloalkyl, OH, $C_1$-$C_6$-alkoxy, $C_1$-$C_6$-alkylthio, ($C_1$-$C_6$-alkyl)sulfinyl, ($C_1$-$C_6$-alkyl)sulfonyl, amino, ($C_1$-$C_6$-alkyl)amino, di($C_1$-$C_6$-alkyl)amino, ($C_1$-$C_6$-alkyl)-carbonyl, ($C_1$-$C_6$-alkoxy)-carbonyl and ($C_1$-$C_6$-alkyl)$C_3$-$C_6$-cycloalkyl;
$R^1$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
phenyl, phenyl-$C_1$-$C_6$-alkyl, phenyl sulfonyl, phenylaminosulfonyl, phenylcarbonyl and phenoxycarbonyl,
wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
$R^2$ is selected from the group consisting of H, halogen, CN, $C_1$-$C_6$-alkyl, $C_1$-$C_6$-haloalkyl, $C_2$-$C_6$-alkenyl, $C_3$-$C_6$-alkynyl, $C_3$-$C_6$-cycloalkyl, ($C_1$-$C_6$-alkyl)$C_3$-$C_6$-cycloalkyl, $C_3$-$C_6$-cycloalkenyl, OH, $C_1$-$C_6$-alkoxy or $C_1$-$C_6$-alkoxy-$C_1$-$C_6$-alkyl;
$R^3$ H, halogen, CN, $C_1$-$C_6$-alkyl, $C_1$-$C_6$-haloalkyl or $C_1$-$C_6$-alkoxy;
$R^4$ H, halogen, CN, $C_1$-$C_6$-alkyl or $C_1$-$C_6$-haloalkyl; or
$R^3$ and $R^4$ together with the carbon atom to which they are attached form a moiety selected from the group consisting of carbonyl, $C_2$-$C_6$-alkenyl, $C_3$-$C_6$-cycloalkyl, $C_3$-$C_6$-cycloalkenyl and three- to six-membered heterocyclyl,
wherein the $C_3$-$C_6$-cycloalkyl, $C_3$-$C_6$-cycloalkenyl or three- to six-membered heterocyclyl is unsubstituted or substituted by one to three substituents selected from halogen, CN, $C_1$-$C_6$-alkyl and $C_1$-$C_6$-alkoxy; and
$R^5$ is selected from the group consisting of H, OH, $S(O)_2NH_2$, CN, $C_1$-$C_6$-alkyl, $C_2$-$C_6$-alkenyl, $C_2$-$C_6$-alkynyl, ($C_3$-$C_6$-cycloalkyl)-$C_1$-$C_4$-alkyl, $C_1$-$C_6$-alkoxy, ($C_1$-$C_6$-alkoxy)-$C_1$-$C_6$-alkyl, ($C_1$-$C_6$-alkyl)-carbonyl, ($C_1$-$C_6$-alkoxy)carbonyl, ($C_1$-$C_6$-alkyl)sulfonyl, ($C_1$-$C_6$-alkylamino)carbonyl, di($C_1$-$C_6$-alkyl)aminocarbonyl, ($C_1$-$C_6$-alkylamino)sulfonyl, di($C_1$-$C_6$-alkyl)aminosulfonyl and ($C_1$-$C_6$-alkoxy)sulfonyl, where the aliphatic and cycloaliphatic parts of the 14 aforementioned radicals are unsubstituted, partly or completely halogenated,
phenyl, phenyl-$C_1$-$C_6$-alkyl, phenyl sulfonyl, phenylaminosulfonyl, phenylcarbonyl and phenoxycarbonyl,
wherein phenyl in the last 6 mentioned radicals are unsubstituted or substituted by 1, 2, 3, 4 or 5 identical or different substituents selected from the group consisting of halogen, CN, $NO_2$, $C_1$-$C_6$-alkyl, $C_1$-$C_6$-haloalkyl, $C_1$-$C_6$-alkoxy and $C_1$-$C_6$-haloalkoxy;
including their agriculturally acceptable salts or N-oxides and at least one further compound selected from herbicide compounds b) and safeners c) and mixtures thereof;
b) where the further herbicidally active compounds b) is selected from the compounds of the following class b1) to b15):
b1) lipid biosynthesis inhibitors;
b2) acetolactate synthase inhibitors;
b3) photosynthesis inhibitors;
b4) protoporphyrinogen-IX oxidase inhibitors,
b5) bleacher herbicides;
b6) enolpyruvyl shikimate 3-phosphate synthase inhibitors;
b7) glutamine synthetase inhibitors;
b8) 7,8-dihydropteroate synthase inhibitors;
b9) mitosis inhibitors;

b10) inhibitors of the synthesis of very long chain fatty acids;
b11) cellulose biosynthesis inhibitors;
b12) decoupler herbicides;
b13) auxinic herbicides;
b14) auxin transport inhibitors and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin, methyl azide, methyl bromide, methyldymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol and its salts and esters including their agriculturally acceptable salts or derivatives.

2. The combination of claim 1, wherein compound (I) comprises at least on compound (I), wherein wherein $R^1$ is H, $R^2$ is H, halogen, $C_1$-$C_6$-alkyl, $C_1$-$C_6$-alkoxy, $C_1$-$C_6$-haloalkyl or $C_1$-$C_6$-haloalkoxy, $R^3$ is H, halogen, CN, $C_1$-$C_6$-alkyl, $C_1$-$C_6$-haloalkyl or $C_1$-$C_6$-alkoxy, $R^4$ is H, halogen, CN, $C_1$-$C_6$-alkyl or $C_1$-$C_6$-haloalkyl, $R^3$ and $R^4$ together with the carbon atom to which they are attached form a $C_3$-$C_6$-cycloalkyl, $R^5$ is H, $R^a$ is H, halogen, CN, $R^b$ is H, halogen, CN, $R^c$ is H, halogen, CN and $R^d$ is H, halogen, CN.

3. The combination of claim 1, wherein compound (I) comprises at least on compound (I), wherein $R^1$ is H, $R^5$ is H, $R^a$, $R^b$, $R^c$, $R^d$, $R^2$, $R^3$, $R^4$ have the following meaning

| $R^a$ | $R^b$ | $R^c$ | $R^d$ | $R^2$ | $R^3$ | $R^4$ |
|---|---|---|---|---|---|---|
| F | F | H | F | $CH_3$ | $CH_3$ | $CH_3$ |
| F | F | F | F | $CH_3$ | $CH_3$ | $CH_3$ |
| F | H | H | H | F | $CH_3$ | $CH_3$ |
| CN | H | H | H | F | $CH_3$ | $CH_3$ |
| Cl | H | H | F | F | $CH_3$ | $CH_3$ |
| F | H | H | Cl | F | $CH_3$ | $CH_3$ |
| F | F | H | F | F | $CH_3$ | $CH_3$ |
| F | F | F | F | F | $CH_3$ | $CH_3$ |
| F | F | Br | F | F | $CH_3$ | $CH_3$ |
| F | F | I | F | F | $CH_3$ | $CH_3$ |
| F | H | H | H | Cl | $CH_3$ | $CH_3$ |
| F | H | H | F | Cl | $CH_3$ | $CH_3$ |
| F | F | H | F | Cl | $CH_3$ | $CH_3$ |
| F | F | F | F | Cl | $CH_3$ | $CH_3$ |
| F | F | Br | F | Cl | $CH_3$ | $CH_3$ |
| F | F | I | F | Cl | $CH_3$ | $CH_3$ |
| F | H | H | H | F | $C_2H_5$ | $CH_3$ |
| CN | H | H | H | F | $C_2H_5$ | $CH_3$ |
| F | H | H | F | F | $C_2H_5$ | $CH_3$ |
| F | F | F | F | F | $C_2H_5$ | $CH_3$ |
| F | F | Br | F | F | $C_2H_5$ | $CH_3$ |
| F | F | I | F | F | $C_2H_5$ | $CH_3$ |
| F | F | H | F | F | $C_2H_5$ | $C_2H_5$ |
| F | F | F | F | F | $C_2H_5$ | $C_2H_5$ |
| F | H | H | H | H | —$(CH_2)_4$— | |
| CN | H | H | H | H | —$(CH_2)_4$— | |
| F | F | H | F | H | —$(CH_2)_4$— | |
| F | F | F | F | H | —$(CH_2)_4$— | |
| F | F | Br | F | H | —$(CH_2)_4$— | |
| F | F | I | F | H | —$(CH_2)_4$— | |
| F | H | H | H | H | —$(CH_2)_5$— | |
| F | F | H | F | H | —$(CH_2)_5$— | |
| F | F | F | F | H | —$(CH_2)_5$— | |
| F | F | Br | F | H | —$(CH_2)_5$— | |
| F | F | I | F | H | —$(CH_2)_5$— | |
| F | F | H | F | $CH_3$ | —$(CH_2)_3$— | |
| F | F | F | F | $CH_3$ | —$(CH_2)_3$— | |
| F | H | H | H | F | —$(CH_2)_4$— | |
| CN | H | H | H | F | —$(CH_2)_4$— | |
| F | F | H | F | F | —$(CH_2)_4$— | |
| F | F | F | F | F | —$(CH_2)_4$— | |
| F | F | Br | F | F | —$(CH_2)_4$— | |
| F | F | I | F | F | —$(CH_2)_4$— | |
| F | H | H | H | F | —$(CH_2)_5$— | |
| CN | H | H | H | F | —$(CH_2)_5$— | |
| F | F | H | F | F | —$(CH_2)_5$— | |
| F | F | F | F | F | —$(CH_2)_5$— | |
| F | F | Br | F | F | —$(CH_2)_5$— | |
| F | F | I | F | F | —$(CH_2)_5$— | |
| F | F | H | F | Cl | —$(CH_2)_3$— | |
| F | F | F | F | Cl | —$(CH_2)_3$— | |
| F | H | H | H | Cl | —$(CH_2)_4$— | |
| CN | H | H | H | Cl | —$(CH_2)_4$— | |
| F | F | H | F | Cl | —$(CH_2)_4$— | |
| F | F | F | F | Cl | —$(CH_2)_4$— | |
| F | F | Br | F | Cl | —$(CH_2)_4$— | |
| F | F | I | F | Cl | —$(CH_2)_4$— | |
| F | H | H | H | $C_2H_5$ | $CH_3$ | H |
| F | H | H | F | $C_2H_5$ | $CH_3$ | H |
| F | F | Br | F | $C_2H_5$ | $CH_3$ | H |
| F | F | I | F | $C_2H_5$ | $CH_3$ | H |
| F | H | H | H | $OCH_3$ | $CH_3$ | H |
| CN | H | H | H | $OCH_3$ | $CH_3$ | H |
| F | F | H | F | $OCH_3$ | $CH_3$ | H |
| F | F | F | F | $OCH_3$ | $CH_3$ | H |
| F | F | Br | F | $OCH_3$ | $CH_3$ | H |
| F | F | I | F | $OCH_3$ | $CH_3$ | H |
| F | H | H | H | $OCH_3$ | $CH_3$ | $CH_3$ |
| CN | H | H | H | $OCH_3$ | $CH_3$ | $CH_3$ |
| F | F | H | F | $OCH_3$ | $CH_3$ | $CH_3$ |
| F | F | F | F | $OCH_3$ | $CH_3$ | $CH_3$ |
| F | F | Br | F | $OCH_3$ | $CH_3$ | $CH_3$ |
| F | F | I | F | $OCH_3$ | $CH_3$ | $CH_3$ |
| F | H | H | F | H | $CH_3$ | $C(CH_3)_3$ |
| F | H | H | F | H | $CH_3$ | $CF_3$ |
| F | H | H | F | H | $CH_3$ | —CH—$CH_2$—$CH_2$— |
| F | H | H | F | F | $CH_3$ | $CH_3$. |

4. The combination of claim 1, wherein
the compounds of group b1) are selected from the group consisting of ACC-herbicides namely alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-chloro-4-cyclo-propyl-2'-fluoro[1,1'-biphenyl]-3-yl)-5-hydroxy-2,2,6,6-tetramethyl-2H-pyran-3(6H)-one; 4-(2',4'-dichloro-4-cyclopropyl [1,1'-biphenyl]-3-yl)-5-hydroxy-2,2,6,6-tetramethyl-2H-pyran -3(6H)-one; 4-(4'-chloro-4-ethyl-2'-fluoro[1,1'-biphenyl]-3-yl)-5-hydroxy-2,2,6,6-tetramethyl-2H-pyran-3(6H)-one; 4-(2',4'-dichloro-4-ethyl[1,1'-biphenyl]-3-yl)-2,2,6,6-tetramethyl-2H-pyran-3,5(4H,6H)-dione; 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one; 5-(acetyloxy)-4-(2',4'-dichloro-4-cyclopropyl-[1,1'-biphenyl]-3-yl)-3,6-dihydro-2,2,6,6- tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one; 5-(acetyloxy)-4-(2',4'-dichloro-4-ethyl[1,1'-biphenyl]-3-yl)-3,6-dihydro-2,2,6,6-tetramethyl-2H-pyran-3-one; 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester; 4-(2',4'-dichloro -4-cyclopropyl-[1,1'-biphenyl]-3-yl)-5,6-dihydro-2,2,6,6-tetramethyl-5-oxo-2H-pyran-3-yl carbonic acid methyl ester; 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester; 4-(2',4'-dichloro-4-ethyl41,1'-biphenyl]-3-yl)-5,6-dihydro-2,2,6,6-tetramethyl-5-oxo-2H-pyran-3-yl carbonic acid methyl ester, non ACC herbicides namely benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate, including their agriculturally acceptable salts an derivatives;

the compounds of group b2) are selected from the group consisting of sulfonylureas namely amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones namely imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates namely bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester, 4-[[[2-[(4,6-dimethoxy-2-pyrimidinyl)oxy]phenyl]methyl]amino]-benzoic acid propyl ester, N-(4-bromophenyl)-2-[(4,6-dimethoxy-2-pyrimidinyl)oxy]benzenemethanamine, sulfonylaminocarbonyl-triazolinone herbicides namely flucarbazone, flucarbazone-sodium, propoxycarbazone, propoxycarbazone-sodium, thiencarbazone and thiencarbazone-methyl; and triafamone, including their agriculturally salts and derivatives;

the compounds of group b3) are selected from the group consisting of amicarbazone, inhibitors of the photosystem II, namely the triazine herbicides, ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea namely chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates namely desmedipham, karbutilat, phenmedipham, phenmedipham-ethyl, nitrile herbicides namely bromofenoxim, bromoxynil and its salts and esters, ioxynil and its salts and esters, uraciles namely bromacil, lenacil and terbacil, and bentazon and bentazon-sodium, pyridate, pyridafol, pentanochlor and propanil and inhibitors of the photosystem I namely diquat, diquat-dibromide, paraquat, paraquat-dichloride and paraquat-dimetilsulfate, including their agriculturally salts and derivatives;

the compounds of group b4) are selected from the group consisting of acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate; N-ethyl-3-(2,6-dichloro-4-trifluoromethylphenoxy)-5-methyl-1H-pyrazole-1-carboxamide, N-tetrahydrofurfuryl-3-(2,6-dichloro-4-trifluoromethylphenoxy)-5-methyl-1H-pyrazole-1-carboxamide, N-ethyl-3-(2-chloro-6-fluoro-4-trifluoromethylphenoxy)-5-methyl-1H-pyrazole-1-carboxamide, N-tetrahydrofurfuryl-3-(2-chloro-6-fluoro-4-trifluoro-methylphenoxy)-5-methyl-1H-pyrazole-1-carboxamide, 347-fluoro-3-oxo-4-(prop-2thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, 1-Methyl-6-trifluoro-methyl-3-(2,2,7-trifluoro-3-oxo-4-prop-2-ynyl-3,4-dihydro-2H-benzo[1,4]oxazin-6-yl)-1H-pyrimidine-2,4-dione, methyl (E)-4-[2-chloro-5-[4-chloro-5-(difluoromethoxy)-1H-methyl-pyrazol-3-yl]-4-fluoro-phenoxy]-3-methoxy-but-2-enoate, and 3-[7-Chloro-5-fluoro-2-(trifluoromethyl)-1H-benzimidazol-4-yl]-1-methyl-6-(trifluoromethyl)-1H-pyrimidine-2,4-dione, including their agriculturally salts and derivatives;

the compounds of group b5) are selected from the group consisting of

PDS inhibitors namely beflubutamid, diflufenican, fluridone, flurochloridone, flurtamone, norflurazon, picolinafen, and 4-(3-trifluoromethylphenoxy)-2-(4-trifluoromethylphenyl)-pyrimidine;

HPPD inhibitors namely benzobicyclon, bicyclopyrone, benzofenap, clomazone, fenquintrione, isoxaflutole, mesotrione, pyrasulfotole, pyrazolynate, pyrazoxyfen, sulcotrione, tefuryltrione, tembotrione, topramezone and bicyclopyrone, bleacher, aclonifen, amitrole and flumeturon, including their agriculturally salts and derivatives;

the compounds of group b6) are selected from the group consisting of glyphosate, glyphosate-isopropylammonium, glyposate-potassium and glyphosate-trimesium, including their agriculturally salts and derivatives;

the compounds of group b7) are selected from the group consisting of bilanaphos, bilanaphos-sodium, glufosinate, glufosinate-P and glufosinate-ammonium, including their agriculturally salts and derivatives;

the compounds of group b8) are selected from the group consisting of asulam, including their agriculturally salts and derivatives;

the compounds of group b9) are selected from the group consisting of

K1 namely dinitroanilines namely benfluralin, butralin, dinitramine, ethafluralin, fluchloralin, oryzalin, pendimethalin, prodiamine and trifluralin, phosphoramidates namely amiprophos, amiprophos-methyl, and butamiphos, benzoic acid herbicides namely chlorthal, chlorthal-dimethyl, pyridines namely dithiopyr and thiazopyr, benzamides namely propyzamide and tebutam; compounds of group K2 namely chlorpropham, propham and carbetamide including their agriculturally salts and derivatives;

the compounds of group b 10) are selected from the group consisting of chloroacetamides namely acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides namely flufenacet and mefenacet, acetanilides namely diphenamid, naproanilide, napropamide and napropamide-M, tetrazolinones namely fentrazamide, and other herbicides namely anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

II.1
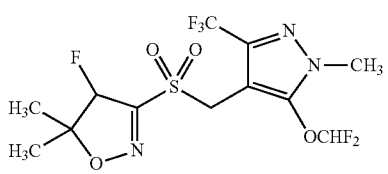

II.2
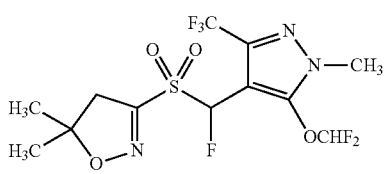

II.3
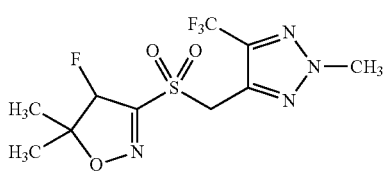

II.4
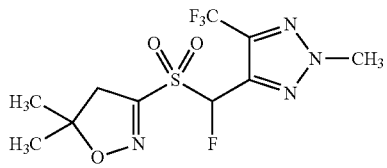

II.5
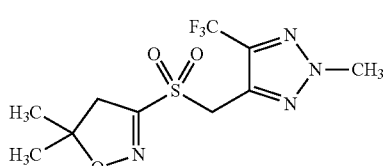

II.6
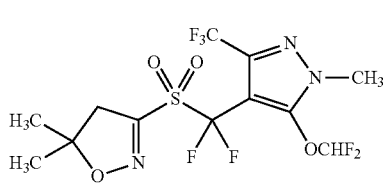

II.7
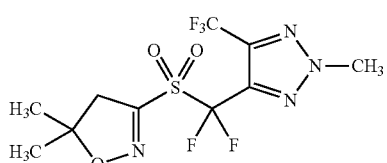

II.8
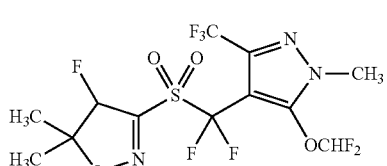

II.9
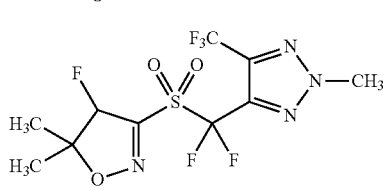

including their agriculturally salts and derivatives;

the compounds of group b11) are selected from the group consisting of chlorthiamid, dichlobenil, flupoxam, triaziflam, indaziflam, isoxaben and 1-Cyclohexyl-5-pentafluorphenyloxy-1$^4$-[1,2,4,6]thiatriazin-3-ylamine including their agriculturally salts and derivatives;

the compounds of group b12) are selected from the group consisting of dinoseb, dinoterb and DNOC and its salts including their agriculturally salts and derivatives;

the compounds of group b13) are selected from the group consisting of 2,4-D and its salts and esters namely clacyfos, 2,4-DB and its salts and esters, aminocyclopyrachlor and its salts and esters, aminopyralid and its salts namely aminopyralid-dimethylammonium, aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters; MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters, triclopyr and its salts and esters;

the compounds of group b14) are selected from the group consisting of diflufenzopyr, diflufenzopyr-sodium, naptalam and naptalam-sodium including their agriculturally salts and derivatives and the compounds of group b15) are selected from the group consisting of bromobutide, chlorflurenol, chlorflurenol-methyl, cinmethylin, cumyluron, cyclopyrimorate and its salts and esters, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin, methyl azide, methyl bromide, methyl-dymron, methyl iodide, MSMA, oleic acid, oxaziclomefone, pelargonic acid, pyributicarb, quinoclamine, triaziflam and tridiphane including their agriculturally salts and derivatives.

5. The combination of claim 1, wherein active compound (II) comprises at least one compound (II) selected from the compounds of group b 1).

6. The combination of claim 5, wherein b1) is selected from the group consisting of clodinafop-propargyl, cycloxydim, cyhalofop-butyl, fenoxaprop-P-ethyl, pinoxaden, profoxydim, tepraloxydim, tralkoxydim, 4-(4'-chloro-4-cyclopropyl-2'-fluoro[1,1'-biphenyl]-3-yl)-5-hydroxy-2,2,6,6-tetramethyl-2H-pyran-3(6H)-one; 4-(2',4'-dichloro-4-cyclopropyl[1,1'-biphenyl]-3-yl)-5-hydroxy-2,2,6,6-tetramethyl-2H-pyran-3(6H)-one; 4-(4'-chloro-4-ethyl-2'-fluoro[1,1'-biphenyl]-3-yl)-5-hydroxy-2,2,6,6-tetramethyl-2H-pyran-3(6H)-one; 4-(2',4'-dichloro-4-ethyl[1,1'-biphenyl]-3-yl)-2,2,6,6-tetramethyl-2H-pyran-3,5(4H,6H)-dione; 5-(acetyloxy)-4-(4'-chloro-4-cyclopropyl-2'-fluoro[1,1'-biphenyl]-3-yl)-3,6-dihydro-2,2,6,6-tetramethyl-2H-pyran-3-one; 5-(acetyloxy)-4-(2',4'-dichloro-4-cyclopropyl-[1,1'-biphenyl]-3-yl)-3,6-dihydro-2,2,6,6-tetramethyl-2H-pyran-3-one; 5-(acetyloxy)-4-(4'-chloro-4-ethyl-2'-fluoro[1,1'-biphenyl]-3-yl)-3,6-dihydro-2,2,6,6-tetramethyl-2H-pyran-3-one; 5-(acetyloxy)-4-(2',4'-dichloro-4-ethyl[1,1'-biphenyl]-3-yl)-3,6-dihydro-2,2,6,6-tetramethyl-2H-pyran-3-one; 4-(4'-chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester; 4-(2',4'-dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-chloro-4-ethyl-2'-fluoro[1,1'-biphenyl]-3-yl)-5,6-dihydro-2,2,6,6-tetramethyl-5-oxo-2H-pyran-3-yl carbonic acid methyl ester; 4-(2',4'-dichloro-4-ethyl[1,1'-biphenyl]-3-yl)-5,6-dihydro-2,2,6,6-tetramethyl-5-oxo-2H-pyran-3-yl carbonic acid methyl ester; esprocarb, prosulfocarb, thiobencarb and triallate.

7. The combination of claim 1, wherein active compound b) comprises at least one compound (II) selected from the compounds of group b6).

8. The combination of claim 7, wherein b6) is selected from the group consisting of glyphosate, glyphosate-isopropylammonium and glyphosate-trimesium.

9. The combination of claim 1, wherein active compound b) comprises at least one compound (II) selected from the compounds of group b9).

10. The combination of claim 9, wherein b9) is selected from the group consisting of pendimethalin and trifluralin.

11. The combination of claim 1, wherein active compound b) comprises at least one compound b) selected from the compounds of group b10).

12. The combination of claim 11, wherein b10) is selected from the group consisting of acetochlor, cafenstrole, dimethenamid-P, fentrazamide, flufenacet, mefenacet, metazachlor, metolachlor, S-metolachlor, fenoxasulfone, ipfencarbazone, pyroxasulfone and isoxazoline compounds of the formulae II.1, II.2, II.3, II.4, II.5, II.6, II.7, II.8 and II.9 as defined in claim 4.

13. The combination of claim 1, wherein active compound b) comprises at least one compound b) selected from the compounds of b11).

14. The combination of claim 13, wherein b11) is selected from the group consisting of isoxaben.

15. The combination of claim 1 further comprising a safener compound c).

16. The combination of claim 15, wherein the safener compound c) is selected from the group consisting of benoxacor, cloquintocet, cyometrinil, cyprosulfamide, dichlormid, dicyclonon, diethalate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane, 2,2,5-trimethyl-3-(dichloroacetyl)-1,3-oxazolidine and N-(2-methoxybenzoyl)-4-[(methylaminocarbonyl)amino]benzenesulfon-amide.

17. A method for controlling unwanted or undesired plants or vegetation, which method comprises applying the combination of claim 1 on plants, their environment or to the seed of said plants.

18. The method of claim 17 wherein said unwanted or undesired plants or vegetation are controlled in crop plants.

19. A herbicide formulation comprising a combination of claim 1 and at least one solid or liquid carrier.

20. A compound selected from the group consisting of 6-(1-methylbutyl)-N4-(2,3,5,6-tetrafluorophenyl)-1,3,5-triazine-2,4-di amine, N4-(2,3,5,6-tetrafluorophenyl)-6-(1,2,2-trimethylpropyl)-1,3,5-triazine-2,4-diamine, 6-(cyclopropylmethyl)-N4-(2,4,6-trifluorophenyl)-1,3,5-triazine-2,4-diamine or/and an agriculturally acceptable salt or N-oxide thereof.

* * * * *